(12) United States Patent
Honda et al.

(10) Patent No.: US 10,695,412 B2
(45) Date of Patent: *Jun. 30, 2020

(54) COMPOSITIONS AND METHODS FOR THE INDUCTION OF CD8+ T-CELLS

(71) Applicants: Keio University, Tokyo (JP); The University of Tokyo, Tokyo (JP)

(72) Inventors: Kenya Honda, Tokyo (JP); Takeshi Tanoue, Tokyo (JP); Masahira Hattori, Tokyo (JP); Yutaka Kawakami, Tokyo (JP)

(73) Assignees: Keio University, Tokyo (JP); The University of Tokyo, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/421,578

(22) Filed: May 24, 2019

(65) Prior Publication Data

US 2019/0381111 A1 Dec. 19, 2019

Related U.S. Application Data

(63) Continuation of application No. PCT/JP2017/046232, filed on Dec. 22, 2017.

(60) Provisional application No. 62/574,446, filed on Oct. 19, 2017, provisional application No. 62/491,062, filed on Apr. 27, 2017, provisional application No. 62/484,607, filed on Apr. 12, 2017, provisional application No. 62/438,793, filed on Dec. 23, 2016.

(51) Int. Cl.
| | |
|---|---|
| *A61K 35/74* | (2015.01) |
| *A61K 31/7036* | (2006.01) |
| *A61P 35/00* | (2006.01) |
| *C07K 16/28* | (2006.01) |
| *A61K 39/02* | (2006.01) |
| *A61K 39/114* | (2006.01) |
| *A61K 39/395* | (2006.01) |
| *A61K 35/12* | (2015.01) |
| *A61K 9/00* | (2006.01) |
| *A61K 9/19* | (2006.01) |
| *A61K 35/742* | (2015.01) |
| *A61K 39/08* | (2006.01) |
| *C12N 1/20* | (2006.01) |
| *C12Q 1/689* | (2018.01) |
| *A61K 39/00* | (2006.01) |
| *A61K 35/00* | (2006.01) |

(52) U.S. Cl.
CPC ........ *A61K 39/0208* (2013.01); *A61K 9/0053* (2013.01); *A61K 9/19* (2013.01); *A61K 31/7036* (2013.01); *A61K 35/12* (2013.01); *A61K 35/74* (2013.01); *A61K 35/742* (2013.01); *A61K 39/0216* (2013.01); *A61K 39/08* (2013.01); *A61K 39/114* (2013.01); *A61K 39/3955* (2013.01); *A61K 39/39558* (2013.01); *A61P 35/00* (2018.01); *C07K 16/2818* (2013.01); *C12N 1/20* (2013.01); *C12Q 1/689* (2013.01); *A61K 2035/11* (2013.01); *A61K 2035/115* (2013.01); *A61K 2039/505* (2013.01); *A61K 2039/52* (2013.01); *A61K 2039/542* (2013.01); *A61K 2039/585* (2013.01)

(58) Field of Classification Search
CPC .. A61K 38/20; A61K 2039/542; A61K 35/74; A61K 31/7036; A61K 35/12; A61K 2035/11; A61P 31/04; A61P 35/00; C12Q 1/689; C12N 15/09; C01K 16/2818
See application file for complete search history.

(56) References Cited

U.S. PATENT DOCUMENTS

2019/0343944 A1  11/2019 Honda et al.

FOREIGN PATENT DOCUMENTS

| WO | WO 2013/080561 A1 | 6/2013 |
| WO | WO 2014/121298 A2 | 8/2014 |
| WO | WO 2015/077794 A1 | 5/2015 |
| WO | WO 2015/156419 A1 | 10/2015 |
| WO | WO 2016/196605 A1 | 12/2016 |

OTHER PUBLICATIONS

Tanoue T. et al., "A defined commensal consortium elicits CD8 T cells and anti-cancer immunity", Nature, vol. 565, published on Jan. 31, 2019, pp. 600-605 (with supplemental data; total pp. 25). (Year: 2019).*
Genbank accession No. AB247141. Hasegawa et al. Jan. 19, 2006.
Genbank accession No. AB249652. Tamura et al. Oct. 17, 2012.
Genbank accession No. AB261128. Sakamoto et al. Nov. 9, 2012.
Genbank accession No. AB490801. Watanabe et al. Aug. 6, 2010.
Genbank accession No. AB331897. Morotomi et al. Aug. 19, 2009.
Genbank accession No. AB470343. Sakamoto et al. Nov. 9, 2012.
Genbank accession No. AB595134. Sakamoto et al. Nov. 9, 2012.
Genbank accession No. AF139525. Gregg et al. Jun. 2, 1999.
Genbank accession No. AY608696. Song et al. Dec. 2, 2005.
Genbank accession No. CP011531. Russell et al. May 3, 2016.
Genbank accession No. CR626927. Cerdano-Tarraga et al. Feb. 6, 2015.
Genbank accession No. KR822463. Asao et al. Oct. 27, 2016.
Genbank accession No. LN998073. Ndongo et al. Feb. 6, 2016.

(Continued)

*Primary Examiner* — Satyendra K Singh
(74) *Attorney, Agent, or Firm* — Wolf, Greenfield & Sacks, P.C.

(57) ABSTRACT

Provided herein are compositions and methods for the induction and/or proliferation of CD8+ T-cells. The disclosure also provides methods of treatment of diseases that can be treated by the induction and/or proliferation of CD8+ T-cells.

20 Claims, 83 Drawing Sheets

Specification includes a Sequence Listing.

(56) References Cited

OTHER PUBLICATIONS

Genbank accession No. NR_112933. Sakamoto et al. Feb. 3, 2015.
Genbank accession No. NR_112935. Sakamoto et al. Feb. 3, 2015.
Genbank accession No. NR_112945. Sakamoto et al. Feb. 3, 2015.
Genbank accession No. NR_113076. Sakamoto et al. Feb. 3, 2015.
Genbank accession No. HE974920. Sjoberg et al. Jul. 1, 2013.
Genbank accession No. NZ_CAEG00000000. Apr. 8, 2017.
Genbank accession No. NZ_ACWB00000000. Apr. 17, 2017.
Genbank accession No. NZ_ACWW00000000. Jun. 19, 2017.
Pitt et al., Fine-Tuning Cancer Immunotherapy: Optimizing the Gut Microbiome. Cancer Res. Aug. 15, 2016;76(16):4602-7. doi: 10.1158/0008-5472.CAN-16-0448. Epub Jul. 29, 2016.

* cited by examiner

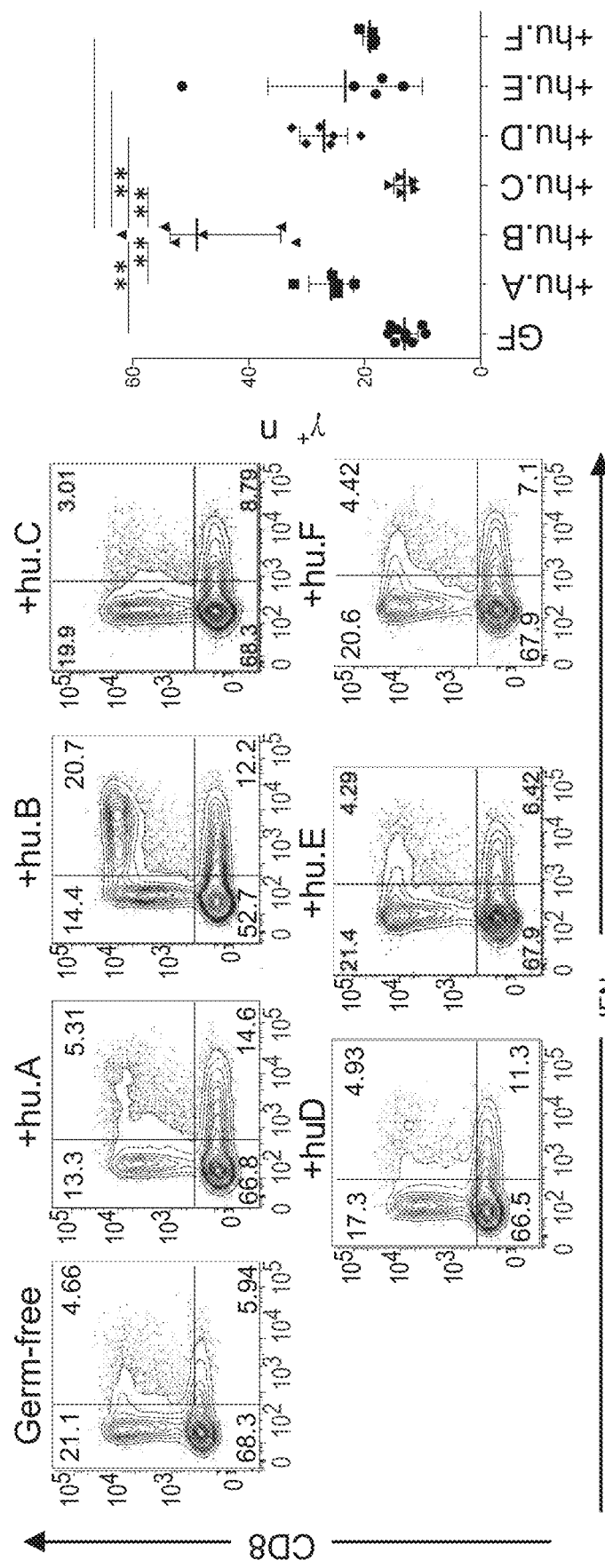

| ID | S_ab score | sequence name | # |
|---|---|---|---|
| 1A1 | 1 | Clostridium innocuum | 26 |
| 1F3 | 0.99 | Ruminococcus sp. | 25 |
| 1E6 | 0.99 | Clostridium lavalense | 24 |
| 1G1 | 0.99 | Hungatella hathewayi | 23 |
| 3F2 | 0.79 | Lachnospiraceae bacterium HGA0140 | 22 |
| 1H8 | 0.99 | Bacteriodes sp. | 21 |
| 2E8 | 0.99 | Parabacteroides goldsteinii | 20 |
| 2D2 | 0.98 | Clostridium sp. | 19 |
| 2B11 | 0.99 | Bacteroides eggerthii | 18 |
| 1A2 | 0.99 | Bacteroides uniformis | 17 |
| 2A12 | 0.99 | Bacteroides fragilis | 16 |
| 2A3 | 0.99 | Bacteroides salyersiae | 15 |
| 1B4 | 1 | Anaerostipes caccae | 14 |
| 2C1 | 0.99 | Bacteroides clarus | 13 |
| 2B7 | 0.99 | Bacteroides cellulosilyticus | 12 |
| 2G9 | 0.99 | Parabacteroides distasonis | 11 |
| 1C1 | 0.99 | Eubacterum limosum | 10 |
| 1H9 | 0.97 | Parabacteroides gordonii | 9 |
| 1E7 | 0.97 | Alistipes sp. | 8 |
| 2F11 | 0.99 | Parabacteroides johnsonii | 7 |
| 2A6 | 0.99 | Paraprevotella xylaniphila | 6 |
| 2B1 | 1 | Subdoligranulum sp. | 5 |
| 2G1 | 0.99 | Bacteroides uniformis | 4 |
| 1B11 | 1 | Bacteroides dorei | 3 |
| 1A6 | 0.99 | Fusobacterium ulcerans | 2 |
| 2G5 | 0.99 | Phascolarctobacterium faecium | 1 |

- negatively correlated with IFNγ + CD8T
- positively correlated with IFNγ + CD8T
- detected in Chloro. B#5
- corresponding to isolated strains

Fig. 7B

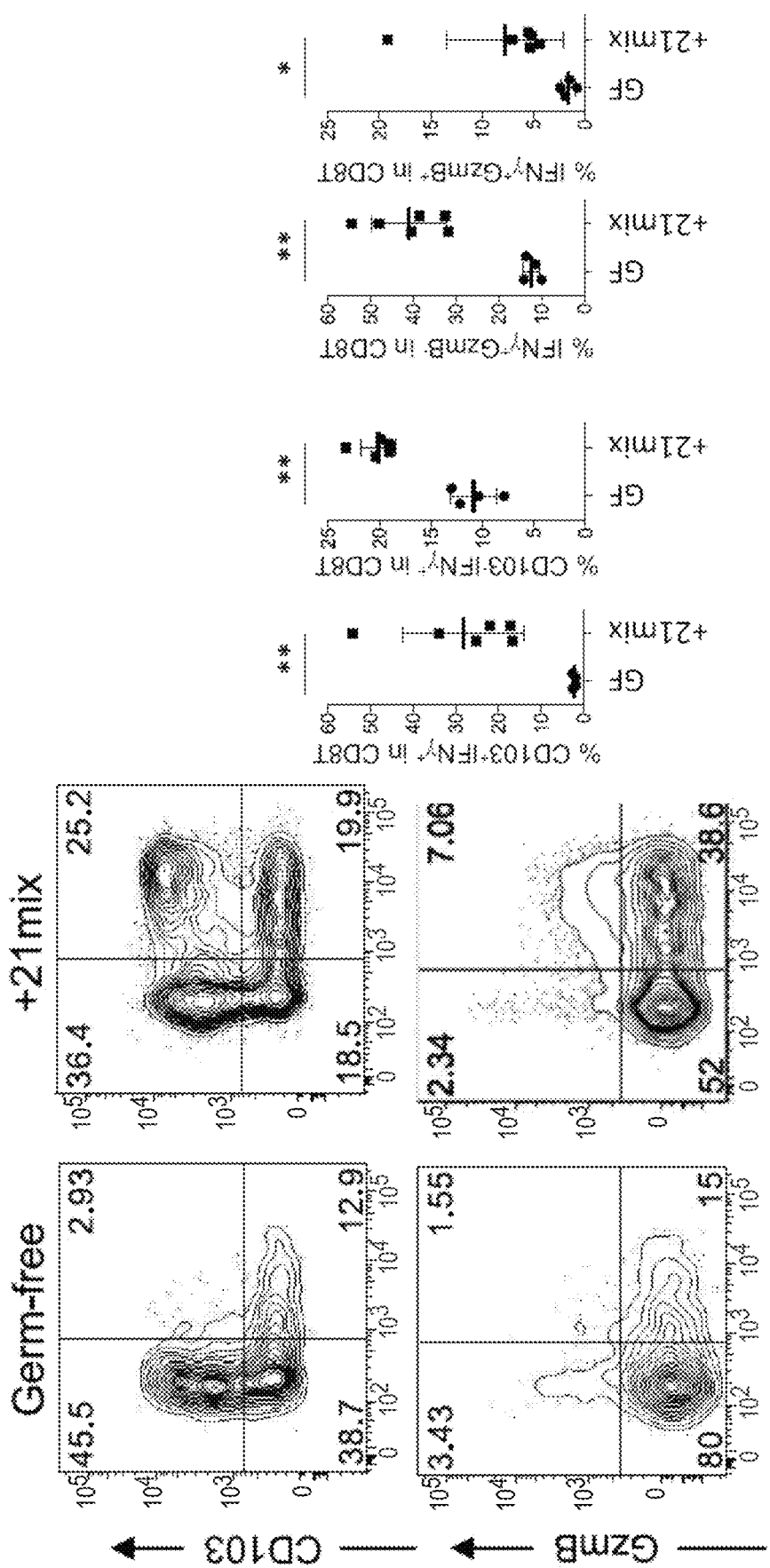

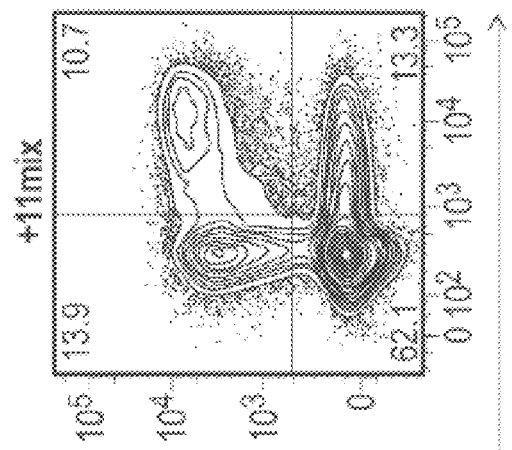
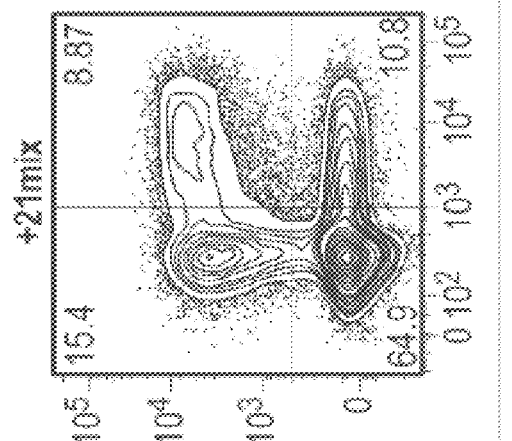
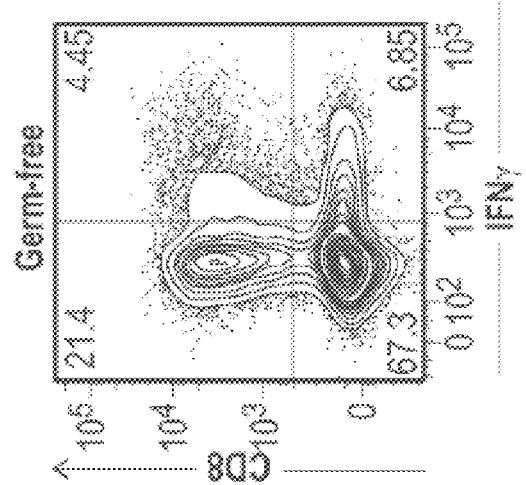
Fig. 10A
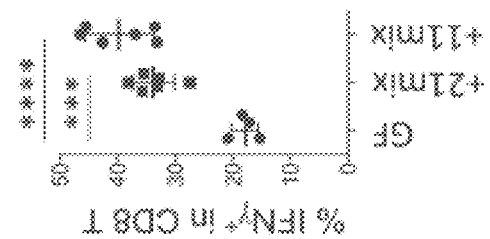
Fig. 10B

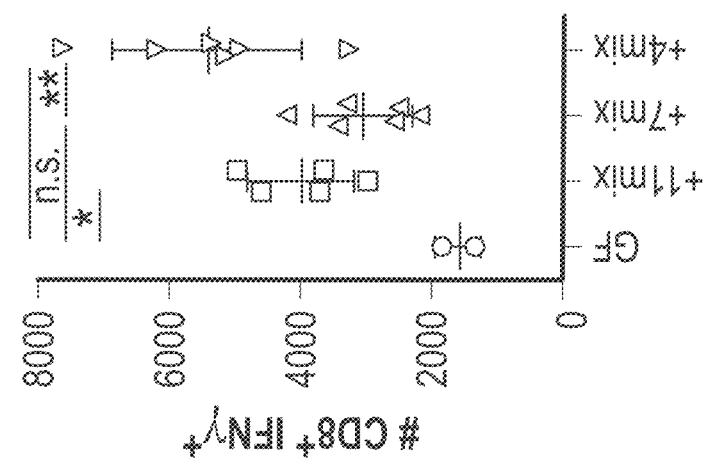
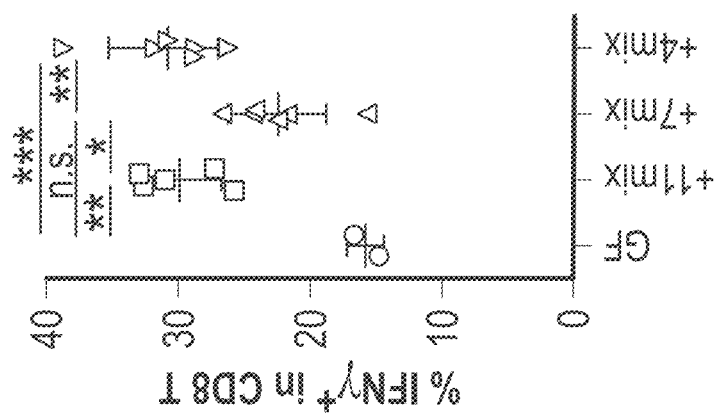
Fig. 14B
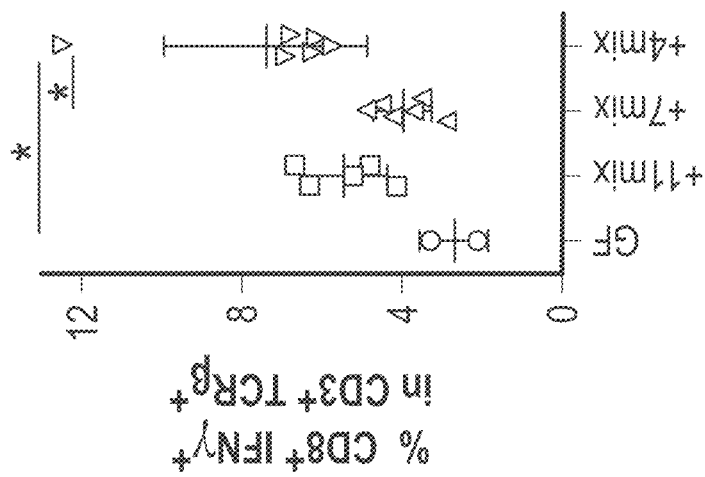

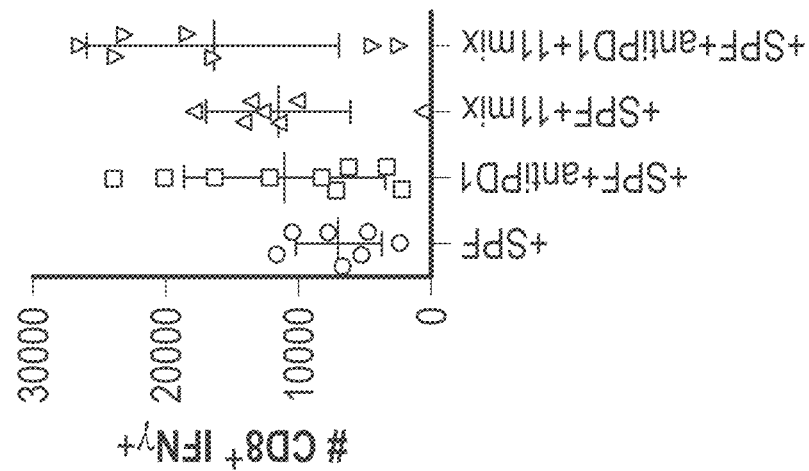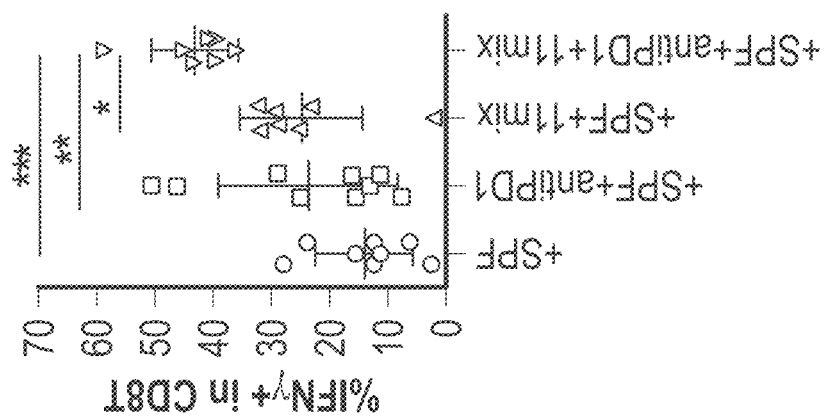
Fig. 16B
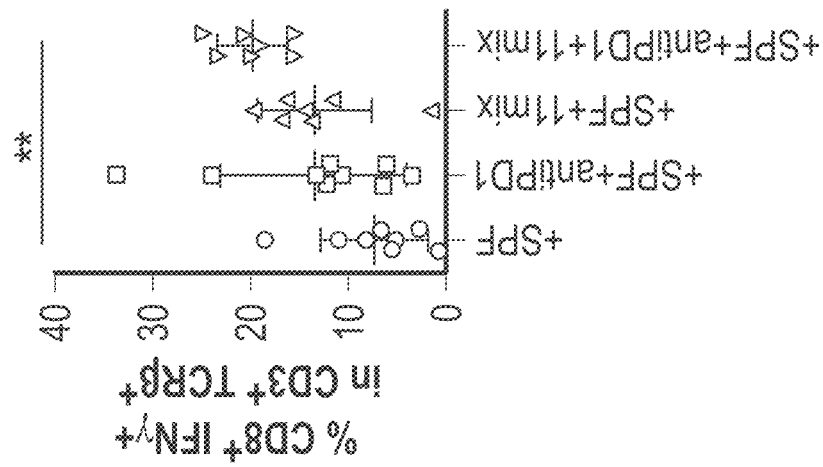

Fig. 20

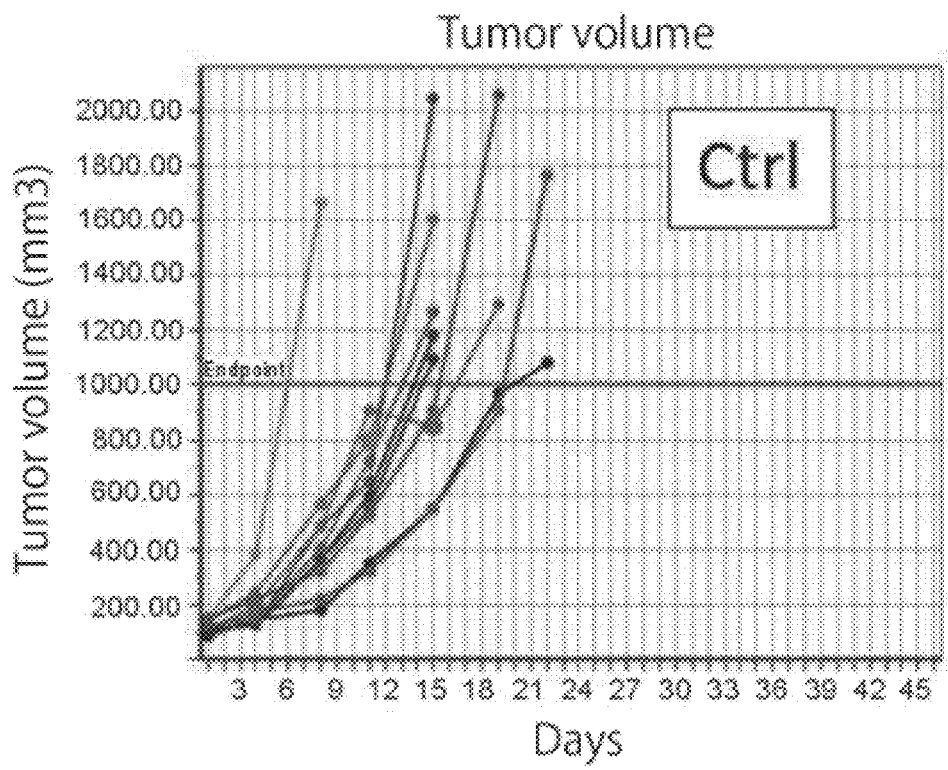
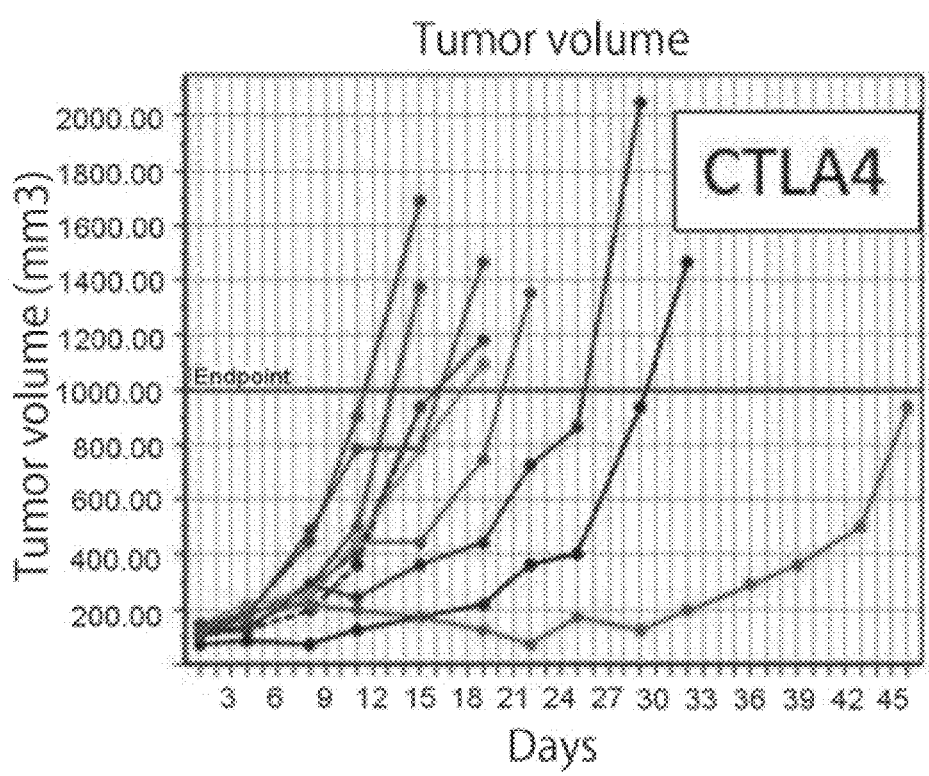
Fig. 27

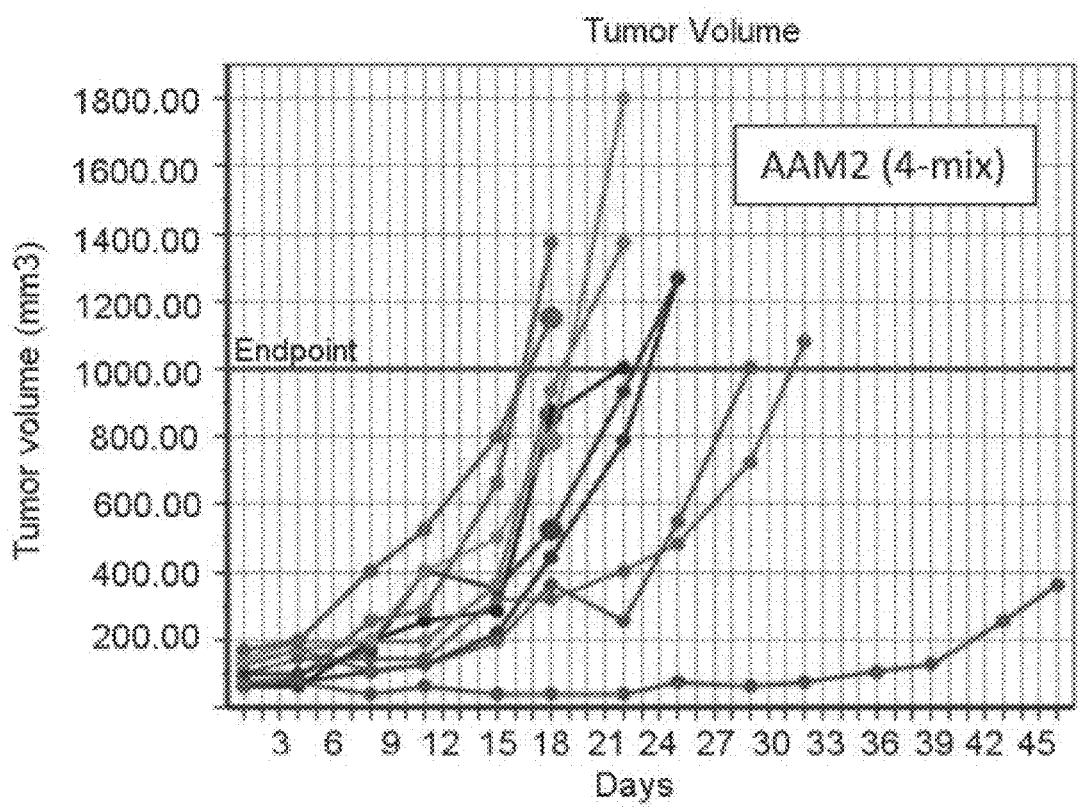
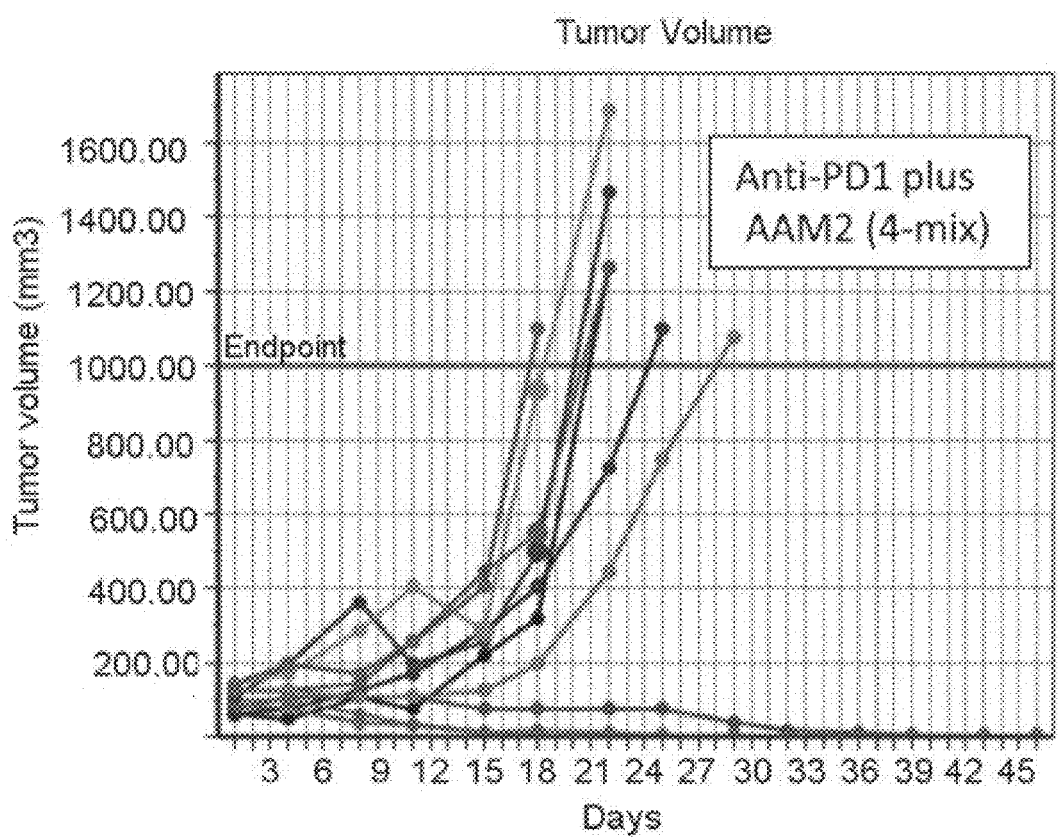
Fig. 32 (Continued)

One mouse in SPF feces group (among 8 mice) died at day 6. %BW of 11mix group is significantly (P<0.05) higher than the other 2 groups at day3-5.

SEQUENCE LISTING

<160> NUMBER OF SEQ ID NOS: 64

<210> SEQ ID NO 1
<211> LENGTH: 1440
<212> TYPE: DNA
<213> ORGANISM: Phascolarctobacterium faecium

<400> SEQUENCE: 1

```
gacgaacgct ggcggcgtgc ctaacacatg caagtcgaac ggagaatttt atttcggtag      60
aattcttagt ggcgaacggg tgagtaacgc gtaggcaacc taccctttag acggggacaa     120
cattccgaaa ggagtgctaa taccggatgt gatcatcttg ccgcatggca ggatgaagaa     180
agatggcctc tacaagtaag ctatcgctaa aggatgggcc tgcgtctgat tagctagttg     240
gtagtgtaac ggactaccaa ggcgatgatc agtagccggt ctgagaggat gaacggccac     300
attgggactg agacacggcc caaactccta cgggaggcag cagtggggaa tcttccgcaa     360
tggacgaaag tctgacggag caacgccgcg tgagtgatga aggatttcgg tctgtaaagc     420
tctgttgttt atgacgaacg tgcagtgtgt gaacaatgca ttgcaatgac ggtagtaaac     480
gaggaagcca cggctaacta cgtgccagca gccgcggtaa tacgtaggtg gcgagcgttg     540
tccggaatta ttgggcgtaa agagcatgta ggcggcttaa taagtcgagc gtgaaaatgc     600
ggggctcaac cccgtatggc gctggaaact gttaggcttg agtgcaggag aggaaagggg     660
aattcccagt gtagcggtga aatgcgtaga tattgggagg aacaccagtg gcgaaggcgc     720
ctttctggac tgtgtctgac gctgagatgc gaaagccagg gtagcgaacg ggattagata     780
ccccggtagt cctggccgta aacgatgggt actaggtgta ggaggtatcg accccttctg     840
tgccggagtt aacgcaataa gtaccccgcc tggggagtac ggccgcaagg ttgaaactca     900
aaggaattga cgggggcccg cacaagcggt ggagtatgtg gtttaattcg acgcaacgcg     960
aagaacctta ccaaggcttg acattgattg aacgctctag agatagagat ttcccttcgg    1020
ggacaagaaa acaggtggtg catggctgtc gtcagctcgt gtcgtgagat gttgggttaa    1080
gtcccgcaac gagcgcaacc cctatcctat gttaccagca agtaaagttg gggactcatg    1140
ggagactgcc agggacaacc tggaggaagg cggggatgac gtcaagtcat catgcccctt    1200
atgtcttggg ctacacacgt actacaatgg tcggaaacag agggaagcga agccgcgagg    1260
cagagcaaac cccagaaacc cgatctcagt tcggatcgca ggctgcaacc cgcctgcgtg    1320
aagtcggaat cgctagtaat cgcaggtcag catactgcgg tgaatacgtt cccgggcctt    1380
gtacacaccg cccgtcacac cacgaaagtt ggtaacaccc gaagccggtg aggtaaccta    1440
```

<210> SEQ ID NO 2
<211> LENGTH: 1392
<212> TYPE: DNA
<213> ORGANISM: Fusobacterium ulcerans

<400> SEQUENCE: 2

```
gatgaacgct gacagaatgc ttaacacatg caagtctact tgatccttcg ggtgaaggtg      60
gcggacgggt gagtaacgcg taaagaactt gccttacaga ctgggacaac atttggaaac     120
gaatgctaat accggatatt atgattgggt cgcatgatct gattatgaaa gctatatgcg     180
ctgtgagaga gctttgcgtc ccattagtta gttggtgagg taacggctca ccaagacgat     240
```

```
gatgggtagc cggcctgaga gggtgaacgg ccacaagggg actgagacac ggcccttact      300
cctacgggag gcagcagtgg ggaatattgg acaatggacc aaaagtctga tccagcaatt      360
ctgtgtgcac gaagaagttt tcggaatgt aaagtgcttt cagttgggaa gaagtcagtg       420
acggtaccaa cagaagaagc gacggctaaa tacgtgccag cagccgcggt aatacgtatg      480
tcgcaagcgt tatccggatt tattgggcgt aaagcgcgtc taggcggctt agtaagtctg      540
atgtgaaaat gcggggctca accccgtatt gcgttggaaa ctgctaaact agagtactgg      600
agaggtaggc ggaactacaa gtgtagaggt gaaattcgta gatatttgta ggaatgccga      660 tgggaagcc agcctactgg acagatactg acgctaaagc gcgaaagcgt gggtagcaaa       720
caggattaga taccctggta gtccacgccg taaacgatga ttactaggtg ttgggggtcg      780
aacctcagcg cccaagctaa cgcgataagt aatccgcctg ggagtacgt acgcaagtat       840 gaaactcaaa ggaattgacg gggacccgca caagcggtgg agcatgtggt ttaattcgac      900
gcaacgcgag gaaccttacc agcgtttgac atcccaagaa gttaacagag atgttttcgt      960
gcctcttcgg aggaacttgg tgacaggtgg tgcatggctg tcgtcagctc gtgtcgtgag     1020
atgttgggtt aagtcccgca acgagcgcaa ccccttcgt atgttaccat cattaagttg      1080
gggactcatg cgagactgcc tgcgatgagc aggaggaagg tggggatgac gtcaagtcat     1140
catgcccctt atacgctggg ctacacacgt gctacaatgg gtagtacaga gagctgcaaa     1200
cctgcgaggg taagctaatc tcataaaact attcttagtt cggattgtac tctgcaactc     1260
gagtacatga agttggaatc gctagtaatc gcaaatcagc tatgttgcgg tgaatacgtt     1320
ctcgggtctt gtacacaccg cccgtcacac cacgagagtt ggttgcacct gaagtaacag     1380
gcctaaccgt aa                                                         1392

<210> SEQ ID NO 3
<211> LENGTH: 1443
<212> TYPE: DNA
<213> ORGANISM: Bacteroides dorei
<220> FEATURE:
<221> NAME/KEY: misc_feature
<222> LOCATION: (7)..(9)
<223> OTHER INFORMATION: n is a, c, g, or t

<400> SEQUENCE: 3
agtttgnnnt atggctcagg atgaacgcta gctacaggct taacacatgc aagtcgaggg       60
gcagcatggt cttagcttgc taaggctgat ggcgaccggc gcacgggtga gtaacacgta      120
tccaacctgc cgtctactct tggccagcct tctgaaagga agattaatcc aggatgggat      180
catgagttca catgtccgca tgattaaagg tattttccgg tagacgatgg ggatgcgttc      240
cattagatag taggcgggt aacgccac ctagtcaacg atggataggg gttctgagag         300
gaaggtcccc cacattggaa ctgagacacg gtccaaactc ctacgggagg cagcagtgag     360
gaatattggt caatgggcga tggcctgaac cagccaagta gcgtgaagga tgactgccct      420
atgggttgta aacttctttt ataaaggaat aaagtcgggt atgcataccc gtttgcatgt      480
actttatgaa taaggatcgg ctaactccgt gccagcagcc gcggtaatac ggaggatccg      540
agcgttatcc ggatttattg ggtttaaagg gagcgtagat ggatgtttaa gtcagttgtg      600
aaagtttgcg gctcaaccgt aaaattgcag ttgatactgg atgtcttgag tgcagttgag      660
gcaggcggaa ttcgtggtgt agcggtgaaa tgcttagata tcacgaagaa ctccgattgc      720
gaaggcagcc tgctaagctg caactgacat tgaggctcga agtgtgggt atcaaacagg       780 attagatacc ctggtagtcc acacggtaaa cgatgaatac tcgctgtttg cgatatacgg      840
```

```
caagcggcca agcgaaagcg ttaagtattc cacctgggga gtacgccggc aacggtgaaa        900
ctcaaaggaa ttgacggggg cccgcacaag cggaggaaca tgtggtttaa ttcgatgata        960
cgcgaggaac cttacccggg cttaaattgc actcgaatga tccggaaacg gttcagctag       1020
caatagcgag tgtgaaggtg ctgcatggtt gtcgtcagct cgtgccgtga ggtgtcggct       1080
taagtgccat aacgagcgca acccttgttg tcagttacta acaggtgatg ctgaggactc       1140
tgacaagact gccatcgtaa gatgtgagga aggtggggat gacgtcaaat cagcacggcc       1200
cttacgtccg gggctacaca cgtgttacaa tggggggtac agagggccgc taccacgcga       1260
gtggatgcca atccctaaaa cccctctcag ttcggactgg agtctgcaac ccgactccac       1320
gaagctggat tcgctagtaa tcgcgcatca gccacggcgc ggtgaatacg ttcccgggcc       1380
ttgtacacac cgcccgtcaa gccatgggag ccggggtac ctgaagtgcg taaccgcgag       1440
gat                                                                    1443
```

<210> SEQ ID NO 4
<211> LENGTH: 1420
<212> TYPE: DNA
<213> ORGANISM: Bacteroides uniformis

<400> SEQUENCE: 4

```
gatgaacgct agctacaggc ttaacacatg caagtcgagg ggcagcatga acttagcttg         60
ctaagtttga tggcgaccgg cgcacgggtg agtaacacgt atccaacctg ccgatgactc        120
ggggatagcc tttcgaaaga aagattaata cccgatggca tagttcttcc gcatggtaga       180
actattaaag aatttcggtc atcgatgggg atgcgttcca ttaggttgtt ggcggggtaa       240
cggcccacca agccttcgat ggatagggggt tctgagagga aggtcccca cattggaact       300 gagacacggt ccaaactcct acgggaggca gcagtgagga atattggtca atggacgaga       360
gtctgaacca gccaagtagc gtgaaggatg actgccctat ggttgtaaa ctttcttttat       420 acgggaataa agtgaggcac gtgtgccttt ttgtatgtac cgtatgaata aggatcggct       480
aactccgtgc cagcagccgc ggtaatacga aggatccgag cgttatccgg atttattggg       540
tttaaaggga gcgtaggcgg acgcttaagt cagttgtgaa agtttgcggc tcaaccgtaa       600
aattgcagtt gatactgggt gtcttgagta cagtagaggc aggcggaatt cgtggtgtag       660
cggtgaaatg cttagatatc acgaagaact ccgattgcga aggcagcctg ctggactgta       720
actgacgctg atgctcgaaa gtgtgggtat caaacaggat tagataccct ggtagtccac       780
accagtaaac gatgaatact cgctgtttgc gatatacagt aagcggccaa gcgaaagcgt       840
taagtattcc acctggggag tacgccggca acggtgaaac tcaaaggaat tgacggggggc       900 ccgcacaagc ggaggaacat gtggtttaat tcgatgatac gcgaggaacc ttacccgggc       960
ttgaattgca actgaatgat gtggagacat gtcagccgca aggcagttgt gaaggtgctg      1020
catggttgtc gtcagctcgt gccgtgaggt gtcggcttaa gtgccataac gagcgcaacc      1080
cttatcgata gttaccatca ggtgatgctg gggactctgt cgagactgcc gtcgtaagat      1140
gtgaggaagg tggggatgac gtcaaatcag cacggccctt acgtccgggg ctacacacgt      1200
gttacaatgg ggggtacaga aggcagctac acggcgacgt gatgctaatc ccgaaagcct      1260
ctctcagttc ggattggagt ctgcaacccg actccatgaa gctggattcg ctagtaatcg      1320
cgcatcagcc acggcgcggt gaatacgttc cgggcttg tacacaccgc ccgtcaagcc      1380
atgaaagccg ggggtacctg aagtgcgtaa ccgcaaggag                            1420
```

<210> SEQ ID NO 5
<211> LENGTH: 1410
<212> TYPE: DNA
<213> ORGANISM: Subdoligranulum sp.

<400> SEQUENCE: 5

| | | |
|---|---|---|
| gacgaacgct ggcggcgcgc ctaacacatg caagtcgaac ggagctgttt tctctgaagt | 60 |
| tttcggatgg aagagagttc agcttagtgg cgaacgggtg agtaacacgt gagcaacctg | 120 |
| cctttcagtg ggggacaaca tttggaaacg aatgctaata ccgcataaga ccacagtgtc | 180 |
| gcatggcaca ggggtcaaag gatttatccg ctgaaagatg ggctcgcgtc cgattagcta | 240 |
| gatggtgagg taacggccca ccatggcgac gatcggtagc cggactgaga ggttgaacgg | 300 |
| ccacattggg actgagacac ggcccagact cctacgggag gcagcagtgg ggaatattgc | 360 |
| acaatggggg aaaccctgat gcagcgacgc cgcgtggagg aagaaggtct tcggattgta | 420 |
| aactcctgtc ccaggggacg ataatgacgg taccctggga ggaagcaccg gctaactacg | 480 |
| tgccagcagc cgcggtaaaa cgtagggtgc aagcgttgtc cggaattact gggtgtaaag | 540 |
| ggagcgcagg cggattggca agttgggagt gaaatctatg ggctcaaccc ataaattgct | 600 |
| ttcaaaactg tcagtcttga gtggtgtaga ggtaggcgga attcccggtg tagcggtgga | 660 |
| atgcgtagat atcgggagga acaccagtgg cgaaggcggc ctactgggca ctaactgacg | 720 |
| ctgaggctcg aaagcatggg tagcaaacag gattagatac cctggtagtc catgccgtaa | 780 |
| acgatgatta ctaggtgtgg gaggattgac cccttccgtg ccgcagttaa cacaataagt | 840 |
| aatccacctg gggagtacga ccgcaaggtt gaaactcaaa ggaattgacg ggggcccgca | 900 |
| caagcagtgg agtatgtggt ttaattcgaa gcaacgcgaa gaaccttacc aggtcttgac | 960 |
| atcggatgca tacctaagag attagggaag tccttcggga catccagaca ggtggtgcat | 1020 |
| ggttgtcgtc agctcgtgtc gtgagatgtt gggttaagtc ccgcaacgag cgcaacccct | 1080 |
| atcgttagtt actacgcaag aggactctag cgagactgcc gttgacaaaa cggaggaagg | 1140 |
| tggggatgac gtcaaatcat catgcccttt atgacctggg ctacacacgt actacaatgg | 1200 |
| ctattaacag agagaagcga taccgcgagg tggagcaaac ctcacaaaaa tagtctcagt | 1260 |
| tcggatcgca ggctgcaacc cgcctgcgtg aagccggaat tgctagtaat cgcggatcag | 1320 |
| catgccgcgg tgaatacgtt cccgggcctt gtacacaccg cccgtcacac catgagagcc | 1380 |
| gggggggaccc gaagtcggta gtctaaccgc | 1410 |

<210> SEQ ID NO 6
<211> LENGTH: 1418
<212> TYPE: DNA
<213> ORGANISM: Paraprevotella xylaniphila
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (1411)..(1412)
<223> OTHER INFORMATION: n is a, c, g, or t

<400> SEQUENCE: 6

| | | |
|---|---|---|
| gatgaacgct agctacaggc ttaacacatg caagtcgagg ggcagcatga acttagcttg | 60 |
| ctaagtttga tggcgaccgg cgcacgggtg agtaacgcgt atccaacctg ccctttaccc | 120 |
| ggggatagcc ttctgaaaag gaagtttaat acccgatgaa ttcgtttagt cgcatggctn | 180 |
| gatgaataaa gattaattgg taaaggatgg ggatgcgtcc cattagcttg ttggcggggt | 240 |

```
aacggcccac caaggcgacg atgggtaggg gttctgagag gaaggtcccc cacattggaa      300
ctgagacacg gtccaaactc ctacgggagg cagcagtgag gaatattggt caatgggcgc      360
gagcctgaac cagccaagta gcgtggagga cgacggccct acgggttgta aactccttt       420 ataagggat aaagttggcc atgtatggcc atttgcaggt accttatgaa taagcatcgg       480
ctaattccgt gccagcagcc gcggtaatac ggaagatgcg agcgttatcc ggatttattg      540
ggtttaaagg gagcgtaggc gggctgtcaa gtcagcggtc aaatggcgcg gctcaaccgc      600
gttccgccgt tgaaactggc agccttgagt atgcacaggg tacatggaat cgtggtgta      660 gcggtgaaat gcttagatat cacgaggaac tccgatcgcg caggcattgt accgggcat       720 tactgacgct gaggctcgaa ggtgcgggta tcaaacagga ttagataccc tggtagtccg      780
cacagtaaac gatgaatgcc cgctgtcggc gacatagtgt cggcggccaa gcgaaagcgt      840
taagcattcc acctggggag tacgccggca acggtgaaac tcaaaggaat tgacggggc       900 ccgcacaagc ggaggaacat gtggtttaat tcgatgatac gcgaggaacc ttacccgggc      960
ttgaatcgca ggtgcatggg ccggagacgg ccctttcctt cgggactcct gcgaaggtgc     1020
tgcatggttg tcgtcagctc gtgccgtgag gtgtcggctt aagtgccata acgagcgcaa     1080 ccccctccc cagttgccac cgggtaatgc cgggcacttt ggggacactg ccaccgcaag     1140
gtgcgaggaa ggtggggatg acgtcaaatc agcacggccc ttacgtccgg ggcgacacac     1200
gtgttacaat gggggtaca gagggccgct gcccggtgac ggttggccaa tccctaaaac      1260
ccctctcagt tcggactgga gtctgcaacc cgactccacg aagctggatt cgctagtaat     1320
cgcgcatcag ccatggcgcg gtgaatacgt tcccgggcct tgtacacacc gcccgtcaag     1380
ccatgaaagc cgggggtgcc tgaagtccgt nnccgcga                              1418

<210> SEQ ID NO 7
<211> LENGTH: 1419
<212> TYPE: DNA
<213> ORGANISM: Parabacteroides johnsonii

<400> SEQUENCE: 7
gatgaacgct agcgacaggc ttaacacatg caagtcgagg ggcagcatgg taagtagcaa       60
tacttattga tggcgaccgg cgcacgggtg agtaacgcgt atgcaactta cctatcagag     120
ggggatagcc cggcgaaagt cggattaata ctccataaaa caggggttcc gcatgggact     180
atttgttaaa gattcatcgc tgatagatag gcatgcgttc cattaggcag ttggcggggt     240
aacggcccac caaaccgacg atggataggg gttctgagag gaaggtcccc cacattggta     300
ctgagacacg gaccaaactc ctacgggagg cagcagtgag gaatattggt caatggccga     360
gaggctgaac cagccaagtc gcgtgaagga tgaaggatct atggtttgta aacttctttt     420 atagggaat aaagtgtggg acgtgttcca ttttgtatgt accctatgaa taagcatcgg     480
ctaactccgt gccagcagcc gcggtaatac ggaggatgcg agcgttatcc ggatttattg     540
ggtttaaagg gtgcgtaggt ggtaatttaa gtcagcggtg aaagtttgtg gctcaaccat     600
aaaattgccg ttgaaactgg gttacttgag tgtgtttgag gtaggcggaa tgcgtggtgt     660
agcggtgaaa tgcatagata tcacgcagaa ctccaattgc gaaggcagct tactaaacca     720
taactgacac tgaagcacga aagcgtgggt atcaaacagg attagatacc ctggtagtcc     780
acgcagtaaa cgatgattac taggagtttg cgatacacag taagctctac agcgaaagcg     840
ttaagtaatc cacctgggga gtacgccggc aacggtgaaa ctcaaaggaa ttgacggggg     900
```

```
cccgcacaag cggaggaaca tgtggtttaa ttcgatgata cgcgaggaac cttacccggg    960
tttgaacgta gtcagaccga ccttgaaaga ggttttctag caatagctga ttacgaggtg   1020
ctgcatggtt gtcgtcagct cgtgccgtga ggtgtcggct taagtgccat aacgagcgca   1080
acccttatca ctagttacta acaggttaag ctgaggactc tggtgagact gccagcgtaa   1140
gctgtgagga aggtggggat gacgtcaaat cagcacggcc cttacatccg ggcgacaca    1200
cgtgttacaa tggcatggac aaagggcagc tacctggcga caggatgcta atctctaaac   1260
catgtctcag ttcggatcgg agtctgcaac tcgactccgt gaagctggat tcgctagtaa   1320
tcgcgcatca gccatggcgc ggtgaatacg ttcccgggcc ttgtacacac cgcccgtcaa   1380
gccatgggag ccgggggtac ctgaagtccg taaccgcaa                          1419
```

<210> SEQ ID NO 8
<211> LENGTH: 1414
<212> TYPE: DNA
<213> ORGANISM: Alistipes sp. JC136
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t

<400> SEQUENCE: 8

```
gatgaacgct agcggcaggc ctaacacatg caagtcgagg ggcagcggga ttgaagcttg     60
cttcagttgc cggcgaccgg cgcacgggtg cgtaacgcgt atgcaaccta cccataacag    120
ggggataaca ctgagaaatc ggtactaata tcccataaca tcaagagggg catccctttt    180
ggttgaaaac tccggtggtt atggatgggc atgcgttgta ttagctagtt ggtgaggtaa    240
cggctcacca aggcgacgat acataggggg actgagaggt taaccccccca cattggtact    300
gagacacgga ccaaactcct acgggaggca gcagtgagga atattggtca atggacgcaa    360
gtctgaacca gccatgccgc gtgcaggatg acggctctat gagttgtaaa ctgcttttgt    420
acgagggtaa acccggatac gtgtatccgg ctgaaagtat cgtacgaata aggatcggct    480
aactccgtgc cagcagccgc ggtaatacgg aggattcaag cgttatccgg atttattggg    540
tttaagggt gcgtaggcgg tttgataagt tagaggtgaa ataccggtgc ttaacaccgg    600
aactgcctct aatactgttg agctagagag tagttgcggt aggcggaatg tatggtgtag    660
cggtgaaatg cttagagatc atacagaaca ccgattgcng aaggcagctt accaaactat    720
atctgacgtt ngaggcacga aagcgtgggg gagcaaacag gattagatac cctggtagtc    780
cacgcagtaa acgatgataa ctcgctgtcg gcgatacaca gtcggtggct aagcgaaagc    840
gataagttat ccacctgggg agtacgttcg caagaatgaa actcaaagga attgacgggg    900
gcccgcacaa gcggaggaac atgtggttta attcgatgat acgcgaggaa ccttacccgg    960
gcttgaaagt tactgacgat tctggaaaca ggatttccct tcggggcagg aaactaggtg   1020
ctgcatggtt gtcgtcagct cgtgccgtga ggtgtcgggt taagtcccat aacgagcgca   1080
acccctaccg ttagttgcca tcaggtcaag ctgggcactc tggcgggact gccggtgtaa   1140
gccgagagga aggtggggat gacgtcaaat cagcacggcc cttacgtccg ggctacaca    1200
cgtgttacaa tggtaggtac agagggcagc tacccagtga tgggatgcga atctcgaaag   1260
cctatctcag ttcggattgg aggctgaaac ccgcctccat gaagtggat tcgctagtaa    1320
tcgcgcatca gccatggcgc ggtgaatacg ttcccgggcc ttgtacacac cgcccgtcaa   1380
```

```
gccatggaag ctgggggtgc ctgaagttcg tgac                              1414
```

<210> SEQ ID NO 9
<211> LENGTH: 1416
<212> TYPE: DNA
<213> ORGANISM: Parabacteroides gordonii
<220> FEATURE:
<221> NAME/KEY: misc_feature
<222> LOCATION: (1408)..(1408)
<223> OTHER INFORMATION: n is a, c, g, or t

<400> SEQUENCE: 9

```
gatgaacgct agcgacaggc ttaacacatg caagtcgagg ggcagcagga agtagcaata    60
ctttgctggc gaccggcgca cgggtgagta acgcgtatgc aacctaccta tcagaggggg   120
ataacccggc gaaagtcgga ctaataccgc ataaaacagg ggtcccgcat gggaatattt   180
gttaaagatt tattgctgat agatgggcat gcgttccatt agatagttgg tgaggtaacg   240
gctcaccaag tcttcgatgg ataggggttc tgagaggaag gtcccccaca ctggtactga   300
gacacggacc agactcctac gggaggcagc agtgaggaat attggtcaat gggcgagagc   360
ctgaaccagc caagtcgcgt gaaggatgaa ggatctatgg ttcgtaaact tcttttatag   420
gggaataaag tgcaggacgt gtcctgtttt gtatgtaccc tatgaataag gatcggctaa   480
ctccgtgcca gcagccgcgg taatacgag gatccgagcg ttatccggat ttattgggtt   540
taaagggtgc gtaggtggct ttttaagtca gcggtgaaag tttgtggctc aaccataaaa   600
ttgccgttga aactggaggg cttgagtata tttgaggtag gcggaatgcg tggtgtagcg   660
gtgaaatgca tagatatcac gcagaactcc aattgcgaag gcagcttact aaactataac   720
tgacactgaa gcacgaaagc gtggggatca aacaggatta taccctgg tagtccacgc    780
agtaaacgat gattactagg agtttgcgat acacagtaag ctctacagcg aaagcgttaa   840
gtaatccacc tggggagtac gccggcaacg gtgaaactca aaggaattga cgggggcccg   900
cacaagcgga ggaacatgtg gtttaattcg atgatacgcg aggaaccta cccgggtttg   960
aacgtaagtt gaccggagtg gaaacactct ttctagcaat agcaatttac gaggtgctgc   1020
atggttgtcg tcagctcgtg ccgtgaggtg tcggcttaag tgccataacg agcgcaaccc   1080
ttatctttag ttactaacag gtcgagctga ggactctaaa gagactgcca gcgtaagctg   1140
tgaggaaggt ggggatgacg tcaaatcagc acggccctta catccggggc gacacacgtg   1200
ttacaatggt ggggacaaag ggcagctacc tggcgacagg atgctaatct ccaaacccca   1260
tctcagttcg gatcgaagtc tgcaacccga cttcgtgaag ctggattcgc tagtaatcgc   1320
gcatcagcca tggcgcggtg aatacgttcc cgggccttgt acacaccgcc cgtcaagcca   1380
tgggagttgg gggtacctaa agtccgtnac cgcaag                             1416
```

<210> SEQ ID NO 10
<211> LENGTH: 1419
<212> TYPE: DNA
<213> ORGANISM: Eubacterium limosum

<400> SEQUENCE: 10

```
gacgaacgct ggcggtatgc ttaacacatg caagtcgaac gagaaggttt tgatggatcc    60
ttcgggtgac attagaactg gaaagtggcg aacgggtgag taacgcgtgg gtaacctgcc   120
ctatggaaag gaatagcctc gggaaactgg gagtaaagcc ttatattatg gttttgtcgc   180
atggcaagat catgaaaact ccggtgccat aggatggacc cgcgtcccat tagctagttg   240
```

-continued

| | |
|---|---|
| gtgagataac agcccaccaa ggcgacgatg gtaaccggt ctgagagggc gaacggtcac | 300 |
| actggaactg agacacggtc cagactccta cgggaggcag cagtggggaa tattgcgcaa | 360 |
| tgggggcaac cctgacgcag caataccgcg tgagtgaaga aggttttcgg atcgtaaagc | 420 |
| tctgttattg gggaagaaga atgacggtac ccaatgagga agtcccggct aactacgtgc | 480 |
| cagcagccgc ggtaatacgt aggggacaag cgttgtccgg aatgactggg cgtaaagggc | 540 |
| gcgtaggcgt ctattaagt ctgatgtgaa aggtaccggc tcaaccggtg aagtgcattg | 600 |
| gaaactggta gacttgagta ttggagaggc aagtggaatt cctagtgtag cggtgaaatg | 660 |
| cgtagatatt aggaggaaca ccagtggcga aggcggcttg ctggacaaat actgacgctg | 720 |
| aggtgcgaaa gcgtggggag cgaacaggat tagataccct ggtagtccac gccgtaaacg | 780 |
| atgaatgcta ggtgttgggg aaactcagtg ccgcagttaa cacaataagc attccgcctg | 840 |
| gggagtacga ccgcaaggtt gaaactcaaa ggaattgacg ggacccgca caagcagcgg | 900 |
| agcatgtggt ttaattcgaa gcaacgcgaa gaaccttacc aggtcttgac atcctctgac | 960 |
| gagcctagag ataggaagtt ccttcgggga acagagagac aggtggtgca tggttgtcgt | 1020 |
| cagctcgtgt cgtgagatgt tgggttaagt cccgcaacga gcgcaacccc tgcctttagt | 1080 |
| tgccagcatt aagttgggca ctctagaggg actgccgtag acaatacgga ggaaggtggg | 1140 |
| gacgacgtca atcatcatg ccccttatga cctgggctac acacgtgcta caatggtctg | 1200 |
| aacagagggc gcgaagccg cgaggtgaag caaatccctt aaaacagatc ccagttcgga | 1260 |
| ttgcaggctg caactcgcct gcatgaagtt ggagttgcta gtaatcgcgg atcagaatgc | 1320 |
| cgcggtgaat gcgttcccgg gtcttgtaca caccgcccgt cacaccacga gagttggcaa | 1380 |
| caccccgaagc ctgtgagaga accgtaagga ctcagcagt | 1419 |

<210> SEQ ID NO 11
<211> LENGTH: 1413
<212> TYPE: DNA
<213> ORGANISM: Parabacteroides distasonis
<220> FEATURE:
<221> NAME/KEY: misc_feature
<222> LOCATION: (1387)..(1387)
<223> OTHER INFORMATION: n is a, c, g, or t

<400> SEQUENCE: 11

| | |
|---|---|
| gatgaacgct agcgacaggc ttaacacatg caagtcgagg ggcagcacag gtagcaatac | 60 |
| cgggtggcga ccggcgcacg ggtgagtaac gcgtatgcaa cttgcctatc agaggggggat | 120 |
| aacccggcga aagtcggact aataccgcat gaagcagggg ccccgcatgg ggatatttgc | 180 |
| taaagattca tcgctgatag ataggcatgc gttccattag gcagttggcg gggtaacggc | 240 |
| ccaccaaacc gacgatggat aggggttctg agaggaaggt cccccacatt ggtactgaga | 300 |
| cacggaccaa actcctacgg gaggcagcag tgaggaatat tggtcaatgg ccgagaggct | 360 |
| gaaccagcca gtcgcgtga gggatgaagg ttctatggat cgtaaacctc ttttataagg | 420 |
| gaataaagtg cgggacgtgt cccgttttgt atgtaccta tgaataagga tcggctaact | 480 |
| ccgtgccagc agccgcggta atacggagga tccgagcgtt atccggattt attgggttta | 540 |
| aagggtgcgt aggcggcctt ttaagtcagc ggtgaaagtc tgtggctcaa ccatagaatt | 600 |
| gccgttgaaa ctggggggct tgagtatgtt tgaggcaggc ggaatgcgtg gtgtagcggt | 660 |
| gaaatgcata gatatcacgc agaaccccga ttgcgaaggc agcctgccaa gccattactg | 720 |
| acgctgatgc acgaaagcgt ggggatcaaa caggattaga taccctggta gtccacgcag | 780 |
| taaacgatga tcactagctg tttgcgatac actgtaagcg gcacagcgaa agcgttaagt | 840 |

```
gatccacctg gggagtacgc cggcaacggt gaaactcaaa ggaattgacg ggggcccgca      900
caagcggagg aacatgtggt ttaattcgat gatacgcgag gaaccttacc cgggtttgaa      960
cgcattcgga ccgaggtgga aacacctttt ctagcaatag ccgtttgcga ggtgctgcat     1020
ggttgtcgtc agctcgtgcc gtgaggtgtc ggcttaagtg ccataacgag cgcaacccctt   1080 gccactagtt actaacaggt aaagctgagg actctggtgg gactgccagc gtaagctgcg    1140
aggaaggcgg ggatgacgtc aaatcagcac ggcccttaca tccggggcga cacacgtgtt   1200
acaatggcgt ggacaaaggg aagccacctg gcgacaggga gcgaatcccc aaaccacgtc   1260
tcagttcgga tcggagtctg caacccgact ccgtgaagct ggattcgcta gtaatcgcgc   1320
atcagccatg gcgcggtgaa tacgttcccg ggccttgtac acaccgcccg tcaagccatg   1380
ggagccnggg gtacctgaag tccgtaaccg cga                                 1413
```

<210> SEQ ID NO 12
<211> LENGTH: 1406
<212> TYPE: DNA
<213> ORGANISM: Bacteroides cellulosilyticus

<400> SEQUENCE: 12

```
gatgaacgct agctacaggc ttaacacatg caagtcgagg ggcagcatga cctagcaata      60
ggttgatggc gaccggcgca cgggtgagta acacgtatcc aacctaccgg ttattccggg     120
atagcctttc gaaagaaaga ttaataccgg atagtataac gagaaggcat cttttttgtta    180 ttaaagaatt tcgataaccg atggggatgc gttccattag tttgttggcg ggtaacggc     240 ccaccaagac atcgatggat aggggttctg agaggaaggt cccccacatt ggaactgaga    300
cacggtccaa actcctacgg gaggcagcag tgaggaatat tggtcaatgg acgagagtct    360
gaaccagcca agtagcgtga aggatgactg ccctatgggt tgtaaacttc ttttatatgg    420
gaataaagtg agccacgtgt ggcttttttgt atgtaccata cgaataagga tcggctaact  480
ccgtgccagc agccgcggta atacggagga tccgagcgtt atccggattt attgggttta    540
aagggagcgt aggcggacta ttaagtcagc tgtgaaagtt tgcggctcaa ccgtaaaatt    600
gcagttgata ctggtcgtct tgagtgcagt agaggtaggc ggaattcgtg gtgtagcggt    660
gaaatgctta gatatcacga gaactccga ttgcgaaggc agcttactgg actgtaactg     720
acgctgatgc tcgaaagtgt gggtatcaaa caggattaga taccctggta gtccacacag     780
taaacgatga atactcgctg tttgcgatat acagcaagcg ccaagcgaa agcattaagt    840 attccacctg gggagtacgc cggcaacggt gaaactcaaa ggaattgacg ggggcccgca    900
caagcggagg aacatgtggt ttaattcgat gatacgcgag gaaccttacc cgggcttaaa    960
ttgcatctga ataatttgga aacagattag ccgtaaggca gatgtgaagg tgctgcatgg   1020
ttgtcgtcag ctcgtgccgt gaggtgtcgg cttaagtgcc ataacgagcg caacccttat   1080
ctttagttac taacaggtca tgctgaggac tctagagaga ctgccgtcgt aagatgtgag  1140
gaaggtgggg atgacgtcaa atcagcacgg cccttacgtc cggggctaca cacgtgttac  1200 aatgggggt acagaaggca gctacacagc gatgtgatgc taatcccaaa agcctctctc    1260
agttcggatt ggagtctgca acccgactcc atgaagctgg attcgctagt aatcgcgcat   1320
cagccacggc gcggtgaata cgttcccggg ccttgtacac accgcccgtc aagccatgaa   1380
agccgggggt acctgaagtc cgtaac                                         1406
```

<210> SEQ ID NO 13

```
<211> LENGTH: 1415
<212> TYPE: DNA
<213> ORGANISM: Bacteroides clarus

<400> SEQUENCE: 13
gatgaacgct agctacaggc ttaacacatg caagtcgagg ggcagcgggg ttgaagcttg    60
cttcaaccgc cggcgaccgg cgcacgggtg agtaacacgt atccaacctg ccgataactc   120
cgggatagcc tttcgaaaga aagattaata ccggatggca tagttttccc gcatggaata   180
actattaaag aatttcggtt atcgatgggg atgcgttcca ttaggcagtt ggcggggtaa   240
cggcccacca aaccgacgat ggataggggg tctgagagga aggtcccccca cattggaact   300
gagacacggt ccaaactcct acgggaggca gcagtgagga atattggtca atggacgaga   360
gtctgaacca gccaagtagc gtgaaggatg actgccctat ggttgtaaa cttcttttat    420
acgggaataa agttggccac gtgtggtttt ttgcatgtac cgtatgaata aggatcggct   480
aactccgtgc cagcagccgc ggtaatacgg aggatccgag cgttatccgg atttattggg   540
tttaaaggga gcgtaggcgg gtattaagt cagttgtgaa agtttgcggc tcaaccgtaa   600
aattgcagtt gatactggta tccttgagtg cagcagaggt gggcggaatt cgtggtgtag   660
cggtgaaatg cttagatatc acgaagaact ccgattgcga aggcagctca ctggagtgta   720
actgacgctg atgctcgaaa gtgtgggtat caaacaggat tagataccct ggtagtccac   780
acagtaaacg atgaatactc gctgttggcg atacaatgtc agcggccaag cgaaagcatt   840
aagtattcca cctggggagt acgccggcaa cggtgaaact caaggaatt gacggggggcc   900
cgcacaagcg aggaacatg tggtttaatt cgatgatacg cgaggaacct tacccgggct   960
tgaattgcaa ctgactgagc tggaaacagt tctttcttcg acagttgtg aaggtgctgc   1020
atggttgtcg tcagctcgtg ccgtgaggtg tcggcttaag tgccataacg agcgcaaccc   1080
ttatctatag ttaccatcag gtcatgctgg ggactctatg gagactgccg tcgtaagatg   1140
tgaggaaggt ggggatgacg tcaaatcagc acggccctta cgtccggggc tacacacgtg   1200
ttacaatggg gggtacagaa ggcagctaca cggcgacgtg atgctaatcc caaaaacctc   1260
tctcagttcg gattggagtc tgcaacccga ctccatgaag ctggattcgc tagtaatcgc   1320
gcatcagcca cggcgcggtg aatacgttcc cgggccttgt acacaccgcc cgtcaagcca   1380
tgaaagccgg gggtacctga agtacgtaac cgcaa                               1415

<210> SEQ ID NO 14
<211> LENGTH: 938
<212> TYPE: DNA
<213> ORGANISM: Anaerostipes sp.
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (899)..(901)
<223> OTHER INFORMATION: n is a, c, g, or t

<400> SEQUENCE: 14
gatgaacgct ggcggcgtgc ttaacacatg caagtcgaac gaagcattta ggattgaagt    60
tttcggatgg atttcctata tgactgagtg gcggacgggt gagtaacgcg tggggaacct   120
gccctataca gggggataac agctggaaac ggctgctaat accgcataag cgcacagaat   180
cgcatgattc agtgtgaaaa gcctggcag tataggatgg tccgcgtct gattagctgg    240
ttggtgaggt aacggctcac caaggcgacg atcagtagcc ggcttgagag agtgaacggc   300
```

```
cacattggga ctgagacacg gcccaaactc ctacgggagg cagcagtggg gaatattgca      360
caatggggga aaccctgatg cagcgacgcc gcgtgagtga agaagtattt cggtatgtaa      420
agctctatca gcaggaaga aaacagacgg tacctgacta agaagcccg gctaactacg        480 tgccagcagc cgcggtaata cgtagggggc aagcgttatc cggaattact gggtgtaaag      540
ggtgcgtagg tggcatggta agtcagaagt gaaagcccgg ggcttaaccc cgggactgct     600
tttgaaactg tcatgctgga gtgcaggaga ggtaagcgga attcctagtg tagcggtgaa      660
atgcgtagat attaggagga acaccagtgg cgaaggcggc ttactggact gtcactgaca      720
ctgatgcacg aaagcgtggg gagcaaacag gattagatac cctggtagtc cacgccgtaa      780
acgatgaata ctaggtgtcg gggccgtaga ggcttcggtg ccgcagcaaa cgcagtaagt      840
attccacctg gggagtacgt tcgcaagaat gaaactcaaa gganttgacg gggaccgcnn      900
nagcggtgga gcatgtggtt aattcgaagc acgcgaag                              938

<210> SEQ ID NO 15
<211> LENGTH: 1406
<212> TYPE: DNA
<213> ORGANISM: Bacteroides salyersiae

<400> SEQUENCE: 15
gatgaacgct agctacaggc ttaacacatg caagtcgagg ggcatcaggg tgtagcaata       60
caccgctggc gaccggcgca cgggtgagta acacgtatcc aacctgccct ttactcgggg      120
atagcctttc gaaagaaaga ttaatacccg atggtataac atgacctcct ggttttgtta      180
ttaaagaatt tcggtagagg atggggatgc gttccattag gcagttggcg gggtaacggc      240
ccaccaaacc ttcgatggat aggggttctg agaggaaggt cccccacatt ggaactgaga      300
cacggtccaa actcctacgg gaggcagcag tgaggaatat tggtcaatgg gcgagagcct      360
gaaccagcca gtagcgtgaa ggatgaccgc ccctatgggt tgtaaacttc ttttatatgg      420
gaataaagtc tgccacgtgt ggcattttgt atgtaccata tgaataagga tcggctaact      480
ccgtgccagc agccgcggta atacggagga tccgagcgtt atccggattt attgggttta      540
aagggagcgt aggtggacat gtaagtcagt tgtgaaagtt tgcggctcaa ccgtaaaatt      600
gcagttgaaa ctgcgtgtct tgagtacagt agaggtgggc ggaattcgtg gtgtagcggt      660
gaaatgctta gatatcacga agaactccga ttgcgaaggc agctcactgg actgcaactg      720
acactgatgc tcgaaagtgt gggtatcaaa caggattaga taccctggta gtccacacag      780
taaacgatga atactcgctg tttgcgatat acagtaagcg gccaagcgaa agcattaagt      840
attccacctg gggagtacgc cggcaacggt gaaactcaaa ggaattgacg ggggcccgca      900
caagcggagg aacatgtggt ttaattcgat gatacgcgag gaaccttacc cgggcttaaa      960
ttgcaaatga atatgccgga aacggcatag ccgcaaggca tttgtgaagg tgctgcatgg     1020
ttgtcgtcag ctcgtgccgt gaggtgtcgg cttaagtgcc ataacgagcg caacccttat     1080
cttcagttac taacaggtca tgctgaggac tctggagaga ctgccgtcgt aagatgtgag     1140
gaaggtgggg atgacgtcaa atcagcacgg cccttacgtc ggggctaca cacgtgttac      1200 aatggggggt acagaaggcc gctacacagc gatgtgatgc caatccctaa agcccctctc     1260
agttcggatc gaagtctgca acccgacttc gtgaagctgg attcgctagt aatcgcgcat     1320
cagccacggc gcggtgaata cgttcccggg ccttgtacac accgcccgtc aagccatggg     1380 agccggggggt acctgaagta cgtaac                                         1406
```

<210> SEQ ID NO 16
<211> LENGTH: 1417
<212> TYPE: DNA
<213> ORGANISM: Bacteroides fragilis

<400> SEQUENCE: 16

| | |
|---|---:|
| gatgaacgct agctacaggc ttaacacatg caagtcgagg ggcatcagga agaaagcttg | 60 |
| ctttctttgc tggcgaccgg cgcacgggtg agtaacacgt atccaacctg cccttactc | 120 |
| ggggatagcc tttcgaaaga aagattaata cccgatagca taatgattcc gcatggtttc | 180 |
| attattaaag gattccggta aaggatgggg atgcgttcca ttaggttgtt ggtgaggtaa | 240 |
| cggctcacca agccttcgat ggatagggt tctgagagga aggtccccca cattggaact | 300 |
| gagacacggt ccaaactcct acgggaggca gcagtgagga atattggtca atgggcgcta | 360 |
| gcctgaacca gccaagtagc gtgaaggatg aaggctctat gggtcgtaaa cttctttat | 420 |
| ataagaataa agtgcagtat gtatactgtt ttgtatgtat tatatgaata aggatcggct | 480 |
| aactccgtgc cagcagccgc ggtaatacg aggatccgag cgttatccgg atttattggg | 540 |
| tttaaaggga gcgtaggtgg actggtaagt cagttgtgaa agtttgcggc tcaaccgtaa | 600 |
| aattgcagtt gatactgtca gtcttgagta cagtagaggt gggcggaatt cgtggtgtag | 660 |
| cggtgaaatg cttagatatc acgaagaact ccgattgcga aggcagctca ctggactgca | 720 |
| actgacactg atgctcgaaa gtgtgggtat caaacaggat tagataccct ggtagtccac | 780 |
| acagtaaacg atgaatactc gctgtttgcg atatacagta agcggccaag cgaaagcatt | 840 |
| aagtattcca cctggggagt acgccggcaa cggtgaaact caaaggaatt gacggggggcc | 900 |
| cgcacaagcg gaggaacatg tggtttaatt cgatgatacg cgaggaacct tacccgggct | 960 |
| taaattgcag tggaatgatg tggaaacatg tcagtgagca atcaccgctg tgaaggtgct | 1020 |
| gcatggttgt cgtcagctcg tgccgtgagg tgtcggctta agtgccataa cgagcgcaac | 1080 |
| ccttatcttt agttactaac aggttatgct gaggactcta gagagactgc cgtcgtaaga | 1140 |
| tgtgaggaag gtggggatga cgtcaaatca gcacggccct tacgtccggg ctacacacg | 1200 |
| tgttacaatg gggggtacag aaggcagcta acgggtgacc gtatgctaat cccaaaagcc | 1260 |
| tctctcagtt cggatcgaag tctgcaaccc gacttcgtga agctggattc gctagtaatc | 1320 |
| gcgcatcagc cacggcgcgg tgaatacgtt cccgggcctt gtacacaccg cccgtcaagc | 1380 |
| catgggagcc gggggtacct gaagtacgta accgcaa | 1417 |

<210> SEQ ID NO 17
<211> LENGTH: 1407
<212> TYPE: DNA
<213> ORGANISM: Bacteroides uniformis

<400> SEQUENCE: 17

| | |
|---|---:|
| gatgaacgct agctacaggc ttaacacatg caagtcgagg ggcatcagga agaaagcttg | 60 |
| ctttctttgc tggcgaccgg cgcacgggtg agtaacacgt atccaacctg ccgatgactc | 120 |
| ggggatagcc tttcgaaaga aagattaata cccgatggta tatctgaaag gcatctttca | 180 |
| gctattaaag aatttcggtc attgatgggg atgcgttcca ttaggttgtt ggcggggtaa | 240 |
| cggcccacca agccatcgat ggatagggt tctgagagga aggtccccca cattggaact | 300 |
| gagacacggt ccaaactcct acgggaggca gcagtgagga atattggtca atggacgaga | 360 |
| gtctgaacca gccaagtagc gtgaaggatg actgccctat gggttgtaaa cttctttat | 420 |
| acgggaataa agttaggcac gtgtgccttt ttgtatgtac cgtatgaata aggatcggct | 480 |

```
aactccgtgc cagcagccgc ggtaatacgg aggatccgag cgttatccgg atttattggg      540
tttaaaggga gcgtaggcgg atgcttaagt cagttgtgaa agtttgcggc tcaaccgtaa      600
aattgcagtt gatactgggt gtcttgagta cagtagaggc aggcggaatt cgtggtgtag      660
cggtgaaatg cttagatatc acgaagaact ccgattgcga aggcagcttg ctggactgta      720
actgacgctg atgctcgaaa gtgtgggtat caaacaggat tagataccct ggtagtccac      780
acagtaaacg atgaatactc gctgtttgcg atatacagta agcggccaag cgaaagcgtt      840
aagtattcca cctggggagt acgccggcaa cggtgaaact caaaggaatt gacggggggcc     900 cgcacaagcg gaggaacatg tggtttaatt cgatgatacg cgaggaacct acccgggct       960 taaattgcaa atgaatgttc tggaaacaga tcagccgcaa ggcatttgtg aaggtgctgc     1020
atggttgtcg tcagctcgtg ccgtgaggtg tcggcttaag tgccataacg agcgcaaccc     1080
ttatcgatag ttaccatcag gttatgctgg ggactctgtc gagactgccg tcgtaagatg     1140
tgaggaaggt ggggatgacg tcaaatcagc acggccctta cgtccggggc tacacacgtg     1200
ttacaatggg gggtacagaa ggcagctaca cggcgacgtg atgctaatcc ctaaaacctc     1260
tctcagttcg gattggagtc tgcaacccga ctccatgaag ctggattcgc tagtaatcgc     1320
gcatcagcca cggcgcggtg aatacgttcc cgggccttgt acacaccgcc cgtcaagcca     1380
tgaaagccgg gggtacctga agtgcgt                                         1407
```

<210> SEQ ID NO 18
<211> LENGTH: 1420
<212> TYPE: DNA
<213> ORGANISM: Bacteroides eggerthii
<220> FEATURE:
<221> NAME/KEY: misc_feature
<222> LOCATION: (220)..(220)
<223> OTHER INFORMATION: n is a, c, g, or t

<400> SEQUENCE: 18

```
gatgaacgct agctacaggc ttaacacatg caagtcgagg ggcagcatga ttgaagcttg       60
cttcaatcga tggcgaccgg cgcacgggtg agtaacacgt atccaacctg ccgataactc      120
ggggatagcc tttcgaaaga aagattaata cccgatagca tagtatttcc gcatggtttc      180
actattaaag aatttcggtt atcgatgggg atgcgttccn ttagatagtt ggcggggtaa      240
cggcccacca agtcaacgat ggatagggggt tctgagagga aggtcccccca cattggaact      300 gagacacggt ccaaactcct acgggaggca gcagtgagga atattggtca atggacgaga      360
gtctgaacca gccaagtagc gtgaaggatg actgccctat gggttgtaaa cttcttttat      420
acgggaataa agtggagtat gcatactcct ttgtatgtac cgtatgaata aggatcggct      480
aactccgtgc cagcagccgc ggtaatacgg aggatccgag cgttatccgg atttattggg      540
tttaaaggga gcgtaggcgg gtgcttaagt cagttgtgaa agtttgcggc tcaaccgtaa      600
aattgcagtt gatactgggc gccttgagtg cagcataggt aggcggaatt cgtggtgtag      660
cggtgaaatg cttagatatc acgaagaact ccgattgcga aggcagctta ctggactgta      720
actgacgctg atgctcgaaa gtgtgggtat caaacaggat tagataccct ggtagtccac      780
acagtaaacg atgaatactc gctgttggcg atacacagtc agcggccaag cgaaagcatt      840
aagtattcca cctggggagt acgccggcaa cggtgaaact caaaggaatt gacggggggcc     900 cgcacaagcg gaggaacatg tggtttaatt cgatgatacg cgaggaacct acccgggct       960 taaattgcag cggaatgtag tggaaacatt acagccttcg ggccgctgtg aaggtgctgc     1020
```

```
atggttgtcg tcagctcgtg ccgtgaggtg tcggcttaag tgccataacg agcgcaaccc    1080
ttatctatag ttactatcag gtcatgctga ggactctatg gagactgccg tcgtaagatg    1140
tgaggaaggt ggggatgacg tcaaatcagc acggcccta cgtccggggc tacacacgtg    1200
ttacaatggg gggtacagaa ggcagctacc tggcgacagg atgctaatcc ctaaaacctc    1260
tctcagttcg gattggagtc tgcaacccga ctccatgaag ctggattcgc tagtaatcgc    1320
gcatcagcca cggcgcggtg aatacgttcc cgggccttgt acacaccgcc cgtcaagcca    1380
tgaaagccgg gggtacctga agtacgtaac cgcaaggagc                          1420

<210> SEQ ID NO 19
<211> LENGTH: 1408
<212> TYPE: DNA
<213> ORGANISM: Clostridium sp.

<400> SEQUENCE: 19
gatgaacgct ggcggcgtgc ctaatacatg caagtcggac gcaatgcttc ggcattgagt      60
ggcgaacggg tgagtaatac ataagcaacc tgccctgtg aggggataa ctgctggaaa      120 cggcagctaa gaccgcatat gcatacatga cgcatgtcga gtatgttaaa tatccacgg      180 gatagcacag ggatgggctt atgacgcatt agctagctgg tgaggtagag gctcaccagg     240
gcgacgatgc gtagccggcc tgagagggtg gacggccaca ctgggactga gacacggccc     300
agactcctac gggaggcagc agtagggaat tttcggcaat gggcgaaagc ctgaccgagc     360
aacgccgcgt gaaggaagaa gtcattcgtg atgtaaactt ctgttataaa ggaagaacgg     420
cgcctgtagg gaatgacagg cgagtgacgg tactttatga ggaagccacg gctaactacg     480
tgccagcagc cgcggtaata cgtaggtggc gagcgttatc cggaatcatt gggcgtaaag     540
agggagcagg cggcagtgca ggtctgcggt gaaagcccga agctaaactt cggtaagccg     600
tggaaaccgc acagctagag agcatcagag gatcgcggaa ttccatgtgt agcggtgaaa     660
tgcgtagata tatggaggaa caccagtggc gaaggcggcg gtctggggtg cagctgacgc     720
tcagtcccga aagcgtgggg agcaaatagg attagatacc ctagtagtcc acgccgtaaa     780
cgatgagtgc taagtgttgg gggtcagacc tcagtgctgc agttaacgca ataagcactc     840
cgcctgagta gtacgttcgc aagaatgaaa ctcaaaggaa ttgacggggg cccgcacaag     900
cggtggagca tgtggtttaa ttcgaagcaa cgcgaagaac cttaccaggt cttgacatgg     960
agataaaggc tctggagaca gagagatagg tatatctcac acaggtggtg catggttgtc    1020
gtcagctcgt gtcgtgagat gttgggttaa gtcccgcaac gagcgcaacc cctgttgcca    1080
gttgccagca ttaggttggg gactctggcg agactgcctc tgcaaggagg aggaaggcgg    1140
ggatgacgtc aaatcatcat gccccttatg acctgggcta cacacgtgct acaatggacg    1200
gatcagaggg aggcgaagcc gcgaggtgga gcgaaaccca gaaacccgtt cacagttcgg    1260
actgcagtct gcaactcgac tgcacgaagc tggaatcgct agtaatcgcg aatcagcatg    1320
tcgcggtgaa tacgttctcg ggccttgtac acaccgcccg tcacaccatg agagttggta    1380
acacccgaag ccggtggccc aaccgcaa                                        1408

<210> SEQ ID NO 20
<211> LENGTH: 1413
<212> TYPE: DNA
<213> ORGANISM: Parabacteroides goldsteinii

<400> SEQUENCE: 20
gatgaacgct agcgacaggc ttaacacatg caagtcgagg ggcagcacga tgtagcaata      60
```

```
cattggtggc gaccggcgca cgggtgagta acgcgtatgc aacctaccta tcagagggga    120
ataacccggc gaaagtcgga ctaataccgc ataaaacagg ggttccacat ggaaatattt    180
gttaaagaat tatcgctgat agatgggcat gcgttccatt agatagttgg tgaggtaacg    240
gctcaccaag tccacgatgg atagggggttc tgagaggaag gtcccccaca ctggtactga    300
gacacggacc agactcctac gggaggcagc agtgaggaat attggtcaat gggcgagagc    360
ctgaaccagc caagtcgcgt gaaggatgaa ggatctatgg tttgtaaact tcttttatat    420
gggaataaag tgaggaacgt gttccttttt gtatgtacca tatgaataag catcggctaa    480
ctccgtgcca gcagccgcgg taatacgagg atgcgagcg ttatccggat ttattgggtt    540
taaagggtgc gtaggtggtt aattaagtca gcggtgaaag tttgtggctc aaccataaaa    600
ttgccgttga aactggttga cttgagtata tttgaggtag gcggaatgcg tggtgtagcg    660
gtgaaatgca tagatatcac gcagaactcc gattgcgaag gcagcttact aaactataac    720
tgacactgaa gcacgaaagc gtggggatca aacaggatta atacccctgg tagtccacgc    780
agtaaacgat gattactagc tgtttgcgat acacagtaag cggcacagcg aaagcgttaa    840
gtaatccacc tggggagtac gccggcaacg gtgaaactca aaggaattga cgggggcccg    900
cacaagcgga ggaacatgtg gtttaattcg atgatacgcg aggaaccta cccgggtttg    960 aacgcatatt gacagctctg gaaacagagt ctctagtaat agcaatttgc gaggtgctgc   1020
atggttgtcg tcagctcgtg ccgtgaggtg tcggcttaag tgccataacg agcgcaaccc   1080
ttatcactag ttactaacag gtcatgctga ggactctagt gagactgcca gcgtaagctg   1140
tgaggaaggt ggggatgacg tcaaatcagc acggccctta catccggggc gacacacgtg   1200
ttacaatggt ggggacaaag ggcagctacc gtgtgagcgg atgcaaatct ccaaacccca   1260
tctcagttcg gatcgaagtc tgcaacccga cttcgtgaag ctggattcgc tagtaatcgc   1320
gcatcagcca tggcgcggtg aatacgttcc cgggccttgt acacaccgcc cgtcaagcca   1380
tgggagttgg gggtacctaa agtccgtaac cgc                                1413
```

<210> SEQ ID NO 21
<211> LENGTH: 1145
<212> TYPE: DNA
<213> ORGANISM: Bacteroides sp.
<220> FEATURE:
<221> NAME/KEY: misc_feature
<222> LOCATION: (167)..(167)
<223> OTHER INFORMATION: n is a, c, g, or t

<400> SEQUENCE: 21

```
gatgaacgct agctacaggc ttaacacatg caagtcgagg ggcagcattt cagtttgctt     60
gcaaactgga gatggcgacc ggcgcacggg tgagtaacac gtatccaacc tgccgataac    120
tcggggatag cctttcgaaa gaaagattaa tacccgatgg tataatnaga ccgcatggtc    180
ttgttattaa agaatttcgg ttatcgatgg ggatgcgttc cattaggcag ttggtgaggt    240
aacggctcac caaaccttcg atggataggg gttctgagag gaaggtcccc cacattggaa    300
ctgagacacg gtccaaactc ctacggggagg cagcagtgag gaatattggt caatgggcgc    360
aggcctgaac cagccaagta gcgtgaagga tgactgccct atgggttgta aacttctttt    420
atatgggaat aaagtttttcc acgtgtggaa ttttgtatgt accatatgaa taaggatcgg    480
ctaactccgt gccagcagcc gcggtaatac ggaggatccg agcgttatcc ggatttattg    540
ggtttaaagg gagcgtaggt ggacagttaa gtcagttgtg aaagtttgcg gctcaaccgt    600
```

-continued

```
aaaattgcag ttgatactgg ctgtcttgag tacagtagag gtgggcggaa ttcgtggtgt    660
agcggtgaaa tgcttagata tcacgaagaa ctccgattgc gaaggcagct cactggactg    720
caactgacac tgatgctcga aagtgtgggt atcaaacagg attagatacc ctggtagtcc    780
acacagtaaa cgatgaatac tcgctgtttg cgatatacag taagcggcca agcgaaagca    840
ttaagtattc cacctgggga gtacgccggc aacggtgaaa ctcaaaggaa ttgacggggg    900
cccgcacaag cggaggaaca tgtggtttaa ttcgatgata cgcgaggaac cttacccggg    960
cttaaattgc atttgaatat attggaaaca gtatagccgt aaggcaaatg tgaaggtgct   1020
gcatggttgt cgtcagctcg tgccgtgagg tgtcggctta agtgccataa cgagcgcaac   1080
ccttatcttt agttactaac aggtcatgct gaggactcta gagagactgc cgtcgtaaga   1140
tgtga                                                               1145
```

<210> SEQ ID NO 22
<211> LENGTH: 965
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (156)..(157)
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (879)..(880)
<223> OTHER INFORMATION: n is a, c, g, or t
<220> FEATURE:
<221> NAME/KEY: misc_feature
<222> LOCATION: (913)..(913)
<223> OTHER INFORMATION: n is a, c, g, or t
<220> FEATURE:
<221> NAME/KEY: misc_feature
<222> LOCATION: (927)..(929)
<223> OTHER INFORMATION: n is a, c, g, or t
<220> FEATURE:
<221> NAME/KEY: misc_feature
<222> LOCATION: (937)..(937)
<223> OTHER INFORMATION: n is a, c, g, or t
<220> FEATURE:
<221> NAME/KEY: misc_feature
<222> LOCATION: (939)..(942)
<223> OTHER INFORMATION: n is a, c, g, or t
<220> FEATURE:
<221> NAME/KEY: misc_feature
<222> LOCATION: (953)..(953)
<223> OTHER INFORMATION: n is a, c, g, or t
<220> FEATURE:
<221> NAME/KEY: misc_feature
<222> LOCATION: (956)..(957)
<223> OTHER INFORMATION: n is a, c, g, or t
<220> FEATURE:
<221> NAME/KEY: misc_feature
<222> LOCATION: (959)..(962)
<223> OTHER INFORMATION: n is a, c, g, or t
<220> FEATURE:
<221> NAME/KEY: misc_feature
<222> LOCATION: (965)..(965)
<223> OTHER INFORMATION: n is a, c, g, or t

```
<400> SEQUENCE: 22
nnnnnnnnnt gcagtcgaac gaagcgattt gaatgaagtt ttcggatgga tttcaanttg    60
actgagtggc ggacgggtga gtaacgcgtg ggtaacctgc cccatacagg gggataacag   120
ttagaaatga ctgctaatac cgcataagac cacagnnccg catggtgcag gggtaaaaac   180
tccggtggta tgggatggac ccgcgtctga ttagcttgtt ggcggggtaa cggcccacca   240
aggcgacgat cagtagccga cctgagaggg tgaccggcca cattgggact gagacacggc   300
ccaaactcct acgggaggca gcagtgggga atattgcaca atgggggaaa ccctgatgca   360
gcgacgccgc gtgagtgatg aagtatttcg gtatgtaaag ctctatcagc agggaagaaa   420
atgacggtac ctgactaaga agccccggct aactacgtgc cagcagccgc ggtaatacgt   480
aggggggcaag cgttatccgg atttactggg tgtaaaggga gcgtagacgg ctgtgcaagt   540
ctggagtgaa agcccggggc tcaaccccgg gactgctttg gaaactgtac ggctggagtg   600
ctggagaggc aagcggaatt cctagtgtag cggtgaaatg cgtagatatt aggaggaaca   660
ccagtggcga aggcggcttg ctggacagta actgacgttg aggctcgaaa gcgtggggag   720
caaacaggat tagataccct ggtagtccac gccgtaaacg atgaatgcta ggtgtcgggg   780
agcaaagctc ttcggtgccg ccgcaaacgc aataagcatt ccacctgggg agtacgttcg   840
caagaatgaa actcaaagga nttgacgggg accgcacann ggtggagcat gtggttattc   900
gagcacgcga aancttacca gtcttgnnnc ccctgangnn nngtatgtcg ctnctnngnn   960
nnggn                                                               965

<210> SEQ ID NO 23
<211> LENGTH: 1457
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1440)..(1440)
<223> OTHER INFORMATION: n is a, c, g, or t
<220> FEATURE:
<221> NAME/KEY: misc_feature
<222> LOCATION: (1451)..(1457)
<223> OTHER INFORMATION: n is a, c, g, or t

<400> SEQUENCE: 23
agtttgatta tggctcagga tgaacgctgg cggcgtgctt aacacatgca agtcgagcga    60
agcggtttca atgaagtttt cggatggatt tgaaattgac ttagcggcgg acgggtgagt   120
aacgcgtggg taacctgcct tacactgggg gataacagtt agaaatgact gctaataccg   180
cataagcgca cagggccgca tggtccggtg tgaaaaactc cggtggtgta agatggaccc   240
gcgtctgatt aggtagttgg cggggtaacg gcccaccaag ccgacgatca gtagccgacc   300
tgagagggtg accggccaca ttgggactga gacacgccc aaactcctac gggaggcagc   360
agtggggaat attgacaat gggcgaaagc ctgatccagc gacgccgcgt gagtgaagaa   420
gtatttcggt atgtaaagct ctatcagcag ggaagaaaat gacggtacct gactaagaag   480
ccccggctaa ctacgtgcca gcagccgcgg taatacgtag gggcaagcg ttatccggat   540
ttactgggtg taagggagc gtagacggtt tagcaagtct gaagtgaaag cccggggctc   600
aaccccggta ctgctttgga aactgttaga cttgagtgca ggagaggtaa gtggaattcc   660
tagtgtagcg gtgaaatgcg tagatattag gaggaacacc agtggcgaag gcggcttact   720
```

```
ggactgtaac tgacgttgag gctcgaaagc gtggggagca acaggattta gataccctgg    780
tagtccacgc cgtaaacgat gaatactagg tgtcggggg  caaagccctt cggtgccgcc    840
gcaaacgcaa taagtattcc acctggggag tacgttcgca agaatgaaac tcaaaggaat    900
tgacggggac ccgcacaagc ggtggagcat gtggtttaat tcgaagcaac gcgaagaacc    960
ttaccaagtc ttgacatccc actgaaaaca ctttaaccgg tgtccctctt cggagcagtg   1020
gagacaggtg gtgcatggtt gtcgtcagct cgtgtcgtga gatgttgggt taagtcccgc   1080
aacgagcgca acccttatcc ttagtagcca gcgagtagag tcgggcactc tggggagact   1140
gccagggata acctggagga aggtggggat gacgtcaaat catcatgccc cttatgattt   1200
gggctacaca cgtgctacaa tggcgtaaac aaagggaggc aaaggagcga tctggagcaa   1260
accccaaaaa taacgtctca gttcggattg caggctgcaa ctcgcctgca tgaagctgga   1320
atcgctagta atcgcgaatc agaatgtcgc ggtgaatacg ttcccgggtc ttgtacacac   1380
cgcccgtcac accatgggag ttggtaacgc ccgaagtcag tgacccaacc gcaaggaggn   1440
agctgccgaa nnnnnnn                                                  1457

<210> SEQ ID NO 24
<211> LENGTH: 1456
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(11)
<223> OTHER INFORMATION: n is a, c, g, or t
<220> FEATURE:
<221> NAME/KEY: misc_feature
<222> LOCATION: (1314)..(1315)
<223> OTHER INFORMATION: n is a, c, g, or t
<220> FEATURE:
<221> NAME/KEY: misc_feature
<222> LOCATION: (1358)..(1358)
<223> OTHER INFORMATION: n is a, c, g, or t
<220> FEATURE:
<221> NAME/KEY: misc_feature
<222> LOCATION: (1407)..(1407)
<223> OTHER INFORMATION: n is a, c, g, or t
<220> FEATURE:
<221> NAME/KEY: misc_feature
<222> LOCATION: (1440)..(1440)
<223> OTHER INFORMATION: n is a, c, g, or t
<220> FEATURE:
<221> NAME/KEY: misc_feature
<222> LOCATION: (1444)..(1444)
<223> OTHER INFORMATION: n is a, c, g, or t
<220> FEATURE:
<221> NAME/KEY: misc_feature
<222> LOCATION: (1449)..(1450)
<223> OTHER INFORMATION: n is a, c, g, or t
<220> FEATURE:
<221> NAME/KEY: misc_feature
<222> LOCATION: (1452)..(1456)
<223> OTHER INFORMATION: n is a, c, g, or t

<400> SEQUENCE: 24
agtttgnnnn ngctcaggat gaacgctggc ggcgtgccta acacatgcaa gtcgaacgaa     60
gcatttcaga tgaagttttc ggatggattc tgagatgact gagtggcgga cgggtgagta    120
acacgtggat aacctgcctc acactggggg acaacagtta gaaatgactg ctaataccgc    180
ataagcgcac agtaccgcat ggtacagtgt gaaaaactcc ggtggtgtga gatggatccg    240
cgtctgatta gccagttggc ggggtaacgg cccaccaaag cgacgatcag tagccgacct    300
gagagggtga ccggccacat tgggactgag acacggccca aactcctacg ggaggcagca   360
```

```
gtggggaata ttgcacaatg ggcgaaagcc tgatgcagcg acgccgcgtg agtgaagaag      420
tatttcggta tgtaaagctc tatcagcagg gaagataatg acggtacctg actaagaagc      480
cccggctaac tacgtgccag cagccgcggt aatacgtagg gggcaagcgt tatccggatt      540
tactgggtgt aaagggagcg tagacggcat ggcaagtctg aagtgaaaac ccagggctca      600
accctgggac tgctttggaa actgtcaagc tagagtgcag gagaggtaag tggaattcct      660
agtgtagcgg tgaaatgcgt agatattagg aggaacacca gtggcgaagg cggcttactg      720
gactgtaact gacgttgagg ctcgaaagcg tggggagcaa acaggattag ataccctggt      780
agtccacgcc gtaaacgatg agtgctaggt gttgggggggc aaagcccttc ggtgccgtcg      840
caaacgcaat aagcactcca cctggggagt acgttcgcaa gaatgaaact caaaggaatt      900
gacggggacc cgcacaagcg gtggagcatg tggtttaatt cgaagcaacg cgaagaacct      960
taccaagtct tgacatcctc ttgaccggcg tgtaacggcg ccttccttc gggacaagag     1020 agacaggtgg tgcatggttg tcgtcagctc gtgtcgtgag atgttgggtt aagtcccgca     1080
acgagcgcaa cccttatcct tagtagccag cattaagatg ggcactctag ggagactgcc     1140
agggacaacc tggaggaagg tggggatgac gtcaaatcat catgccccttt atgatttggg     1200 ctacacacgt gctacaatgg cgtaaacaaa gggaagcgac cctgcgaagg tgagcaaatc     1260
tcaaaaataa cgtcccagtt cggactgtag tctgcaaccc gactacacga agcnngaatc     1320
gctagtaatc gcgaatcaga atgtcgcggt gaatacgntc ccgggtcttg tacacaccgc     1380
ccgtcacacc atgggagtca gcaacgnccg aagtcagtga cccaaccgaa aggagggagn     1440
tgcngaagnn gnnnnn                                                    1456

<210> SEQ ID NO 25
<211> LENGTH: 1455
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1443)..(1455)
<223> OTHER INFORMATION: n is a, c, g, or t

<400> SEQUENCE: 25
agtttgannt tggctcagga tgaacgctgg cggcgtgcct aacacatgca agtcgagcga       60
agcgctgttt tcagaatctt cggaggaaga ggacagtgac tgagcggcgg acgggtgagt      120
aacgcgtggg caacctgcct catacagggg gataacagtt agaaatgact gctaataccg      180
cataagcgca caggaccgca tggtgtagtg tgaaaaactc cggtggtatg agatggaccc      240
gcgtctgatt aggtagttgg tgggtaaag gcctaccaag ccgacgatca gtagccgacc      300
tgagagggtg accggccaca ttgggactga gacacggccc aaactcctac gggaggcagc      360
agtggggaat attgcacaat gggggaaacc ctgatgcagc gacgccgcgt gaaggaagaa      420
gtatttcggt atgtaaactt ctatcagcag ggaagaagat gacggtacct gagtaagaag      480
caccggctaa atacgtgcca gcagccgcgg taatacgtat ggtgcaagcg ttatccggat      540
```

```
ttactgggtg taaagggagc gtagacggat aggcaagtct ggagtgaaaa cccagggctc    600
aactctggga ctgctttgga aactgcagat ctggagtgcc ggagaggtaa gcggaattcc    660
tagtgtagcg gtgaaatgcg tagatattag gaggaacacc agtggcgaag gcggcttact    720
ggacggtgac tgacgttgag gctcgaaagc gtggggagca acaggatta gatacctgg     780 tagtccacgc cgtaaacgat gactactagg tgtcggtgtg caaagcacat cggtgccgca    840
gcaaacgcaa taagtagtcc acctgggag tacgttcgca agaatgaaac tcaaaggaat    900
tgacggggac ccgcacaagc ggtggagcat gtggtttaat tcgaagcaac gcgaagaacc    960
ttacctggtc ttgacatccg gatgacgggc gagtaatgtc gccgtccctt cggggcatcc    1020
gagacaggtg gtgcatggtt gtcgtcagct cgtgtcgtga gatgttgggt taagtcccgc    1080
aacgagcgca acccttatct tcagtagcca gcatataagg tgggcactct ggagagactg    1140
ccagggagaa cctggaggaa ggtggggatg acgtcaaatc atcatgcccc ttatggccag    1200
ggctacacac gtgctacaat ggcgtaaaca aagggaagcg agagggtgac ctgaagcgaa    1260
tcccaaaaat aacgtctcag ttcggattgt agtctgcaac tcgactacat gaagctggaa    1320
tcgctagtaa tcgcggatca gcatgccgcg gtgaatacgt tcccgggtct tgtacacacc    1380
gcccgtcaca ccatgggagt cagtaacgcc cgaagccant gacccaacct tagaggaggg    1440
agnnnnnnnn nnnnn                                                    1455

<210> SEQ ID NO 26
<211> LENGTH: 1458
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1439)..(1439)
<223> OTHER INFORMATION: n is a, c, g, or t
<220> FEATURE:
<221> NAME/KEY: misc_feature
<222> LOCATION: (1445)..(1449)
<223> OTHER INFORMATION: n is a, c, g, or t
<220> FEATURE:
<221> NAME/KEY: misc_feature
<222> LOCATION: (1452)..(1457)
<223> OTHER INFORMATION: n is a, c, g, or t

<400> SEQUENCE: 26
agtttgatta tggctcagga tgaacgctgg cggcatgcct aatacatgca agtcgaacga    60
agtttcgagg aagcttgctt ccaaagagac ttagtggcga acgggtgagt aacacgtagg    120
taacctgccc atgtgtccgg gataactgct ggaaacggta gctaaaaccg gataggtata    180
cagagcgcat gctcagtata ttaaagcgcc catcaaggcg tgaacatgga tggacctgcg    240
gcgcattagc tagttggtga ggtaacggcc caccaaggcg atgatgcgta gccggcctga    300
gagggtaaac ggccacattg ggactgagac acggcccaaa ctcctacggg aggcagcagt    360
agggaatttt cgtcaatggg ggaaaccctg aacgagcaat gccgcgtgag tgaagaaggt    420
cttcggatcg taaagctctg ttgtaagtga agaacggctc atagaggaaa tgctatggga    480
gtgacggtag cttaccagaa agccacggct aactacgtgc cagcagccgc ggtaatacgt    540
aggtggcaag cgttatccgg aatcattggg cgtaaagggt gcgtaggtgg cgtactaagt    600
ctgtagtaaa aggcaatggc tcaaccattg taagctatgg aaactggtat gctgagtgc    660 agaagagggc gatggaattc catgtgtagc ggtaaaatgc gtagatatat ggaggaacac    720
cagtggcgaa ggcggtcgcc tggtctgtaa ctgacactga ggcacgaaag cgtggggagc    780
```

```
aaataggatt agataccta gtagtccacg ccgtaaacga tgagaactaa gtgttggagg      840
aattcagtgc tgcagttaac gcaataagtt ctccgcctgg ggagtatgca cgcaagtgtg    900
aaactcaaag gaattgacgg gggcccgcac aagcggtgga gtatgtggtt taattcgaag    960
caacgcgaag aaccttacca ggccttgaca tggaaacaaa taccctagag ataggggat    1020 aattatggat cacacaggtg gtgcatggtt gtcgtcagct cgtgtcgtga gatgttgggt   1080
taagtcccgc aacgagcgca acccttgtcg catgttacca gcatcaagtt ggggactcat   1140
gcgagactgc cggtgacaaa ccggaggaag gtggggatga cgtcaaatca tcatgcccct   1200
tatggcctgg gctacacacg tactacaatg gcgaccacaa agagcagcga cacagtgatg   1260
tgaagcgaat ctcataaagg tcgtctcagt tcggattgaa gtctgcaact cgacttcatg   1320
aagtcggaat cgctagtaat cgcagatcag catgctgcgg tgaatacgtt ctcgggcctt   1380
gtacacaccg cccgtcaaac catgggagtc agtaataccc gaagccggtg gcataaccnt   1440
aaggnnnnnc cnnnnnna                                                 1458
```

<210> SEQ ID NO 27
<211> LENGTH: 1217
<212> TYPE: RNA
<213> ORGANISM: Phascolarctobacterium faecium

<400> SEQUENCE: 27

```
agaggaccgg ccaggacgaa cgcggcggcg gccaacacag caagcgaacg gagaaacgga     60
gaacagggcg aacggggaga acgcgaggca accgcccaga cggggacaac accgaaagga    120
ggcaaaccgg aggacacggc cgcaggcagg agaagaaaga ggcccacaag aagcacgcaa    180
aggagggccg cgcgaagcag ggaggaacgg acaccaaggc gagacagagc cggcgagagg    240
agaacggcca cagggacgag acacggccca aacccacggg aggcagcagg gggaacccgc    300
aaggacgaaa gcgacggagc aacgccgcgg aggagaagga cggcgaaagc cggagacgaa    360 cggcaggga acaagcagca agacggagaa acgaggaagc cacggcaaca cggccagcag    420
ccgcggaaac gaggggcgag cggccggaaa gggcgaaaga gcagaggcgg caaaagcgag    480
cggaaaagcg gggccaaccc cgaggcgcgg aaacgaggcg aggcaggaga ggaaagggga    540
acccaggagc gggaaagcga gaagggagga acaccagggc gaaggcgccc ggacggcgac    600
gcgagagcga aagccaggga gcgaacggga agaaccccgg agccggccga aacgagggac    660
agggaggagg acgaccccg gccggagaac gcaaagacc ccgccgggga gacggccgca     720
agggaaacca aaggaagacg ggggcccgca caagcgggga gagggaacga cgcaacgcga    780
agaaccacca aggcgacaga gaacgccaga gaagagcccc cggggacaag aaaacagggg    840
gcaggcgcgc agccggcgga gagggaagc ccgcaacgag cgcaaccccca ccagaccagc    900 aagaaagggg gaccagggag acgccaggga caaccggagg aaggcgggga gacgcaagca    960
cagccccagc gggcacacac gacacaaggc ggaaacagag ggaagcgaag ccgcgaggca   1020
gagcaaaccc cagaaacccg accagcggac gcaggcgcaa cccgccgcgg aagcggaacg   1080
cagaacgcag gcagcaacgc gggaaacgcc cgggccgaca caccgcccgc acaccacgaa   1140
agggaacacc cgaagccggg aggaaccaag gagccagccg caagggggc cgagaggggg    1200 aagcgaacaa ggagccg                                                 1217
```

<210> SEQ ID NO 28
<211> LENGTH: 1104
<212> TYPE: RNA

<213> ORGANISM: Fusobacterium ulcerans

<400> SEQUENCE: 28

| | |
|---|---|
| gccaggagaa cgcgacagaa gcaacacagc aagcacgacc cggggaaggg gcggacgggg | 60 |
| agaacgcgaa agaacgccac agacgggaca acaggaaacg aagcaaaccg gaaagagggc | 120 |
| gcagacgaag aaagcaagcg cggagagagc gcgcccaaga gggdaggaac ggccaccaag | 180 |
| acgagaggga gccggccgag aggggaacgg ccacaagggg acgagacacg gcccacccac | 240 |
| gggaggcagc aggggaaag dacaaggacc aaaagcgacc agcaacgggc acgagaagcg | 300 |
| gaagaaaggc caggggaaga agcaggacgg accaacagaa gaagcgacgg caaaacggcc | 360 |
| agcagccgcg gaaacgagcg caagcgaccg gaagggcgaa agcgcgcagg cggcagaagc | 420 |
| gaggaaaagc ggggccaacc ccgagcggga aacgcaaaca gagacggaga ggaggcggaa | 480 |
| cacaaggaga gggaaacgag aagaggaagc cgaggggaag ccagccacgg acagaacgac | 540 |
| gcaaagcgcg aaagcgggga gcaaacagga agaaacccgga gccacgccga aacgagaaca | 600 |
| ggggggggcg aacccagcgc ccaagcaacg cgaaagaacc gccggggaga cgacgcaaga | 660 |
| gaaaccaaag gaagacgggg acccgcacaa gcggggagca gggaacgacg caacgcgagg | 720 |
| aaccaccagc ggacacccaa gaagaacaga gagcggcccc ggaggaacgg gacaggggc | 780 |
| aggcgcgcag ccggcggaga ggggaagccc gcaacgagcg caaccccga gaccacaaag | 840 |
| ggggaccagc gagacgccgc gagagcagga ggaagggggg agacgcaagc acagccccaa | 900 |
| cgcgggcaca cacggcacaa gggagacaga gagcgcaaac cgcgagggaa gcaaccaaaa | 960 |
| acacagcgga gaccgcaacc gagacagaag ggaacgcaga acgcaaacag caggcggaa | 1020 |
| acgccgggcg acacaccgcc cgcacaccac gagagggggca ccgaagaaca ggccaaccga | 1080 |
| aggagggagc cgagggggaa gcga | 1104 |

<210> SEQ ID NO 29
<211> LENGTH: 1202
<212> TYPE: RNA
<213> ORGANISM: Bacteroides dorei

<400> SEQUENCE: 29

| | |
|---|---|
| aacaagaaga ggaccggcca ggagaacgca gcacaggcaa cacagcaagc gaggggcagc | 60 |
| aggcagcgca aggcgaggcg accggcgcac ggggagaaca cgaccaaccg ccgcaccggc | 120 |
| cagcccgaaa ggaagaaacc aggagggaca gagcacagcc gcagaaaagg accggagacg | 180 |
| aggggagcgc caagaagagg cggggaacgg cccaccagca acgaggaagg ggcgagagga | 240 |
| aggcccccac aggaacgaga cacggccaaa cccacgggag gcagcaggag gaaaggcaag | 300 |
| ggcgaggccg aaccagccaa gagcggaagg agacgcccag gggaaaccaa aaggaaaaag | 360 |
| cgggagcaac ccggcagaca gaaaaggacg gcaacccggc cagcagccgc ggaaacggag | 420 |
| gaccgagcga ccggaaggga aagggagcga gaggagaagc agggaaaggc ggccaaccga | 480 |
| aaagcaggaa cggagcgagg caggaggcag gcggaacggg gagcgggaaa gcagaacacg | 540 |
| aagaacccga gcgaaggcag ccgcaagcgc aacgacagag gccgaaaggg gacaaacag | 600 |
| gaagaacccg gagccacacg gaaacgagaa accgcgcgca acggcaagc ggccaagcga | 660 |
| aagcgaagac caccggggag acgccggcaa cgggaaacca aggaagacg ggggcccgca | 720 |
| caagcggagg aacagggaac gagaacgcga ggaaccaccc gggcaaagca ccgaagaccg | 780 |
| gaaacggcag cagcaaagcg agggaagggc caggggcgca gccggccgga gggcggcaag | 840 |
| gccaaacgag cgcaacccgg cagacaacag ggagcgagga ccgacaagac gccacgaaga | 900 |

| | |
|---|---:|
| ggaggaaggg gggagacgca aacagcacgg cccacgccgg ggcacacacg gacaaggggg | 960 |
| gacagagggc cgcaccacgc gagggagcca acccaaaacc ccccagcgga cggagcgcaa | 1020 |
| cccgacccac gaagcggacg cagaacgcgc acagccacgg cgcgggaaac gcccgggccg | 1080 |
| acacaccgcc cgcaagccag ggagccgggg gaccgaaggc gaaccgcgag gacgcccagg | 1140 |
| gaaaacggga cggggcaagc gaacaaggag ccgaccggaa gggcggcgga acaccccgg | 1200 |
| ag | 1202 |

<210> SEQ ID NO 30
<211> LENGTH: 1148
<212> TYPE: RNA
<213> ORGANISM: Bacteroides uniformis

<400> SEQUENCE: 30

| | |
|---|---:|
| cggccaggag aacgcagcac aggcaacaca gcaagcgagg ggcagcagaa cagcgcaagg | 60 |
| aggcgaccgg cgcacgggga gaacacgacc aaccgccgag accggggaag cccgaaagaa | 120 |
| agaaaacccg aggcaagccc gcaggagaac aaaagaacgg cacgagggga gcgccaaggg | 180 |
| ggcggggaac ggcccaccaa gcccgaggaa ggggcgagag gaaggccccc acaggaacga | 240 |
| gacacggcca aacccacggg aggcagcagg aggaaaggca aggacgagag cgaaccagcc | 300 |
| aagagcggaa ggagacgccc aggggaaacc aacgggaaaa aggaggcacg ggccgagacc | 360 |
| gagaaaagga cggcaacccg gccagcagcc gcggaaacgg aggaccgagc gaccggaagg | 420 |
| gaaagggagc gaggcggacg caagcaggga aaggcggcca accgaaaagc aggaacgggg | 480 |
| cgagacagag aggcaggcgg aacggggagc gggaaagcag aacacgaaga acccgagcga | 540 |
| aggcagcgcg gacgaacgac gcgagccgaa aggggggacaa acaggaagaa cccggagcca | 600 |
| cacagaaacg agaaaccgcg gcgaaacaga agcggccaag cgaaagcgaa gaccaccggg | 660 |
| gagacgccgg caacgggaaa ccaaaggaag acggggggccc gcacaagcgg aggaacaggg | 720 |
| aacgagaacg cgaggaacca cccgggcgaa gcaacgaaga gggagacagc agccgcaagg | 780 |
| cagggaaggg cgcagggcgc agccggccgg agggcggcaa ggccaaacga gcgcaaccca | 840 |
| cgaagaccac aggagcgggg accgcgagac gccgcgaaga ggaggaaggg gggagacgca | 900 |
| aacagcacgg cccacgccgg ggcacacacg gacaagggg gacagaaggc agcacacggc | 960 |
| gacgagcaa cccaaagccc ccagcggagg agcgcaaccc gacccagaag cggacgcaga | 1020 |
| acgcgcacag ccacggcgcg ggaaacgccc gggccgacac accgcccgca agccagaaag | 1080 |
| ccgggggacc gaaggcgaac cgcaaggagc gcccagggaa acgggaggg gcaagcgaac | 1140 |
| aaggaacc | 1148 |

<210> SEQ ID NO 31
<211> LENGTH: 1219
<212> TYPE: RNA
<213> ORGANISM: Subdoligranulum sp.

<400> SEQUENCE: 31

| | |
|---|---:|
| agaggaccgg ccaggacgaa cgcggcggcg cgccaacaca gcaagcgaac ggagcgccga | 60 |
| agcggaggaa gagagcagca gggcgaacgg ggagaacacg gagcaaccgc caggggga | 120 |
| caacaggaaa cgaagcaaac cgcaaagacc acaggcgcag gcacagggc aaggaaccg | 180 |
| cgaaagaggg ccgcgccgaa gcagaggagg gaacggccca ccaggcgacg acggagccgg | 240 |
| acgagaggga acgccacag ggacgagaca cggcccagac ccacgggagg cagcaggggg | 300 |

```
aaagcacaag ggggaaaccc gagcagcgac gccgcgggag gaagaaggcc ggagaaaccc      360
gcccagggga cgaaagacgg acccggggag aagcaccggc aacacggcca gcagccgcgg      420
aaaacgaggg gcaagcggcc ggaaacgggg aaagggagcg caggcggagg caaggggagg      480
aaacagggcc aacccaaaag ccaaaacgca gcgaggggga aggaggcgga acccgggagc      540
ggggaagcga gaacgggagg aacaccaggg cgaaggcggc cacgggcaca acgacgcgag      600
gccgaaagca gggagcaaac aggaagaacc cggagccagc cgaaacgaga cagggggga      660 ggagaccccc cggccgcaga acacaaaaga accaccgggg agacgaccgc aagggaaacc      720
aaaggaagac gggggcccgc acaagcaggg agagggaacg aagcaacgcg aagaaccacc      780
aggcgacacg gagcaaccaa gagaagggaa gcccgggaca ccagacaggg ggcagggcgc      840
agccggcgga gaggggaagc ccgcaacgag cgcaacccac gagacacgca agaggaccag      900
cgagacgccg gacaaaacgg aggaagggggg gagacgcaaa cacagcccag accgggcaca      960
cacgacacaa gcaaacaga gagaagcgaa ccgcgagggg agcaaaccca caaaaaagcc     1020
agcggacgca ggcgcaaccc ccgcggaag ccggaagcag aacgcggaca gcagccgcgg     1080
gaaacgcccg ggccgacaca ccgcccgcac accagagagc cggggggacc cgaagcggag     1140
caaccgaagg aggacgccgc cgaaggaaaa cgggagggggg aagcgaacaa ggagccgacg     1200
gaagggcggc ggacacccc                                                  1219

<210> SEQ ID NO 32
<211> LENGTH: 1186
<212> TYPE: RNA
<213> ORGANISM: Paraprevotella xylaniphila

<400> SEQUENCE: 32
agaggaccgg ccaggagaac gcagcacagg caacacagca agcgaggggc agcagaacag       60
cgcaaggagg cgaccggcgc acggggagaa cgcgaccaac cgcccacgcg gggaagcccg      120
aaaggaagaa acccgagaac gagcgcaggc gagaaaaaga acagaaagga ggggagcgcc      180
caagcgggcg gggaacggcc caccaaggcg acagggagg ggcgagagga aggcccccac      240
aggaacgaga cacggccaaa cccacgggag gcagcaggga gaaaggcaag ggcgcgagcc      300
gaaccagcca agagcgggag gacgacggcc cacggggaaa cccaaagggg aaaagggcca      360
gaggccagca ggaccagaaa agcacggcaa ccggccagca gccgcggaaa cggaagagcg      420
agcgaccgga agggaaaggg agcgaggcgg gcagcaagca gcggcaaagg cgcggccaac      480
cgcgccgccg gaaacggcag ccgagagcac agggacagga acgggagcg ggaaagcaga      540 acacgaggaa cccgacgcgc aggcagaccg gggcaacgac gcgaggccga agggcgggac      600
aaacaggaag aacccggagc cgcacagaaa cgagaagccc gcgcggcgac aaggcggcgg      660
ccaagcgaaa gcgaagcacc accggggaga cgccggcaac gggaaaccaa aggaagacgg      720
gggcccgcac aagcggagga acagggaacg agaacgcgag gaaccaccccg ggcgaacgca      780 gggcagggcc ggagacggcc ccccgggacc cgcgaagggc gcaggcgca gccggccgga      840 gggcggcaag gccaaacgag cgcaacccc ccccaggcc acgggaagcc gggcacgggg      900
acacgccacc gcaagggcga ggaagggggg agacgcaaac agcacggccc acgccggggc      960
gacacacgga caaggggggga cagagggccg cgcccgggac ggggccaacc caaagccccc     1020
cagcggacgc agcgcaaccc gacccacgaa gcggacgcag aacgcgcaca gcaggcgcg     1080 ggaaacgccc gggccgacac accgcccgca agccagaaag ccggggggcc gaagccggac     1140
cgcgagggcg gccaggagaa accgggaggg gcaagcgaac aaggaa                    1186
```

<210> SEQ ID NO 33
<211> LENGTH: 1165
<212> TYPE: RNA
<213> ORGANISM: Parabacteroides johnsonii

<400> SEQUENCE: 33

| | | | | | |
|---|---|---|---|---|---|
| agaggaccgg | ccaggagaac | gcagcgacag | gcaacacagc | aagcgagggg | cagcaggaag | 60 |
| agcaaacaga | ggcgaccggc | gcacgggag | aacgcgagca | acaccacaga | gggggaagcc | 120 |
| cggcgaaagc | ggaaaaccca | aaaacagggg | ccgcagggac | agaaagacac | gcgaagaagg | 180 |
| cagcgccaag | gcagggcggg | gaacggccca | ccaaaccgac | gaggaagggg | cgagaggaag | 240 |
| gcccccacag | gacgagacac | ggaccaaacc | cacgggaggc | agcaggagga | aaggcaaggc | 300 |
| cgagaggcga | accagccaag | cgcggaagga | gaaggacagg | gaaaccaagg | ggaaaaaggg | 360 |
| ggacggccag | agacccagaa | aagcacggca | acccggccag | cagccgcgga | aacggaggag | 420 |
| cgagcgaccg | gaagggaaag | gggcgagggg | aaaagcagcg | ggaaagggc | caaccaaaaa | 480 |
| gccggaaacg | ggacgagggg | aggaggcgga | agcgggagc | gggaaagcaa | gaacacgcag | 540 |
| aacccaagcg | aaggcagcac | aaaccaaacg | acacgaagca | cgaaagcggg | gacaaacagg | 600 |
| aagaacccgg | agccacgcag | aaacgagaac | aggaggcgaa | cacagaagcc | acagcgaaag | 660 |
| cgaagaacca | ccggggagac | gccggcaacg | ggaaaccaaa | ggaagacggg | ggcccgcaca | 720 |
| agcggaggaa | cagggaacga | gaacgcgagg | aaccacccgg | ggaacgagca | gaccgaccga | 780 |
| aagaggccag | caaagcgaac | gagggcgcag | ggcgcagccg | gccggagggc | ggcaaggcca | 840 |
| aacgagcgca | acccacacag | acaacaggca | agcgaggacc | gggagacgcc | agcgaagcgg | 900 |
| aggaaggggg | gagacgcaaa | cagcacggcc | cacaccgggg | cgacacacgg | acaaggcagg | 960 |
| acaaagggca | gcaccggcga | caggagcaac | caaaccagcc | agcggacgga | gcgcaaccga | 1020 |
| cccggaagcg | gacgcagaac | gcgcacagcc | aggcgcggga | aacgcccggg | ccgacacacc | 1080 |
| gcccgcaagc | cagggagccg | ggggaccgaa | gccgaaccgc | aaggacggcc | agggaaaacg | 1140 |
| ggacggggca | agcgaacaag | gaacc | | | | 1165 |

<210> SEQ ID NO 34
<211> LENGTH: 1181
<212> TYPE: RNA
<213> ORGANISM: Alistipes sp

<400> SEQUENCE: 34

| | | | | | |
|---|---|---|---|---|---|
| agaggaccgg | ccaggagaac | gcagcggcag | gccaacacag | caagcgaggg | gcagcgggag | 60 |
| aagcgccaac | gccggcgacc | ggcgcacggg | gcgaacgcga | gcaaccaccc | agaacagggg | 120 |
| gaaacacgag | aaaggacaaa | cccaaacaca | aaggggcacc | cggaaaaccc | ggggcggag | 180 |
| ggcagcggaa | gcggggagg | aacggccacc | aaggcaacga | acaagggga | cgagaggaac | 240 |
| cccccacagg | acgagacacg | gaccaaaccc | acggaggca | gcaggaggaa | aggcaaggac | 300 |
| gcaagcgaac | cagccagccg | cggcaggaag | acggccagag | gaaacgcgac | agggaaacca | 360 |
| gaacgcgacg | acgaaagaag | acgaaaagga | ccggcaaccc | ggccagcagc | cgcggaaacg | 420 |
| gagggccaag | cgaccggaag | ggaaaggggc | gaggcggaga | agagaggga | aaaccgggca | 480 |
| acaccggaac | gcccaaacga | gcagagaaag | gcggaggsgg | aagagggagc | gggaaagcag | 540 |
| agacaacaga | acaccgagcg | aaggcagcac | caagcacgac | ggaggcacga | aagcggggga | 600 |
| gcaaacagga | agaacccgga | gccacgcaga | aacgagaaac | cgcgcggcga | acacagcggc | 660 |

```
ggcaagcgaa agcgaaagac caccggggag acgcgcaaga agaaaccaaa ggaagacggg      720
ggcccgcaca agcggaggaa cagggaacga gaacgcgagg aaccacccgg gcgaaagacg      780
acgacggaaa caggaccccg gggcaggaaa cagggcgcag ggcgcagccg gccggagggc      840
gggaagccca acgagcgca accccaccga ggccacaggc aagcgggcac cgacgggacg       900
ccgggaagcc gagaggaagg ggggagacgc aaacagcacg gcccacgccg gggcacacac      960
ggacaaggag gacagagggc agcacccgcg aaggagcga accgaaagcc accagcggac       1020
ggaggcgaaa cccgccccgg aagggacgca gaacgcgcac agccaggcgc gggaaacgcc      1080
cgggccgaca caccgcccgc aagccaggaa gcggggggcc gaagcggacc gcaaggagcg      1140
accagggcaa aaccgggacg gggcaagcga acaaggagcc g                         1181
```

<210> SEQ ID NO 35
<211> LENGTH: 1157
<212> TYPE: RNA
<213> ORGANISM: Parabacteroides gordonii

<400> SEQUENCE: 35

```
agaggaccgg ccaggagaac gcagcgacag gcaacacagc aagcgagggg cagcaggaag       60
agcaaacgcg gcgaccggcg cacggggaga acgcgagcaa ccaccacaga gggggaaacc      120
cggcgaaagc ggacaaaccg caaaaacagg ggcccgcagg gaaagaaaga aagcgaagag      180
ggcagcgcca agaaggggaag gaacggcacc aagcgcgagg aaggggcgag aggaaggccc      240
ccacacggac gagacacgga ccagacccac gggaggcagc aggaggaaag gcaagggcga      300
gagccgaacc agccaagcgc ggaaggagaa ggacaggcga aaccaagggg aaaaaggcgg      360
acggccggag accagaaaag gacggcaacc cggccagcag ccgcggaaac ggaggaccga      420
gcgaccggaa gggaaagggg cgaggggaaa gcagcgggaa aggggccaac caaaaagccg      480
gaaacggaac gagaagagga ggcggaagcg gggagcggga aagcaagaac acgcagaacc      540
caagcgaagg cagcacaaac aaacgacacg aagcacgaaa gcggggacca aacaggaaga      600
acccggagcc acgcagaaac gagaacagga ggcgaacaca gaagccacag cgaaagcgaa      660
gaaccaccgg ggagacgccg gcaacgggaa accaaaggaa gacggggccc cgcacaagcg      720
gaggaacagg gaacgagaac gcgaggaacc acccggggaa cgcaggacag ccgaaagagg      780
accagcaaag ccagcgaggg cgcagggcgc agccggccgg agggcggcaa ggccaaacga      840
gcgcaaccca cagacaacag gcgcgaggac caaagagacg ccagcgaagc ggaggaaggg      900
gggagacgca aacagcacgg cccacaccgg ggcgacacac ggacaagggg ggacaaaggg      960
cagcacacag cgaggagcaa cccaaacccc accagcggac gaagcgcaac ccgaccggaa     1020
gcggacgcag aacgcgcaca gccaggcgcg ggaaacgccc gggccgacac accgcccgca     1080
agccagggag gggggaccaa agccgaaccg caaggacggc caggaaaacc gagacggggc     1140
aagcgaacca aggaacc                                                    1157
```

<210> SEQ ID NO 36
<211> LENGTH: 1189
<212> TYPE: RNA
<213> ORGANISM: Eubacterium limosum

<400> SEQUENCE: 36

```
agaggaccgg ccaggacgaa cgcggcggag caacacagca agcgaacgag aagggaggac       60
ccggggacaa gaacgaaaag ggcgaacggg gagaacgcgg ggaaccgccc aggaaaggaa      120
agcccgggaa acgggagaaa gccaaagggc gcaggcaaga cagaaaaccc gggccaagga      180
```

-continued

```
ggacccgcgc ccaagcaggg gagaaacagc ccaccaaggc gacgagggaa ccggcgagag    240
ggcgaacggc acacggaacg agacacggcc agacccacgg gaggcagcag ggggaaagcg    300 caaggggggca acccgacgca gcaaaccgcg gaggaagaag gcggacgaaa gccgagggga    360
agaagaagac ggacccaaga ggaagcccgg caacacggcc agcagccgcg gaaacgaggg    420
gacaagcggc cggaagacgg gcgaaagggc gcgaggcggc aaagcgagga aggaccggc     480 caaccgggaa ggcaggaaac ggagacgaga ggagaggcaa gggaaccagg agcgggaaag    540
cgagaaagga ggaacaccag ggcgaaggcg gcgcggacaa aacgacgcga gggcgaaagc    600
gggggagcga acaggaagaa cccggagcca cgccgaaacg agaagcaggg ggggaaacca    660
ggccgcagaa cacaaaagca ccgccgggga gacgaccgca agggaaacca aaggaagacg    720
gggacccgca caagcagcgg agcagggaac gaagcaacgc gaagaaccac caggcgacac    780
ccgacgagcc agagaaggaa gcccgggaac agagagacag ggggcagggc gcagccggcg    840
gagaggggaa gcccgcaacg agcgcaaccc cgccaggcca gcaaaggggc accagaggga    900
cgccgagaca aacggaggaa gggggggacga cgcaaacaca gccccagacc gggcacacac    960
ggcacaaggc gaacagaggg ccgcgaagcc gcgagggaag caaacccaaa acagacccag   1020
cggagcaggc gcaaccgccg cagaagggag gcagaacgcg gacagaagcc gcgggaagcg   1080
cccgggcgac acaccgcccg cacaccacga gagggcaaca cccgaagccg gagagaaccg   1140
caaggaccag cagcgaaggg gggcagaagg gggaagcgaa caaggaacc                1189
```

<210> SEQ ID NO 37
<211> LENGTH: 1190
<212> TYPE: RNA
<213> ORGANISM: Parabacteroides distasonis

<400> SEQUENCE: 37

```
agaggaccgg ccaggagaac gcagcgacag gcaacacagc aagcgagggg cagcggggga     60
gcaaacaccg ccggcgaccg gcgcacgggg agaacgcgag caacgccaca gagggggaaa    120
cccggcgaaa gcggacaaac cgcagaagca gggacccgca gggaaagcaa agacacgcga    180
agaaggcagc gccaaggcag ggcggggaac ggcccaccaa accgacgagg aaggggcgag    240
aggaaggccc ccacaggacg agacacggac caaacccacg ggaggcagca ggaggaaagg    300
caagggcgaa gccgaaccag ccaagcgcgg agggagaagg caggacgaaa cccaaaggga    360
aaaaggcggg acggcccgga gaccagaaaa ggacggcaac ccggccagca gccgcggaaa    420
cggaggaccg agcgaccgga agggaaaggg gcgaggcggc caagcagcgg gaaagcgggc    480
caaccaagaa gccggaaacg gggggcgaga ggaggcaggc ggaagcgggg agcgggaaag    540
caagaacacg cagaaccccg agcgaaggca gccgccaagc caacgacgcg agcacgaaag    600 cggggggacaa acaggaagaa cccggagcca cgcagaaacg agacacagcg gcgaacacga    660
agcggcacag cgaaagcgaa ggaccaccgg ggagacgccg gcaacgggaa accaaaggaa    720
gacgggggcc cgcacaagcg gaggaacagg gaacgagaac gcgaggaacc acccggggaa    780
cgcacggacc gaggggaaac acccagcaaa gccggcgagg gcgcagggcg cagccggccg    840
gagggcggca aggccaaacg agcgcaaccc gccacagaca acaggaggcg aggaccgggg    900
gacgccagcg aagcgcgagg aaggcgggga gacgcaaaca gcacggccca caccggggcg    960
acacacggac aaggcgggac aaagggaggc caccggcgac agggagcgaa ccccaaacca   1020
cgccagcgga cggagcgcaa cccgacccgg aagcggacgc agaacgcgca cagccaggcg   1080
```

```
cgggaaacgc ccgggccgac acaccgcccg caagccaggg agccggggga ccgaagccga    1140
accgaaagga cggccaggga aaacgggacg gggcaagcga acaaggaacc               1190
```

<210> SEQ ID NO 38
<211> LENGTH: 1141
<212> TYPE: RNA
<213> ORGANISM: Bacteroides cellulosilyticus

<400> SEQUENCE: 38

```
agaggaccgg ccaggagaac gcagcacagg caacacagca agcgaggggc agcagaccag     60
caaagggagg cgaccggcgc acggggagaa cacgaccaac caccggaccg ggaagcccga    120
aagaaagaaa accggaagaa acgagaaggc acgaaaagaa cgaaaccgag gggagcgcca    180
aggggcgggg aacggcccac caagacacga ggaaggggcg agaggaaggc ccccacagga    240
acgagacacg gccaaaccca cgggaggcag caggaggaaa ggcaaggacg agagcgaacc    300
agccaagagc ggaaggagac gcccagggga accaaggga aaaggagcc acggggcgag      360 accaacgaaa aggacggcaa cccggccagc agccgcggaa acgaggacc gagcgaccgg     420 aagggaaagg gagcgaggcg gacaaagcag cggaaaggcg gccaaccgaa aagcaggaac    480
ggcgcgaggc agagaggagg cggaacgggg agcgggaaag cagaacacga agaacccgag    540
cgaaggcagc acggacgaac gacgcgagcc gaaaggggga caaacaggaa gaacccggag    600
ccacacagaa acgagaaacc gcggcgaaac agcaagcggc caagcgaaag caaagaccac    660
cggggagacg ccggcaacgg gaaaccaaag gaagacgggg gcccgcacaa gcggaggaac    720
agggaacgag aacgcgagga accacccggg caaagcacga aaaggaaaca gaagccgcaa    780
ggcagaggaa gggcgcaggg cgcagccggc cggagggcgg caaggccaaa cgagcgcaac    840
ccacagacaa caggcagcga ggaccagaga acgccgcga agaggaggaa gggggagac     900 gcaaacagca cggcccacgc cggggcacac acggacaagg gggacagaa ggcagcacac     960 agcgaggagc aacccaaaag ccccagcgg aggagcgcaa cccgacccag aagcggagcg    1020
agaacgcgca cagccacggc gcgggaaacg cccgggccga cacccgcccc gcaagccaga    1080
aagccggggg accgaagccg aaccgcaagg agcggccagg gaaaacggaa ggggcaagcg    1140
a                                                                   1141
```

<210> SEQ ID NO 39
<211> LENGTH: 1155
<212> TYPE: RNA
<213> ORGANISM: Bacteroides clarus

<400> SEQUENCE: 39

```
gagaacgcag cacaggcaac acagcaagcg agggcagcg ggggaagcgc caaccgccgg      60
cgaccggcgc acggggagaa cacgaccaac cgccgaaacc cgggaagccc gaaagaaaga    120
aaaccggagg caagcccgca ggaaaacaaa agaacggacg aggggagcgc caaggcaggg    180
cggggaacgg cccaccaaac cgacgaggaa ggggcgagag gaaggccccc acaggaacga    240
gacacggcca aacccacggg aggcagcagg aggaaaggca aggacgagag cgaaccagcc    300
aagagcggaa ggagacgccc aggggaaacc aacgggaaaa agagccacgg gggcagaccg    360
agaaaaggac ggcaacccgg ccagcagccg cggaaacgga ggaccgagcg accggaaggg    420 aagggagcg aggcggggaa agcagggaaa gcggccaac cgaaaagcag gaacggaccg      480
aggcagcaga ggggcggaa cggggagcgg gaaagcagaa cacgaagaac ccgagcgaag     540
gcagccacgg aggaacgacg cgagccgaaa ggggacaaa caggaagaac ccggagccac     600
```

```
acagaaacga gaaaccgcgg gcgaacaagc agcggccaag cgaaagcaaa gaccaccggg      660
gagacgccgg caacgggaaa ccaaaggaag acggggggccc gcacaagcgg aggaacaggg     720
aacgagaacg cgaggaacca cccgggcgaa gcaacgacgg aaggaaacag cccggacagg      780
gaagggcgca gggcgcagcc ggccggaggg cggcaaggcc aaacgagcgc aacccacgaa      840
gaccacaggc agcggggacc acgagacgcc gcgaagagga ggaaggggggg agacgcaaac    900
agcacggccc acgccgggc acacgcgac aaggggggac agaaggcagc acacggcgac       960
ggagcaaccc caaaacccccc agcggaggag cgcaacccga cccagaagcg gacgcagaac   1020
gcgcacagcc acggcgcggg aaacgcccgg gccgacacac cgcccgcaag ccagaaagcc    1080
gggggaccga agacgaaccg caaggagcgc cagggaaaac gggagggggca agcgaacaag   1140
gagccgaccg gaagg                                                     1155

<210> SEQ ID NO 40
<211> LENGTH: 408
<212> TYPE: RNA
<213> ORGANISM: Anaerostipes caccae

<400> SEQUENCE: 40
gaccaagacg agggcggacg gggagaacgc gggggaaccg cccaacaggg ggaaacagcg     60
gaaacggcgc aaaccgcaaa gcgcacagaa cgcagacagg gaaaagcccg gcagaaggag   120
gcccgcgcga agcggggggag gaacggccac caaggcgacg acagagccgg cgagagagga  180
acggccacag ggacgagaca cggcccaaac ccacgggagg cagcagggggg aaagcacaag  240
gggaaacccc gagcagcgac gccgcggagg aagaagacgg agaaagccac agcagggaag   300
aaaacagacg gaccgacaag aagccccggc aacacggcca gcagccgcgg aaacgagggg   360
gcaagcgacc ggaaacgggg aaaggggcga ggggcaggaa gcagaagg                 408

<210> SEQ ID NO 41
<211> LENGTH: 1111
<212> TYPE: RNA
<213> ORGANISM: Bacteroides salyersiae

<400> SEQUENCE: 41
aggagaacgc agcacaggca acacagcaag cgaggggcac aggggagcaa acaccgcggc     60
gaccggcgca cggggagaac acgaccaacc gcccaccggg gaagcccgaa agaaagaaaa   120
cccgaggcaa acagaccccg ggaaaagaac ggagaggagg ggagcgccaa ggcagggcgg  180
ggaacgcccc accaaacccg aggaaggggc gagaggaagg cccccacagg aacgagacac  240
ggccaaaccc acgggaggca gcaggaggaa aggcaagggc gagagccgaa ccagccaaga   300
gcggaaggag accgcccagg ggaaaccaag ggaaaagggg gccacggggc agagaccaag   360
aaaaggacgg caacccggcc agcagccgcg gaaacggagg accgagcgac cggaagggaa   420
agggagcgag gggacagaag caggggaaagg cggccaaccg aaaagcagga aacgcggcga  480
gacagagagg gggcggaacg gggagcggga aagcagaaca cgaagaaccc gagcgaaggc   540
agccacggac gcaacgacac gagccgaaag ggggacaaac aggaagaacc cggagccaca   600
cagaaacgag aaaccgcggc gaaacagaag cggccaagca aaagcaaaga ccaccgggga   660
gacgccggca acgggaaacc aaaggaagac ggggccgc acaagcggag gaacagggaa    720
cgagaacgcg aggaaccacc cgggcaaagc aaagaaagcc ggaacggca agccgcaagg   780
caggaagggc gcagggcgca gccggccgga gggcggcaag gccaaacgag cgcaacccac   840
```

| | | |
|---|---|---|
| cagacaacag gcagcgagga ccggagagac gccgcgaaga ggaggaaggg gggagacgca | 900 | |
| aacagcacgg cccacgccgg ggcacacacg gacaaggggg gacagaaggc cgcacacagc | 960 | |
| gaggagccaa cccaaagccc cccagcggac gaagcgcaac ccgaccggaa gcggacgcag | 1020 | |
| aacgcgcaca gccacggcgc gggaaacgcc cgggccgaca caccgcccgc aagccaggga | 1080 | |
| gccggggggac cgaagacgaa ccgcaaggag c | 1111 | |

<210> SEQ ID NO 42
<211> LENGTH: 1146
<212> TYPE: RNA
<213> ORGANISM: Bacteroides fragilis
<220> FEATURE:
<221> NAME/KEY: misc_feature
<222> LOCATION: (205)..(205)
<223> OTHER INFORMATION: n is a, c, g, or u

<400> SEQUENCE: 42

| | | |
|---|---|---|
| agaggaccgg ccaggagaac gcagcacagg caacacagca agcgaggggc acaggaagaa | 60 | |
| agcgccgcgg cgaccggcgc acgggagaaa cacgaccaac cgcccaccgg ggaagcccga | 120 | |
| aagaaagaaa acccgaagca aagaccgcag gcaaaaagga ccggaaagga ggggagcgcc | 180 | |
| aaggggggag gaacggccac caagnccgag gaaggggcga gaggaaggcc cccacaggaa | 240 | |
| cgagacacgg ccaaacccac gggaggcagc aggaggaaag gcaagggcgc agccgaacca | 300 | |
| gccaagagcg gaaggagaag gccagggcga aaccaaaaga aaaaggcaga gaacggagaa | 360 | |
| agaaaaggac ggcaacccgg ccagcagccg cggaaacgga ggaccgagcg accggaaggg | 420 | |
| aaagggagcg aggggacgga agcagggaaa ggcggccaac cgaaaagcag gaacgcagcg | 480 | |
| agacagagag ggggcggaac ggggagcggg aaagcagaac acgaagaacc cgagcgaagg | 540 | |
| cagccacgga cgcaacgaca cgagccgaaa ggggacaaa caggaagaac ccggagccac | 600 | |
| acagaaacga gaaaccgcgg cgaaacagaa gcggccaagc gaaagcaaag accaccgggg | 660 | |
| agacgccggc aacggaaaac caaaggaaga cgggggcccg cacaagcgga ggaacaggga | 720 | |
| acgagaacgc gaggaaccac ccgggcaaag cagggaagag ggaaacagca ggagcaacac | 780 | |
| cgcggaaggg cgcagggcgc agccggccgg agggcggcaa ggccaaacga gcgcaaccca | 840 | |
| cagacaacag gagcgaggac cagagagacg ccgcgaagag gaggaagggg ggagacgcaa | 900 | |
| acagcacggc ccacgccggg gcacacacgg acaagggggg acagaaggca gcagcgggga | 960 | |
| ccgagcaacc caaaagcccc cagcggacga agcgcaaccc gaccggaagc ggacgcagaa | 1020 | |
| cgcgcacagc cacggcgcgg gaaacgcccg ggccgacaca ccgcccgcaa gccagggagc | 1080 | |
| cggggggaccg aagacgaacc gcaaggacgc cagggaaaac gggacggggc aagcgaacaa | 1140 | |
| ggaacc | 1146 | |

<210> SEQ ID NO 43
<211> LENGTH: 1150
<212> TYPE: RNA
<213> ORGANISM: Bacteroides uniformis

<400> SEQUENCE: 43

| | | |
|---|---|---|
| agaggaccgg ccaggagaac gcagcacagg caacacagca agcgaggggc acaggaagaa | 60 | |
| agcgccgcgg cgaccggcgc acggggagaa cacgaccaac cgccgagacc ggggaagccc | 120 | |
| gaaagaaaga aacccgagg aacgaaaggc accagcaaaa gaacggcaga ggggagcgcc | 180 | |
| aaggggggcg ggaacggccc accaagccac gaggaagggg cgagaggaag gcccccacag | 240 | |
| gaacgagaca cggccaaacc cacgggaggc agcaggagga aaggcaagga cgagagcgaa | 300 | |

```
ccagccaaga gcggaaggag acgcccaggg gaaaccaacg ggaaaaagag gcacgggccg      360
agaccgagaa aaggacggca acccggccag cagccgcgaa acggaggac cgagcgaccg       420 gaagggaaag ggagcgaggc ggagcaagca gggaaaggcg gccaaccgaa aagcaggaac      480
ggggcgagac agagaggcag gcggaacggg gagcgggaaa gcagaacacg aagaacccga     540
gcgaaggcag cgcggacgaa cgacgcgagc cgaaggggg acaaacagga agaacccgga       600
gccacacaga aacgagaaac cgcggcgaaa cagaagcggc caagcgaaag cgaagaccac     660
cggggagacg ccggcaacgg gaaaccaaag gaagacgggg gcccgcacaa gcggaggaac     720
agggaacgag aacgcgagga accacccggg caaagcaaag aagcggaaac agacagccgc      780
aaggcaggaa gggcgcaggg cgcagccggc cggagggcgg caaggccaaa cgagcgcaac     840
ccacgaagac cacaggagcg gggaccgcga gacgccgcga agaggaggaa gggggggagac    900 gcaaacagca cggcccacgc cggggcacac acggacaagg ggggacagaa ggcagcacac    960
gggacggagc aacccaaaac ccccagcgga ggagcgcaac ccgacccaga agcggacgca    1020
gaacgcgcac agccacggcg cgggaaacgc ccggccgac acaccgcccg caagccagaa      1080
agccggggga ccgaaggcga accgcgagga gcgcccaggg aaaacgggag gggcaagcga    1140
acaaggaacc                                                             1150

<210> SEQ ID NO 44
<211> LENGTH: 1154
<212> TYPE: RNA
<213> ORGANISM: Bacteroides eggerthii

<400> SEQUENCE: 44
agaggaccgg ccaggagaac gcagcacagg caacacagca agcgaggggc agcagagaag       60
cgccaacgag gcgaccggcg cacgggagag acacgaccaa ccgccgaaac cggggaagcc     120
cgaaagaaag aaaacccgaa gaagccgcag gcacaaaaga acggacgagg ggagcgccaa     180
gaagggcggg gaacggccca ccaagcaacg aggaagggc gagaggaagg ccccccacagg     240 aacgagacac ggccaaaccc acgggaggca gcaggaggaa aggcaaggac gagagcgaac     300
cagccaagag cggaaggaga cgcccagggg aaaccaacgg gaaaagggga gagcaacccg     360
agaccgagaa aaggacggca acccggccag cagccgcgga aacggaggac cgagcgaccg    420
gaagggaaag ggagcgaggc ggggcaagca gggaaaggcg gccaaccgaa aagcaggaac     480
gggcgccgag gcagcaagga ggcggaacgg ggagcgggaa agcagaacac gaagaacccg    540
agcgaaggca gcacggacga acgacgcgag ccgaaggggg acaaacagg aagaacccgg      600 agccacacag aaacgagaaa ccgcgggcga acacagcagc ggccaagcga agcaaagac     660 caccggggag acgccggcaa cgggaaacca aggaagacg ggggcccgca caagcggagg     720
aacagggaac gagaacgcga ggaaccaccc gggcaaagca gcggaagagg gaaacaacag    780
cccgggccgc ggaagggcgc agggcgcagc cggccggagg gcggcaaggc caaacgagcg   840
caacccacaa gacacaggca gcgaggacca ggagacgccg cgaagaggag gaaggggga     900 gacgcaaaca gcacggccca cgccggggca cacacggaca agggggggaca gaaggcagca    960 ccggcgacag gagcaacccg aaaacccca gcggaggagc gcaacccgac ccagaagcgg    1020
acgcagaacg cgcacagcca cggcgcggga aacgcccggg ccgacacacc gcccgcaagc   1080
cagaaagccg ggggaccgaa gacgaaccgc aaggagcgcc agggaaaacg ggaggggcaa    1140
gcgaacaagg aacc                                                     1154
```

<210> SEQ ID NO 45
<211> LENGTH: 1162
<212> TYPE: RNA
<213> ORGANISM: Clostridium sp.

<400> SEQUENCE: 45

| | | | | | |
|---|---|---|---|---|---|
| acagcaagcg | gacgcaagcc | ggcagagggc | gaacggggag | aagacaaagc | aaccgccccg | 60 |
| gagggggaaa | cgcggaaacg | gcagcaagac | cgcaaggcaa | gaggacgcag | cgacagaaaa | 120 |
| cccacgggaa | gcacagggag | ggcagacgca | agccagcggg | aggaacggcc | accagggcga | 180 |
| cgagcgagcc | ggccgagagg | gggacggcca | cacgggacga | gacacggccc | agacccacgg | 240 |
| gaggcagcag | agggaacggc | aagggcgaaa | gccgaccgag | caacgccgcg | gaaggaagaa | 300 |
| gcacggagaa | accgagaagg | aagaacggca | gaggagggaa | gccaggcgga | cggaccagag | 360 |
| gaagccacgg | caacacggcc | agcagccgcg | gaaacgaggg | gcgagcgacc | ggaacagggc | 420 |
| gaaagaggga | gcaggcggca | ggcaggcgcg | ggaaagaccg | gagcaaaccg | gaagccggga | 480 |
| aaccgcacag | cagagagcac | agaggacgcg | gaaccaggag | cggaaagcg | agaaaggagg | 540 |
| aacaccaggg | cgaaggcggc | ggcggggca | gcgacgccag | cccgaaagcg | ggggagcaaa | 600 |
| aggaagaacc | cagagccacg | ccgaaacgag | aggcaagggg | gggcagaccc | aggcggagaa | 660 |
| cgcaaaagca | cccgccgaga | gacgcgcaag | aagaaaccaa | aggaagacgg | gggcccgcac | 720 |
| aagcggggag | cagggaacga | agcaacgcga | agaaccacca | ggcgacagga | gaaaaggccc | 780 |
| ggagacaggg | agaagaaacc | acacaggggg | cagggcgcag | ccggcggaga | ggggaagccc | 840 |
| gcaacgagcg | caaccccggc | caggccagca | agggggggacc | ggcgagacgc | cgcaaggag | 900 |
| gaggaaggcg | gggagacgca | aacacagccc | cagaccgggc | acacacggca | caaggacgga | 960 |
| cagagggagg | cgaagccgcg | aggggagcga | aacccagaaa | cccgcacagc | ggacgcagcg | 1020 |
| caaccgacgc | acgaagcgga | acgcagaacg | cgaacagcag | cgcgggaaac | gccgggccga | 1080 |
| cacaccgccc | gcacaccaga | gagggaacac | ccgaagccgg | ggcccaaccg | caaggaggga | 1140 |
| gcgcaagggg | gacgagaggg | gg | | | | 1162 |

<210> SEQ ID NO 46
<211> LENGTH: 1153
<212> TYPE: RNA
<213> ORGANISM: Parabacteroides goldsteinii

<400> SEQUENCE: 46

| | | | | | |
|---|---|---|---|---|---|
| ggccaggaga | acgcagcgac | aggcaacaca | gcaagcgagg | ggcagcacga | gagcaaacag | 60 |
| gggcgaccgg | cgcacgggga | gaacgcgagc | aaccaccaca | gagggaaaaa | cccggcgaaa | 120 |
| gcggacaaac | cgcaaaaaca | ggggccacag | gaaaagaaag | aaacgcgaag | agggcagcgc | 180 |
| caagaagggg | aggaacggcc | accaagccac | gaggaagggg | cgagaggaag | gcccccacac | 240 |
| ggacgagaca | cggaccagac | ccacggggag | cagcaggagg | aaaggcaagg | gcgagagccg | 300 |
| aaccagccaa | gcgcggaagg | agaaggacag | ggaaaccaag | ggaaaaagga | ggaacggccg | 360 |
| agaccaagaa | aagcacggca | acccggccag | cagccgcgga | aacggaggag | cgagcgaccg | 420 |
| gaagggaaag | gggcgagggg | aaaagcagcg | ggaaaggggc | caaccaaaaa | gccggaaacg | 480 |
| ggacgagaag | aggaggcgga | agcggggagc | gggaaagcaa | gaacacgcag | aacccgagcg | 540 |
| aaggcagcac | aaacaaacga | cacgaagcac | gaaagcgggg | gacaaacagg | aagaacccgg | 600 |
| agccacgcag | aaacgagaac | agcggcgaac | acagaagcgg | cacagcgaaa | gcgaagaacc | 660 |
| accggggaga | cgccggcaac | gggaaaccaa | aggaagacgg | gggcccgcac | aagcggagga | 720 |

-continued

| | |
|---|---|
| acagggaacg agaacgcgag gaaccacccg gggaacgcaa gacagccgga aacagagcca | 780 |
| gaaagcaagc gagggcgcag ggcgcagccg gccggagggc ggcaaggcca aacgagcgca | 840 |
| acccacacag acaacaggca gcgaggacca ggagacgcca gcgaagcgga ggaagggggg | 900 |
| agacgcaaac agcacggccc acaccggggc gacacacgga caaggggga caaagggcag | 960 |
| caccgggagc ggagcaaccc aaacccacca gcggacgaag cgcaacccga ccggaagcgg | 1020 |
| acgcagaacg cgcacagcca ggcgcgggaa acgcccgggc cgacacaccg cccgcaagcc | 1080 |
| agggagggg gaccaaagcc gaaccgcaag gacggccagg gaaaaccgag acggggcaag | 1140 |
| cgaacaagga acc | 1153 |

<210> SEQ ID NO 47
<211> LENGTH: 1125
<212> TYPE: RNA
<213> ORGANISM: Bacteroides thetaiotaomicron

<400> SEQUENCE: 47

| | |
|---|---|
| caggagaacg cagcacaggc aacacagcaa gcgaggggca gcacaggcgc aaacggagag | 60 |
| gcgaccggcg cacggggaga acacgaccaa ccgccgaaac cggggaagcc cgaaagaaag | 120 |
| aaaacccgag gaaacagacc gcaggcgaaa agaacggacg aggggagcgc caaggcaggg | 180 |
| gaggaacggc caccaaaccc gaggaagggg cgagaggaag gccccacag gaacgagaca | 240 |
| cggccaaacc cacgggaggc agcaggagga aaggcaaggg cgcaggccga accagccaag | 300 |
| agcggaagga gacgcccagg ggaaaccaag ggaaaaagcc acggggaaga gaccaagaaa | 360 |
| aggacggcaa cccggccagc agccgcggaa acggaggacc gagcgaccgg aagggaaagg | 420 |
| gagcgagggg acagaagcag ggaaaggcgg ccaaccgaaa agcaggaacg gcgcgagaca | 480 |
| gagaggggc ggaacgggga gcgggaaagc agaacacgaa gaacccgagc gaaggcagcc | 540 |
| acggacgcaa cgacacgagc cgaaagggg acaaacagga agaacccgga gccacacaga | 600 |
| aacgagaaac cgcggcgaaa cagaagcggc caagcgaaag caaagaccac cggggagacg | 660 |
| ccggcaacgg gaaaccaaag gaagacgggg gcccgcacaa gcggaggaac agggaacgag | 720 |
| aacgcgagga accacccggg caaagcagaa aaggaaacag aagccgaagg caaaggaagg | 780 |
| gcgcagggcg cagccggccg gagggcggca aggccaaacg agcgcaaccc acagacaaca | 840 |
| ggcagcgagg accagagaga cgccgcgaag aggaggaagg gggagacgc aaacagcacg | 900 |
| gcccacgccg ggcacacac ggacaagggg ggacagaagg cagcaccggg acaggagcaa | 960 |
| cccaaaagcc cccagcggac gaagcgcaac ccgaccggaa gcggacgcag aacgcgcaca | 1020 |
| gccaggcgcg ggaaacgccc gggccgacac accgcccgca agccagaaag ccggggggacc | 1080 |
| gaagacgaac cgcaaggagc gccagggaaa acggaagggg caagc | 1125 |

<210> SEQ ID NO 48
<211> LENGTH: 420
<212> TYPE: RNA
<213> ORGANISM: Lachnospiraceae bacterium

<400> SEQUENCE: 48

| | |
|---|---|
| gacgagcggc ggacggggag aacgcgggga accgcccaac agggggaaac agggaaacgg | 60 |
| cgcaaaccgc aaagcgcaca gaccgcagga ccgggaaaaa cccgggggaga gaggacccgc | 120 |
| gcgaagcagg gggggaacgg ccaccaaggc gacgacagag ccgaccgaga ggggaccggc | 180 |
| cacagggacg agacacggcc caaacccacg ggaggcagca gggggaaagc acaaggggga | 240 |

| aacccgagca gcgacgccgc ggagcgagaa gacggagaaa gccacagcag ggaagaaaag | 300 |
| acggaccgac aagaagcccc ggcaacacgg ccagcagccg cggaaacgag ggggcaagcg | 360 |
| accggaacgg ggaaagggag cgagacggca ggcaagccag aggaaagccc ggggccaacc | 420 |

<210> SEQ ID NO 49
<211> LENGTH: 1203
<212> TYPE: RNA
<213> ORGANISM: Clostridium hathewayi
<220> FEATURE:
<221> NAME/KEY: misc_feature
<222> LOCATION: (150)..(150)
<223> OTHER INFORMATION: n is a, c, g, or u
<220> FEATURE:
<221> NAME/KEY: misc_feature
<222> LOCATION: (166)..(166)
<223> OTHER INFORMATION: n is a, c, g, or u
<220> FEATURE:
<221> NAME/KEY: misc_feature
<222> LOCATION: (193)..(193)
<223> OTHER INFORMATION: n is a, c, g, or u
<220> FEATURE:
<221> NAME/KEY: misc_feature
<222> LOCATION: (791)..(791)
<223> OTHER INFORMATION: n is a, c, g, or u

<400> SEQUENCE: 49

| ccaggagaac gcggcggcgg caacacagca agcgagcgaa gcggcaagaa gcggaggaga | 60 |
| aagacagcgg cggacgggga gaacgcgggg aaccgccaca cggggggaaac agagaaagac | 120 |
| gcaaaccgca aagcgcacag ggccgcaggn cggggaaaaa cccggnggga agaggacccg | 180 |
| cgcgaaggag ggnggggaac ggcccaccaa gccgacgaca gagccgaccg agaggggacc | 240 |
| ggccacaggg acgagacacg gcccaaaccc acgggaggca gcaggggaa aggacaaggg | 300 |
| cgaaagccga ccagcgacgc cgcggaggaa gaagacggag aaagccacag cagggaagaa | 360 |
| aagacggacc gacaagaagc cccggcaaca cggccagcag ccgcggaaac gaggggcaa | 420 |
| gcgaccggaa cggggaaagg gagcgagacg gagcaagcga aggaaagccc ggggccaacc | 480 |
| ccggacgcgg aaacgagacg aggcaggaga ggaagggaac caggagcggg aaagcgagaa | 540 |
| aggaggaaca ccagggcgaa ggcggcacgg acgaacgacg gaggccgaaa gcgggggagc | 600 |
| aaacaggaag aacccggagc cacgccgaaa cgagaaacag ggcggggggc aaagcccggg | 660 |
| gccgccgcaa acgcaaaaga ccaccgggga gacgcgcaag aagaaaccaa aggaagacgg | 720 |
| ggacccgcac aagcggggag cagggaacga agcaacgcga agaaccacca agcgacacccc | 780 |
| acgaaaacac naaccggacc cccggagcag ggagacaggg ggcagggcgc agccggcgga | 840 |
| gaggggaagc ccgcaacgag cgcaacccac cagagccagc gagagagcgg gcaccgggga | 900 |
| gacgccaggg aaaccggagg aagggggggag acgcaaacac agcccagag ggcacacacg | 960 |
| gcacaaggcg aaacaaaggg aggcaaagga gcgacggagc aaaccccaaa aaaacgccag | 1020 |
| cggagcaggc gcaaccgccg cagaagcgga acgcagaacg cgaacagaag gcgcgggaaac | 1080 |
| gcccgggcga cacaccgccc gcacaccagg gagggaacgc ccgaagcagg acccaaccga | 1140 |
| aaggagggag cgccgaaggc gggacgaaac gggggaagcg aacaaggagc cgacggaagg | 1200 |
| gcg | 1203 |

<210> SEQ ID NO 50
<211> LENGTH: 1177
<212> TYPE: RNA
<213> ORGANISM: Clostridium lavalense
<220> FEATURE:
<221> NAME/KEY: misc_feature

```
<222> LOCATION: (887)..(887)
<223> OTHER INFORMATION: n is a, c, g, or u

<400> SEQUENCE: 50
gccaggagaa cgcggcggcg gccaacacag caagcgaacg aagcayagag aagcggagga      60
cgagagacga gggcggacgg ggagaacacg ggaaaccgcc cacacggggg acaacagaga     120
aagacgcaaa ccgcaaagcg cacagaccgc aggacaggga aaaacccggg gggagaggac     180
cgcgcgaagc cagggcgggg aacgcccac  caaagcgacg acagagccga ccgagagggg     240
accggccaca gggacgagac acggcccaaa cccacgggag gcagcagggg gaaagcacaa     300
gggcgaaagc cgagcagcga cgccgcggag gaagaagacg gagaaagcca cagcagggaa     360
gaaagacgga ccgacaagaa gccccggcaa cacggccagc agccgcggaa acgaggggc      420 aagcgaccgg aacggggaaa gggagcgaga cggcaggcaa gcgaaggaaa acccagggcc     480
aacccgggac gcggaaacgc aagcagaggc aggagaggaa gggaaccagg agcgggaaag     540
cgagaaagga ggaacaccag ggcgaaggcg gcacggacga acgacggagg ccgaaagcgg     600
gggagcaaac aggaagaacc cggagccacg ccgaaacgag aggcaggggg gggcaaagc      660 cccgggccgc gcaaacgcaa aagcacccac cggggagacg cgcaagaaga aaccaaagga     720
agacggggac ccgcacaagc ggggagcagg gaacgaagca acgcgaagaa ccaccaagcg     780
acacccgacc ggcggaacgg cgcccccggg acaagagaga caggggggcag ggcgcagccg     840 gcggagaggg gaagcccgca acgagcgcaa cccaccagag ccagcanrag agggcaccag     900
ggagacgcca gggacaaccg gaggaagggg ggagacgcaa acacagcccc agagggcaca     960
cacggcacaa ggcgaaacaa agggaagcga cccgcgaagg gagcaaacca aaaaaacgcc    1020
cagcggacga gcgcaacccg acacacgaag cggaacgcag aacgcgaaca gaagcgcggg    1080
aaacgcccgg gcgacacacc gcccgcacac cagggagcag caacgcccga agcaggaccc    1140
aaccgcaaga gagggagcgc cgaaggcggg gcaggaa                             1177

<210> SEQ ID NO 51
<211> LENGTH: 1204
<212> TYPE: RNA
<213> ORGANISM: Ruminococcus sp

<400> SEQUENCE: 51
gaacgcggcg gcggccaaca cagcaagcga gcgaagcgcg cagaaccgga ggaagaggac      60
aggacgagcg gcggacgggg agaacgcggg gcaaccgccc aacaggggga aacagagaaa     120
gacgcaaacc gcaaagcgca caggaccgca gggagggaaa aacccgggga gagaggaccc     180
gcgcgaagga ggggggggaaa ggccaccaag ccgacgacag agccgaccga gaggggaccg     240
gccacaggga cgagacacgg cccaaaccca cggggaggcag caggggggaaa gcacaagggg     300 gaaacccgag cagcgacgcc gcggaaggaa gaagacggag aaaccacagc agggaagaag     360
agacggaccg agaagaagca ccggcaaaac ggccagcagc cgcggaaacg agggcaagcg     420
accggaacgg ggaaagggag cgagacggaa ggcaagcgga ggaaaaccca gggccaaccc     480
gggacgcgga acgcagacg  gaggccggag aggaagcgga accaggagcg ggaaagcgag     540
aaaggaggaa caccagggcg aaggcggcac ggacgggacg acgaggccg  aaagcggggg     600 agcaaacagg aagaacccgg agccacgccg aaacgagaca cagggcgggg caaagcacac     660
gggccgcagc aaacgcaaaa gagccaccgg ggagacgcgc aagaagaaac caaaggaaga     720
cggggacccg cacaagcggg gagcagggaa cgaagcaacg cgaagaacca ccggcgacac     780
```

```
cggagacggg cgagaagcgc cgccccgggg caccgagaca gggggcaggg cgcagccggc    840
ggagagggga agcccgcaac gagcgcaacc caccagagcc agcaaaaggg ggcaccggag    900
agacgccagg gagaaccgga ggaagggggg agacgcaaac acagcccag gccagggcac     960 acacggcaca aggcgaaaca aagggaagcg agagggggacc ggagcgaacc caaaaaaacg   1020
ccagcggaga gcgcaaccga cacagaagcg gaacgcagaa cgcggacagc agccgcggga   1080
aacgcccggg cgacacaccg cccgcacacc agggagcaga acgcccgaag ccaggaccca   1140
accagaggag ggagcgcgaa ggcgggacgg aaacggggga agcgaacaag gagccgacgg   1200
aagg                                                                1204
```

<210> SEQ ID NO 52
<211> LENGTH: 1170
<212> TYPE: RNA
<213> ORGANISM: Clostridium innocuum

<400> SEQUENCE: 52

```
gaccggccag gagaacgcgg cggcagccaa acagcaagcg aacgaagcga ggaagcgccc     60
aaagagacag ggcgaacggg gagaacacga ggaaccgccc aggccgggaa acgcggaaac    120
ggagcaaaac cggaaggaac agagcgcagc cagaaaaagc gcccacaagg cggaacagga    180
ggaccgcggc gcaagcaggg gaggaacggc ccaccaaggc gagagcgagc cggccgagag    240
ggaaacggcc acagggacga gacacggccc aaacccacgg gaggcagcag agggaacgca    300 aggggggaaac ccgaacgagc aagccgcgga ggaagaaggc cggacgaaag ccggaaggaa    360
gaacggccaa gaggaaagca gggaggacgg agcaccagaa agccacggca acacggccag    420
cagccgcgga aacgagggc aagcgaccgg aacagggcga aaggggcgag gggcgacaag     480
cgagaaaagg caaggccaac cagaagcagg aaacggagcg gaggcagaag agggcgagga    540
accaggagcg gaaaagcgag aaaggaggaa caccagggcg aaggcggcgc cggcgaacga    600
cacgaggcac gaaagcgggg gagcaaaagg aagaacccag agccacgccg aaacgagaga    660 acaagggggag gaacaggcgc agaacgcaaa agcccgccgg ggagagcacg caagggaaac    720
caaaggaaga cggggggcccg cacaagcggg gagagggaac gaagcaacgc gaagaaccac    780
caggccgaca ggaaacaaaa cccagagaag ggggaaaagg acacacaggg ggcagggcgc    840
agccggcgga gagggggaagc ccgcaacgag cgcaacccgc gcagaccagc acaagggga     900 ccagcgagac gccgggacaa accggaggaa gggggggagac gcaaacacag ccccaggccg    960
ggcacacacg acacaaggcg accacaaaga gcagcgacac aggaggaagc gaaccaaaag   1020
gcgccagcgg agaagcgcaa ccgaccagaa gcggaacgca gaacgcagac agcagcgcgg   1080
gaaacgccgg gccgacacac cgcccgcaaa ccagggagca gaaacccgaa gccggggcaa   1140
accgaaggag gagccgcgaa ggaggaccga                                    1170
```

<210> SEQ ID NO 53
<211> LENGTH: 8
<212> TYPE: PRT
<213> ORGANISM: Artificial Sequence
<220> FEATURE:
<223> OTHER INFORMATION: Synthetic polynucleotide

<400> SEQUENCE: 53

Lys Ser Pro Trp Phe Thr Thr Leu
1               5

<210> SEQ ID NO 54

<211> LENGTH: 1161
<212> TYPE: RNA
<213> ORGANISM: Artificial Sequence
<220> FEATURE:
<223> OTHER INFORMATION: Synthetic polynucleotide

<400> SEQUENCE: 54

| | | | | | |
|---|---|---|---|---|---|
| cgaagaggac | cggccaggag | aacgcgacag | aagcaacaca | gcaagcacga | cccggggaag | 60 |
| gggcggacgg | ggagaacgcg | aaagaacgcc | acagacggga | caacaggaaa | cgaagcaaac | 120 |
| cggaaagagg | gcgcagacga | agaaagcaag | cgcggagaga | gcgcgcccaa | gaggggagga | 180 |
| acggccacca | agacgagagg | gagccggccg | agagggggaac | ggccacaagg | ggacgagaca | 240 |
| cggcccaccc | acggggaggca | gcaggggggaa | aggacaagga | ccaaaagcga | ccagcaacgg | 300 |
| gcacgaagaa | gcggaagaaa | ggccagggga | agaagcagga | cggaccaaca | gaagaagcga | 360 |
| cggcaaaacg | gccagcagcc | gcggaaacga | gcgcaagcga | ccggaagggc | gaaagcgcgc | 420 |
| aggcggcaga | agcgaggaaa | agcggggcca | accccgagcg | ggaaacgcaa | acagagacgg | 480 |
| agaggaggcg | gaacacaagg | agagggaaac | gagaagagga | agccgagggg | aagccagcca | 540 |
| cggacagaac | gacgcaaagc | gcgaaagcgg | ggagcaaaca | ggaagaaccc | ggagccacgc | 600 |
| cgaaacgaga | acagggggggg | gcgaacccag | cgcccaagca | acgcgaaaga | accgccgggg | 660 |
| agacgacgca | agagaaacca | aaggaagacg | gggacccgca | caagcgggga | gcagggaacg | 720 |
| acgcaacgcg | aggaaccacc | agcggacacc | caagaagaac | agagagcggc | cccggaggaa | 780 |
| cgggacaggg | ggcaggcgcg | cagccggcgg | agaggggaag | cccgcaacga | gcgcaacccc | 840 |
| cgagaccaca | aaggggggacc | agcgagacgc | cgcgagagca | ggaggaaggg | gggagacgca | 900 |
| agcacagccc | caacgcgggc | acacacggca | caagggagac | agagagcgca | aaccgcgagg | 960 |
| gaagcaacca | aaaacacagc | ggagaccgca | accgagacag | aagggaacgc | agaacgcaaa | 1020 |
| cagcaggcgg | gaaacgccgg | gcgacacacc | gcccgcacac | cacgagaggg | gcaccgaaga | 1080 |
| acaggccaac | cgaaggaggg | agccgagggg | gaagcgaggg | ggaagcgaac | aaggaccgac | 1140 |
| gggaacggcg | gaggacaccc | c | | | 1161 |

<210> SEQ ID NO 55
<211> LENGTH: 1190
<212> TYPE: RNA
<213> ORGANISM: Artificial Sequence
<220> FEATURE:
<223> OTHER INFORMATION: Synthetic polynucleotide

<400> SEQUENCE: 55

| | | | | | |
|---|---|---|---|---|---|
| cgaagaggac | cggccaggag | aacgcagcga | caggcaacac | agcaagcgag | gggcacagga | 60 |
| agagcaaaca | gaggcgaccg | gcgcacgggg | agaacgcgag | caacaccaca | gaggggggaag | 120 |
| cccggcgaaa | gcggaaaacc | caaaaacagg | ggccgcaggg | acagaaagac | acgcgaagaa | 180 |
| ggcagcgcca | aggcagggcg | gggaacggcc | caccaaaccg | acgaggaagg | ggcgagagga | 240 |
| aggcccccac | aggacgagac | acggaccaaa | cccacgggag | gcagcaggag | gaaaggcaag | 300 |
| gccgagaggc | gaaccagcca | agcgcggaag | gagaaggaca | gggaaaccaa | ggggaaaaag | 360 |
| ggggacggcc | agagacccag | aaaagcacgg | caacccggcc | agcagccgcg | gaaacggagg | 420 |
| agcgagcgac | cggaagggaa | aggggcgagg | ggaaaagcag | cgggaaaggg | gccaaccaaa | 480 |
| aagccggaaa | cgggacgagg | ggaggaggcg | gaagcgggga | gcgggaaagc | aagaacacgc | 540 |
| agaacccaag | cgaaggcagc | acaaaccaaa | cgacacgaag | cacgaaagcg | gggacaaaca | 600 |
| ggaagaaccc | ggagccacgc | agaaacgaga | acaggaggcg | aacacagaag | ccacagcgaa | 660 |

```
agcgaagaac caccggggag acgccggcaa cgggaaacca aaggaagacg ggggcccgca    720
caagcggagg aacagggaac gagaacgcga ggaaccaccc ggggaacgag cagaccgacc    780
gaaagaggca gcaaagcgaa cgagggcgca gggcgcagcc ggccggaggg cggcaaggcc    840
aaacgagcgc aacccacaca gacaacagga agcgaggacc gggagacgcc agcgaagcgg    900
aggaaggggg gagacgcaaa cagcacggcc cacaccgggg cgacacacgg acaaggcagg    960
acaaagggca gcaccggcga caggagcaac caaaccagcc agcggacgga gcgcaaccga   1020
cccggaagcg gacgcagaac gcgcacagcc aggcgcggga aacgcccggg ccgacacacc   1080
gcccgcaagc cagggagccg ggggaccgaa gccgaaccgc aaggacggcc agggaaaacg   1140
ggacggggca agcgaacaag gagccgaccg gaagggcggc ggaacacccc               1190

<210> SEQ ID NO 56
<211> LENGTH: 1061
<212> TYPE: RNA
<213> ORGANISM: Artificial Sequence
<220> FEATURE:
<223> OTHER INFORMATION: Synthetic polynucleotide

<400> SEQUENCE: 56
aaaaagaaag gaaggagggg gagcgcccaa gcgggcgggg aacggcccac caaggcgacg     60
agggaggggc gagaggaagg cccccacagg aacgagacac ggccaaaccc acggaggca    120 gcaggaggaa aggcaagggc gcgagccgaa ccagccaaga gcgggaggac gacggcccac    180
ggggaaaccc aaaggggaaa agggccagag gccagcagga ccagaaaagc acggcaaccg    240
gccagcagcc gcggaaacgg aagagcgagc gaccggaagg gaaagggagc gaggcgggca    300
gcaagcagcg gcaaaggcgc ggccaaccgc gccgccggaa acggcagccg agagcacagg    360
gacaggaacg gggagcggga aagcagaaca cgaggaaccc gacgcgcagg cagaccgggg    420
caacgacgcg aggccgaagg gcgggacaaa caggaagaac ccggagccgc acagaaacga    480
gaagcccgcg cggcgacaag gcggcggcca agcgaaagcg aagcaccacc ggggagacgc    540
cggcaacggg aaaccaaagg aagacggggg cccgcacaag cggaggaaca gggaacgaga    600
acgcgaggaa ccacccgggc gaacgcaggg cagggccgga gacggccccc gggacccgc    660 gaagggcgca gggcgcagcc ggccggaggg cggcaaggcc aaacgagcgc aacccccccc    720
ccaggccacc gggaagccgg gcacggggac acgccaccgc aagggcgagg aaggggggag    780
acgcaaacag cacggcccac gccggggcga cacacggaca aggggggaca gagggccgcg    840
cccgggacgg ggccaacccca aaaccccca gcggacggag cgcaacccga cccacgaagc    900
ggacgcagaa cgcgcacagc caggcgcggg aaacgcccgg gccgacacac cgcccgcaag    960
ccagaaagcc ggggggccga agccggaccg cgagggcggc cagggaaaac cgggagggc   1020 aagcgaacaa ggagccgacc ggaagggcgg cggaacaccc c                       1061

<210> SEQ ID NO 57
<211> LENGTH: 1219
<212> TYPE: RNA
<213> ORGANISM: Artificial Sequence
<220> FEATURE:
<223> OTHER INFORMATION: Synthetic polynucleotide

<400> SEQUENCE: 57
cgaagaggac cggccaggag aacgcagcga caggcaacac agcaagcgag ggcagcaca     60 ggagcaaacc gggggcgacc ggcgcacggg gagaacgcga gcaacgccac agaggggaa    120
```

| | | |
|---|---|---|
| acccggcgaa agcggacaaa ccgcagaagc aggggcccccg caggggaagc aaagacacgc | 180 |
| gaagaaggca gcgccaaggc agggcgggga acggcccacc aaaccgacga ggaaggggcg | 240 |
| agaggaaggc ccccacagga cgagacacgg accaaaccca cgggaggcag caggaggaaa | 300 |
| ggcaaggccg agaggcgaac cagccaagcg cggaggraga aggcaggacg aaacccaaag | 360 |
| ggaaaaaggc gggacggccc ggagaccaga aaaggacggc aacccggcca gcagccgcgg | 420 |
| aaacggagga ccgagcgacc ggaagggaaa ggggcgaggc ggccaagcag cgggaaagcg | 480 |
| ggccaaccaa gaagccggaa acgggggggcg agaggaggca ggcggaagcg gggagcggga | 540 |
| aagcaagaac acgcagaacc ccgagcgaag gcagccgcca agccaacgac gcagagcacga | 600 |
| aagcggggga caaacaggaa gaacccggag ccacgcagaa acgagacaca gcggcgaaca | 660 |
| cgaagcggca cagcgaaagc gaaggaccac cggggagacg ccggcaacgg gaaaccaaag | 720 |
| gaagacgggg gcccgcacaa gcggaggaac agggaacgag aacgcgagga accacccggg | 780 |
| gaacgcacgg accgaggga aacacccagc aaagccggcg agggcgcagg gcgcagccgg | 840 |
| ccggagggcg gcaaggccaa acgagcgcaa cccgccacag acaacaggaa agcgaggacc | 900 |
| gggggacgcc agcgaagcgc gaggaaggcg gggagacgca aacagcacgg cccacaccgg | 960 |
| ggcgacacac ggacaaggcg ggacaaaggg aagccaccgg cgacagggag cgaacccaa | 1020 |
| accacgccag cggacggagc gcaacccgac ccggaagcgg acgcagaacg cgcacagcca | 1080 |
| ggcgcgggaa acgcccgggc cgacacaccg cccgcaagcc agggagccgg gggaccgaag | 1140 |
| ccgaaccgcg aggacggcca gggaaaacgg gacggggcaa gcgaacaagg agccgaccgg | 1200 |
| aagggcggcg gaacaccccc | 1219 |

<210> SEQ ID NO 58
<211> LENGTH: 1205
<212> TYPE: RNA
<213> ORGANISM: Artificial Sequence
<220> FEATURE:
<223> OTHER INFORMATION: Synthetic polynucleotide

<400> SEQUENCE: 58

| | | |
|---|---|---|
| aggagaggac cggccaggag aacgcagcgg caggccaaca cagcaagcga ggggcagcgg | 60 |
| gagaagcgcc aggccggcga ccggcgcacg gggcgaacgc gagcaaccac ccaaacaggg | 120 |
| ggaaacacga gaaacggaca aacccaaaca caagaggggc acccgggaaa acccggggag | 180 |
| gagggcagcg gaagcagggg aggaacggcc accaaggcga cgaacaaggg ggacgagagg | 240 |
| aacccccccac aggacgagac acggaccaaa cccacgggag gcagcaggag gaaaggcaag | 300 |
| gacgcaagcg aaccagccag ccgcggcagg agacggccag aggaaacgcg acgagggaaa | 360 |
| cccggaacgg accggcgaaa gacgacgaaa aggacggcaa cccggccagc agccgcggaa | 420 |
| acggaggaca agcgaccgga agggaaaggg gcgaggcggg aaagagaggg aaaaccgggc | 480 |
| aacaccggaa cgcccaaacg gagcagagag aggcggaggc ggaagaggga gcgggaaagc | 540 |
| agagacaaca gaacaccgag cgaaggcagc accaaacaac gacggaggca cgaaagcggg | 600 |
| ggagcaaaca ggaagaaccc ggagccacgc agaaacgaga accgcgcgg cgaacacagc | 660 |
| ggggcaagcg aaagcgaaag accaccgggg agacgcgcaa gaagaaacca aggaagacg | 720 |
| ggggcccgca caagcggagg aacagggaac gagaacgcga ggaaccaccc gggcgaaaga | 780 |
| cgacgacgga aacaggaccc cggggcagga acagggcgc agggcgcagc cggccggagg | 840 |
| gcgggaagcc caaacgagcg caaccccacc gaggccacag gcaagcgggc accggcggga | 900 |
| cgccgggaag ccgagaggaa gggggggagac gcaaacagca cggcccacgc cggggcacac | 960 |

| | |
|---|---|
| acggacaagg aggacagagg gcagcaccca ggagggagcg aaccgaaagc caccagcgga | 1020 |
| ggaggcgaaa cccgcccag aagggacgca gaacgcgcac agccaggcgc gggaaacgcc | 1080 |
| cgggccgaca caccgcccgc aagccaggaa gcggggggcc gaagcggacc gcaaggagcg | 1140 |
| accagggcaa aaccgggacg gggcaagcga acaaggagcc gaccggaagg gcggcggaac | 1200 |
| acccc | 1205 |

<210> SEQ ID NO 59
<211> LENGTH: 1213
<212> TYPE: RNA
<213> ORGANISM: Artificial Sequence
<220> FEATURE:
<223> OTHER INFORMATION: Synthetic polynucleotide

<400> SEQUENCE: 59

| | |
|---|---|
| agagaggacc ggccaggacg aacgcggcgg agcaacacag caagcgaacg agaagggagg | 60 |
| acccggggaa cagaacggaa agggcgaacg gggagaaccgc ccaggaaagg | 120 |
| aaagcccggg aaacgggaga agccaaagg gcgcaggcaa gacagaaaac ccgggccaag | 180 |
| gaggacccgc gcccaagcag gggagaaaca gcccaccaag gcgacgaggg aaccggcgag | 240 |
| agggcgaacg gcacacggaa cgagacacgg ccagacccac ggggaggcagc aggggggaaag | 300 |
| cgcaaggggg caacccgacg cagcaaaccg cggaggaaga aggcggacga agccgagggg | 360 |
| gaagaagaag acggacccaa gaggaagccc ggcaacacgg ccagcagccg cggaaacgag | 420 |
| gggacaagcg gccggaagac gggcgaaagg gcgcgaggcg gcaaagcgag gaaaggaccg | 480 |
| gccaaccggg aaggcaggaa acggagacga gaggagaggc aagggaacca ggagcgggaa | 540 |
| agcgagaaag gaggaacacc agggcgaagg cggcgcggac aaaacgacgc gagggcgaaa | 600 |
| gcggggggagc gaacaggaag aaccccggagc cacgccgaaa cgagaagcag ggggggaaac | 660 |
| caggccgcag aacacaaaag caccgccggg gagacgaccg caagggaaac caaaggaaga | 720 |
| cggggacccg cacaagcagc ggagcaggga acgaagcaac gcgaagaacc accaggcgac | 780 |
| acccgacgag ccagagaagg aagcccggga acagagagac aggggggcagg gcgcagccgg | 840 |
| cggagagggg aagcccgcaa cgagcgcaac cccgccaggc cagcaaaggg gcaccagagg | 900 |
| gacgccgaga caaacggagg aaggggggac gacgcaaaca cagccccaga ccgggcacac | 960 |
| acggcacaag gcgaacagag ggccgcgaag ccgcgaggga agcaaaccca aaacagaccc | 1020 |
| agcggagcag gcgcaaccgc cgcagaaggg aggcagaacg cggacagaag ccgcgggaag | 1080 |
| cgcccgggcg acacaccgcc cgcacaccac gagagggcaa cacccgaagc cggagagaac | 1140 |
| cgaaggacca gcagcgaagg ggggcagaag ggggaagcga acaaggagcc gacggaaggg | 1200 |
| cggcggacac ccc | 1213 |

<210> SEQ ID NO 60
<211> LENGTH: 1193
<212> TYPE: RNA
<213> ORGANISM: Artificial Sequence
<220> FEATURE:
<223> OTHER INFORMATION: Synthetic polynucleotide

<400> SEQUENCE: 60

| | |
|---|---|
| agaagaggac cggccaggag aacgcagcac aggcaacaca gcaagcgagg ggcagcaggc | 60 |
| agcgcaaggc gaggcgaccg gcgcacgggg agaacacgac caaccgccgc accggccagc | 120 |
| ccgaaaggaa gaaaccagga gggacagagc acagccgcag aaaaggaccg gagacgaggg | 180 |

| | |
|---|---|
| gagcgccaag aagaggcggg gaacggccca ccagcaacga ggaagggggcg agaggaaggc | 240 |
| ccccacagga acgagacacg gccaaaccca cggaggcag caggaggaaa ggcaagggcg | 300 |
| aggccgaacc agccaagagc ggaaggagac gcccagggga aaccaaaagg aaaaagcggg | 360 |
| agcaacccgg cagacagaaa aggacggcaa cccggccagc agccgcggaa acggaggacc | 420 |
| gagcgaccgg aagggaaagg gagcgagagg agaagcaggg aaaggcggcc aaccgaaaag | 480 |
| caggaacgga gcgaggcagg aggcaggcgg aacgggagc gggaaagcag aacacgaaga | 540 |
| acccgagcga aggcagccgc aagcgcaacg acagaggccg aaggggac aaacaggaag | 600 |
| aacccggagc cacacggaaa cgagaaaccg cggcgaaacg gcaagcggcc aagcgaaagc | 660 |
| gaagaccacc ggggagacgc cggcaacggg aaaccaaagg aagacggggg cccgcacaag | 720 |
| cggaggaaca gggaacgaga acgcgaggaa ccacccgggc aaagcaccga agaccggaaa | 780 |
| cggcagcagc aaagcgaggg aagggcgcag ggcgcagccg gccggagggc ggcaaggcca | 840 |
| aacgagcgca acccggcaga caacaggag cgaggaccga caagacgcca cgaagaggag | 900 |
| gaagggggga gacgcaaaca gcacggccca cgccggggca cacacggaca aggggggaca | 960 |
| gagggccgca ccacgcgagg gagccaaccc aaaaccccc agcggacgga gcgcaacccg | 1020 |
| acccacgaag cggacgcaga acgcgcacag ccacggcgcg ggaaacgccc gggccgacac | 1080 |
| accgcccgca agccagggag ccgggggacc gaaggcgaac cgcgaggacg cccagggaaa | 1140 |
| acgggacggg gcaagcgaac aaggagccga ccggaagggc ggcggaacac ccc | 1193 |

<210> SEQ ID NO 61
<211> LENGTH: 1191
<212> TYPE: RNA
<213> ORGANISM: Artificial Sequence
<220> FEATURE:
<223> OTHER INFORMATION: Synthetic polynucleotide

<400> SEQUENCE: 61

| | |
|---|---|
| cgaagaggac cggccaggag aacgcagcga caggcaacac agcaagcgag gggcagcagg | 60 |
| aagagcaaac gcggcgaccg gcgcacgggg agaacgcgag caaccaccac agaggggggaa | 120 |
| acccggcgaa agcggacaaa ccgcaaaaac aggggcccgc agggaaagaa agaagcgaag | 180 |
| agggcagcgc caagaagggg aggaacggcc accaagccga ggaaggggcg agaggaaggc | 240 |
| ccccacacgg acgagacacg gaccagaccc acggaggca gcaggaggaa aggcaagggc | 300 |
| gagagccgaa ccagccaagc gcggaaggag aaggacaggc gaaaccaagg ggaaaaaggc | 360 |
| aggacggccg gagacccaga aaaggacggc aacccggcca gcagccgcgg aaacggagga | 420 |
| ccgagcgacc ggaagggaaa ggggcgaggg gcaagcagcg ggaaagggggc caaccaaaaa | 480 |
| gccgaaaacg gagggcgaga agaggaggcg gaagcgggga gcgggaaagc aagaacacgc | 540 |
| agaacccaag cgaaggcagc acaaacaaac gacacgaagc acgaaagcgg gggacaaaca | 600 |
| ggaagaaccc ggagccacgc agaaacgaga acaggaggcg aacacagaag ccacagcgaa | 660 |
| agcgaagaac caccggggag acgccggcaa cgggaaacca aggaagacg ggggcccgca | 720 |
| caagcggagg aacagggaac gagaacgcga ggaaccaccc ggggaacgaa ggaccggagg | 780 |
| gaaacaccca gcaaagcaaa cgagggcgca gggcgcagcc ggccgagggg cggcaaggcc | 840 |
| aaacgagcgc aacccacaga caacaggcga gcgaggacca aagagacgcc agcgaagcgg | 900 |
| aggaagggggg gagacgcaaa cagcacggcc cacaccgggg cgacacacgg acaagggggg | 960 |
| acaaagggca gcaccggcga caggagcaac ccaaacccca ccagcggacg aagcgcaacc | 1020 |
| cgaccggaag cggacgcaga acgcgcacag ccaggcgcgg gaaacgcccg ggccgacaca | 1080 |

```
ccgcccgcaa gccagggagg ggggaccaaa gccgaaccgc aaggacggcc agggaaaacc      1140
gagacggggc aagcgaacaa ggagccgacc ggaagggcgg cggaacaccc c               1191
```

<210> SEQ ID NO 62
<211> LENGTH: 1224
<212> TYPE: RNA
<213> ORGANISM: Artificial Sequence
<220> FEATURE:
<223> OTHER INFORMATION: Synthetic polynucleotide

<400> SEQUENCE: 62

```
aagaagagga ccggccagga cgaacgcggc ggcgcgccaa cacagcaagc gaacggagcg       60
ccgaagcgga ggaagagagc agcagggcga acggggagaa cacggagcaa ccgcccaggg      120
gggacaacag gaaacgaagc aaaccgcaaa gaccacaggc gcaggcacag gggcaaggga      180
accgcgaaag agggccgcgc cgaagcagag ggaggaacgg cccaccaggc gacgacggag      240
ccggacgaga gggaacggcc acagggacga gacacggccc agaccacggg gaggcagcag      300
ggggaaagca caagggggaa acccgagcag cgacgccgcg ggaggaagaa ggccggagaa      360
acccgcccag gggacgaaag acggacccgg gaggaagcac cggcaacacg gccagcagcc      420
gcggaaaacg aggggcaagc ggccggaaac ggggaagggg agcgcaggcg gaggcaaggg      480
gaggaaacag ggccaacccaaaagccaaaa cgcagcgagg ggagaggagg cggaacccgg      540
gagcggggaa gcgagaacgg gaggaacacc agggcgaagg cggccacggg cacaacgacg      600
cgaggccgaa agcaggagc aaacaggaag aacccgagc cagccgaaac gagaacaggg      660
gggaggagac cccccggccg cagaacacaa aagaaccacc ggggagacga ccgcaaggga      720
aaccaaagga gacggggc cgcacaagc agggagaggg aacgaagcaa cgcgaagaac      780
caccaggcga cacggagcaa ccaagagaag ggaagcccgg acaccagac aggggcagg      840 gcgcagccgg cggagagggg aagcccgcaa cgagcgcaac ccacgagaca cgcaagagga      900
ccagcgagac gccggacaaa acggaggaag gggggagacg caaacacagc ccagaccggg      960
cacacacgac acaaggcaaa cagagagaag cgaaccgcga ggggagcaaa cccacaaaaa     1020
agccagcgga cgcaggcgca acccgccgcg gaagccggaa gcagaacgcg acagcagcc     1080 gcgggaaacg cccgggccga cacaccgccc gcacaccaga gagccggggg gacccgaagc     1140
ggagcaaccg caaggaggac gccgccgaag gaaaacggga ggggaagcg aacaaggagc     1200 cgacggaagg gcggcggaca cccc                                          1224
```

<210> SEQ ID NO 63
<211> LENGTH: 1186
<212> TYPE: RNA
<213> ORGANISM: Artificial Sequence
<220> FEATURE:
<223> OTHER INFORMATION: Synthetic polynucleotide

<400> SEQUENCE: 63

```
agaagaggac cggccaggag aacgcagcac aggcaacaca gcaagcgagg ggcagcagaa       60
cagcgcaagg aggcgaccgg cgcacgggga gaacacgacc aaccgccgag accgggaag      120 cccgaaagaa agaaaacccg aggcaagccc gcagggaac aaaagaacgg cacgagggga      180
```

| | | |
|---|---|---|
| gcgccaaggg ggcggggaac ggcccaccaa gcccgaggaa ggggcgagag gaaggccccc | 240 | |
| acaggaacga gacacggcca aacccacggg aggcagcagg aggaaaggca aggacgagag | 300 | |
| cgaaccagcc aagagcggaa ggagacgccc aggggaaacc aacgggaaaa aggaggcacg | 360 | |
| ggccgagacc gagaaaagga cggcaacccg gccagcagcc gcggaaacgg aggaccgagc | 420 | |
| gaccggaagg gaaagggagc gaggcggacg caagcaggga aaggcggcca accgaaaagc | 480 | |
| aggaacgggg cgagacagag aggcaggcgg aacggggagc gggaaagcag aacacgaaga | 540 | |
| acccgagcga aggcagccgc ggacgaacga cgcgagccga aaggggggaca aacaggaaga | 600 | |
| acccggagcc acacagaaac gagaaaccgc ggcgaaacag aagcggccaa gcgaaagcga | 660 | |
| agaccaccgg ggagacgccg gcaacgggaa accaaaggaa gacgggggcc cgcacaagcg | 720 | |
| gaggaacagg gaacgagaac gcgaggaacc acccgggcga agcaacgaag agggagacag | 780 | |
| cagccgcaag gcagggaagg gcgcagggcg cagccggccg gagggcggca aggccaaacg | 840 | |
| agcgcaaccc acgaagacca cagggagcgg ggaccgcgag acgccgcgaa gaggaggaag | 900 | |
| gggggagacg caaacagcac ggcccacgcc ggggcacaca cggacaaggg gggacagaag | 960 | |
| gcagcacacg gcgacggagc aacccgaaag ccccccagcgg aggagcgcaa cccgacccag | 1020 | |
| aagcggacgc agaacgcgca cagccacggc gcgggaaacg cccgggccga cacaccgccc | 1080 | |
| gcaagccaga aagccggggg accgaaggcg aaccgcaagg agcgcccagg gaaaacggga | 1140 | |
| ggggcaagcg aacaaggagc cgaccggaag ggcggcggaa caccccc | 1186 | |

<210> SEQ ID NO 64
<211> LENGTH: 1241
<212> TYPE: RNA
<213> ORGANISM: Artificial Sequence
<220> FEATURE:
<223> OTHER INFORMATION: Synthetic polynucleotide

<400> SEQUENCE: 64

| | | |
|---|---|---|
| aggagaggac cggccaggac gaacgcggcg gcggccaaca cagcaagcga acggagaaac | 60 | |
| ggagaacagg gcgaacgggg agaacgcgag gcaaccaccc agacggggac aacaccgaaa | 120 | |
| ggaggcaaac cggaggacac gccgcaggca ggagaagaaa gaggcccaca agaagcacgc | 180 | |
| aaaggagggc cgcgcgaagc agggaggaac ggacaccaag gcgagacaga gccggcgaga | 240 | |
| ggagaacggc cacagggacg agacacggcc caaacccacg ggaggcagca gggggaaccc | 300 | |
| gcaaggacga aagcgacgga gcaacgccgc ggaggagaag gacggcgaaa gccggagacg | 360 | |
| aacggcaggg gaacaagcag caagacggag aaacgaggaa gccacggcaa cacggccagc | 420 | |
| agccgcggaa acgaggggcg agcggccgga aagggcgaaa gagcagaggc ggcaaaagcg | 480 | |
| agcggaaaag cggggccaac cccgaggcgc ggaaacgagg cgaggcagga gaggaaaggg | 540 | |
| gaacccagga gcgggaaagc gagaagggag gaacaccagg gcgaaggcgc ccggacggcg | 600 | |
| acgcgagagc gaaagccagg gagcgaacgg gaagaacccc ggagccggcc gaaacgaggg | 660 | |
| acagggagga ggacgacccc cggccggaga acgcaaaaga ccccgccggg gagacggccg | 720 | |
| caagggaaac caaaggaaga cgggggcccg cacaagcggg gagagggaac gacgcaacgc | 780 | |
| gaagaaccac caaggcgaca gagaacgcca gagaagagac cccggggaca agaaaacagg | 840 | |
| gggcaggcgc gcagccggcg gagagggaa gcccgcaacg agcgcaaccc caccagacca | 900 | |
| gcaagaaagg gggaccaggg agacgccagg gacaaccgga ggaaggcggg gagacgcaag | 960 | |
| cacagccccca gcgggcacac acgacacaag gcggaaacag agggaagcga agccgcgagg | 1020 | |
| cagagcaaac cccagaaacc cgaccagcgg acgcaggcgc aacccgccgc ggaagcggaa | 1080 | |

-continued

```
cgcagaacgc aggcagcaac gcgggaaacg cccgggccga cacaccgccc gcacaccacg    1140
aaagggaaca cccgaagccg ggaggaacca aggagccagc cgcaaggggg gccgagaggg    1200
ggaagcgaac aaggagccga cggaagggcg gcggacaccc c                       1241
```

COMPOSITIONS AND METHODS FOR THE INDUCTION OF CD8+ T-CELLS

RELATED APPLICATIONS

This application is a continuation of international application number PCT/JP2017/046232, filed Dec. 22, 2017 which claims the benefit under 35 U.S.C. § 119(e) of U.S. provisional application No. 62/438,793, filed Dec. 23, 2016; U.S. provisional application No. 62/484,607, filed Apr. 12, 2017; U.S. provisional application No. 62/491,062, filed Apr. 27, 2017; and U.S. provisional application No. 62/574,446, filed Oct. 19, 2017. The entire contents of each of these referenced applications are incorporated by reference herein.

TECHNICAL FIELD

The disclosure relates to compositions and methods for the induction and/or proliferation of CD8+ T-cells. The disclosure also provides methods of treatment of diseases that can be treated by the induction and/or proliferation of CD8+ T-cells.

BACKGROUND ART

Animals, including humans, harbor a multitude of microbes (collectively referred to as the microbiota) in anatomical locations including the mouth, esophagus, stomach, small intestine, large intestine, caecum, vagina, skin, nasal cavities, ear, and lungs. The human microbiota is responsible for a multitude of critical processes, including the development of the immune system, metabolism of carbohydrates, proteins and xenobiotics, formation and regeneration of the epithelium, fat storage, production of hormones, production of vitamins, and protection from pathogen infections, among others (See e.g., LeBlanc et al. Curr. Opin. Biotechnol. (2013) 24(2):160-168; Hooper et al. Science (2012) 336(60801268-1273; Hughes et al. Am. J. Gastroenterol. (2013) 108(7):1066-1074). Modification of the human microbiota, which can be caused by a number of factors such as antibiotic use, excessive hygiene, diet, genetic background or combinations of the above, has been associated with a number of unwanted effects including the occurrence of infectious diseases (e.g., *C. difficile* infections), inflammatory, autoimmune and allergic diseases (e.g., ulcerative colitis, Crohn's disease, Type I diabetes, food allergies, asthma, rheumatoid arthritis) and metabolic diseases (e.g., Type II diabetes, metabolic syndrome, obesity, malnutrition), and cancer, among others. For instance, modifications of the microbiota can lead to a loss of tolerance against harmless food antigens or commensal bacterial antigens, subsequent excessive inflammatory responses, metabolic dysregulation, and damage to the intestinal tissue, which compromises its ability to serve as a barrier between the gut lumen and the systemic circulation.

Manipulation of the immune response is of great importance in the treatment of cancer and in vaccination. Cancer therapies that target the immune system have attained improvements in survival rates. However, a large percentage of patients do not respond to cancer immunotherapies. Similarly, large population subsets (e.g., the elderly) cannot mount strong immune responses to vaccines.

Approaches for countering the harmful effects of microbiota modifications on health are limited, despite the role that such modifications play in promoting human pathology. Interventions known to modulate the microbiota include antibiotics, prebiotics, probiotics and fecal transplants, each of which has limitations and potential adverse effects. Additional approaches to counter the detrimental effects of microbiome modification on human health are clearly needed. Furthermore, approaches for promoting stronger immune responses to cancer and to vaccines are also needed.

SUMMARY OF INVENTION

The inventors joined the Innovative Advanced Research and Development Support Project Incubation Type of Japan Agency for Medical Research and Development (AMED) in 2016, whose Research and Development Subject entitled "Creating New Drugs Using Intestinal Bacterial Strain Cocktail" (AMED-LEAP Research Program), and obtained the present invention as the result of the AMED-LEAP Research Program. The disclosure relates to compositions of bacterial strains and methods for the induction and/or proliferation of CD8+ T-cells by administering these compositions. The disclosure also provides compositions and methods for the treatment of diseases that can be treated by the induction and/or proliferation of CD8+ T-cells. Diseases that can be treated by the induction and/or proliferation of CD8+ T-cells include infectious diseases and cancers.

As disclosed herein, for the first-time compositions of human-derived bacterial strains are provided which activate the immune system through the induction of interferon gamma producing CD8+ T cells (also referred to herein as IFNγ+CD8+ T cells, CD8+ IFNγ+ T cells, CD8+ T cells or CD8 positive T-cells). While microbial-based compositions for inducing proliferation or accumulation of regulatory T-cells (WO2011/152566), and composition for inducing Th17 cells (WO2015/156419) were previously reported, this disclosure is the first report on microbial species which induce IFNγ+CD8+ T-cells. IFNγ+CD8+ T-cells play important roles in the immune system, in particular the surveillance of infections (e.g., viral infections) and cancer cell development. The compositions provided herein can therefore be used in, for instance, the treatment of infectious diseases and cancer immunotherapy.

In one aspect, the disclosure provides compositions comprising a purified bacterial mixture comprising one or more bacterial strains of species selected from the group consisting of *Phascolarctobacterium faecium*, *Fusobacterium ulcerans*, *Bacteroides dorei*, *Bacteroides uniformis*, *Subdoligranulum* sp., *Paraprevotella xylaniphila*, *Parabacteroides johnsonii*, *Alistipes* sp., *Parabacteroides gordonii*, *Eubacterum limosum*, *Parabacteroides distasonis*, *Bacteroides cellulosilyticus*, *Bacteroides clarus*, *Anaerostipes caccae*, *Bacteroides salyersiae*, *Bacteroides fragilis*, *Bacteroides uniformis*, *Bacteroides eggerthii*, *Clostridium* sp., *Parabacteroides goldsteinii*, *Bacteroides* sp., *Lachnospiraceae bacterium* HGA0140, *Hungatella hathewayi*, *Clostridium lavalense*, *Ruminococcus* sp., and *Clostridium innocuum*. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains of species selected from the group consisting of *Phascolarctobacterium faecium*, *Fusobacterium ulcerans*, *Bacteroides dorei*, *Bacteroides uniformis*, *Subdoligranulum* sp., *Paraprevotella xylaniphila*, *Parabacteroides johnsonii*, *Alistipes* sp., *Parabacteroides gordonii*,

*Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*. In one aspect, the disclosure provides compositions comprising a purified bacterial mixture consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*.

In one aspect, the disclosure provides compositions comprising a purified bacterial mixture essentially consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*. In one aspect, the disclosure provides compositions comprising a purified bacterial mixture comprising one or more bacterial strains of species selected from the group consisting of *Phascolarctobacterium faecium, Phascolarctobacterium* sp. CAG:207, *Fusobacterium ulcerans, Fusobacterium varium, Bacteroides dorei, Bacteroides fluxus, Bacteroides uniformis, Bacteroides* sp. D20 *Subdoligranulum* sp., *Ruthenibacterium lactatiformans, Ruminococcaceae bacterium* cv2, *Gemminger formicilis, Paraprevotella xylaniphila, Parabacteroides johnsonii, Alistipes* sp., *Alistipes timonensis, Alistipes senegalesis, Parabacteroides gordonii, Parabacteroides* sp. HGS0025, *Eubacterum limosum, Parabacteroides* sp. CAG:2 and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising:
1) *Phascolarctobacterium faecium*, or *Phascolarctobacterium* sp. CAG:207,
2) *Fusobacterium ulcerans*, or *Fusobacterium varium*,
3) *Bacteroides dorei*, or *Bacteroides fluxus*,
4) *Bacteroides uniformis*, or *Bacteroides* sp. D20,
5) *Subdoligranulum* sp., *Ruthenibacterium lactatiformans, Ruminococcaceae bacterium* cv2, or *Gemminger formicilis*,
6) *Paraprevotella xylaniphila*,
7) *Parabacteroides johnsonii*,
8) *Alistipes* sp., *Alistipes timonensis*, or *Alistipes senegalesis*,
9) *Parabacteroides gordonii*, or *Parabacteroides* sp. HGS0025,
10) *Eubacterum limosum*, and
11) *Parabacteroides* sp. CAG:2 or *Parabacteroides distasonis*.

In one aspect, the disclosure provides compositions comprising a purified bacterial mixture consisting of:
1) *Phascolarctobacterium faecium*, or *Phascolarctobacterium* sp. CAG:207,
2) *Fusobacterium ulcerans*, or *Fusobacterium varium*,
3) *Bacteroides dorei*, or *Bacteroides fluxus*,
4) *Bacteroides uniformis*, or *Bacteroides* sp. D20,
5) *Subdoligranulum* sp., *Ruthenibacterium lactatiformans, Ruminococcaceae bacterium* cv2, or *Gemminger formicilis*,
6) *Paraprevotella xylaniphila*,
7) *Parabacteroides johnsonii*,
8) *Alistipes* sp., *Alistipes timonensis*, or *Alistipes senegalesis*,
9) *Parabacteroides gordonii*, or *Parabacteroides* sp. HGS0025, 10) *Eubacterum limosum*, and
11) *Parabacteroides* sp. CAG:2 or *Parabacteroides distasonis*.

In one aspect, the disclosure provides compositions comprising a purified bacterial mixture comprising one or more bacterial strains of species selected from the group consisting of *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum,* and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum,* and *Parabacteroides distasonis*.

In one aspect, the disclosure provides compositions comprising a purified bacterial mixture consisting of *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum,* and *Parabacteroides distasonis*. In one aspect, the disclosure provides compositions comprising a purified bacterial mixture essentially consisting of *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum,* and *Parabacteroides distasonis*.

In one aspect, the disclosure provides compositions comprising a purified bacterial mixture comprising one or more bacterial strains of species selected from the group consisting of *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum,* and *Parabacteroides* sp. CAG:2. In some embodiments of the compositions provided herein, the purified bacterial mixture comprises at least 2, at least 3, at least 4, at least 5, at least 6, at least 7, at least 8, at least 9, at least 10, or at least 11 bacterial strains. In one aspect, the disclosure provides compositions comprising a purified bacterial mixture comprising *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum,* and *Parabacteroides* sp. CAG:2.

In one aspect, the disclosure provides compositions comprising a purified bacterial mixture consisting of *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum,* and *Parabacteroides* sp. CAG:2. In one aspect, the disclosure provides compositions comprising a purified bacterial mixture essentially consisting of *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum,* and *Parabacteroides* sp. CAG:2.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum,* and *Parabacteroides distasonis*. In some embodiments of the compositions provided herein, the purified bacterial mixture comprises at least 3, at least 4, at least 5, at least 6, at least 7, at least 8, at least 9, at least 10, or at least 11 bacterial strains. In one aspect, the disclosure provides compositions comprising a purified bacterial mixture comprising two or more bacterial strains of species selected from the group consisting of *Phascolarctobacterium faecium, Phascolarctobacterium* sp. CAG:207, *Fusobacterium ulcerans, Fusobacterium varium, Bacteroides dorei, Bacteroides fluxus, Bacteroides uniformis, Bacteroides* sp. D20 *Subdoligranulum* sp., *Ruthenibacterium lactatiformans, Ruminococcaceae bacterium* cv2, *Gemminger formicilis, Paraprevotella xylaniphila, Parabacteroides johnsonii, Alistipes* sp., *Alistipes senegalesis, Parabacteroides gordonii, Parabacteroides* sp. HGS0025, *Eubacterum limosum, Parabacteroides* sp. CAG:2 and *Parabacteroides distasonis*. In some embodiments of the compositions provided herein, the purified bacterial mixture comprises, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum,* and *Parabacteroides distasonis*. In some embodiments of the compositions provided herein, the purified bacterial mixture comprises at least 3, at least 4, at least 5, at least 6, at least 7, at least 8, at least 9, at least 10, or at least 11 bacterial strains. In one aspect, the disclosure provides compositions comprising a purified bacterial mixture comprising two or more bacterial strains of species selected from the group consisting of *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum,* and *Parabacteroides* sp. CAG:2. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains. In one aspect, the disclosure provides compositions comprising a purified bacterial mixture comprising two or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii,* and *Bacteroides* sp. In some embodiments of the compositions provided herein, the purified bacterial mixture comprises at least 2, at least 3, at least 4, at least 5, at least 6, at least 7, at least 8, at least 9, or at least 10 bacterial strains. In one aspect, the disclosure provides compositions comprising a purified bacterial mixture comprising two or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii,* and *Bacteroides* sp. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains of species selected from the group consisting of *Phascolarctobacterium faecium, Fusobacterium ulcerans, Subdoligranulum* sp., and *Eubacterum limosum*. In some embodiments of the compositions provided herein, the purified bacterial mixture comprises at least 2, at least 3, or at least 4 bacterial strains. In one aspect, the disclosure provides compositions comprising a purified bacterial mixture comprising two or more bacterial strains of species selected from the group consisting of *Phascolarctobacterium faecium, Fusobacterium ulcerans, Subdoligranulum* sp., and *Eubacterum limosum*. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains of species selected from the group consisting of *Bacteroides dorei, Bacteroides uniformis, Paraprevotella xylaniphila, Parabacteroides johnsonii, Alistipes* sp., *Parabacteroides gordonii,* and *Parabacteroides distasonis*. In some embodiments of the compositions provided herein, the purified bacterial mixture comprises at least 2, at least 3, at least 4, at least 5, at least 6, or at least 7 bacterial strains. In one aspect, the disclosure provides compositions comprising a purified bacterial mixture comprising two or more bacterial strains of species selected from the group consisting of *Bacteroides dorei, Bacteroides uniformis, Paraprevotella xylaniphila, Parabacteroides johnsonii, Alistipes* sp., *Parabacteroides gordonii,* and *Parabacteroides distasonis*. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the one or more bacterial strain comprises 16S rDNA sequences of at least 96%, at least 97%, at least 98%, or at least 99% sequence identity with SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains. In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains. In one aspect, the disclosure provides compositions comprising a purified bacterial mixture comprising two or more bacterial strains comprising 16S rDNA sequences of at least 95% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 3, at least 4, at least 5, at least 6, at least 7, at least 8, at least 9, at least 10, or at least 11 bacterial strains. In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture comprising:
a bacterial strain comprising a 16S rDNA sequence of at least 97% homology to SEQ ID NO:1,
a bacterial strain comprising a 16S rDNA sequence of at least 97% homology to SEQ ID NO:2,
a bacterial strain comprising a 16S rDNA sequence of at least 97% homology to SEQ ID NO:3,
a bacterial strain comprising a 16S rDNA sequence of at least 97% homology to SEQ ID NO:4,
a bacterial strain comprising a 16S rDNA sequence of at least 97% homology to SEQ ID NO:5,
a bacterial strain comprising a 16S rDNA sequence of at least 97% homology to SEQ ID NO:6,
a bacterial strain comprising a 16S rDNA sequence of at least 97% homology to SEQ ID NO:7,
a bacterial strain comprising a 16S rDNA sequence of at least 97% homology to SEQ ID NO:8, a bacterial strain comprising a 16S rDNA sequence of at least 97% homology to SEQ ID NO:9,
a bacterial strain comprising a 16S rDNA sequence of at least 97% homology to SEQ ID NO:10, and
a bacterial strain comprising a 16S rDNA sequence of at least 97% homology to SEQ ID NO:11.

In one aspect, the disclosure provides compositions comprising a purified bacterial mixture consisting of bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture consisting of:
a bacterial strain comprising a 16S rDNA sequence of at least 97% homology to SEQ ID NO:1,
a bacterial strain comprising a 16S rDNA sequence of at least 97% homology to SEQ ID NO:2,
a bacterial strain comprising a 16S rDNA sequence of at least 97% homology to SEQ ID NO:3,
a bacterial strain comprising a 16S rDNA sequence of at least 97% homology to SEQ ID NO:4,
a bacterial strain comprising a 16S rDNA sequence of at least 97% homology to SEQ ID NO:5,
a bacterial strain comprising a 16S rDNA sequence of at least 97% homology to SEQ ID NO:6,
a bacterial strain comprising a 16S rDNA sequence of at least 97% homology to SEQ ID NO:7,
a bacterial strain comprising a 16S rDNA sequence of at least 97% homology to SEQ ID NO:8,
a bacterial strain comprising a 16S rDNA sequence of at least 97% homology to SEQ ID NO:9,
a bacterial strain comprising a 16S rDNA sequence of at least 97% homology to SEQ ID NO:10, and
a bacterial strain comprising a 16S rDNA sequence of at least 97% homology to SEQ ID NO:11.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 3, at least 4, at least 5, at least 6, at least 7, at least 8, at least 9, at least 10, or at least 11 bacterial strains. In one aspect, the disclosure provides compositions comprising a purified bacterial mixture comprising two or more bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture comprising bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture comprising:
a bacterial strain comprising a 16S rDNA sequence of at least 97% sequence identity with SEQ ID NO:1,
a bacterial strain comprising a 16S rDNA sequence of at least 97% sequence identity with SEQ ID NO:2,
a bacterial strain comprising a 16S rDNA sequence of at least 97% sequence identity with SEQ ID NO:3,
a bacterial strain comprising a 16S rDNA sequence of at least 97% sequence identity with SEQ ID NO:4,
a bacterial strain comprising a 16S rDNA sequence of at least 97% sequence identity with SEQ ID NO:5,
a bacterial strain comprising a 16S rDNA sequence of at least 97% sequence identity with SEQ ID NO:6,
a bacterial strain comprising a 16S rDNA sequence of at least 97% sequence identity with SEQ ID NO:7,
a bacterial strain comprising a 16S rDNA sequence of at least 97% sequence identity with SEQ ID NO:8,
a bacterial strain comprising a 16S rDNA sequence of at least 97% sequence identity with SEQ ID NO:9,
a bacterial strain comprising a 16S rDNA sequence of at least 97% sequence identity with SEQ ID NO:10, and
a bacterial strain comprising a 16S rDNA sequence of at least 97% sequence identity with SEQ ID NO:11.

In one aspect, the disclosure provides compositions comprising a purified bacterial mixture comprising:
a bacterial strain comprising a 16S rDNA sequence of at least 99% sequence identity with SEQ ID NO:1,
a bacterial strain comprising a 16S rDNA sequence of at least 99% sequence identity with SEQ ID NO:2,
a bacterial strain comprising a 16S rDNA sequence of at least 99% sequence identity with SEQ ID NO:3,
a bacterial strain comprising a 16S rDNA sequence of at least 99% sequence identity with SEQ ID NO:4,
a bacterial strain comprising a 16S rDNA sequence of at least 99% sequence identity with SEQ ID NO:5,
a bacterial strain comprising a 16S rDNA sequence of at least 99% sequence identity with SEQ ID NO:6,
a bacterial strain comprising a 16S rDNA sequence of at least 99% sequence identity with SEQ ID NO:7,
a bacterial strain comprising a 16S rDNA sequence of at least 99% sequence identity with SEQ ID NO:8,
a bacterial strain comprising a 16S rDNA sequence of at least 99% sequence identity with SEQ ID NO:9,
a bacterial strain comprising a 16S rDNA sequence of at least 99% sequence identity with SEQ ID NO:10, and
a bacterial strain comprising a 16S rDNA sequence of at least 99% sequence identity with SEQ ID NO:11.

In one aspect, the disclosure provides compositions comprising a purified bacterial mixture comprising bacterial strains comprising 16S rDNA sequences with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11. In one aspect, the disclosure provides compositions comprising a purified bacterial mixture consisting of bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11. In one aspect, the disclosure provides compositions comprising a purified bacterial mixture consisting of bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture consisting of:
a bacterial strain comprising a 16S rDNA sequence of at least 97% sequence identity with SEQ ID NO:1,
a bacterial strain comprising a 16S rDNA sequence of at least 97% sequence identity with SEQ ID NO:2,
a bacterial strain comprising a 16S rDNA sequence of at least 97% sequence identity with SEQ ID NO:3,
a bacterial strain comprising a 16S rDNA sequence of at least 97% sequence identity with SEQ ID NO:4,
a bacterial strain comprising a 16S rDNA sequence of at least 97% sequence identity with SEQ ID NO:5,
a bacterial strain comprising a 16S rDNA sequence of at least 97% sequence identity with SEQ ID NO:6,
a bacterial strain comprising a 16S rDNA sequence of at least 97% sequence identity with SEQ ID NO:7,
a bacterial strain comprising a 16S rDNA sequence of at least 97% sequence identity with SEQ ID NO:8,
a bacterial strain comprising a 16S rDNA sequence of at least 97% sequence identity with SEQ ID NO:9,
a bacterial strain comprising a 16S rDNA sequence of at least 97% sequence identity with SEQ ID NO:10, and
a bacterial strain comprising a 16S rDNA sequence of at least 97% sequence identity with SEQ ID NO:11.

In one aspect, the disclosure provides compositions comprising a purified bacterial mixture consisting of:
a bacterial strain comprising a 16S rDNA sequence of at least 99% sequence identity with SEQ ID NO:1,
a bacterial strain comprising a 16S rDNA sequence of at least 99% sequence identity with SEQ ID NO:2,
a bacterial strain comprising a 16S rDNA sequence of at least 99% sequence identity with SEQ ID NO:3,
a bacterial strain comprising a 16S rDNA sequence of at least 99% sequence identity with SEQ ID NO:4,
a bacterial strain comprising a 16S rDNA sequence of at least 99% sequence identity with SEQ ID NO:5,
a bacterial strain comprising a 16S rDNA sequence of at least 99% sequence identity with SEQ ID NO:6,
a bacterial strain comprising a 16S rDNA sequence of at least 99% sequence identity with SEQ ID NO:7,
a bacterial strain comprising a 16S rDNA sequence of at least 99% sequence identity with SEQ ID NO:8,
a bacterial strain comprising a 16S rDNA sequence of at least 97% sequence identity with SEQ ID NO:9,
a bacterial strain comprising a 16S rDNA sequence of at least 99% sequence identity with SEQ ID NO:10, and
a bacterial strain comprising a 16S rDNA sequence of at least 99% sequence identity with SEQ ID NO:11.

In one aspect, the disclosure provides compositions comprising a purified bacterial mixture consisting of bacterial strains comprising 16S rDNA sequences with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11. In one aspect, the disclosure provides compositions comprising a purified bacterial mixture comprising two or more bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 99% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture comprising bacterial strains comprising 16S rDNA sequences of at least 99% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture comprising:
a bacterial strain comprising a 16S rDNA sequence of at least 97% sequence identity with SEQ ID NO:54,
a bacterial strain comprising a 16S rDNA sequence of at least 97% sequence identity with SEQ ID NO:55,
a bacterial strain comprising a 16S rDNA sequence of at least 97% sequence identity with SEQ ID NO:56,
a bacterial strain comprising a 16S rDNA sequence of at least 97% sequence identity with SEQ ID NO:57,
a bacterial strain comprising a 16S rDNA sequence of at least 97% sequence identity with SEQ ID NO:58,
a bacterial strain comprising a 16S rDNA sequence of at least 97% sequence identity with SEQ ID NO:59,
a bacterial strain comprising a 16S rDNA sequence of at least 97% sequence identity with SEQ ID NO:60,
a bacterial strain comprising a 16S rDNA sequence of at least 97% sequence identity with SEQ ID NO:61,
a bacterial strain comprising a 16S rDNA sequence of at least 97% sequence identity with SEQ ID NO:62,
a bacterial strain comprising a 16S rDNA sequence of at least 97% sequence identity with SEQ ID NO:63, and
a bacterial strain comprising a 16S rDNA sequence of at least 97% sequence identity with SEQ ID NO:64.

In one aspect, the disclosure provides compositions comprising a purified bacterial mixture comprising:
a bacterial strain comprising a 16S rDNA sequence of at least 99% sequence identity with SEQ ID NO:54,
a bacterial strain comprising a 16S rDNA sequence of at least 99% sequence identity with SEQ ID NO:55,
a bacterial strain comprising a 16S rDNA sequence of at least 99% sequence identity with SEQ ID NO:56,
a bacterial strain comprising a 16S rDNA sequence of at least 99% sequence identity with SEQ ID NO:57,
a bacterial strain comprising a 16S rDNA sequence of at least 99% sequence identity with SEQ ID NO:58,
a bacterial strain comprising a 16S rDNA sequence of at least 99% sequence identity with SEQ ID NO:59, a bacterial strain comprising a 16S rDNA sequence of at least 99% sequence identity with SEQ ID NO:60,
a bacterial strain comprising a 16S rDNA sequence of at least 99% sequence identity with SEQ ID NO:61,
a bacterial strain comprising a 16S rDNA sequence of at least 99% sequence identity with SEQ ID NO:62,
a bacterial strain comprising a 16S rDNA sequence of at least 99% sequence identity with SEQ ID NO:63, and
a bacterial strain comprising a 16S rDNA sequence of at least 99% sequence identity with SEQ ID NO:64.

In one aspect, the disclosure provides compositions comprising a purified bacterial mixture comprising bacterial strains comprising 16S rDNA sequences with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In one aspect, the disclosure provides compositions comprising a purified bacterial mixture consisting of bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture consisting of bacterial strains comprising 16S rDNA sequences of at least 99% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture consisting of:
a bacterial strain comprising a 16S rDNA sequence of at least 97% sequence identity with SEQ ID NO:54,
a bacterial strain comprising a 16S rDNA sequence of at least 97% sequence identity with SEQ ID NO:55,
a bacterial strain comprising a 16S rDNA sequence of at least 97% sequence identity with SEQ ID NO:56,
a bacterial strain comprising a 16S rDNA sequence of at least 97% sequence identity with SEQ ID NO:57,
a bacterial strain comprising a 16S rDNA sequence of at least 97% sequence identity with SEQ ID NO:58,
a bacterial strain comprising a 16S rDNA sequence of at least 97% sequence identity with SEQ ID NO:59,
a bacterial strain comprising a 16S rDNA sequence of at least 97% sequence identity with SEQ ID NO:60,
a bacterial strain comprising a 16S rDNA sequence of at least 97% sequence identity with SEQ ID NO:61,
a bacterial strain comprising a 16S rDNA sequence of at least 97% sequence identity with SEQ ID NO:62,
a bacterial strain comprising a 16S rDNA sequence of at least 97% sequence identity with SEQ ID NO:63, and
a bacterial strain comprising a 16S rDNA sequence of at least 97% sequence identity with SEQ ID NO:64.

In one aspect, the disclosure provides compositions comprising a purified bacterial mixture consisting of:
a bacterial strain comprising a 16S rDNA sequence of at least 99% sequence identity with SEQ ID NO:54,
a bacterial strain comprising a 16S rDNA sequence of at least 99% sequence identity with SEQ ID NO:55,
a bacterial strain comprising a 16S rDNA sequence of at least 99% sequence identity with SEQ ID NO:56,
a bacterial strain comprising a 16S rDNA sequence of at least 99% sequence identity with SEQ ID NO:57,
a bacterial strain comprising a 16S rDNA sequence of at least 99% sequence identity with SEQ ID NO:58,
a bacterial strain comprising a 16S rDNA sequence of at least 99% sequence identity with SEQ ID NO:59,
a bacterial strain comprising a 16S rDNA sequence of at least 99% sequence identity with SEQ ID NO:60,
a bacterial strain comprising a 16S rDNA sequence of at least 99% sequence identity with SEQ ID NO:61,
a bacterial strain comprising a 16S rDNA sequence of at least 99% sequence identity with SEQ ID NO:62,
a bacterial strain comprising a 16S rDNA sequence of at least 99% sequence identity with SEQ ID NO:63, and
a bacterial strain comprising a 16S rDNA sequence of at least 99% sequence identity with SEQ ID NO:64.

In one aspect, the disclosure provides compositions comprising a purified bacterial mixture consisting of bacterial strains comprising 16S rDNA sequences with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture comprising one or more bacterial strains comprising 16S rDNA sequences of at least 95% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 95% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains. In one aspect, the disclosure provides compositions comprising a purified bacterial mixture comprising two or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains. In one aspect, the disclosure provides compositions comprising one or more bacterial strains comprising 16S rDNA sequences of at least 95% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising one or more bacterial strains comprising 16S rDNA sequences of at least 95% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains. In one aspect, the disclosure provides compositions comprising two or more bacterial strains comprising 16S rDNA sequences of at least 95% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 95% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, or at least 10 bacterial strains. In one aspect, the disclosure provides compositions comprising two or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains. In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:5, or SEQ ID NO:10.

In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:5, or SEQ ID NO:10. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, or at least 4 bacterial strains. In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:5, or SEQ ID NO:10. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 95% sequence identity with SEQ ID NO:1, SEQ ID NO:2, SEQ ID NO:5, or SEQ ID NO:10. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, or at least 4 bacterial strains. In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:5, or SEQ ID NO:10. In some embodiments of the compositions provided herein, the purified bacterial mixture comprises at least 3, or at least 4 bacterial strains. In one aspect, the disclosure provides compositions comprising a purified bacterial mixture comprising two or more bacterial strains comprising 16S rDNA sequences of at least 97% sequence identity with the SEQ ID NO:1, SEQ ID NO:2, SEQ ID NO:5, or SEQ ID NO:10. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains comprising 16S rDNA sequences of at least 95% homology to SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, or at least 7 bacterial strains. In one aspect, the disclosure provides compositions comprising a purified bacterial mixture comprising one or more bacterial strains comprising 16S rDNA sequences of at least 95% sequence identity with SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 95% homology to SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, or at least 7 bacterial strains. In one aspect, the disclosure provides compositions comprising a purified bacterial mixture comprising two or more bacterial strains comprising 16S rDNA sequences of at least 95% sequence identity with SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% homology to SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 3, at least 4, at least 5, at least 6, or at least 7 bacterial strains. In one aspect, the disclosure provides compositions comprising a purified bacterial mixture comprising two or more bacterial strains comprising 16S rDNA sequences of at least 97% sequence identity with SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains. In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains. In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the one or more bacterial strain comprises 16S rDNA sequences of at least 96%, at least 97%, at least 98%, or at least 99% sequence identify with the SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains. In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains. In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains. In one aspect, the disclosure provides compositions comprising a purified bacterial mixture comprising two or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, or at least 10 bacterial strains. In one aspect, the disclosure provides compositions comprising a purified bacterial mixture comprising two or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:31 or SEQ ID NO:36. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:31 or SEQ ID NO:36. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, or at least 4 bacterial strains. In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:31 or SEQ ID NO:36. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:31 or SEQ ID NO:36. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, or at least 4 bacterial strains. In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:31 or SEQ ID NO:36. In some embodiments of the compositions provided herein, the purified bacterial mixture comprises at least 3, or at least 4 bacterial strains. In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:31 or SEQ ID NO:36. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains comprising 16S rDNA sequences of at least 95% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, or at least 7 bacterial strains. In one aspect, the disclosure provides compositions comprising a purified bacterial mixture comprising one or more bacterial strains comprising 16S rDNA sequences of at least 95% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 95% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, or at least 7 bacterial strains. In one aspect, the disclosure provides compositions comprising a purified bacterial mixture comprising two or more bacterial strains comprising 16S rDNA sequences of at least 95% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains. In some embodiments of the compositions provided herein, at least 50% of the bacterial strains belong to the order of Bacteriodales. In some embodiments of the compositions provided herein, one or more of the bacterial strains belong to the order of Bacteriodales and one or more of the bacterial strains belong to the order of Clostridiales. In some embodiments of the compositions provided herein, at least 25% of the bacterial strains belong to the family of Bacteroidaceae. In some embodiments of the compositions provided herein, one or more of the bacterial strains belongs to the genus *Bacteroides*. In some embodiments of the compositions provided herein, the composition does not include bacterial strains that belong to the order of Bacteriodales. In some embodiments of the compositions provided herein, one or more of the bacterial strains is a spore-former. In some embodiments of the compositions provided herein, one or more of the bacterial strains is in spore form. In some embodiments of the compositions provided herein, one or more of the bacterial strains is a non-spore former. In some embodiments of the compositions provided herein, the composition comprises only obligate anaerobic bacterial strains. In some embodiments of the compositions provided herein, one or more of the bacterial strains does not have an antibiotic resistance gene. In some embodiments of the compositions provided herein, the antibiotic resistance gene renders the bacterial strain resistant to vancomycin. In some embodiments of the compositions provided herein, the bacterial strains are human-derived bacteria. In some embodiments of the compositions provided herein, the bacterial strains are derived from more than one human donor. In some embodiments of the compositions provided herein, the composition induces proliferation and/or accumulation of CD8+T-cells.

In some embodiments of the compositions provided herein, the composition is a pharmaceutical composition. In some embodiments of the pharmaceutical compositions provided herein, the pharmaceutical composition comprises a pharmaceutically acceptable excipient. In some embodiments of the pharmaceutical compositions provided herein, the pharmaceutical composition is formulated for oral administration. In some embodiments of the pharmaceutical compositions provided herein, the pharmaceutical composition is formulated for rectal administration. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon. In some embodiments of the pharmaceutical compositions provided herein, one or more of the bacterial strains is lyophilized. In some embodiments of the pharmaceutical compositions provided herein, the pharmaceutical composition is in the form of a capsule. In some embodiments of the pharmaceutical compositions provided herein, the pharmaceutical composition further comprises a pH sensitive composition comprising one or more enteric polymers. In one aspect, the disclosure provides a food product comprising any of the compositions provided herein and a nutrient.

In some embodiments of the compositions provided herein, the composition further comprises one or more anticancer agents. In some embodiments of the compositions provided herein, the anticancer agent is a chemotherapy agent. In some embodiments of the compositions provided herein, the anticancer agent is cancer immunotherapy agent. In some embodiments of the compositions provided herein, the cancer immunotherapy agent is an immune checkpoint inhibitor. In some embodiments of the compositions provided herein, the immune checkpoint inhibitor is a PD-1 inhibitor, PD-L-1 inhibitor, or CTLA-4 inhibitor. In some embodiments of the compositions provided herein, the immune checkpoint inhibitor is a PD-1 inhibitor. In some embodiments of the compositions provided herein, the immune checkpoint inhibitor is a CTLA-4 inhibitor. In some embodiments of the compositions provided herein, the composition further comprises one or more cytokines. In some embodiments of the compositions provided herein, the cytokine is IL-2, IL-15, or IL-21. In some embodiments of the compositions provided herein, the composition further comprises one or more costimulatory agents. In some embodiments of the compositions provided herein, the costimulatory agent is a CD-28, OX-40, 4-1BB, or CD40 antibody. In some embodiments of the compositions provided herein, the composition further comprises one or more vaccines. In some embodiments of the compositions provided herein, the vaccine is a dendritic cell vaccine. In some embodiments of the compositions provided herein, the composition is combined with adoptive cell transfer therapy. In some embodiments of the compositions provided herein, the adoptive cell transfer therapy is the use of engineered T-cell receptors or chimeric antigen receptors.

In one aspect, the disclosure provides a vaccine comprising any of the compositions provided herein and an antigen. In some embodiments of the vaccines provided herein, the antigen is an HIV antigen. In some embodiments of the vaccines provided herein, the antigen is a hepatitis antigen. In some embodiments of the compositions provided herein, the composition further comprises one or more anti-inflammatory agents. In some embodiments of the compositions provided herein, the anti-inflammatory agent is an NSAID.

In some embodiments of the compositions provided herein, administration of the composition to a subject results in the induction of proliferation and/or accumulation of CD8+ T-cells in the intestine of the subject. In some embodiments of the compositions provided herein, administration of the composition to a subject results in an increase in IFNγ production in the intestine of a subject. In some embodiments of the compositions provided herein, administration of the composition to a subject results in the presence of one or more bacterial strains of the administered composition in the intestine of the subject. In some embodiments of the compositions provided herein, the one or more bacterial strains of the administered composition was not previously present in the intestine of the subject. In some embodiments of the compositions provided herein, administration of the composition to a subject results in the engraftment of one or more bacterial strains of the administered composition in the intestine of the subject. In some embodiments of the compositions provided herein, the one or more bacterial strains of the administered composition was not previously engrafted in the intestine of the subject. In some embodiments of the compositions provided herein, administration of the composition to a subject results in an increase in the number of the bacterial strains of the administered composition in the intestine of the subject. In some embodiments of the compositions provided herein, administration of the composition to a subject results in an increase in the number of the bacterial strains of the administered composition engrafted in the intestine of the subject. In some embodiments of the compositions provided herein, administration of the composition to a subject results in an increase in the amount of bacteria of the bacterial strains of the administered composition in the intestine of the subject. In some embodiments of the compositions provided herein, administration of the composition to a subject results in an increase in the amount of bacteria of the bacterial strains of the administered composition engrafted in the intestine of the subject.

In one aspect, the disclosure provides a method of treating a disease in a subject comprising administering any of the compositions provided herein to the subject in an effective amount to treat the disease. In some embodiments of the methods provided herein, the administration of the composition to the subject results in the induction of proliferation and/or accumulation of CD8+ T-cells in the intestine of the subject. In some embodiments of the methods provided herein, the proliferation and/or accumulation of CD8+ T-cells in the intestine of the subject is increased by at least 10%, at least 20%, at least 30%, at least 40%, at least 50%, at least 100%, or at least 200% when compared to the proliferation and/or accumulation of CD8+ T-cells in the intestine of the subject before the administration of the composition. In some embodiments of the methods provided herein, the administration of the composition to the subject results in an increase of IFNγ production in the intestine of the subject when compared to the IFNγ production in the intestine of the subject before the administration of the composition. In some embodiments of the methods provided herein, the administration of the composition to the subject results in an increase of IFNγ production in the intestine of the subject by at least 10%, at least 20%, at least 30%, at least 40%, at least 50%, at least 100%, or at least 200% when compared to the IFNγ production in the intestine of the subject before the administration of the composition.

In some embodiments of the methods provided herein, the subject has cancer. In some embodiments of the methods provided herein, the cancer is carcinoma, glioma, mesothelioma, melanoma, lymphoma, leukemia, adenocarcinoma, breast cancer, ovarian cancer, cervical cancer, glioblastoma, multiple myeloma, prostate cancer, Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease, AIDS-associated primary effusion lymphoma, neuroectodermal tumors, or rhabdomyosarcoma. In some embodiments of the methods provided herein, the cancer is prostate cancer, bladder cancer, non-small cell lung cancer, urothelial carcinoma, melanoma, or renal cell carcinoma. In some embodiments of the methods provided herein, the subject is undergoing radiation treatment.

In some embodiments of the methods provided herein, the method further includes administering one or more anticancer agents. In some embodiments of the methods provided herein, the anticancer agent is a chemotherapy agent. In some embodiments of the methods provided herein, the anticancer agent is a cancer immunotherapy agent. In some embodiments of the methods provided herein, the cancer immunotherapy agent is an immune checkpoint inhibitor. In some embodiments of the methods provided herein, the immune checkpoint inhibitor is a PD-1 inhibitor, PD-L-1 inhibitor, or CTLA-4 inhibitor. In some embodiments of the methods provided herein, the immune checkpoint inhibitor is a PD-1 inhibitor. In some embodiments of the methods provided herein, the immune checkpoint inhibitor is a CTLA-4 inhibitor. In some embodiments of the methods provided herein, the method further includes administering one or more cytokines. In some embodiments of the methods provided herein the cytokine is IL-2, IL-15, or IL-21.

In some embodiments of the methods provided herein, the method further includes administering one or more costimulatory agents. In some embodiments of the methods provided herein the costimulatory agent is a CD-28, OX-40, 4-1BB, or CD40 antibody. In some embodiments of the methods provided herein, the method further includes administering one or more vaccines. In some embodiments of the methods provided herein, the vaccine is a dendritic cell vaccine. In some embodiments of the methods provided herein, the method further includes administering adoptive cell transfer therapy. In some embodiments of the methods provided herein, the adoptive cell transfer therapy is the use of engineered T-cell receptors or chimeric antigen receptors. In some embodiments of the methods provided herein, the subject has an infectious disease. In some embodiments of the methods provided herein, the infectious disease is a bacterial infection, a viral infection, a parasitic infection, or a fungal infection. In some embodiments of the methods provided herein, the infectious disease is a viral infection. In some embodiments of the methods provided herein, the viral infection is HIV. In some embodiments of the methods provided herein, the infection is an infection by a hepatitis virus. In some embodiments of the methods provided herein, the subject has an autoimmune disease or an allergic disease. In some embodiments of the methods provided herein, the composition further includes one or more anti-inflammatory agents. In some embodiments of the methods provided herein, the anti-inflammatory is an NSAID. In some embodiments of the methods provided herein, the composition may be administered as one or more dose.

In one aspect, the disclosure provides a method that includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject. In some embodiments of the methods provided herein, the subject is undergoing, or will be undergoing, cancer treatment. In one aspect, the disclosure provides a method for determining if a subject is expected to respond positively to cancer treatment, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the subject is not expected to respond positively to cancer treatment. In some embodiments of the methods provided herein, the cancer treatment is cancer immunotherapy treatment. In one aspect, the disclosure provides a method for reducing the risk of a viral infection in a subject, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject, thereby reducing the risk of a viral infection in the subject.

In some embodiments of the methods provided herein, determining the presence of one or more of the bacterial species is done by sequencing fecal matter of the subject. In some embodiments of the methods provided herein, determining the presence of one or more of the bacterial species is done by sequencing the 16S rDNA sequences of fecal matter of the subject. In one aspect, the disclosure provides compositions and methods to induce activation of CD8+ IFNγ-producing T-cells in the intestinal tract. In one aspect, the disclosure provides a composition comprising a purified bacterial mixture comprising one or more bacterial strains comprising 16S rDNA sequences of at least 95% homology to the sequences of the following NCBI accession numbers: LN998073, KR822463, CP011531, NR_112945, NZ-ACWW00000000, AB331897, AB261128, NZ-CAEG00000000, AB470343, AB595134, HE974920, NR_112933, AB490801, NZ-ACWB00000000, AY608696, CR626927, AB247141, NR_112935, AB249652, NR_113076 and AF139525. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In some embodiments of the compositions provided herein, the one or more bacterial strains comprises 16S rDNA sequences with at least 96%, at least 97%, at least 98%, or at least 99% homology with sequences provided herein.

In one aspect, the disclosure provides a composition that induces or activates CD8+ IFNγ-producing T-cells, the composition comprising (i) one or more purified bacterial strains collected from human stool which possesses resistance to ampicillin, or (ii) a culture supernatant of (i). In some embodiments of the compositions provided herein, the composition comprises (a) a purified bacterial mixture comprising one or more bacterial strains of species selected from the group consisting of

*Phascolarctobacterium faecium*; LN998073,
*Fusobacterium ulcerans*; KR822463,
*Bacteroides dorei*; CP011531,
*Bacteroides uniformis*; NR_112945,
*Subdoligranulum* sp. 4_3_54A2FAA; NZ-ACWW00000000,
*Paraprevotella xylaniphila*; AB331897,
*Parabacteroides johnsonii*; AB261128,
*Alistipes* sp. JC136; NZ-CAEG00000000,
*Parabacteroides gordonii*; AB470343,
*Eubacterium limosum*; AB595134,
*Parabacteroides distasonis*; HE974920,
*Bacteroides cellulosilyticus*; NR_112933,
*Bacteroides clarus*; AB490801,
*Anaerostipes* sp. 3_2_56FAA; NZ-ACWB00000000,
*Bacteroides salyersiae*; AY608696,
*Bacteroides fragilis*; CR626927,
*Bacteroides uniformis*; AB247141,
*Bacteroides eggerthii*; NR_112935,
*Clostridium* sp. TM-40; AB249652,
*Parabacteroides goldsteinii*; NR_113076, and
*Bacteroides* sp. AR29; AF139525, or (b) one or more bacterial strains comprising a 16S rRNA sequence having at least 97% homology to a 16S rRNA sequence of a species selected from the group consisting of
*Phascolarctobacterium faecium*; LN998073,
*Fusobacterium ulcerans*; KR822463,
*Bacteroides dorei*; CP011531,
*Bacteroides uniformis*; NR_112945,
*Subdoligranulum* sp. 4_3_54A2FAA; NZ-ACWW00000000,
*Paraprevotella xylaniphila*; AB331897,
*Parabacteroides johnsonii*; AB261128,
*Alistipes* sp. JC136; NZ-CAEG00000000,
*Parabacteroides gordonii*; AB470343,
*Eubacterium limosum*; AB595134,
*Parabacteroides distasonis*; HE974920,
*Bacteroides cellulosilyticus*; NR_112933,
*Bacteroides clarus*; AB490801,
*Anaerostipes* sp. 3_2_56FAA; NZ-ACWB00000000,
*Bacteroides salyersiae*; AY608696,
*Bacteroides fragilis*; CR626927,
*Bacteroides uniformis*; AB247141,
*Bacteroides eggerthii*; NR_112935,
*Clostridium* sp. TM-40; AB249652,
*Parabacteroides goldsteinii*; NR_113076, and
*Bacteroides* sp. AR29; AF139525

In some embodiments of the compositions provided herein, the composition comprises a purified bacterial mixture comprising (a) one or more bacterial strains of species selected from the group consisting of
*Phascolarctobacterium faecium*; LN998073,
*Fusobacterium ulcerans*; KR822463,
*Bacteroides dorei*; CP011531,
*Bacteroides uniformis*; NR_112945,
*Subdoligranulum* sp. 4_3_54A2FAA; NZ-ACWW00000000,
*Paraprevotella xylaniphila*; AB331897,
*Parabacteroides johnsonii*; AB261128,
*Alistipes* sp. JC136; NZ-CAEG00000000,
*Parabacteroides gordonii*; AB470343,
*Eubacterium limosum*; AB595134, and
*Parabacteroides distasonis*; HE974920; or (b) one or more bacterial strains comprising a 16S rRNA sequence of a species belonging to the group consisting of *Phascolarctobacterium faecium*; LN998073,
*Fusobacterium ulcerans*; KR822463,
*Bacteroides dorei*; CP011531,
*Bacteroides uniformis*; NR_112945,
*Subdoligranulum* sp. 4_3_54A2FAA; NZ-ACWW00000000,
*Paraprevotella xylaniphila*; AB331897,
*Parabacteroides johnsonii*; AB261128,
*Alistipes* sp. JC136; NZ-CAEG00000000,

*Parabacteroides gordonii*; AB470343,
*Eubacterium limosum*; AB595134, and
*Parabacteroides distasonis*; HE974920.

In some embodiments of the compositions provided herein, the CD8+ IFNγ-producing T-cells express CD103 or Granzyme B.

In some embodiments of the compositions provided herein, the composition activates the immune system. In one aspect, the disclosure provides a method for activating the immune system, the method comprising administration of one or more of the compositions provided herein. In one aspect, the disclosure provides a method for activating CD8+ IFNγ-producing T-cells, the method comprising administration of one or more of the compositions provided herein to a subject. In one aspect, the disclosure provides a method for inducing the proliferation and/or accumulation of CD8+ T cells in the intestine, comprising administering to a subject any one or more of the compositions provided herein, wherein the administering results in the induction of proliferation and/or accumulation of CD8+ T cells in the intestine of the subject. In one aspect, the disclosure provides a method for assisting in treatment, and/or preventing cancer or viral infection, comprising administering to a subject any one or more of the compositions provided herein, wherein the administering prevents, treats, assists in treatment, and/or prevents cancer or viral infection. In one aspect, the disclosure provides vaccine compositions which induce immune response against bacterial strains of any one of the compositions disclosed herein. In one aspect, the disclosure provides a vaccine composition containing antigen derived from constituents and/or metabolites of bacterial species of any one of the compositions provided herein.

In one aspect, the disclosure provides a method for inducing an immune response in a subject, comprising administering to the subject any of the vaccines provided herein, wherein the administering results in the induction of immune response of the subject. In one aspect, the disclosure provides immune suppressive compositions. In one aspect, the disclosure provides a composition comprising a chemical substance that possesses antibacterial activity towards bacterial species of any one of the compositions provided herein, or a chemical substance which binds a physiologically active substance secreted from bacterial species of any one of the compositions provided herein. In some embodiments of the compositions provided herein, administration of the composition to a subject results in suppression of activity of CD8+ and IFNγ-producing T-cells in the subject. In one aspect, the disclosure provides a method for suppressing CD8+ and IFNγ-producing T-cells in the subject, the method comprising administration of one or more of the compositions provided herein to the subject. In one aspect, the disclosure provides a method for prevention, treatment or improvement in a disease originated by over-activation of CD8+ and IFNγ-producing T-cells of the subject the method comprising administering to the subject any one or more of the compositions provided herein to the subject. In one aspect, the disclosure provides substances derived from the bacterial strains disclosed herein. In one aspect, the disclosure provides a physiologically active substance derived from a bacterial species of any one of the compositions provided herein. In one aspect, the disclosure provides a bacterial specific antigen of any one of the bacterial species of any one of the compositions provided herein.

In one aspect, the disclosure provides an antibody that specifically binds a bacterial species of any one of the compositions provided herein. In one aspect, the disclosure provides a bacterial-specific nucleotide sequence contained in any one of the bacterial species of the compositions provided herein. In one aspect, the disclosure provides animal models and test kits. In one aspect, the disclosure provides an animal model comprising a non-human mammal, wherein the intestinal tract of the non-human mammal has been inoculated with the bacterial species of any one of the compositions provided herein. In some embodiments of the animal model provided herein, the non-human mammal has a disease originated by irregularity of CD8+ IFNγ-producing T-cells. In one aspect, the disclosure provides a kit for evaluating the activation of CD8+ IFNγ-producing T cells, the kit comprising: intestinal epithelial cells, peripheral blood mononuclear cells, and a bacterial species of any one of the compositions provided herein. In one aspect, the disclosure provides methods of detection of CD8+ IFNγ-producing T cells in the human intestinal tract. In one aspect, the disclosure provides kits for evaluating activation of CD8+ IFNγ-producing T cells. In some embodiments, the kits comprise intestinal epithelial cells, peripheral mononuclear cells, and the bacterial species of any of the compositions described herein.

In one aspect, the disclosure provides a method for screening bacteria or a physiologically active substance derived from human intestinal bacteria, wherein the substance induces activation of CD8+ IFNγ-producing T cells in the intestinal tract, comprising (i) allowing a non-human germ-free animal to ingest a physiologically active substance derived from human intestinal bacteria or bacteria, (ii) detecting the number, or activity of, CD8+ IFNγ-producing T cells in the intestinal tract of the non-human aseptic animal, wherein if activation of CD8+ IFNγ-producing T cells is detected, the physiologically active substance is identified as a substance that can activate CD8+ IFNγ-producing T cells. In one aspect, the disclosure provides a method for screening bacteria or a physiologically active substance derived from human intestinal bacteria a, wherein the substance induces proliferation or activation of CD8+ IFNγ-producing T cells in intestinal tract, comprising (i) adding a physiologically active substance derived from human intestinal bacteria or bacteria to the intestinal epithelial cells in a system comprising intestinal epithelial cells and peripheral blood mononuclear cells; (ii) detecting the number or activity of CD8+ IFNγ-producing T cells in said system, wherein if the activation of CD8+ IFNγ-producing T cells is detected, the physiologically active substance is identified as a substance that can activate CD8+ IFN γ-producing T cells.

In one aspect, the disclosure provides a method for screening for a substance that induces activation of CD8+ IFNγ-producing T cells in intestinal tract, comprising (i) adding a physiologically active substance derived from bacteria or bacteria contained in a composition provided herein to a system containing intestinal epithelial cells and peripheral blood mononuclear cells, (ii) adding a test substance, (iii) detecting the number or activity of CD8+ IFNγ-producing T cells in said system, wherein if the number or activity of CD8+ IFNγ-producing T cells detected in the is increased, the test substance is identified as a substance that induces activation of CD8+ IFNγ-producing T cells. In one aspect, the disclosure provides a method for screening a substance that induces activation of CD8+ IFNγ-producing T cells in intestinal tract, comprising (i) the method for screening a non-human animal provided herein, (ii) detecting the number or activity of CD8+ IFNγ-producing T cells in the intestinal tract of the non-human animal, wherein if the number or activity of CD8+ IFNγ-producing T cells detected in the above step is increased, the test substance is identified as a substance that induces activation of CD8+ IFNγ-producing T cells. In one aspect, the disclosure provides a composition for stimulating immunity, the composition comprising, as an active ingredient, a human intestinal bacterium or a physiologically active substance derived from a bacterium obtained by the screening methods provided herein. In some embodiments of the compositions provided herein, the composition induces the activation of CD8+ IFNγ-producing T cells.

In one aspect, the disclosure provides a vaccine composition comprising, as an active ingredient, human intestinal bacteria obtained by any of the screening methods provided herein, or an antigen specific to said bacterium. In one aspect, the disclosure provides a method for screening a substance having an activity of inducing or exacerbating a disease caused by CD8+ IFNγ-producing T cells, comprising (i) allowing a test substance to be ingested by a non-human animal provided herein, (ii) detecting the degree of a disease-associated damage caused by CD8+ IFNγ-producing T cells in said non-human animal, wherein the test substance is identified as a substance that induces a disease caused by CD8+ IFNγ-producing T cells when the extent of the lesion detected in the above step is increased as compared to when no compound or placebo was added. In one aspect, the disclosure provides a composition for inducing or exacerbating a disease caused by CD8+ IFNγ-producing T cells, wherein the composition comprises, as an active ingredient, the substance obtained by any one of the screening methods provided herein. In one aspect, the disclosure provides a composition comprising a processed human fecal sample, wherein the processed human fecal sample is obtained by contacting a human fecal sample with ampicillin, and wherein the processed human fecal sample induces the proliferation and/or accumulation of CD8+ T-cells. In some embodiments, the disclosure provides a method of treatment of a disease in a subject, the method comprising administering to the subject any one of the compositions provided herein in an effective amount to treat the disease in the subject. In some embodiments of the methods provided herein, the disease is cancer or an infection (e.g., a viral infection).

In one aspect, the disclosure provides a method comprising inoculating a human fecal sample in germ free mice, and determining if the human fecal sample induces the proliferation and/or accumulation of CD8+ T-cells. In one aspect, the disclosure provides a method for determining if a human fecal sample induces proliferation and/or accumulation of CD8+ T cells, comprising inoculating germ-free mice with a human fecal sample, and determining if the human fecal sample induces the proliferation and/or accumulation of CD8+ T-cells. In one aspect, the disclosure provides a method for identifying a human fecal donor, comprising inoculating germ-free mice with a human fecal sample, and determining if the human fecal sample induces the proliferation and/or accumulation of CD8+ T-cells, wherein if the fecal sample induces the proliferation and/or accumulation of CD8+ T-cells, the human subject is identified as a human fecal donor. In one aspect, the disclosure provides a method for analyzing expression levels of a marker in lymphocytes in a subject, comprising analyzing the expression levels of the marker, wherein the marker is induced by administering to the subject any of the compositions described herein, wherein the marker is CD44, gp70 MC38 peptide (KSPWFTTL; (SEQ ID NO: 53))-specific TCRβ, tumor antigen derived ligand-specific TCRβ, CD8, IFNγ, and/or GzmB.

In one aspect, the disclosure provides kits for analysis of expression levels of a marker in lymphocytes in a subject after induction, wherein the marker is induced by administering to the subject any of the compositions described herein, wherein the marker is CD44, gp70 MC38 peptide (KSPWFTTL; (SEQ ID NO: 53))-specific TCRβ, tumor antigen derived ligand-specific TCRβ, CD8, IFNγ, and/or GzmB. In one aspect, the disclosure provides methods for screening a bacteria or a physiologically active substance derived from human intestinal bacteria, the method comprising, allowing a tumor-bearing non-human animal to ingest a physiologically active substance derived from human intestinal bacteria or bacteria, detecting the expression of a marker, in lymphocytes isolated from the tumor-bearing non-human animal, wherein if an increase in expression levels of the marker is detected, the physiologically active substance is identified as an immunostimulating agent for the tumor; and wherein the marker is CD44, gp70 MC38 peptide (KSPWFTTL; (SEQ ID NO: 53))-specific TCRβ, tumor antigen derived ligand-specific TCRβ, CD8, IFN and/or GzmB.

In one aspect, the disclosure provides a companion diagnostic method for tumor therapy with an immune checkpoint inhibitor, the method comprising analyzing expression levels of a marker in lymphocytes before and after induction by administering to the subject any of the compositions described herein with or without co-administration of the immune checkpoint inhibitor, wherein if the expression levels of the marker in the lymphocytes of the subject are increased by at least 10%, at least 20%, at least 30%, at least 40%, at least 50%, at least 100%, or at least 200% as compared to the expression levels in the lymphocytes of the subject before the administration of the composition, co-administration of the inhibitor and any of the compositions described herein to the subject, the therapy is continued, wherein if the expression levels in the lymphocytes of the subject are not increased as compared to the expression levels in the lymphocytes of the subject, co-administration of the inhibitor and any of the compositions described herein is discontinued or reanalyzed after repeating the administration of any of the compositions described herein to the subject. In some embodiments, the methods further comprise analyzing expression levels of tumor antigen derived ligand-specific TCRβs in lymphocytes with specific antibodies that bind to the tumor antigen derived ligand-specific TCRβs or MHC multimers that bind to the tumor antigen derived ligand-specific TCRβs. In some embodiments, the methods are use in a tumor therapy with an immune checkpoint inhibitor, wherein the immune checkpoint inhibitor is a PD-1 inhibitor, PD-L1 inhibitor, or CTLA-4 inhibitor. In some embodiments, the methods further comprise assessing PD-1 expression in T-cells in the subject. In some embodiments, the methods further comprise assessing PD-L1 expression in cancer cells in the subject. In some embodiments, the methods further comprise assessing CTLA-4 expression in T-cells in the subject.

In one aspect, the disclosure provides kits for carrying out companion diagnostic methods, wherein the kit comprises one or more molecules for monitoring of the expression levels of a marker in lymphocytes, wherein the marker is CD44, gp70 MC38 peptide (KSPWFTTL; (SEQ ID NO: 53))-specific TCRβ, tumor antigen derived ligand-specific TCRβ, CD8, IFNγ, and/or GzmB. In one aspect, the disclosure provides methods for evaluating the immune activation with the degree of IFNγ production in splenocytes, the method comprising administering to a subject any of the compositions described herein. In one aspect, the disclosure provides kits for evaluating the immune activation with the degree of IFNγ production in splenocytes, comprising one or more IFNγ marker molecules and one or more bacterial species of any of the compositions described herein. In one aspect, the disclosure provides methods for identifying an immunostimulating agent for a tumor the method comprising screening a human intestinal bacteria or a physiologically active substance derived from human intestinal bacteria, the method comprising, (i) allowing a tumor-bearing non-human animal to ingest the human intestinal bacteria or the physiologically active substance derived from the human intestinal bacteria, and (ii) detecting IFNγ in splenocytes isolated from the tumor-bearing non-human animal, wherein if induction of IFNγ is detected, the human intestinal bacteria or physiologically active substance is identified as an immunostimulating agent for the tumor.

In one aspect, the disclosure provides a companion diagnostic method for tumor therapy with an immune checkpoint inhibitor, the method comprising evaluating the immune activation with the degree of IFNγ production in splenocytes before and after induction by administering to the subject any of the compositions described herein with or without co-administration of the inhibitor, wherein if the degree of IFNγ production in the splenocytes in the subject is increased by at least 10%, at least 20%, at least 30%, at least 40%, at least 50%, at least 100%, or at least 200% as compared to the degree of IFNγ production in the splenocytes in the subject before the administration of the composition, co-administration of the inhibitor and any of the compositions described herein to the subject is continued, wherein if the degree of IFNγ production in the splenocytes of the subject is not increased, the co-administration of the inhibitor and any of the compositions described herein is discontinued or reanalyzed after repeat administration of any of the compositions described herein to the subject. In some embodiments, the method further comprises analyzing expression levels of tumor antigens of the therapy target in splenocytes with the specific antibodies or the MHC multimers. In some embodiments, the method is for tumor therapy with an immune checkpoint inhibitor, wherein the tumor inhibitor is a PD-1 inhibitor, PD-L1 inhibitor, or CTLA-4 inhibitor. In some embodiments, the method further comprises assessing PD-1 expression in T-cells in the subject. In some embodiments, the method further comprises assessing PD-L1 expression in cancer cells in the subject. In some embodiments, the method further comprises assessing CTLA-4 expression in T-cells in the subject.

In one aspect, the disclosure provides kits for carrying out the companion diagnostic methods described herein, comprising one or more IFNγ marker molecules. In one aspect, the disclosure provides compositions comprising a purified bacterial mixture comprising one or more bacterial strains of species selected from the group consisting of *Phascolarctobacterium faecium*, *Fusobacterium* sp., *Bacteroides dorei*, bacterium IARFR67, *Ruminococcaceae bacterium*, *Paraprevotella xylaniphila*, *Parabacteroides johnsonii*, *Bacteroides* sp., *Parabacteroides gordonii*, *Eubacterium limosum*, *Parabacteroides distasonis*, *Bacteroides cellulosilyticus*, *Bacteroides clarus*, *Anaerostipes caccae*, *Bacteroides salyersiae*, *Bacteroides fragilis*, *Bacteroides uniformis*, *Bacteroides eggerthii*, *Clostridium* sp., *Parabacteroides goldsteinii*, *Bacteroides* sp., *Lachnospiraceae bacterium* HGA0140, *Hungatella hathewayi*, *Clostridium lavalense*, *Ruminococcus* sp., and *Clostridium innocuum*. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains. In one aspect, the disclosure provides compositions comprising a purified bacterial mixture comprising one or more bacterial strains of species selected from the group consisting of *Phascolarctobacterium faecium*, *Fusobacterium* sp., *Bacteroides dorei*, bacterium IARFR67, *Ruminococcaceae bacterium*, *Paraprevotella xylaniphila*, *Parabacteroides johnsonii*, *Bacteroides* sp., *Parabacteroides gordonii*, *Eubacterum limosum*, *Parabacteroides distasonis*, *Bacteroides cellulosilyticus*, *Bacteroides clarus*, *Anaerostipes caccae*, *Bacteroides salyersiae*, *Bacteroides fragilis*, *Bacteroides uniformis*, *Bacteroides eggerthii*, *Clostridium* sp., *Parabacteroides goldsteinii*, and *Bacteroides* sp. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains of species selected from the group consisting of *Phascolarctobacterium faecium*, *Fusobacterium* sp., *Bacteroides dorei*, bacterium IARFR67, *Ruminococcaceae bacterium*, *Paraprevotella xylaniphila*, *Parabacteroides johnsonii*, *Bacteroides* sp., *Parabacteroides gordonii*, *Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains. In one aspect, the disclosure provides compositions comprising a purified bacterial mixture comprising one or more bacterial strains of species selected from the group consisting of *Phascolarctobacterium faecium*, *Fusobacterium* sp., *Ruminococcaceae bacterium*, and *Eubacterum limosum*. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains of species selected from the group consisting of *Bacteroides dorei*, bacterium IARFR67, *Paraprevotella xylaniphila*, *Parabacteroides johnsonii*, *Bacteroides* sp., *Parabacteroides gordonii*, and *Parabacteroides distasonis*. In some embodiments of the compositions provided herein, the purified bacterial mixture comprises at least 2, at least 3, at least 4, at least 5, at least 6, or at least 7 bacterial strains.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. The figures are illustrative only and are not required for enablement of the disclosure. For purposes of clarity, not every component may be labeled in every drawing. In the drawings:

(FIG. 1A) The expression of CD8 and IFNγ by the gated CD3 and TCRβ positive cells of representative mice. (FIG. 1B) Summarized data of the percentages of IFNγ positive cells within CD3, TCRβ and CD8+ cells. Each plot represents individual mice. ** $P<0.01$ (Student's t-test).

(FIG. 2A) The expression of IFNγ and CD103 (upper row) or GzmB (lower row) by the gated CD8 T cells of representative mice. (FIG. 2B) Summarized data of the percentages of each IFNγ positive cell fraction in CD3, TCRβ and CD8+ cells. Each plot represents individual mice. * $P<0.05$ (Student's t-test).

(FIG. 3A) The expression of CD8 and IFNγ by the gated CD3 and TCRβ positive cells of representative mice. (FIG. 3B) Summarized data of percentages of IFNγ positive cells in CD3, TCRβ and CD8+ cells. Each plot represents individual mice. * $P<0.05$, ** $P<0.01$ (one-way ANOVA).

(FIG. 4A) The expression of CD8 and IFNγ by the gated CD3 and TCRβ positive cells of representative mice. (FIG. 4B) Summarized data of the percentages of IFNγ positive cells in CD3, TCRβ and CD8+ cells. Each plot represents individual mice. * $P<0.05$, ** $P<0.01$ (one-way ANOVA).

FIGS. 5A and 5B show data of experiments with stools from healthy volunteers (A~F) which were orally administered into germ free mice individually in sterile vinyl isolators. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry. (FIG. 5A) The expression of CD8 and IFNγ by the gated CD3 and TCRβ positive cells of representative mice. (FIG. 5B) Summarized data of the percentages of IFNγ positive cells in CD3, TCRβ and CD8+ cells. Each plot represents individual mice. ** $P<0.01$ (one-way ANOVA).

(FIG. 6A) The expression of CD8 and IFNγ by the gated CD3 and TCRβ positive cells of representative mice. (FIG. 6B) Summarized data of the percentages of IFNγ positive cells in CD3, TCRβ and CD8+ cells. Each plot represents individual mice. * $P<0.05$ (one-way ANOVA).

FIGS. 7A and 7B show 16S rRNA gene sequence data of the cecal microbiota of the mice prepared in FIGS. 6A and 6B, which were comprehensively analyzed using the next generation sequencer. (FIG. 7A) Figure of the proportion of operational taxonomic unit (OTU). On the right end, the OTU corresponding to the isolated strains of the B #5-AMP-2 mouse is shown in green. (FIG. 7B) Identification of isolated strains and the homologous bacterial name (Closest sequence) and similarity (S-ab score) are shown.

(FIG. 8A) The expression of CD8 and IFNγ by the gated CD3 and TCRβ positive cells of representative mice. (FIG. 8B) Summarized data of the percentages of IFNγ positive cells in CD3, TCRβ and CD8+ cells. Each plot represents individual mice. ** $P<0.01$ (Student's t-test).

FIGS. 9A and 9B show data on the mixture of 21 isolated strains which was orally administered to germ free mice. Four weeks later, lymphocytes were isolated from the lamina propria of the large intestine and stimulated with PMA/ionomycin for 3.5 hours. CD3, TCRβ, CD8, CD103, IFNγ and GzmB were stained with antibodies and analyzed by flow cytometry. (FIG. 9A) The expression of IFNγ and CD103 (upper row) or GzmB (lower row) by the gated CD8 T cells of representative mice. (FIG. 9B) Summarized data of the percentages of each IFNγ positive cell fraction in CD3, TCRβ and CD8+ cells. Each plot represents individual mice. * $P<0.05$, ** $P<0.01$ (Student's t-test).

FIGS. 10A and 10B show data on the mixture of the 21 strains or 11 strains (11 strain mixture corresponds to strains #1-11; See Table 1), which were orally administered to germ free mice. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry. (FIG. 10A) The expression of CD8 and IFNγ by the gated CD3 and TCRβ positive cells of representative mice. (FIG. 10B) Summarized data of the percentages of IFNγ positive cells in CD3, TCRβ and CD8+ cells. Each plot represents individual mice. * $P<0.001$, **$P<0.0001$ (one-way ANOVA).

(FIG. 12A) The expression of CD8 and IFNγ by the gated CD3 and TCRβ positive cells of representative mice. (FIG. 12B) Summarized data of the percentages of CD8+ IFN+ cells in CD3+ TCRβ+ cells (left), IFNγ+ cells in CD8T cells (middle) and the numbers of CD8+ IFNγ+ cells (right). Each plot represents individual mice.  $P<0.01$, * $P<0.001$, ****$P<0.0001$ (one-way ANOVA).

FIGS. 14A and 14B show data of the mixtures of the 11 strains, 7 or 4 strains mixtures listed in FIG. 13, which were orally administered to germ free mice. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry. (FIG. 14A) The expression of CD8 and IFNγ by the gated CD3 and TCRβ positive cells of representative mice. (FIG. 14B) Summarized data of the percentages of CD8+ IFNγ+ cells in CD3+ TCRβ+ cells (left), IFNγ+ cells in CD8T cells (middle) and the numbers of CD8+ IFNγ+ cells (right). Each plot represents individual mice. * $P<0.05$,  $P<0.01$, * $P<0.001$ (one-way ANOVA).

FIGS. 16A and 16B show data on lymphocytes isolated from tumor cells. At day 23 or 27, lymphocytes were isolated from tumors and stimulated with PMA/ionomycin for 4 hours. CD3, TCRβ, CD8 and IFNγ were stained with antibodies and analyzed by flow cytometry. (FIG. 16A) The expression of CD8 and IFNγ by the gated CD3 and TCRβ positive cells of representative mice. (FIG. 16B) Summarized data of the percentages of CD8+ IFNγ+ cells in CD3+ TCRβ+ cells (left), IFNγ+ cells in CD8T cells (middle) and the numbers of CD8+ IFNγ+ cells (right). Each plot represents individual mice. * $P<0.05$,  $P<0.01$, * $P<0.001$ (one-way ANOVA).

(FIG. 17A) The expression of gp70-specific TCRβ, CD44, GzmB and IFNγ by the gated CD3, TCRβ and CD8+ cells of representative mice. (FIG. 17B). Summarized data of the percentages of each IFN positive cell fraction in CD8T cells. Each plot represents individual mice.  $P<0.01$, * $P<0.001$, **** $P<0.0001$ (one-way ANOVA).

Figure 20:
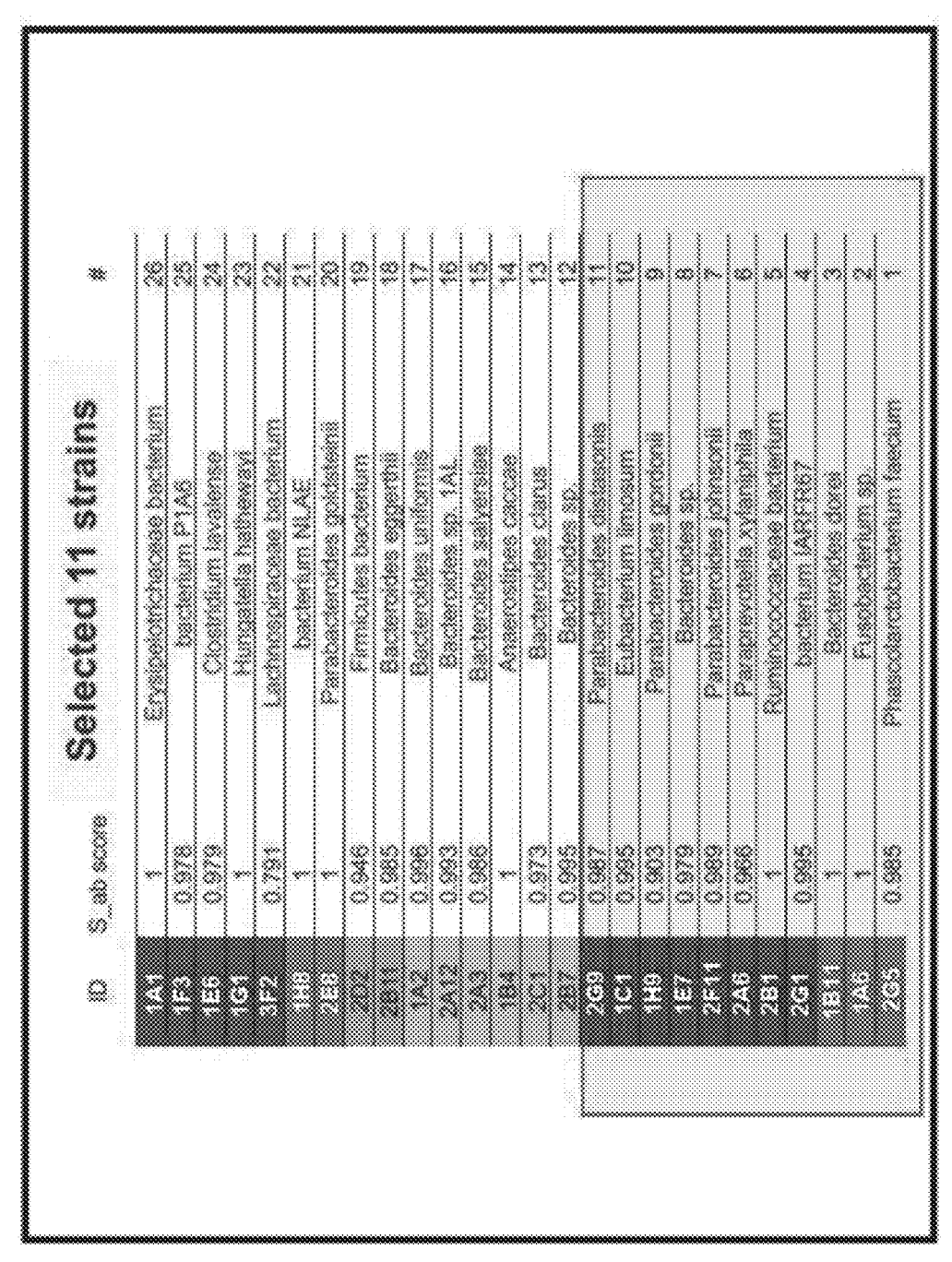

FIG. 20 shows data on 26 isolated strains, including 11 selected strains.

FIG. 37A shows the percentage of CD8+ IFNγ+ cells in the CD3+ TCRβ+ CD8α+ population of cells isolated from the tumors. FIG. 37B shows the number of CD8+ IFNγ+ cells isolated from the tumors. FIG. 37C shows the number of CD8+ IFNγ+ cells per gram of tumors. ** $P<0.01$, * $P<0.05$ (one-way ANOVA).

FIG. 39A shows the percentage of IFNγ+ GzmB+ cells in the CD3+ TCRβ+ CD8α+ population of cells isolated from the tumors. FIG. 39B shows the percentage of Th1 cells in the CD3+ TCRβ+ CD4+ population of cells isolated from the tumors. FIG. 39C shows the percentage of Th17 cells in the CD3+ TCRβ+ CD4+ population of cells isolated from the tumors. FIG. 39D shows the percentage of Treg cells in the CD3+ TCRβ+ CD4+ population of cells isolated from the tumors.

FIG. 41A shows the percentage of CD8+ IFNγ+ cells in the CD3+ TCRβ+ CD8α+ population of cells isolated from the indicated mice. FIG. 41B shows the number of CD8+ IFNγ+ cells isolated from the indicated mice. FIG. 41C shows the percentage of IFNγ+ cells in the population of CD8T cells isolated from the indicated mice.

FIG. 42A shows the percentage of IFNγ+CD103+ cells in the CD3+ TCRβ+ CD8α+ population of cells isolated from the indicated mice. FIG. 42B shows the percentage of Th17 cells in the CD3+ TCRβ+ CD4+ population of cells isolated from the indicated mice. FIG. 42C shows the percentage of Th1 cells in the CD3+ TCRβ+ CD4+ population of cells isolated from the indicated mice.

FIG. 43A shows the percentage of IFNγ+ in the CD3+ TCRβ+CD8α+ (CD8 T cell) population of cells isolated from the indicated mice. FIG. 43B shows the number of CD8+ IFNγ+ cells. FIG. 43C shows the percentage of Th17 cells in the CD3+ TCRβ+CD4+ population of cells isolated from the indicated mice. ** $P<0.0001$, * $P<0.001$, ** $P<0.01$, * $P<0.05$ (one-way ANOVA).

FIG. 44 shows that BATF3 is required for the 11-mix to induce CD8-T cells, as evidenced by the flow cytometry (FIG. 44A), and the percentage of IFNγ+ in the CD3+ TCRβ+ CD8α+ (CD8 T cells) population of cells isolated from the indicated mice (FIG. 44B).

FIG. 45 shows that feces+11-mix is effective in clearing Listeria from infected mice, as evidenced in a decrease in the amount of Listeria CFUs in the feces.

FIG. 46 shows that the body weight of Listeria infected mice treated with feces and the 11-mix is higher than treatment with feces only.

DESCRIPTION OF EMBODIMENTS

Detailed Description

Figure 1A:
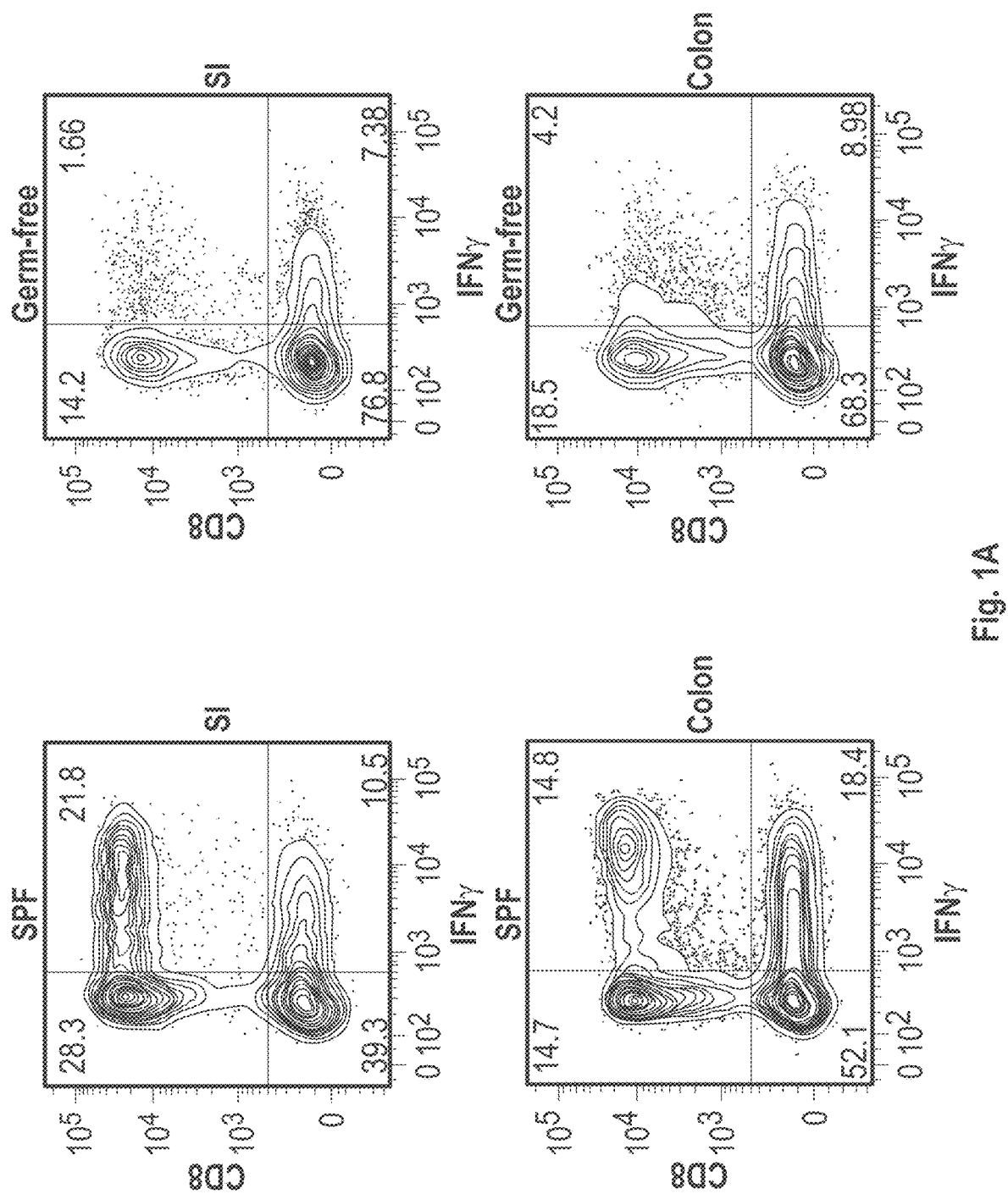
FIGS. 1A and 1B show data of experiments with lymphocytes that were isolated from small intestine (SI) and colon mucosal lamina propria of SPF and germ-free (GF) mice and stimulated with PMA/ionomycin for 3.5 hours. CD3, TCRβ, CD8 and IFNγ were stained with antibodies and analyzed by flow cytometry.

Provided herein are compositions and methods for the induction and/or proliferation of CD8+ T-cells, and methods for the treatment of diseases and conditions that can be treated through the induction and/or proliferation of CD8+ T-cells, including infectious diseases and cancers. In one aspect, the disclosure provides compositions comprising one or more bacterial strains with unique biological properties. In one aspect, the compositions of the bacterial strains disclosed herein, also referred to as bacterial compositions, can induce the proliferation and/or accumulation of CD8+ T-cells. In one aspect, the compositions of the bacterial strains disclosed herein can induce the proliferation and/or accumulation of CD8+ T-cells.

In one aspect, the bacteria of the compositions disclosed herein can be identified by their 16S rRNA (or 16S rDNA) nucleic acid sequence. In general, bacteria are classified as belonging to a specific species and/or genus based on their 16S rRNA nucleic acid sequence. Bacteria, such as bacteria derived from the microbiome, may also be classified into phylogenetic clusters with other closely related strains and species. (See e.g., Rajilic-Stojanovic, M., and de Vos, W. M. (2014). The first 1000 cultured species of the human gastrointestinal microbiota. FEMS Microbiol Rev 38, 996-1047). Methods for determining the identity of specific bacterial species based on their 16S rRNA (or 16S rDNA) nucleic acid sequence are well known in the art (See e.g., Jumpstart Consortium Human Microbiome Project Data Generation Working, G. (2012). Evaluation of 16S rDNA-based community profiling for human microbiome research. PLoS One 7, e39315). In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains. In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains. In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 2, at least 3, at least 4, at least 5, at least 6, at least 7, at least 8, at least 9, at least 10, or at least 11 bacterial strains. In one aspect, the disclosure provides compositions comprising one or more bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 2, at least 3, at least 4, at least 5, at least 6, at least 7, at least 8, at least 9, at least 10, or at least 11 bacterial strains. In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 3, at least 4, at least 5, at least 6, at least 7, at least 8, at least 9, at least 10, or at least 11 bacterial strains. In one aspect, the disclosure provides compositions comprising a purified bacterial mixture comprising two or more bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 3, at least 4, at least 5, at least 6, at least 7, at least 8, at least 9, at least 10, or at least 11 bacterial strains. In one aspect, the disclosure provides compositions comprising a purified bacterial mixture comprising one or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains. In one aspect, the disclosure provides compositions comprising a purified bacterial mixture comprising two or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains. In one aspect, the disclosure provides compositions comprising a purified bacterial mixture comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising one or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 2, at least 3, at least 4, at least 5, at least 6, at least 7, at least 8, at least 9, or at least 10 bacterial strains. In one aspect, the disclosure provides compositions comprising one or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 2, at least 3, at least 4, at least 5, at least 6, at least 7, at least 8, at least 9, or at least 10 bacterial strains. In one aspect, the disclosure provides compositions comprising two or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains. In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:5, or SEQ ID NO:10. In some embodiments of the compositions provided herein, the purified bacterial mixture comprises at least 2, at least 3, or at least 4 bacterial strains. In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:5, or SEQ ID NO:10. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:5, or SEQ ID NO:10. In some embodiments of the compositions provided herein, the purified bacterial mixture comprises at least 3, or at least 4 bacterial strains. In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:5, or SEQ ID NO:10. In some embodiments of the compositions provided herein, the purified bacterial mixture comprises at least 3, or at least 4 bacterial strains. In one aspect, the disclosure provides compositions comprising a purified bacterial mixture comprising one or more bacterial strains comprising 16S rDNA sequences of at least 97% homology to SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 97% sequence identity with SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 2, at least 3, at least 4, at least 5, at least 6, or at least 7 bacterial strains. In one aspect, the disclosure provides compositions comprising a purified bacterial mixture comprising two or more bacterial strains comprising 16S rDNA sequences of at least 97% homology to SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 3, at least 4, at least 5, at least 6, or at least 7 bacterial strains. In one aspect, the disclosure provides compositions comprising a purified bacterial mixture comprising two or more bacterial strains comprising 16S rDNA sequences of at least 97% sequence identity with SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains. In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains. In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 2, least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 2, least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 2, at least 3, at least 4, at least 5, at least 6, at least 7, at least 8, at least 9, at least 10, or at least 11 bacterial strains. In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains. In one aspect, the disclosure provides compositions comprising a purified bacterial mixture comprising one or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains. In one aspect, the disclosure provides compositions comprising a purified bacterial mixture comprising one or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains. In one aspect, the disclosure provides compositions comprising a purified bacterial mixture comprising two or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains. In one aspect, the disclosure provides compositions comprising a purified bacterial mixture comprising one or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 2, at least 3, at least 4, at least 5, at least 6, at least 7, at least 8, at least 9, or at least 10 bacterial strains. In one aspect, the disclosure provides compositions comprising a purified bacterial mixture comprising two or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains. In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:31 or SEQ ID NO:36. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:31 or SEQ ID NO:36. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:31 or SEQ ID NO:36. In some embodiments of the compositions provided herein, the purified bacterial mixture comprises at least 3, or at least 4 bacterial strains. In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:31 or SEQ ID NO:36. In some embodiments of the compositions provided herein, the purified bacterial mixture comprises at least 3, or at least 4 bacterial strains. In one aspect, the disclosure provides compositions comprising a purified bacterial mixture comprising one or more bacterial strains comprising 16S rDNA sequences of at least 97% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 97% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 2, at least 3, at least 4, at least 5, at least 6, or at least 7 bacterial strains. In one aspect, the disclosure provides compositions comprising a purified bacterial mixture comprising two or more bacterial strains comprising 16S rDNA sequences of at least 97% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains. In one aspect, the disclosure provides compositions comprising a purified bacterial mixture comprising two or more bacterial strains comprising 16S rDNA sequences of at least 97% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains.

In one aspect, the disclosure provides compositions comprising a bacterial strain comprising a 16S rDNA sequence with a nucleic acid sequence selected from the group consisting of SEQ ID NOs:1-26. In one aspect, the disclosure provides compositions comprising as an active ingredient a bacterial strain comprising a 16S rDNA sequence with a nucleic acid sequence selected from the group consisting of SEQ ID NOs:1-26. It should be appreciated that for all compositions provided herein, in some embodiments, the bacterial strain or the bacterial strains are the active ingredient of the composition. In one aspect, the disclosure provides compositions comprising a bacterial strain comprising a 16S rDNA sequence with a nucleic acid sequence selected from the group consisting of SEQ ID NOs:1-21. In one aspect, the disclosure provides compositions comprising as an active ingredient a bacterial strain comprising a 16S rDNA sequence with a nucleic acid sequence selected from the group consisting of SEQ ID NOs:1-21. In one aspect, the disclosure provides compositions comprising a bacterial strain comprising a 16S rDNA sequence with a nucleic acid sequence selected from the group consisting of SEQ ID NOs:1-11. In one aspect, the disclosure provides compositions comprising as an active ingredient a bacterial strain comprising a 16S rDNA sequence with a nucleic acid sequence selected from the group consisting of SEQ ID NOs:1-11.

In one aspect, the disclosure provides compositions comprising a bacterial strain comprising a 16S rDNA sequence with a nucleic acid sequence selected from the group consisting of SEQ ID NOs:54-64. In one aspect, the disclosure provides compositions comprising as an active ingredient a bacterial strain comprising a 16S rDNA sequence with a nucleic acid sequence selected from the group consisting of SEQ ID NOs:54-64. It should be appreciated that for all compositions provided herein, in some embodiments, the bacterial strains are purified. Thus, for example the disclosure provides purified bacterial strains comprising a 16S rDNA sequence with a nucleic acid sequence selected from the group consisting of SEQ ID NOs:1-26. In addition, for example, the disclosure provides compositions comprising purified bacterial strains comprising a 16S rDNA sequence with a nucleic acid sequence selected from the group consisting of SEQ ID NOs:1-26. The bacterial strains disclosed herein originally may have been obtained and purified from the microbiota of one or more human individuals or obtained from sources other than the human microbiota, including soil and non-human microbiota. As provided herein, in some embodiments, bacteria isolated from the human microbiota, non-human microbiota, soil, or any alternative source are purified prior to use in the compositions and methods provided herein.

In one aspect, the disclosure provides compositions comprising one or more bacterial strains, wherein the one or more bacterial strains comprise a 16S rDNA sequence with a nucleic acid sequence selected from the group consisting of SEQ ID NOs:1-26. In one aspect, the disclosure provides compositions comprising one or more bacterial strains wherein the one or more bacterial strains comprise 16S rDNA sequences having at least 97% homology with nucleic acid sequences selected from the group consisting of SEQ ID NOs:1-26. As discussed previously, in some embodiments, the bacterial strains are purified. Thus, in one aspect, the disclosure provides compositions comprising one or more purified bacterial strains wherein the one or more purified bacterial strains comprise 16S rDNA sequences having at least 97% homology with nucleic acid sequences selected from the group consisting of SEQ ID NOs:1-26. In one aspect, the disclosure provides compositions comprising one or more bacterial strains wherein the one or more bacterial strains comprise 16S rDNA sequences having at least 97% sequence identity with nucleic acid sequences selected from the group consisting of SEQ ID NOs:1-26. As discussed previously, in some embodiments, the bacterial strains are purified. Thus, in one aspect, the disclosure provides compositions comprising one or more purified bacterial strains wherein the one or more purified bacterial strains comprise 16S rDNA sequences having at least 97% sequence identity with nucleic acid sequences selected from the group consisting of SEQ ID NOs:1-26.

In one aspect, the disclosure provides compositions comprising two or more purified bacterial strains wherein the two or more purified bacterial strains comprise 16S rDNA sequences having at least 97% homology with nucleic acid sequences selected from the group consisting of SEQ ID NOs:1-26. As discussed above, in some embodiments, the bacterial strains are the active ingredient of the composition. Thus, in some embodiments, the disclosure provides compositions comprising as an active ingredient two or more purified bacterial strains wherein the two or more purified bacterial strains comprise 16S rDNA sequences having at least 97% homology with nucleic acid sequences selected from the group consisting of SEQ ID NOs:1-26. In one aspect, the disclosure provides compositions comprising two or more purified bacterial strains wherein the two or more purified bacterial strains comprise 16S rDNA sequences having at least 97% sequence identity with nucleic acid sequences selected from the group consisting of SEQ ID NOs:1-26. As discussed above, in some embodiments, the bacterial strains are the active ingredient of the composition. Thus, in some embodiments, the disclosure provides compositions comprising as an active ingredient two or more purified bacterial strains wherein the two or more purified bacterial strains comprise 16S rDNA sequences having at least 97% sequence identity with nucleic acid sequences selected from the group consisting of SEQ ID NOs:1-26.

In one aspect, the disclosure provides bacterial strains and combinations of bacterial strains that are homologous or have a high percent of homology with bacterial strains comprising 16S rDNA sequences selected from the group consisting of SEQ ID NOs:1-26. As discussed previously, in some embodiments, the bacterial strains are purified. The bacterial strains disclosed herein that have a 16S rDNA sequence with a nucleic acid sequence selected from the group consisting of SEQ ID NOs:1-26 have a high percent of homology (e.g., greater than 90%) or sequence identity, with 16S rDNA sequences of bacterial strains that have been described in various databases (See e.g., the National Center for Biotechnology Information). Table 1 provides the closest known species by homology when the 16S rDNA sequences comprising SEQ ID NOs:1-26 are compared to 16S rDNA sequences of bacterial species available in public databases.

By way of example, the bacterial strain comprising a 16S rDNA sequence with SEQ ID NO:1 disclosed herein has the highest homology with a bacterial strain of the species *Phascolarctobacterium faecium* as defined by NCBI Accession # LN998073 (having 16S rDNA sequence SEQ ID NO:27). While the bacterial strain with SEQ ID NO:1 has homology with other published bacterial strains as well, the highest homology is with a bacterial strain of the species *Phascolarctobacterium faecium* as defined by NCBI Accession # LN998073. It should be appreciated that multiple bacterial strains disclosed herein may have the highest homology with the same species.

It should further be appreciated that the bacterial strains disclosed herein that have a 16S rDNA sequence with a nucleic acid sequence selected from the group consisting of SEQ ID NOs:1-26, are also homologous to other strains based on their whole genome sequence, or subset of their whole genome sequence.

Thus, it should be appreciated that, in one aspect, the disclosure also provides compositions and methods comprising bacterial species with close homology to the bacterial strains that have a 16S rDNA sequence with a nucleic acid sequence selected from the group consisting of SEQ ID NOs:1-26.

In one aspect, the disclosure provides compositions comprising one or more bacterial strains wherein the one or more bacterial strains are of species selected from the group consisting of *Phascolarctobacterium faecium*, *Fusobacterium ulcerans*, *Bacteroides dorei*, *Bacteroides uniformis*, *Subdoligranulum* sp., *Paraprevotella xylaniphila*, *Parabacteroides johnsonii*, *Alistipes* sp., *Parabacteroides gordonii*, *Eubacterum limosum*, *Parabacteroides distasonis*, *Bacteroides cellulosilyticus*, *Bacteroides clarus*, *Anaerostipes caccae*, *Bacteroides salyersiae*, *Bacteroides fragilis*, *Bacteroides uniformis*, *Bacteroides eggerthii*, *Clostridium* sp., *Parabacteroides goldsteinii*, *Bacteroides* sp., *Lachnospiraceae bacterium* HGA0140, *Hungatella hathewayi*, *Clostridium lavalense*, *Ruminococcus* sp., and *Clostridium innocuum* In one aspect, the disclosure provides compositions comprising one or more bacterial strains wherein the one or more bacterial strains are of species selected from the group consisting of *Phascolarctobacterium faecium*, *Fusobacterium ulcerans*, *Bacteroides dorei*, *Bacteroides uniformis*, *Subdoligranulum* sp., *Paraprevotella xylaniphila*, *Parabacteroides johnsonii*, *Alistipes* sp., *Parabacteroides gordonii*, *Eubacterum limosum*, *Parabacteroides distasonis*, *Bacteroides cellulosilyticus*, *Bacteroides clarus*, *Anaerostipes caccae*, *Bacteroides salyersiae*, *Bacteroides fragilis*; *Bacteroides uniformis*, *Bacteroides eggerthii*, *Clostridium* sp., *Parabacteroides goldsteinii*, and *Bacteroides* sp.

In one aspect, the disclosure provides compositions comprising one or more bacterial strains wherein the one or more bacterial strains are of species selected from the group consisting of *Phascolarctobacterium faecium*, *Fusobacterium ulcerans*, *Bacteroides dorei*, *Bacteroides uniformis*, *Subdoligranulum* sp., *Paraprevotella xylaniphila*, *Parabacteroides johnsonii*, *Alistipes* sp., *Parabacteroides gordonii*, *Eubacterum limosum*, and *Parabacteroides distasonis*. In one aspect, the disclosure provides compositions comprising one or more bacterial strains wherein the one or more bacterial strains are of species selected from the group consisting of *Bacteroides cellulosilyticus*, *Bacteroides clarus*, *Anaerostipes caccae*, *Bacteroides salyersiae*, *Bacteroides fragilis*, *Bacteroides uniformis*, *Bacteroides eggerthii*, *Clostridium* sp., *Parabacteroides goldsteinii*, *Bacteroides* sp., *Lachnospiraceae bacterium* HGA0140, *Hungatella hathewayi*, *Clostridium lavalense*, *Ruminococcus* sp., and *Clostridium innocuum*. In one aspect, the disclosure provides compositions comprising one or more bacterial strains wherein the one or more bacterial strains are of species selected from the group consisting of *Bacteroides cellulosilyticus*, *Bacteroides clarus*, *Anaerostipes caccae*, *Bacteroides salyersiae*, *Bacteroides fragilis*, *Bacteroides uniformis*, *Bacteroides eggerthii*, *Clostridium* sp., *Parabacteroides goldsteinii*, and *Bacteroides* sp.

In one aspect, the disclosure provides compositions comprising a purified bacterial mixture comprising two or more bacterial strains of species selected from the group consisting of *Phascolarctobacterium faecium*, *Fusobacterium*

*ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*. In one aspect, the disclosure provides compositions comprising a purified bacterial mixture consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*. In one aspect, the disclosure provides compositions comprising a purified bacterial mixture comprising one or more bacterial strains of species selected from the group consisting of *Phascolarctobacterium faecium, Phascolarctobacterium* sp. CAG:207, *Fusobacterium ulcerans, Fusobacterium varium, Bacteroides dorei, Bacteroides fluxus, Bacteroides uniformis, Bacteroides* sp. D20 *Subdoligranulum* sp., *Ruthenibacterium lactatiformans, Ruminococcaceae bacterium* cv2, *Gemminger formicilis, Paraprevotella xylaniphila, Parabacteroides johnsonii, Alistipes* sp., *Alistipes senegalesis, Parabacteroides gordonii, Parabacteroides* sp. HGS0025, *Eubacterum limosum, Parabacteroides* sp. CAG:2 and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising:
1) *Phascolarctobacterium faecium*, or *Phascolarctobacterium* sp. CAG:207;
2) *Fusobacterium ulcerans*, or *Fusobacterium varium;*
3) *Bacteroides dorei*, or *Bacteroides fluxus,*
4) *Bacteroides uniformis*, or *Bacteroides* sp. D20,
5) *Subdoligranulum* sp., *Ruthenibacterium lactatiformans, Ruminococcaceae bacterium* cv2, or *Gemminger formicilis,*
6) *Paraprevotella xylaniphila,*
7) *Parabacteroides johnsonii,*
8) *Alistipes* sp., *Alistipes timonensis*, or *Alistipes senegalesis,*
9) *Parabacteroides gordonii*, or *Parabacteroides* sp. HGS0025,
10) *Eubacterum limosum*, and
11) *Parabacteroides* sp. CAG:2 or *Parabacteroides distasonis*.

In one aspect, the disclosure provides compositions comprising a purified bacterial mixture consisting of:
1) *Phascolarctobacterium faecium*, or *Phascolarctobacterium* sp. CAG:207;
2) *Fusobacterium ulcerans*, or *Fusobacterium varium;*
3) *Bacteroides dorei*, or *Bacteroides fluxus,*
4) *Bacteroides uniformis*, or *Bacteroides* sp. D20,
5) *Subdoligranulum* sp., *Ruthenibacterium lactatiformans, Ruminococcaceae bacterium* cv2, or *Gemminger formicilis,*
6) *Paraprevotella xylaniphila,*
7) *Parabacteroides johnsonii,*
8) *Alistipes* sp., *Alistipes timonensis*, or *Alistipes senegalesis,*
9) *Parabacteroides gordonii*, or *Parabacteroides* sp. HGS0025,
10) *Eubacterum limosum*, and
11) *Parabacteroides* sp. CAG:2 or *Parabacteroides distasonis*. In one aspect, the disclosure provides compositions comprising a purified bacterial mixture comprising one or more bacterial strains of species selected from the group consisting of *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum*, and *Parabacteroides distasonis*.

In one aspect, the disclosure provides compositions comprising a purified bacterial mixture consisting of *Phascolarctobacterium faecium, Fusobacterium varium, Bacte-* roides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum, and Parabacteroides distasonis. In one aspect, the disclosure provides compositions comprising a purified bacterial mixture comprising one or more bacterial strains of species selected from the group consisting of Phascolarctobacterium sp. CAG:207, Fusobacterium ulcerans, Bacteroides dorei, Bacteroides sp. D20, Ruminococcaceae bacterium cv2, Paraprevotella xylaniphila, Parabacteroides johnsonii, Alistipes senegalesis, Parabacteroides sp. HGS0025, Eubacterum limosum, and Parabacteroides sp. CAG:2. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising Phascolarctobacterium sp. CAG:207, Fusobacterium ulcerans, Bacteroides dorei, Bacteroides sp. D20, Ruminococcaceae bacterium cv2, Paraprevotella xylaniphila, Parabacteroides johnsonii, Alistipes senegalesis, Parabacteroides sp. HGS0025, Eubacterum limosum, and Parabacteroides sp. CAG:2. In one aspect, the disclosure provides compositions comprising a purified bacterial mixture consisting of Phascolarctobacterium sp. CAG:207, Fusobacterium ulcerans, Bacteroides dorei, Bacteroides sp. D20, Ruminococcaceae bacterium cv2, Paraprevotella xylaniphila, Parabacteroides johnsonii, Alistipes senegalesis, Parabacteroides sp. HGS0025, Eubacterum limosum, and Parabacteroides sp. CAG:2. In one aspect, the disclosure provides compositions comprising a purified bacterial mixture comprising two or more bacterial strains of species selected from the group consisting of Phascolarctobacterium faecium, Phascolarctobacterium sp. CAG:207, Fusobacterium ulcerans, Fusobacterium varium, Bacteroides dorei, Bacteroides fluxus, Bacteroides uniformis, Bacteroides sp. D20 Subdoligranulum sp., Ruthenibacterium lactatiformans, Ruminococcaceae bacterium cv2, Gemminger formicilis, Paraprevotella xylaniphila, Parabacteroides johnsonii, Alistipes sp., Alistipes timonensis, Alistipes senegalesis, Parabacteroides gordonii, Parabacteroides sp. HGS0025, Eubacterum limosum, Parabacteroides sp. CAG:2 and Parabacteroides distasonis. In some embodiments of the compositions provided herein, the purified bacterial mixture comprises, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum, and Parabacteroides distasonis. In some embodiments of the compositions provided herein, the purified bacterial mixture comprises at least 2, at least 3, at least 4, at least 5, at least 6, at least 7, at least 8, at least 9, at least 10, or at least 11 bacterial strains. In one aspect, the disclosure provides compositions comprising a purified bacterial mixture comprising two or more bacterial strains of species selected from the group consisting of Phascolarctobacterium sp. CAG:207, Fusobacterium ulcerans, Bacteroides dorei, Bacteroides sp. D20, Ruminococcaceae bacterium cv2, Paraprevotella xylaniphila, Parabacteroides johnsonii, Alistipes senegalesis, Parabacteroides sp. HGS0025, Eubacterum limosum, and Parabacteroides sp. CAG:2. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of Bacteroides cellulosilyticus, Bacteroides clarus, Anaerostipes caccae, Bacteroides salyersiae, Bacteroides fragilis, Bacteroides uniformis, Bacteroides eggerthii, Clostridium sp., Parabacteroides goldsteinii, Bacteroides sp., Lachnospiraceae bacterium HGA0140, Hungatella hathewayi, Clostridium lavalense, Ruminococcus sp., and Clostridium innocuum. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains. In one aspect, the disclosure provides compositions comprising a purified bacterial mixture comprising two or more bacterial strains of species selected from the group consisting of Bacteroides cellulosilyticus, Bacteroides clarus, Anaerostipes caccae, Bacteroides salyersiae, Bacteroides fragilis, Bacteroides uniformis, Bacteroides eggerthii, Clostridium sp., Parabacteroides goldsteinii, and Bacteroides sp. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains of species selected from the group consisting of Phascolarctobacterium faecium, Fusobacterium ulcerans, Subdoligranulum sp., and Eubacterum limosum. In some embodiments of the compositions provided herein, the purified bacterial mixture comprises at least 3, or at least 4 bacterial strains. In one aspect, the disclosure provides compositions comprising a purified bacterial mixture comprising two or more bacterial strains of species selected from the group consisting of Bacteroides dorei, Bacteroides uniformis, Paraprevotella xylaniphila, Parabacteroides johnsonii, Alistipes sp., Parabacteroides gordonii, and Parabacteroides distasonis. In some embodiments of the compositions provided herein, the purified bacterial mixture comprises, at least 3, at least 4, at least 5, at least 6, or at least 7 bacterial strains. It should be appreciated that the compositions may include multiple strains of a particular species. Thus, for illustration, a non-limiting example of the compositions disclosed herein, comprises one strain of Bacteroides salyersiae and two strains of Bacteroides uniformis. The disclosure provides also encompasses compositions comprising bacterial strains that are close in homology to and/or fall within the species Phascolarctobacterium faecium, Fusobacterium ulcerans, Bacteroides dorei, Bacteroides uniformis, Subdoligranulum sp., Paraprevotella xylaniphila, Parabacteroides johnsonii, Alistipes sp., Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium sp., Parabacteroides goldsteinii, Bacteroides sp., Lachnospiraceae bacterium HGA0140, Hungatella hathewayi, Clostridium lavalense, Ruminococcus sp., and Clostridium innocuum.

Thus, in one embodiment, the compositions of the disclosure include one or more bacterial strains comprising 16S rDNA sequences having at least 97% homology with nucleic acid sequences selected from the group consisting of SEQ ID NOs:27-52. In some embodiments, the compositions of the disclosure include two or more bacterial strains comprising 16S rDNA sequences having at least 97% homology with nucleic acid sequences selected from the group consisting of SEQ ID NOs:27-52. Thus, in one embodiment, the compositions of the disclosure include one or more bacterial strains comprising 16S rDNA sequences having at least 97% sequence identity with nucleic acid sequences selected from the group consisting of SEQ ID NOs:27-52. In some embodiments, the compositions of the disclosure include two or more bacterial strains comprising 16S rDNA sequences having at least 97% sequence identity with nucleic acid sequences selected from the group consisting of SEQ ID NOs:27-52.

In one aspect, the compositions of the disclosure include two or more purified bacterial strains comprising 16S rDNA sequences having at least 97% homology with nucleic acid sequences selected from the group consisting of SEQ ID NOs:1-26. In some embodiments, the compositions of the disclosure include two or more purified bacterial strains comprising 16S rDNA sequences having at least 97% sequence identity with nucleic acid sequences selected from the group consisting of SEQ ID NOs:1-26. In some embodiments, the compositions of the disclosure include two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments, the compositions of the disclosure include two or more purified bacterial strains comprising 16S rDNA sequences having at least 97% homology with nucleic acid sequences selected from the group consisting of SEQ ID NO:27-52. In some embodiments, the compositions of the disclosure include two or more purified bacterial strains comprising 16S rDNA sequences having at least 97% sequence identity with nucleic acid sequences selected from the group consisting of SEQ ID NO:27-52.

In some embodiments, the disclosure provides compositions with two or more purified bacterial strains that comprise 16S rDNA sequences with nucleic acid sequences selected from the group consisting of SEQ ID NOs:1-26. In some embodiments, the disclosure provides compositions with five or more purified bacterial strains that comprise 16S rDNA sequences with nucleic acid sequences selected from the group consisting of SEQ ID NOs:1-26. In some embodiments, the disclosure provides compositions with at least ten purified bacterial strains, wherein the bacterial strains comprise 16S rDNA sequences with nucleic acid sequences SEQ ID NOs:1-26, respectively. In some embodiments, the disclosure provides a composition consisting of ten purified bacterial strains, wherein the bacterial strains comprise 16S rDNA sequences with nucleic acid sequences SEQ ID NOs:1-26, respectively. In some embodiments, the disclosure provides a composition essentially consisting of eleven purified bacterial strains, wherein the bacterial strains comprise 16S rDNA sequences with nucleic acid sequences SEQ ID NOs:1-26, respectively. As used herein, essentially consisting of refers to a composition that includes no additional bacterial strains.

In some embodiments, the disclosure provides compositions with bacterial strains that comprise 16S rDNA sequences having at least 97% homology with nucleic acid sequences selected from the group consisting of: SEQ ID NOs:1-26. In some embodiments, the disclosure provides compositions with two or more purified bacterial strains that comprise 16S rDNA sequences having at least 97% homology with nucleic acid sequences selected from the group consisting of SEQ ID NOs:1-26. In some embodiments, the disclosure provides compositions with five or more purified bacterial strains that comprise 16S rDNA having at least 97% homology with nucleic acid sequences selected from the group consisting of SEQ ID NOs:1-26. In some embodiments, the disclosure provides compositions with at least ten purified bacterial strains, wherein the bacterial strains comprise 16S rDNA sequences having at least 97% homology with nucleic acid sequences SEQ ID NOs:1-26, respectively. In some embodiments, the disclosure provides a composition consisting of ten purified bacterial strains, wherein the bacterial strains comprise 16S rDNA sequences having at least 97% homology with nucleic acid sequences SEQ ID NOs:1-26, respectively. In some embodiments, the disclosure provides a composition essentially consisting of ten purified bacterial strains, wherein the bacterial strains comprise 16S rDNA sequences having at least 97% homology with nucleic acid sequences SEQ ID NOs:1-26, respectively.

In some embodiments, the disclosure provides compositions with bacterial strains that comprise 16S rDNA sequences having at least 97% sequence identity with nucleic acid sequences selected from the group consisting of: SEQ ID NOs:1-26. In some embodiments, the disclosure provides compositions with two or more purified bacterial strains that comprise 16S rDNA sequences having at least 97% sequence identity with nucleic acid sequences selected from the group consisting of SEQ ID NOs:1-26. In some embodiments, the disclosure provides compositions with five or more purified bacterial strains that comprise 16S rDNA having at least 97% sequence identity with nucleic acid sequences selected from the group consisting of SEQ ID NOs:1-26. In some embodiments, the disclosure provides compositions with at least ten purified bacterial strains, wherein the bacterial strains comprise 16S rDNA sequences having at least 97% sequence identity with nucleic acid sequences SEQ ID NOs:1-26, respectively. In some embodiments, the disclosure provides a composition consisting of ten purified bacterial strains, wherein the bacterial strains comprise 16S rDNA sequences having at least 97% sequence identity with nucleic acid sequences SEQ ID NOs:1-26, respectively. In some embodiments, the disclosure provides a composition essentially consisting of ten purified bacterial strains, wherein the bacterial strains comprise 16S rDNA sequences having at least 97% sequence identity with nucleic acid sequences SEQ ID NOs:1-26, respectively.

In one aspect, the disclosure provides a composition comprising bacterial strains that are related to the following bacterial species: *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerosti-* pes caccae, Bacteroides salyersiae, Bacteroides fragilis, Bacteroides uniformis, Bacteroides eggerthii, Clostridium sp., Parabacteroides goldsteinii, Bacteroides sp., Lachnospiraceae bacterium HGA0140, Hungatella hathewayi, Clostridium lavalense, Ruminococcus sp., and Clostridium innocuum (See e.g., Table 1). It should be appreciated that multiple bacterial strains of the compositions disclosed herein can have the same related bacterial species. In some embodiments, the disclosure provides compositions with two or more purified bacterial strains comprising 16S rDNA sequences having at least 97% homology with nucleic acid sequences selected from the group consisting of SEQ ID NO:27-52. In some embodiments, the disclosure provides compositions with two or more purified bacterial strains comprising 16S rDNA sequences having at least 97% sequence identity with nucleic acid sequences selected from the group consisting of SEQ ID NO:27-52.

In one aspect, the disclosure provides bacterial strains with 16S rDNA sequences that have homology to a nucleic acid sequence of any one of the sequences of the bacterial strains or species described herein. In some embodiments, the bacterial strain has at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% homology relative to any of the strains or bacterial species described herein over a specified region or over the entire sequence. It would be appreciated by one of skill in the art that the term "homology" or "percent homology," in the context of two or more nucleic acid sequences or amino acid sequences, refers to a measure of similarity between two or more sequences or portion(s) thereof. The homology may exist over a region of a sequence that is at least about 50 nucleotides in length, or more preferably over a region that is 100 to 500 or 1000 or more nucleotides in length. In some embodiments, the homology exists over the length the 16S rRNA or 16S rDNA sequence, or a portion thereof.

Additionally, or alternatively, two or more sequences may be assessed for the identity between the sequences. The terms "identical" or percent "identity" in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman. Proc. Natl. Acad. Sci. USA 85:2444, 1988, by computerized implementations of these algorithms (GAP, BESTFIT, FASTA, and TFASTA in the Wisconsin Genetics Software Package, Genetics Computer Group. Madison. Wis.), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively.

In one aspect, the disclosure provides compositions comprising multiple purified bacterial strains. In one aspect, the 16S rDNA sequences of purified bacterial strains of the compositions were compared to 16S rDNA sequences of known bacterial species/strains in a bacterial genome database to identify the closest known related bacterial species to the bacterial strains disclosed herein (See e.g., Table 1 and Table 3). It should be appreciated that multiple bacterial strains of the compositions disclosed herein may have the same closest related bacterial species. In one aspect, the disclosure provides compositions comprising one or more bacterial strains or species with 16S rDNA sequences that have homology to a nucleic acid sequence of any one of the sequences provided by SEQ ID NOs:1-26. In some embodiments, the species with 16S rDNA sequences with homology to a nucleic acid sequence of any one of the closest related species to any of the strains described herein, correspond to bacterial strains with 16S rDNA sequences provided by SEQ ID NOs:27-52. In one aspect, the disclosure provides compositions comprising one or more bacterial strains or species with 16S rDNA sequences that have homology to a nucleic acid sequence of any one of the sequences provided by SEQ ID NOs:1-21. In some embodiments, the species with 16S rDNA sequences with homology to a nucleic acid sequence of any one of the closest related species to any of the strains described herein, correspond to bacterial strains with 16S rDNA sequences provided by SEQ ID NOs:27-47. In one aspect, the disclosure provides compositions comprising one or more bacterial strains or species with 16S rDNA sequences that have homology to a nucleic acid sequence of any one of the sequences provided by SEQ ID NOs:1-11. In some embodiments, the species with 16S rDNA sequences with homology to a nucleic acid sequence of any one of the closest related species to any of the strains described herein, correspond to bacterial strains with 16S rDNA sequences provided by SEQ ID NOs:27-37. In one aspect, the disclosure provides compositions comprising one or more bacterial strains or species with 16S rDNA sequences that have homology to a nucleic acid sequence of any one of the sequences provided by SEQ ID NOs:12-26. In some embodiments, the species with 16S rDNA sequences with homology to a nucleic acid sequence of any one of the closest related species to any of the strains described herein, correspond to bacterial strains with 16S rDNA sequences provided by SEQ ID NOs:38-52. In one aspect, the disclosure provides compositions comprising one or more bacterial strains or species with 16S rDNA sequences that have homology to a nucleic acid sequence of any one of the sequences provided by SEQ ID NOs:12-21. In some embodiments, the species with 16S rDNA sequences with homology to a nucleic acid sequence of any one of the closest related species to any of the strains described herein, correspond to bacterial strains with 16S rDNA sequences provided by SEQ ID NOs:38-47.

In some embodiments, the compositions disclosed herein provide at least one of the bacterial strains (e.g., purified bacterial strains) described herein. In some embodiments, the compositions that comprise at least one bacterial strain, comprise at least one bacterial strain with a 16S rDNA sequence selected from any one of SEQ ID NOs:1-26. In some embodiments, the compositions that comprise at least one bacterial strain, comprise at least one bacterial strain with a 97% homology to 16S rDNA sequence selected from any one of SEQ ID NOs:1-26. In some embodiments, the compositions that comprise at least one bacterial strain, comprise at least one bacterial strain with a 97% sequence identity with a 16S rDNA sequence selected from any one of SEQ ID NOs:1-26. In some embodiments, the compositions disclosed herein comprise two or more bacterial strains. In some embodiments, the compositions described herein comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 or more bacterial strains (e.g., purified bacterial strains).

In some embodiments of the compositions provided herein, at least 50% of the bacterial strains belong to the order of Bacteriodales. In some embodiments of the compositions provided herein, at least 50% of the bacterial strains belong to the genus *Bacteroides* or *Parabacteroides*. In some embodiments of the compositions provided herein, one or more strains belongs to the genus *Bacteroides* and one or more strains belongs to the genus *Parabacteroides*. In some embodiments of the compositions provided herein, at least 25% of the bacterial strains belong to the family of Bacteroidaceae. In some embodiments of the compositions provided herein, one or more of the bacterial strains belongs to the genus *Bacteroides*. In some embodiments of the compositions provided herein, one or more of the bacterial strains belongs to the genus *Parabacteroides*. *In some embodiments of the compositions provided herein, the composition does not include bacterial strains that belong to the order of Bacteriodales.*

In some embodiments of the compositions provided herein, one or more of the bacterial strains belong to the order of Bacteriodales and one or more of the bacterial strains belong to the order of Clostridiales. In some embodiments of the compositions provided herein, at least 50% of the bacterial strains belong to the order of Bacteriodales and one or more of the bacterial strains belong to the order of Clostridiales. In some embodiments of the compositions provided herein, at least 75% of the bacterial strains belong to the order of Bacteriodales and one or more of the bacterial strains belong to the order of Clostridiales. In some embodiments of the compositions provided herein, at least 90% of the bacterial strains belong to the order of Bacteriodales and one or more of the bacterial strains belong to the order of Clostridiales. In some embodiments, the compositions provided herein do not include *E. coli*. In some embodiments, the compositions provided herein do not include *Bifidobacterium*. In some embodiments, the compositions provided herein do not include *Bacillus*. In some embodiments, the compositions provided herein do not include *Enterococcus*. In some embodiments, the compositions provided herein do not include *Barnesiella*. In some embodiments, the compositions provided herein do not include *B. fragilis*. In some embodiments, the compositions provided herein do not include *B. thetaiotaomicron*. In some embodiments, the compositions provided herein do not include Akkermansia. In some embodiments, the compositions provided herein do not include Proteobacteria. In some embodiments, the compositions provided herein do not include *Burkholderia*. In some embodiments, the compositions provided herein do not include *clostridium* species belonging to Cluster IV. In some embodiments, the compositions provided herein do not include *Faecalibacterium*. In some embodiments, the compositions provided herein do not include *clostridium* species belonging to Cluster XIVa. In some embodiments, the compositions do not comprise fungi, such as *Monilla* species.

In one aspect, the disclosure provides purified fractions of human stool sample that can induce CD8 T cells.

In some embodiments of the compositions provided herein, one or more of the bacterial strains are human-derived bacteria. In some embodiments of the compositions provided herein, all of the bacterial strains are human-derived bacteria. In some embodiments of the compositions provided herein, the bacterial strains are derived from more than one human donor.

The bacterial strains used in the compositions provided herein generally are isolated from the microbiome of healthy individuals. In some embodiments, the compositions include strains originating from a single individual. In some embodiments, the compositions include strains originating from multiple individuals. In some embodiments, the bacterial strains are obtained from multiple individuals, isolated and grown up individually. The bacterial compositions that are grown up individually may subsequently be combined to provide the compositions of the disclosure. It should be appreciated that the origin of the bacterial strains of the compositions provided herein is not limited to the human microbiome from a healthy individual. In some embodiments, the bacterial strains originate from a human with a microbiome in dysbiosis. In some embodiments, the bacterial strains originate from non-human animals or the environment (e.g., soil or surface water). In some embodiments, the combinations of bacterial strains provided herein originate from multiple sources (e.g., human and non-human animals).

In some embodiments of the compositions provided herein, the composition includes one or more anaerobic bacteria. In some embodiments of the compositions provided herein, the composition includes only anaerobic bacteria. In some embodiments of the compositions provided herein, the composition includes one or more facultative anaerobic bacteria. In some embodiments of the compositions provided herein, the composition includes only facultative anaerobic bacteria. In some embodiments of the compositions provided herein, the composition includes one or more obligate anaerobic bacteria. In some embodiments of the compositions provided herein, the composition includes only obligate anaerobic bacteria. In some embodiments of the compositions provided herein, one or more of the bacterial strains does not have an antibiotic resistance gene. In some embodiments of the compositions provided herein, the bacterial strains do not have an antibiotic resistance gene that renders the bacterial strain resistant to vancomycin.

In some embodiments of the compositions provided herein, the compositions do not include bacterial strains that are resistant to one or more antibiotics. It should be appreciated that it may be desirable to have a mechanism to remove the bacterial compositions provided herein from the body after administration. One such mechanism is to remove the bacterial compositions by antibiotic treatment. Thus, in some embodiments, the compositions do not include bacterial strains that are resistant to one or more antibiotics. In some embodiments, the compositions do not include bacterial strains that are resistant to one or more antibiotics selected from the group consisting of penicillin, benzylpenicillin, ampicillin, sulbactam, amoxicillin, clavulanate, tazobactam, piperacillin, cefmetazole, vancomycin, imipenem, meropenem, metronidazole and clindamycin. In some embodiments, the compositions do not include bacterial strains that are resistant to vancomycin.

In some embodiments, the compositions include bacterial strains that are susceptible to at least four antibiotics that are efficacious in humans. In some embodiments, the compositions include bacterial strains that are susceptible to at least three antibiotics that are efficacious in humans. In some embodiments, the compositions include bacterial strains that are susceptible to at least two antibiotics that are efficacious in humans. In some embodiments, the compositions include bacterial strains that are susceptible to at least one antibiotic that is efficacious in humans. In some embodiments, the compositions include only bacterial strains that are susceptible to at least four antibiotics that are efficacious in humans. In some embodiments, the compositions include only bacterial strains that are susceptible to at least three antibiotics that are efficacious in humans. In some embodiments, the compositions include only bacterial strains that are susceptible to at least two antibiotics that are efficacious in humans. In some embodiments, the compositions include bacterial strains that are susceptible to at least one antibiotic that is efficacious in humans. (An "antibiotic that is efficacious in a human" as used herein is an antibiotic that has been used to successfully treat bacterial infections in a human).

In some embodiments of the compositions provided herein, one or more of the bacterial strains is a spore-former. In some embodiments of the compositions provided herein, one or more of the bacterial strains is in spore form. In some embodiments of the compositions provided herein, one or more of the bacterial strains is a non-spore former. In some embodiments, the compositions described herein comprise spore forming and non-spore forming bacterial strains. In some embodiments, the compositions described herein comprise spore-forming bacterial strains. In some embodiments, the compositions described herein comprise only spore-forming bacterial strains. In some embodiments, the compositions described herein comprise only non-spore forming bacterial strains. The spore-forming bacteria can be in spore form (i.e., as spores) or in vegetative form (i.e., as vegetative cells). In spore form, bacteria are generally more resistant to environmental conditions, such as heat, acid, radiation, oxygen, chemicals, and antibiotics. In contrast, in the vegetative state or actively growing state, bacteria are more susceptible to such environmental conditions, compared to in the spore form. In general, bacterial spores are able to germinate from the spore form into a vegetative/actively growing state, under appropriate conditions. For instance, bacteria in spore format may germinate when they are introduced in the intestine.

In some embodiments, at least one (e.g., 1, 2, 3, 4, 5, or more) of the bacterial strains in the composition is a spore former. In some embodiments, at least one (e.g., 1, 2, 3, 4, 5, or more) of the bacterial strains in the composition is in spore form. In some embodiments, at least one (e.g., 1, 2, 3, 4, 5, or more) of the bacterial strains in the composition is a non-spore former. In some embodiments, at least one (e.g., 1, 2, 3, 4, 5, or more) of the bacterial strains in the composition is in vegetative form (as discussed above, spore forming bacteria can also be in vegetative form). In some embodiments, at least one (e.g., 1, 2, 3, 4, 5, or more) of the bacterial strains in the composition is in spore form and at least one (e.g., 1, 2, 3, 4, 5, or more) of the bacterial strains in the composition is in vegetative form. In some embodiments, at least one bacterial strain that is considered able to form spores (i.e., a spore-former) but is present in the composition in vegetative form. In some embodiments, at least one bacterial strain that is considered able to form spores is present in the composition both in spore form and in vegetative form.

It is envisioned that the bacterial strains of the compositions provided herein are alive and will be alive when they reach the target area (e.g., the intestines). Bacterial spores are considered to be alive in this regards. In some embodiments, bacteria that are administered as spores may germinate in the target area (e.g., the intestines). It should further be appreciated that not all of the bacteria are alive and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

In any of the compositions provided herein, in some embodiments, the bacterial strains are purified. In any of the compositions provided herein, in some embodiments, the bacterial strains are isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals. As used herein, the term "isolated" bacteria that have been separated from one or more undesired component, such as another bacterium or bacterial strain, one or more component of a growth medium, and/or one or more component of a sample, such as a fecal sample. In some embodiments, the bacteria are substantially isolated from a source such that other components of the source are not detected. As also used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

In one aspect, the disclosure provides bacterial strains and mixtures of bacterial strains with unique biological properties. In some embodiments of the compositions provided herein, the composition induces proliferation and/or accumulation of CD8+ T-cells. In some embodiments, the bacterial strains of the compositions provided herein can induce proliferation and/or accumulation of CD8+ T-cells, because of the synergy between the bacterial strains. Thus, without being limiting to a specific mechanism, in some embodiments, the combination of the bacterial strains of the compositions provided herein act synergistically in the induction of proliferation and/or accumulation of CD8+ T-cells because the combination of the strains is particularly well-suited to generate metabolites and/or cellular signals that stimulate the induction of proliferation and/or accumulation of CD8+ T-cells. The bacterial compositions may do so, for instance through the use of nutrients in the intestinal tract (e.g., the colon or the cecum), and/or metabolic interactions that result in metabolites and/or cellular signals that stimulate the induction of proliferation and/or accumulation of CD8+ T-cells. In addition, without being limiting to a specific mechanism, in some embodiments, the combination of the bacterial strains of the compositions provided herein act synergistically in the induction of proliferation and/or accumulation of CD8+ T-cells because the combination of the strains is superior in engrafting specific niches in the intestinal tract (e.g., the colon or the cecum) that will result in the induction of proliferation and/or accumulation of CD8+ T-cells (e.g., by providing a favorable microenvironment). In some embodiments, the combination of the bacterial strains of the compositions provided herein act synergistically in the induction of proliferation and/or accumulation of CD8+ T-cells because the combination of the strains is particularly well-suited to generate metabolites and/or cellular signals that stimulate the induction of proliferation and/or accumulation of CD8+ T-cells, and the combination is well suited to engraft in specific niches, that result in localization of the metabolites and/or cellular signals to a target for the induction of proliferation and/or accumulation of CD8+ T-cells Treatment of Diseases Cancer In one aspect, the disclosure includes compositions and methods for the treatment of diseases in a subject. In some embodiments of the methods provided herein, the subject has cancer. In one aspect, the cancers that can be treated according to the compositions and methods provided herein, include without limitation, carcinoma, glioma, mesothelioma, melanoma, lymphoma, leukemia, adenocarcinoma, breast cancer, ovarian cancer, cervical cancer, glioblastoma, multiple myeloma, prostate cancer, Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease, AIDS-associated primary effusion lymphoma, neuroectodermal tumors, or rhabdomyosarcoma. In some embodiments of the methods provided herein, the cancer is prostate cancer, bladder cancer, non-small cell lung cancer, urothelial carcinoma, melanoma, or renal cell carcinoma. In some embodiments of the methods provided herein, the subject is undergoing radiation treatment.

In some embodiments of the methods provided herein, the method further includes administering one or more anticancer agents. In some embodiments of the methods provided herein, the anticancer agent is a chemotherapy agent. In some embodiments of the methods provided herein, the anticancer agent is a cancer immunotherapy agent. In some embodiments of the methods provided herein, the cancer immunotherapy agent is an immune checkpoint inhibitor. In some embodiments of the methods provided herein, the immune checkpoint inhibitor is a PD-1 inhibitor, PD-L-1 inhibitor, or CTLA-4 inhibitor. In some embodiments of the methods provided herein, the immune checkpoint inhibitor is a PD-1 inhibitor. In some embodiments of the methods provided herein, the immune checkpoint inhibitor is a CTLA-4 inhibitor.

In some embodiments of the methods provided herein, the cancer immunotherapy agent is a cancer vaccine that acts to increase the response of a subject's immune system to cancer cells. For example, cancer vaccines include cancer antigen(s) that act to induce or stimulate an immune response against cells bearing the cancer antigen(s). The immune response induced or stimulated can include an antibody (humoral) immune response and/or a T-cell (cell-mediated) immune response. CD8+ T-cells can differentiate into cytotoxic T-cells that kill target cells bearing the antigen recognized by CD8+ T-cells. Induction of CD8+ T-cells can, therefore, enhance the immune response to cancer antigens provided in a cancer vaccine. In some embodiments of the methods provided herein, the cancer immunotherapy agent is a CAR-T therapeutic. CAR-T cells include T-cells taken from a patient that are genetically engineered to produce chimeric antigen receptors (CARs) on their surface. The CARs are engineered to recognize a specific antigen on cancer cells. After the CAR-T cells are infused into the patient, they recognize and kill cancer cells that express the specific antigen on their surfaces. Induction of CD8+ T-cells is useful to provide cells for conversion into CAR-T cells.

In some embodiments of the methods provided herein, the method further includes administering one or more cytokines. In some embodiments of the methods provided herein the cytokine is IL-2, IL-15, or IL-21. In some embodiments of the methods provided herein, the method further includes administering one or more costimulatory agents. In some embodiments of the methods provided herein the costimulatory agent is a CD-28, OX-40, 4-1BB, or CD40 antibody. In some embodiments of the methods provided herein, the method further includes administering one or more vaccines. In some embodiments of the methods provided herein, the vaccine is a dendritic cell vaccine. In some embodiments of the methods provided herein, the method further includes administering adoptive cell transfer therapy. In some embodiments of the methods provided herein, the adoptive cell transfer therapy is the use of engineered T-cell receptors or chimeric antigen receptors.

In some embodiments of the compositions provided herein, the composition further comprises one or more anticancer agents. In some embodiments of the compositions provided herein, the anticancer agent is a chemotherapy agent. In some embodiments of the compositions provided herein, the anticancer agent is cancer immunotherapy agent. In some embodiments of the compositions provided herein, the cancer immunotherapy agent is an immune checkpoint inhibitor. In some embodiments of the compositions provided herein, the immune checkpoint inhibitor is a PD-1 inhibitor, PD-L-1 inhibitor, or CTLA-4 inhibitor. In some embodiments of the compositions provided herein, the immune checkpoint inhibitor is a PD-1 inhibitor, PD-L-1 inhibitor, CTLA-4 inhibitor, IDO1 inhibitor, LAG3 inhibitor or TIM3 inhibitor. In some embodiments of the compositions provided herein, the immune checkpoint inhibitor is a PD-1 inhibitor. In some embodiments, the PD-1 inhibitor is nivolumab. In some embodiments, the PD-1 inhibitor is pembrolizumab. In some embodiments, the PD-1 inhibitor is pidiluzimab. In some embodiments of the compositions provided herein, the immune checkpoint inhibitor is a PD-L-1 inhibitor. In some embodiments, the PD-L-1 inhibitor is atezolizumab. In some embodiments, the PD-L-1 inhibitor is avelumab. In some embodiments, the PD-L-1 inhibitor is durvalumab. In some embodiments of the methods provided herein, the immune checkpoint inhibitor is a CTLA-4 inhibitor. In some embodiments, the CTLA-4 inhibitor is an anti-CTLA-4 antibody. Examples of anti-CTLA-4 antibodies include, without limitation, ipilimumab, tremelimumab (CP-675,206), 9H10, 4F10, and 9D9. In some embodiments, the CTLA-4 inhibitor is ipilimumab. In some embodiments, the CTLA-4 inhibitor is tremelimumab. It should further be appreciated that multiple anticancer agents (e.g., immune checkpoint inhibitors) may be included in the compositions and methods disclosed herein. For instance, in a non-limiting example, the compositions and methods disclosed include both a PD-1 inhibitor and a CTLA-4 inhibitor.

In one aspect, the disclosure provides a composition comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*, and a PD-1 inhibitor. In one aspect, the disclosure provides a composition comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*, and a PD-L-1 inhibitor. In one aspect, the disclosure provides a composition comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*, and a CTLA-4 inhibitor.

In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a PD-1 inhibitor. In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a PD-L-1 inhibitor. In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a CTLA-4 inhibitor.

In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a PD-1 inhibitor. In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a PD-L-1 inhibitor. In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a CTLA-4 inhibitor.

In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, and a PD-1 inhibitor. In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, and a PD-L-1 inhibitor. In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, and a CTLA-4 inhibitor.

In some embodiments of the compositions provided herein, the composition further includes one or more cytokines. In some embodiments of the compositions provided herein, the cytokine is IL-2, IL-15, or IL-21. In some embodiments of the compositions provided herein, the composition further comprises one or more costimulatory agents. In some embodiments of the compositions provided herein, the costimulatory agent is a CD-28, OX-40, 4-1BB, or CD40 antibody. In some embodiments of the compositions provided herein, the composition further comprises one or more vaccines. In some embodiments of the compositions provided herein, the vaccine is a dendritic cell vaccine. In some embodiments of the compositions provided herein, the composition is combined with adoptive cell transfer therapy. In some embodiments of the compositions provided herein, the adoptive cell transfer therapy is the use of engineered T-cell receptors or chimeric antigen receptors.

Infectious Disease

In one aspect, the disclosure includes compositions and methods for the treatment of diseases in a subject. In some embodiments of the methods provided herein, the subject has an infectious disease. In some embodiments of the methods provided herein, the infectious disease is a bacterial infection, a viral infection, a parasitic infection, or a fungal infection. In some embodiments of the methods provided herein, the infectious disease is a viral infection. In some embodiments of the methods provided herein, the viral infection is HIV. In some embodiments of the methods provided herein, the infection is an infection by a hepatitis virus. In some embodiments, the compositions provided herein can be used as a pharmaceutical composition for preventing or treating (reducing, partially or completely the adverse effects of) an infectious disease, such as a bacterial infection, a viral infection, a parasitic infection, and a fungal infection.

Bacterial infections that can be treated according to the methods provided herein include, but are not limited to *P. aeruginosa, E. coli, C. tetani, N. gonorrhoeae, C. botulinum, Klebsiella* sp., *Serratia* sp., *Pseudomanas* sp., *P. cepacia, Acinetobacter* sp., *S. epidermis, E. faecalis, S. pneumonias, S. aureus, S. mutans, Haemophilus* sp., *Neisseria* Sp., *N. meningitides, Bacteroides* sp., *Citrobacter* sp., *Branhamella* sp., *Salmonella* sp., *Shigella* sp., *S. pyogenes, Proteus* sp., *Clostridium* sp., *Erysipelothrix* sp., *Listeria* sp., *Pasteurella multocida, Streptobacillus* sp., *Spirillum* sp., *Fusospirocheta* sp., *Treponema pallidum, Borrelia* sp., *Actinomycetes, Mycoplasma* sp., *Chlamydia* sp., *Rickettsia* sp., *Spirochaeta, Borellia burgdorferi, Legionella* sp., *Mycobacteria* sp, *Ureaplasma* sp, *Streptomyces* sp., *Trichomoras* sp., *P. mirabilis; Vibrio cholera*, enterotoxigenic *Escherichia coli, Clostridium difficile, Salmonella typhi, C. diphtheria, Mycobacterium leprae, Mycobacterium lepromatosi*. Bacterial infections caused by drug resistant bacteria that can be treated according to the methods provided herein include, but are not limited to *Clostridium perfringens; Clostridium botulinum; Clostridium tributrycum; Clostridium sporogenes; Escherichia coli; Pseudomonas aeruginosa*, such as Multidrug Resistant *Pseudomonas aeruginosa*; Vancomycin Resistant Enterococci (VRE); Carbapenem Resistant Enterobacteriaceae (CRE); *Neisseria gonorrheae; Acinetobacter,* Multidrug Resistant *Acinetobacter; Campylobacter*; Multidrug-resistant *Campylobacter; Candida*, Fluconazole-Resistant *Candida*, Extended spectrum beta-lactamase (ESBL) producing Enterobacteriaceae; *Salmonella, Salmonella Typhimurium*, Drug resistant non-typhoid *Salmonella* spp.; Drug resistant *Salmonella Typhi*; Drug resistant *Shigella; Staphylococcus aureus*, such as Methicillin Resistant *S. aureus* or vancomycin resistant *S. aureus*; Drug resistant *Streptococcus pneumoniae*; Drug resistant Tuberculosis; Erythromycin Resistant Group A *Streptococcus*; Clindamycin resistant Group B *Streptococcus*, and any combinations thereof.

Viral infections that can be treated according to the methods provided herein include, but are not limited to, picornaviridae, caliciviridae, togaviridae, flaviviridae, coronaviridae, rhabdoviridae, filoviridae, paramyxoviridae, orthomyxoviridae, bunyaviridae, arenaviridae, reoviridae, retroviridae, hepadnaviridae, parvoviridae, papovaviridae, adenoviridae, herpesviridae, poxviridae, rotavirus, parainfluenza virus, influenza virus A and B, hepatitis virus, syphilis, HIV, rabies virus, Epstein-Barr virus, and herpes simplex virus.

Viral infections that can be treated according to the methods provided herein include, but are not limited to *Plasmodium falciparum, P. vivax, P. ovale, P. malaria, Toxoplasma gondii, Leishmania mexicana, L. tropica, L. major, L. aethiopica, L. donovani, Trypanosoma cruzi, T. brucei, Schistosoma mansoni, S. haematobium, S. japonium, Trichinella spiralis, Wuchereria bancrofti, Brugia malayli, Entamoeba histolytica, Enterobius vermiculoarus, Taenia solium, T. saginata, Trichomonas vaginatis, T. hominis, T. tenax; Giardia lamblia, Cryptosporidium parvum, Pneumocytis carinii, Babesia bovis, B. divergens, B. microti, Isospore belli, L. hominis, Dientamoeba jragiles, Onchocerca volvulus, Ascaris lumbricoides, Necator americanis, Ancylostoma duodenale, Strongyloides stercoralis, Capillaria philippinensis, Angiostrongylus cantonensis, Hymenolepis nana, Diphyllobothrium latum, Echinococcus granulosus, E. multilocularis, Paragonimus westermani, P. caliensis, Chlonorchis sinensis, Opisthorchis felineas, G. Viverini, Fasciola hepatica, Sarcoptes scabiei, Pediculus humanus, Phthirius pubis*, and *Dermatobia hominis*.

Fungal infections that can be treated according to the methods provided herein include, but are not limited to *Cryptococcus neoformans, Blastomyces dermatitidis, Aiellomyces dermatitidis, Histoplasfria capsulatum, Coccidioides immitis, Candida* species, including *C. albicans, C. tropicalis, C. parapsilosis, C. guilliermondii* and *C. krusei, Aspergillus* species, including *A. fumigatus, Aflavus, A. niger, Rhizopus* species, *Rhizomucor* species, *Cunninghammella* species, *Apophysomyces* species, including *A. saksenaea, A. mucor* and *A. absidia, Sporothrix schenckii, Paracoccidioides brasiliensis, Pseudallescheria boydii, Torulopsis glabrata*; and *Dermatophyres* species.

In one aspect, the disclosure provides a vaccine comprising any of the compositions provided herein and an antigen. In some embodiments of the vaccines provided herein, the antigen is an HIV antigen. In some embodiments of the vaccines provided herein, the antigen is a hepatitis antigen. In some embodiments, the bacterial compositions are administered as an adjuvant in combination with antigenic material. The antigenic material can include one or more portions of the protein coat, protein core, or functional proteins and peptides of a pathogen, or a full pathogen (live, killed, inactivated, or attenuated), or may comprise one or a plurality of cancer epitopes or cancer antigens. The antigenic material can be co-administered, administered before, or after the bacterial composition. The bacterial composition may also be administered with existing mucosal vaccines such as influenza vaccines, (e.g. FluMist from Medimmune or NASOVAC from Serum Institute of India), rotavirus vaccines (e.g. RotaTeq from Merck or Rotarix from GlaxoSmithKline), typhoid vaccines (e.g. Vivotif from Crucell, Ty21A), cholera vaccines (e.g. Orochol from Crucell, Shanchol from Shantha Biotechnics), traveller's diarrhea vaccines (e.g. Dukoral from Crucell), and with antigens of live attenuated Influenza A virus HI strain, live attenuated Influenza A virus H3 strain, Influenza B virus, live attenuated H1N1 influenza virus (swine flu), live attenuated rotavirus, mono- and multi-valent poliovirus, live attenuated *Salmonella Typhi*, live recombinant *Vibrio cholerae* lacking cholera toxin subunit A, whole killed *Vibrio cholerae* 01 classical and El Tor biotypes with or without cholera toxin subunit B, cancer antigens, cancer epitopes, and combinations thereof.

Autoimmune Disease or Allergic Disease

In one aspect, the disclosure includes compositions and methods for the treatment of diseases in a subject. In some embodiments of the methods provided herein, the subject has an autoimmune disease or an allergic disease. The compositions and methods of the current disclosure can be used for preventing or treating autoimmune disease and allergic disease. Autoimmune disease that can be treated include, but are not limited to, inflammatory bowel disease, systemic lupus erythematosus, rheumatoid arthritis, multiple sclerosis, or Hashimoto's disease. Allergic diseases that can be treated include, but are not limited to, food allergy, pollenosis, or asthma.

Additional examples of autoimmune and allergic disease that can be treated according to the methods and compositions provided herein include, without limitation, rejection in organ transplantations, such as inflammatory bowel disease (IBD), ulcerative colitis, Crohn's disease, sprue, autoimmune arthritis, rheumatoid arthritis, Type I diabetes, multiple sclerosis, graft vs. host disease following bone marrow transplantation, osteoarthritis, juvenile chronic arthritis, Lyme arthritis, psoriatic arthritis, reactive arthritis, spondyloarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn purpurea, microscopic vasulitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, *chlamydia, yersinia* and *salmonella* associated arthropathy, spondyloarhopathy, atheromatous disease/arteriosclerosis, allergic colitis, atopic allergy, food allergies such as peanut allergy, tree nut allergy, egg allergy, milk allergy, soy allergy, wheat allergy, seafood allergy, shellfish allergy, or sesame seed allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis *nigricans*, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis (all subtypes), insulin dependent diabetes mellitus, sympathetic ophthalmia, pulmonary hypertension secondary to connective tissue disease, Goodpasture's syndrome, pulmonary manifestation of polyarteritis nodosa, acute rheumatoid fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, eosinophilic gastroenteritis, and diarrhea.

In some embodiments of the methods and compositions provided herein, the composition further comprises one or more anti-inflammatory agents. In some embodiments of the methods and compositions provided herein, the anti-inflammatory agent is a non-steroidal anti-inflammatory drug (NSAID). Exemplary NSAIDs include, but are not limited to, aspirin, ibuprofen, naproxen, celecoxib, rofecoxib, diclofenac, diflunisal, etodolac, fenoprofen, flurbiprofen, ketoprofen, ketorolac, mefenamic acid, meloxicam, nabumetone, oxaprozin, piroxicam, sulindac, tolmetin and combinations thereof. In some embodiments, the NSAID is an immune selective anti-inflammatory derivative (ImSAID).

Treatment of Disease

In one aspect, the disclosure provides compositions and methods of treatment for disease in a subject. In one aspect, and without being limiting, the compositions disclosed herein can treat disease because their administration results in the induction of proliferation and/or accumulation of CD8+ T-cells. In some embodiments, the disclosure provides compositions and methods of treatment for disease in a subject for diseases that can be treated by the induction of proliferation and/or accumulation of CD8+ T-cells. In some embodiments, the diseases that can be treated by the induction of proliferation and/or accumulation of CD8+ T-cell is cancer, an infectious disease, an autoimmune disease or allergic disease.

In one aspect, the disclosure provides a method of treating a disease in a subject comprising administering any of the compositions provided herein to the subject in an effective amount to treat the disease. In some embodiments of the methods provided herein, the administration of the composition to the subject results in the induction of proliferation and/or accumulation of CD8+ T-cells in the intestine of the subject. In some embodiments of the methods provided herein, the proliferation and/or accumulation of CD8+ T-cells in the intestine of the subject is increased by at least 10%, at least 20%, at least 30%, at least 40%, at least 50%, at least 100%, or at least 200% when compared to the proliferation and/or accumulation of CD8+ T-cells in the intestine of the subject before the administration of the composition In some embodiments of the methods provided herein, the administration of the composition to the subject results in an increase of IFNγ production in the intestine of the subject when compared to the IFNγ production in the intestine of the subject before the administration of the composition. In some embodiments of the methods provided herein, the administration of the composition to the subject results in an increase of IFNγ production in the intestine of the subject by at least 10%, at least 20%, at least 30%, at least 40%, at least 50%, at least 100%, or at least 200% when compared to the IFN production in the intestine of the subject before the administration of the composition.

Any of the compositions described herein may be administered to a subject in a therapeutically effective amount or a dose of a therapeutically effective amount to treat or prevent a disease (e.g., cancer or infectious disease). The terms "treat" or "treatment" refer to reducing or alleviating one or more of the symptoms associated with a disease (e.g., cancer or infectious disease). The terms "prevent" or "prevention" encompass prophylactic administration and may reduce the incidence or likelihood of the occurrence of the disease (e.g., cancer or infectious disease). For instance, in some embodiments, administration of the compositions provided herein result in a healthy microbiome that induces proliferation and/or accumulation of CD8+ T-cells thereby protecting a subject against cancer and/or infectious disease.

As used herein, a "therapeutically effective amount" of composition, such as a pharmaceutical composition, is any amount that results in a desired response or outcome in a subject, such as those described herein, including but not limited to prevention of infection, an immune response or an enhanced immune response and/or augmentation of cancer treatment. It should be appreciated that the term effective amount may be expressed in number of bacteria or CFUs to be administered. It should further be appreciated that the bacteria can multiply once administered. Thus, administration of even a relatively small amount of bacteria may have therapeutic effects.

In some embodiments, the therapeutically effective amount of any of the compositions described herein is an amount sufficient to treat the disease, e.g., enhance survival of the subject, suppress an infection and/or treat the cancer.

Any of the methods described herein may be for the treatment of cancer in a subject. As used herein, methods of treating cancer involve relieving or alleviating at least one symptom associated with the cancer, or slowing or reversing the cancer progression. A method of treating cancer may, for example, eliminate or reduce a subject's tumor burden, reduce the number or replication of cancer cells, and/or prevent, delay or inhibit metastasis.

Also provided herein are methods for the treatment or prevention of an infectious disease in a subject. As used herein, methods of treating an infectious disease may involve relieving or alleviating at least one symptom associated with infection, or slowing or reversing the progression of the infection. A method of treating an infectious disease may, for example, eliminate or reduce the load of an infectious organism (e.g., bacteria, virus, fungus, or parasite), or inhibit or reduce one or more symptoms of the infection. As also used herein, the terms "prevent," "prevention," and "preventing," include the administration of a composition to a subject to reduce, or delay the onset of the manifestation of clinical or subclinical symptoms, complications, pathologies or biochemical indicia of the infection, or to reduce or inhibit the spread/transmission of the infectious organism (e.g., bacteria, virus, fungus, or parasite).

Aspects of the present disclosure are related to methods for treating a disease or condition in a subject by administering a therapeutically effective amount of any of the compositions described herein. In some embodiments, the subject is a mammalian subject, such as a human, non-human primate, rodent, rabbit, sheep, pig, dog, cat, horse, or cow. In some embodiments, the subject is a human subject. The compositions and methods described herein may be utilized in conjunction with other types of therapy (i.e., combination treatment), such as additional therapeutic agents. Examples of additional combination therapies include, without limitation, surgery, radiation, gene therapy, and administration of additional therapeutic agents, such as chemotherapeutics, antibiotics, antivirals, anti-fungals, anti-parasitics, immunomodulatory agents, anti-inflammatory agents. In general, combination therapies can be administered simultaneously or sequentially (in any order) with the compositions and methods described herein. In some embodiments, any of the compositions described herein is administered simultaneously with one or more additional therapeutic agents, for example in a single dose or in multiple doses that are administered at substantially the same time.

In some embodiments, the compositions described herein are administered to a subject concomitantly with one or more additional therapeutic agents. In some embodiments, the compositions described herein are administered to a subject followed by administration of one or more additional therapeutic agent. In some embodiments, any of the compositions described herein is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of the one or more additional therapeutic agent. Alternatively, in some embodiments, one or more therapeutic agent administered to a subject followed by administration of any of the compositions described herein. In some embodiments, one or more therapeutic agent is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of any the compositions described herein.

Additional Methods

Also within the scope of the present disclosure are methods of assessing whether one or more bacterial strains of any of the compositions described herein are present in the intestine of a subject. In some embodiments, if fewer than a threshold number of bacterial strains are detected in the intestine of the subject, any of the compositions described herein are administered to the subject to increase the number of the bacterial strains in the intestine of the subject. In some embodiments, the method further comprises identifying the subject as a candidate for a treatment of the disease based on the number of bacterial strains detected in the intestine. Measuring the levels of the biomarker sets may also be useful in the evaluation and treatment of a disease. In general, the bacterial population of the intestine (e.g., presence or absence of one or more bacterial strains) may be determined by assessing a sample obtained from the subject, such as a fecal sample.

In some embodiments of the compositions provided herein, administration of the composition to a subject results in the induction of proliferation and/or accumulation of CD8+ T-cells in the intestine of the subject. In some embodiments of the compositions provided herein, administration of the composition to a subject results in an increase in IFNγ production in the intestine of a subject. In some embodiments of the compositions provided herein, administration of the composition to a subject results in the presence of one or more bacterial strains of the administered composition in the intestine of the subject. In some embodiments of the compositions provided herein, the one or more bacterial strains of the administered composition was not previously present in the intestine of the subject. In some embodiments of the compositions provided herein, administration of the composition to a subject results in the engraftment of one or more bacterial strains of the administered composition in the intestine of the subject. In some embodiments of the compositions provided herein, the one or more bacterial strains of the administered composition was not previously engrafted in the intestine of the subject. In some embodiments of the compositions provided herein, administration of the composition to a subject results in an increase in the number of the bacterial strains of the administered composition in the intestine of the subject. In some embodiments of the compositions provided herein, administration of the composition to a subject results in an increase in the engrafted number of the bacterial strains of the administered composition in the intestine of the subject. In some embodiments of the compositions provided herein, administration of the composition to a subject results in an increase in the abundance of total bacteria of the bacterial strains of the administered composition in the intestine of the subject. In some embodiments of the compositions provided herein, administration of the composition to a subject results in an increase in the engrafted total bacterial strains of the administered composition in the intestine of the subject.

In one aspect, the disclosure provides a method that includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject. In some embodiments of the methods provided herein, the subject is undergoing, or will be undergoing, cancer treatment. In one aspect, the disclosure provides a method for determining if a subject is expected to respond positively to cancer treatment, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the subject is not expected to respond positively to cancer treatment. In some embodiments of the methods provided herein, the cancer treatment is cancer immunotherapy treatment.

In one aspect, the disclosure provides a method for reducing the risk of a viral infection in a subject, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject, thereby reducing the risk of a viral infection in the subject. In some embodiments of the methods provided herein, determining the presence of one or more of the bacterial species is done by sequencing fecal matter of the subject.

Pharmaceutical Compositions

In one aspect, the disclosure provides pharmaceutical compositions comprising the bacterial strains and combinations of bacterial strains provided herein. In some embodiments of the compositions provided herein, the composition is a pharmaceutical composition. In some embodiments of the pharmaceutical compositions provided herein, the pharmaceutical composition comprises a pharmaceutically acceptable excipient. In some embodiments of the pharmaceutical compositions provided herein, the pharmaceutical composition is formulated for oral administration. In some embodiments of the pharmaceutical compositions provided herein, the pharmaceutical composition is formulated for rectal administration. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon. In some embodiments of the pharmaceutical compositions provided herein, one or more of the bacterial strains is lyophilized. In some embodiments of the pharmaceutical compositions provided herein, the pharmaceutical composition is in the form of a capsule. In some embodiments of the pharmaceutical compositions provided herein, the pharmaceutical composition further comprises a pH sensitive composition comprising one or more enteric polymers.

Any of the compositions described herein, including the pharmaceutical compositions and food products comprising the compositions, may contain bacterial strains in any form, for example in an aqueous form, such as a solution or a suspension, embedded in a semi-solid form, in a powdered form or freeze dried form. In some embodiments, the composition or the bacterial strains of the composition are lyophilized. In some embodiments, a subset of the bacterial strains in a composition is lyophilized. Methods of lyophilizing compositions, specifically compositions comprising bacteria, are well known in the art. See, e.g., U.S. Pat. Nos. 3,261,761; 4,205,132; PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strain or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

The bacterial strains of the composition can be manufactured using fermentation techniques well known in the art. In some embodiments, the active ingredients are manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art. In some embodiments, the composition of bacterial strains may be formulated for administration as a pharmaceutical composition. The term "pharmaceutical composition" as used herein means a product that results from the mixing or combining of at least one active ingredient, such as any two or more purified bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

In some embodiments, the bacteria are formulated for delivery to the intestines (e.g., the small intestine and/or the colon). In some embodiments, the bacteria are formulated with an enteric coating that increases the survival of the bacteria through the harsh environment in the stomach. The enteric coating is one which resists the action of gastric juices in the stomach so that the bacteria which are incorporated therein will pass through the stomach and into the intestines. The enteric coating may readily dissolve when in contact with intestinal fluids, so that the bacteria enclosed in the coating will be released in the intestinal tract. Enteric coatings may consist of polymer and copolymers well known in the art, such as commercially available EUDRAGIT (Evonik Industries). (See e.g., Zhang, AAPS PharmSciTech, 2016, 17 (1), 56-67).

The bacteria may also be formulated for rectal delivery to the intestine (e.g., the colon). Thus, in some embodiments, the bacterial compositions may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., Int J Pharm 2015, 487 (1-2): 314-9).

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease. Another example of a system enabling the delivery to the intestine (e.g., the colon) is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose). A further example of a system enabling the delivery of a composition to the intestine (e.g., the colon), is a composition that includes a coating that can be removed by an enzyme present in the gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or the colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon). The compositions comprising bacterial strains are formulated into pharmaceutically acceptable dosage forms by conventional methods known to those of skill in the art. Dosage regimens are adjusted to provide the optimum desired response (e.g., the prophylactic or therapeutic effect). In some embodiments, the dosage form of the composition is a tablet, pill, capsule, powder, granules, solution, or suppository. In some embodiments, the pharmaceutical composition is formulated for oral administration. In some embodiments, the pharmaceutical composition is formulated such that the bacteria of the composition, or a portion thereof, remain viable after passage through the stomach of the subject. In some embodiments, the pharmaceutical composition is formulated for rectal administration, e.g. as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect (e.g., treatment of a pathogenic infection, reduction of bacterial burden of pathogenic infection, reduction or inhibition of toxin production) is achieved. In general, effective doses of the compositions disclosed herein, for the prophylactic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy. In some embodiments, the dosing regimen entails oral administration of a dose of any of the compositions described herein. In some embodiments, the dosing regimen entails oral administration of multiple doses of any of the compositions described herein. In some embodiments, the composition is administered orally the subject once, twice, 3 times, 4 times, 5 times, 6 times, 7 times, 8 times, 9 times, or at least 10 times.

The compositions, including the pharmaceutical compositions disclosed herein, include compositions with a range of active ingredients (e.g., live bacteria, bacteria in spore format). The amount of bacteria in the compositions may be expressed in weight, number of bacteria and/or CFUs (colony forming units). In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacteria of the composition per dosage amount. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacteria per dosage amount. It should further be appreciated that the bacteria of the compositions may be present in different amounts. Thus, for instance, as a non-limiting example, a composition may include $10^3$ of bacteria A, $10^4$ of bacteria B and $10^6$ of bacteria C. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs of each of the bacteria in the composition per dosage amount. In some embodiments, the pharmaceutical compositions disclosed herein contain about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs in total for all of the bacteria combined per dosage amount. As discussed above, bacteria of the compositions may be present in different amounts. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams of each of the bacteria in the composition per dosage amount. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams in total for all of the bacteria combined per dosage amount. In some embodiment, the dosage amount is one administration device (e.g., one table, pill or capsule). In some embodiment, the dosage amount is the amount that is administered in a particular period (e.g., one day or one week).

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total bacteria per dosage amount.

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between 104 and 105, between 10 and 104, between 102 and 104, between $10^3$ and $10^4$, between 10 and $10^3$, between $10^2$ and $10^3$, or between 10 and $10^2$ CFUs of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total CFUs per dosage amount.

In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of each of the bacteria in the composition per dosage amount. In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of all of the bacteria combined per dosage amount.

In one aspect, the disclosure provides a food product comprising any of the compositions provided herein and a nutrient. Also with the scope of the present disclosure are food products comprising any of the bacterial strains described herein and a nutrient. Food products are, in general, intended for the consumption of a human or an animal. Any of the bacterial strains described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

Food products containing bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product. Examples of food products which may be formulated to contain any of the bacterial strains described herein include, without limitation, a beverage, a drink, a bar, a snack, a dairy product, a confectionery product, a cereal product, a ready-to-eat product, a nutritional formula, such as a nutritional supplementary formulation, a food or beverage additive.

In some embodiments, the subject has not received a dose of an antibiotic prior to administration of the bacterial composition. In some embodiments, the subject has not been administered an antibiotic at least 1, at least 2, at least 3, at least 5, at least 10, at least 15, at least 20, at least 25, at least 30, at least 60, at least 90, at least 120, at least 180 or at least 360 days prior to administration of the compositions provided herein. In some embodiments, the subject may be administered one or more doses of an antibiotic prior to or concurrently with a bacterial composition. Antibiotics may be administered for a variety of reasons. For instance, antibiotics may be administered to remove bacterial species from the colon and/or intestine prior to administration of the bacterial compositions provided herein. Antibiotics may also be administered to suppress unwanted infections in the case of cancer treatment. In some instances, antibiotics may be administered as a treatment method for an infectious disease. In some embodiments, the subject is administered a single dose of an antibiotic prior to the bacterial composition. In some embodiments, the subject is administered multiple doses of an antibiotic prior to the bacterial composition. In some embodiments, the subject is administered at least 2, 3, 4, 5 or more doses of an antibiotic prior to the bacterial composition. In some embodiments, the subject is administered a dose of an antibiotic at substantially the same time as the bacterial composition. Examples of antibiotics that can be administered include, without limitation, kanamycin, gentamicin, colistin, metronidazole, vancomycin, clindamycin, fidaxomicin, and cefoperazone.

Diagnostics and Prognostic Methods

Also described herein are diagnostic methods (e.g., companion diagnostics) for use in determining whether a subject should receive a treatment, such as a composition as described herein and/or any of the immune checkpoint inhibitors described herein. Such methods can be used for diagnosing a disease, monitoring the progress of a disease, assessing the efficacy of a treatment for the disease, and/or identifying patients suitable for a particular treatment. Accordingly, the methods described herein are based on the level of a marker in a sample (e.g., a biological sample containing lymphocytes) obtained from a subject. In some embodiments, the methods involve analyzing the presence and/or level of a marker in one or more samples from a subject.

In some embodiments, the level of the marker in a sample obtained from a subject can then be compared with a reference sample or a control sample to determine a value indicating the amount of the marker in the sample. In some embodiments, a value for a marker is obtained by comparing the level of a marker in a sample to the level of another marker (e.g., an internal control or internal standard) in the sample. The value of the marker can be compared to a reference value to determine whether the subject has or is at risk for the disease. In some embodiments, the level of the marker is compared to a predetermined threshold for the marker, a deviation from which may indicate the subject has a disease. In some embodiments, if the level or value of the marker is higher than a reference level or value, the subject can be identified as having or at risk for a disease, as described herein. In some embodiments, if the level or value of the marker is lower than a reference level or value, the subject can be identified as having or at risk for a disease, as described herein. In some embodiments, the level of the marker in a sample from a subject is compared to the level of the marker in another sample obtained from the same subject, for example, a sample obtained from the subject at a different time. In some embodiments, the level of the marker in a sample from a subject is compared to the level of the marker in a sample obtained from the subject at an earlier time, such as prior to administration of any of the compositions described herein. In some embodiments, the level of the marker in a sample from a subject is compared to the level of the marker in a sample obtained from the subject at a later time, such as after administration of any of the compositions described herein.

In some embodiments, if the level or value of the marker is higher in a sample as compared to the level or value of the marker in a sample from the subject obtained prior to administration of a composition described herein, the subject is administered an immune checkpoint inhibitor and a composition described herein. In some embodiments, if the level or value of the marker is higher in a sample as compared to the level or value of the marker in a sample from the subject obtained prior to administration of a composition described herein, the subject continues a therapy involving administration of an immune checkpoint inhibitor and a composition described herein. In some embodiments, the level or value of the marker in a sample is enhanced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of the marker in a sample prior to administration of a composition as described herein.

In some embodiments, if the level or value of the marker is not increased (e.g., equal to or lower) in a sample as compared to the level or value of the marker in a sample from the subject obtained prior to administration of a composition described herein, administration of an immune checkpoint inhibitor and a composition described herein is discontinued. In some embodiments, if the level or value of the marker is not increased (e.g., equal to or lower) in a sample as compared to the level or value of the marker in a sample from the subject obtained prior to administration of a composition described herein, the administration of an immune checkpoint inhibitor and a composition described herein is reanalyzed after administration of a composition as described herein. In some embodiments, the level or value of the marker in a sample is reduced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of the marker in a sample prior to administration of a composition as described herein. In some embodiments, the level of the marker is determined by analyzing the expression of the marker (e.g., protein or nucleic acid level) and/or the cell type in which the marker is expressed. Any method known the art may be used to analyze the expression of the marker and/or cell type in which the marker is expressed.

Also provided herein are methods based on the level or degree of IFNγ production in a sample (e.g., a biological sample containing splenocytes) obtained from a subject. In some embodiments, the methods involve analyzing the presence and/or level of IFN production in one or more samples from a subject. In some embodiments, the level of IFNγ production in a sample obtained from a subject can then be compared with a reference sample or a control sample to determine a value indicating the amount of the IFNγ production in the sample. In some embodiments, a value for IFNγ production is obtained by comparing the level of IFN production in a sample to the level of another molecule (e.g., an internal control or internal standard) in the sample. The value of IFNγ production can be compared to a reference value to determine whether the subject has or is at risk for the disease. In some embodiments, the level of IFNγ production is compared to a predetermined threshold for IFNγ production, a deviation from which may indicate the subject has a disease. In some embodiments, if the level or value of IFNγ production is higher than a reference level or value, the subject can be identified as having or at risk for a disease, as described herein. In some embodiments, if the level or value of IFNγ production is lower than a reference level or value, the subject can be identified as having or at risk for a disease, as described herein.

In some embodiments, the level of IFNγ production in a sample from a subject is compared to the level of IFNγ production in another sample obtained from the same subject, for example, a sample obtained from the subject at a different time. In some embodiments, the level of IFNγ production in a sample from a subject is compared to the level of IFNγ production in a sample obtained from the subject at an earlier time, such as prior to administration of any of the compositions described herein. In some embodiments, the level of IFNγ production in a sample from a subject is compared to the level of IFNγ production in a sample obtained from the subject at a later time, such as after administration of any of the compositions described herein. In some embodiments, if the level or value of IFNγ production is higher in a sample as compared to the level or value of IFNγ production in a sample from the subject obtained prior to administration of a composition described herein, the subject is administered an immune checkpoint inhibitor and a composition described herein. In some embodiments, if the level or value of IFNγ production is higher in a sample as compared to the level or value of IFNγ production in a sample from the subject obtained prior to administration of a composition described herein, the subject continues a therapy involving administration of an immune checkpoint inhibitor and a composition described herein. In some embodiments, the level or value of IFN production in a sample is enhanced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of IFNγ production in a sample prior to administration of a composition as described herein.

In some embodiments, if the level or value of IFNγ production is not increased (e.g., equal to or lower) in a sample as compared to the level or value of IFNγ production in a sample from the subject obtained prior to administration of a composition described herein, administration of an immune checkpoint inhibitor and a composition described herein is discontinued. In some embodiments, if the level or value of IFNγ production is not increased (e.g., equal to or lower) in a sample as compared to the level or value of IFNγ production in a sample from the subject obtained prior to administration of a composition described herein, the administration of an immune checkpoint inhibitor and a composition described herein is reanalyzed after administration of a composition as described herein. In some embodiments, the level or value of IFNγ production in a sample is reduced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of IFNγ production in a sample prior to administration of a composition as described herein.

In some embodiments, the level of IFNγ production is determined by analyzing the expression of IFNγ (e.g., protein or nucleic acid level) and/or the cell type by which IFNγ is produced. Any method known the art may be used to analyze the expression of IFNγ and/or identify the cell type that produces IFNγ. The control level can also be a predetermined level or threshold. Such a predetermined level can represent the level of the marker or IFNγ production in a population of subjects that do not have or are not at risk for the target disease. It can also represent the level of the marker or IFNγ production in a population of subjects that have the target disease. The predetermined level can take a variety of forms. For example, it can be single cut-off value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the levels of the metabolite in a control population.

As used herein, "an elevated level" or "an increased level" means that the level of the marker or IFNγ production is higher than a reference value or the level in another sample, such as a sample obtained from the subject prior to administration of any of the compositions described herein. An elevated level of a marker or IFNγ production includes a level of the marker or IFNγ production that is, for example, 1%, 5%, 10%, 20%, 30%, 40%, 50%, 60%, 70%, 80%, 90%, 100%, 150%, 200%, 300%, 400%, 500% or more above a reference value or above the level in another sample from the subject. In some embodiments, the level of the marker or IFNγ production in the test sample is at least 1.1, 1.2, 1.3, 1.4, 15, 1.6, 1.7, 1.8, 1.9, 2, 2.5, 3, 3.5, 4, 4.5, 5, 5.5, 6, 7, 8, 9, 10, 50, 100, 150, 200, 300, 400, 500, 1000, 10000-fold or more, higher than the level in a reference sample or the level in another sample from the subject. As used herein, "a decreased level" means that the level of the marker or IFNγ production is lower than a reference value or the level in another sample, such as a sample obtained from the subject prior to administration of any of the compositions described herein. A decreased level of the marker or IFNγ production includes a level of the marker or IFNγ production that is, for example, 1%, 5%, 10%, 20%, 30%, 40%, 50%, 60%, 70%, 80%, 90%, 100%, 150%, 200%, 300%, 400%, 500% or more lower than a reference value or the level in another sample from the subject. In some embodiments, the level of the marker or IFNγ production in the test sample is at least 1.1, 1.2, 1.3, 1.4, 15, 1.6, 1.7, 1.8, 1.9, 2, 2.5, 3, 3.5, 4, 4.5, 5, 5.5, 6, 7, 8, 9, 10, 50, 100, 150, 200, 300, 400, 500, 1000, 10000-fold or more lower than the level of the marker or IFNγ production in a reference sample or the level in another sample from the subject.

A subject identified in the methods described herein may be subject to a suitable treatment, such as treatment with a combination of an immune checkpoint inhibitor and any of the composition, as described herein. The assay methods and kits described herein also can be applied for evaluation of the efficacy of a treatment for a disease, such as those described herein, given the correlation between the level of the marker or IFNγ production and such diseases. For examples, multiple biological samples can be collected from a subject to whom a treatment is performed either before and after the treatment or during the course of the treatment. The levels of a marker or IFNγ production may be indicative as to whether the treatment is effective. If the subject is identified as not responsive to the treatment, a higher dose and/or frequency of dosage of the composition and/or immune checkpoint inhibitors are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment. In other embodiments, the values of a marker or IFNγ production can also be relied on to identify a disease may be treatable, for example by administering the compositions described herein.

Screening Methods

Provided herein are methods for screening bacteria or physiologically active substances derived from bacteria to identify bacteria or physiologically active substances thereof that produce a desired response. For example, in some embodiments, the screening methods are used to identify bacteria or physiologically active substances derived from bacteria that induce activation of CD8+ IFNγ-producing T cells. In some embodiments, the screening methods are used to identify bacteria or physiologically active substances derived from bacteria that induce activation of CD8+ IFNγ-producing T cells. In some embodiments, the screening methods are used to identify bacteria or physiologically active substances derived from bacteria as an immunostimulatory agent. Also provided herein are methods for screening test substances to identify substances that induce activation induce or exacerbate a disease caused by CD8+ IFNγ-producing T cells. In general, the screening methods may be performed in vitro (e.g., using cells) or in vivo (e.g., using non-human animal models). In some embodiments, the methods involve contacting a population of cells (e.g., intestinal epithelial cells, peripheral blood mononuclear cells) with a test substance (e.g., bacteria or physiologically active substances thereof) and assessing a response. In some embodiments, the response is the number and/or activity of a desired cell population (e.g., CD8+ IFNγ T cells).

In some embodiments, the methods involve inoculating a non-human animal model with a test substance (e.g., bacteria or physiologically active substances thereof) and assessing a response. In some embodiments, the non-human animal model ingests the test substance. In some embodiments, the response is the number and/or activity of a desired cell population (e.g., CD8+ IFNγ T cells). In some embodiments, the response is an improvement of a disease or symptom thereof, or induction/exacerbation of a disease or symptom thereof.

In some embodiments, the bacteria and/or the physiologically active substances derived from bacteria identified in any of the screening methods described herein may be administered to a subject, for example for the treatment of a disease.

Kits

The present disclosure also provides kits for use in evaluating the immune system activation, for example based on the degree or level of IFNγ production in splenocytes, involving administering to a subject any of the compositions as described herein. In some embodiments, a sample may be obtained from the subject prior to, during, and/or after administration of any of the compositions described herein. In some embodiments, the kit contains one or more molecules for detecting and/or measuring the amount of IFNγ production in a sample. In some embodiments, the molecule that detects or measures the amount of IFNγ production can comprise one or more binding agents that specifically bind to IFNγ. In some embodiments, the binding agent is an antibody that specifically binds to IFNγ. In some embodiments, the binding agent is part of a reporter system, such as a receptor on a cell that binds to the IFNγ and induces expression of a gene encoding a reporter molecule. In some embodiments, the kit also contains a standard or control sample to which the amount of IFNγ in the sample(s) obtained from the subject may be compared.

In some embodiments, the kit may be for carrying out any of the companion diagnostic methods described herein. In some embodiments, the kit contains one or more molecules for detecting and/or measuring the amount or presence of any one of the bacterial species described herein, or component thereof. In some embodiments, the molecule that detects or measures the amount of a bacterial strain can comprise one or more binding agents that specifically bind to the bacterial strain. In some embodiments, the binding agent specifically binds to a feature of one or more bacterial species that identifies the bacterial species. In some embodiments, the binding agent is a nucleic acid that specifically binds to a nucleic acid sequence of one or more of the bacterial species described herein, such as a specific 16S rRNA sequence. In some embodiments, the kit also contains a standard or control sample to which the sample(s) obtained from the subject may be compared.

The present disclosure also provides kits for use in determining a treatment method, for example, a tumor therapy, involving analyzing the expression of a marker (e.g., CD44, CD8, IFNγ, GzmB, gp70 MC38 peptide (KSP-WFTTL; SEQ ID NO: 53))-specific TCRβ, or an antigen-derived ligand-specific TCRβ), prior to, during, and/or after administration of any of the compositions described herein. Also provided herein are kits comprising companion diagnostics for tumor therapy with an immune checkpoint inhibitor (e.g., a PD-1 inhibitor). In some embodiments, the kit includes one or more components for analyzing or monitoring expression levels of a marker, such as CD44, CD8, IFNγ, GzmB, or a tumor antigen-derived ligand-specific TCRβ. In some embodiments, the marker is analyzed by detecting the presence of the marker, by measuring the level (amount) of the marker, and/or a specific cell type on which the marker is presented. In some embodiments, the molecule that detects or measures the amount of the marker can comprise one or more binding agents that specifically bind to the marker. In some embodiments, the binding agent is an antibody that specifically binds to the marker. In some embodiments, the binding agent is an MHC multimer that specifically binds to the marker.

In some embodiments, the marker is analyzed by detecting the presence of a nucleic acid encoding the marker, by measuring the level (amount) of a nucleic acid encoding the marker, and/or a specific cell type in which the nucleic acid encoding the marker is expressed. In some embodiments, the kit includes one or more reagents for the isolation of nucleic acids (e.g., RNA) from a sample obtained from subject. In some embodiments, the kits further comprise a detection agent (e.g., an antibody binding to the binding agent) for detecting binding of the agent to the target (e.g., IFNγ, bacterial species) in the sample. The detection agent can be conjugated to a label. In some embodiments, the detection agent is an antibody that specifically binds to at least one of the binding agents. In some embodiments, the binding agent comprises a tag that can be identified and, directly or indirectly, bound by a detection agent.

In some embodiments, the kit may further include one or more therapeutics and/or compositions for administering to the subject. For example, in some embodiments, the kit may include one or more immune checkpoint inhibitor (e.g., PD-1 inhibitor, PD-L1 inhibitor, CTLA-4 inhibitor). In some embodiments, the kit may include a composition comprising one or more of the bacterial strains described herein. In some embodiments, the kits may be for screening bacteria or substances derived from bacteria, for example of activation of CD8+ IFNγ-producing T cells. In some embodiments, the kits include cells, such as cells of a cell line. In some embodiments, the cells are intestinal epithelial cells, peripheral blood mononuclear cells. In some embodiments, the kit or device further includes a support member. In some embodiments, the support member is a membrane, such as a nitrocellulose membrane, a polyvinylidene fluoride (PVDF) membrane, or a cellulose acetate membrane. In some examples, the immunoassay may be in a Western blot assay format or a lateral flow assay format.

In some embodiments, the support member is a multi-well plate, such as an ELISA plate. In some embodiments, the immunoassays described herein can be carried out on high throughput platforms. In some embodiments, multi-well plates, e.g., 24-, 48-, 96-, 384- or greater well plates, may be used for high throughput detection assays. In the kit or detecting device, one or more of the binding agents may be immobilized on a support member, which can be a membrane, a bead, a slide, or a multi-well plate. Selection of an appropriate support member for the immunoassay will depend on various factor such as the number of samples and method of detecting the signal released from label conjugated to the second agent. The kit can also comprise one or more buffers as described herein but not limited to a coating buffer, a blocking buffer, a wash buffer, and/or a stopping buffer.

In some embodiments, the kit can comprise instructions for use in accordance with any of the methods described herein. The instructions relating to the use of the kit generally include information as to the amount of each component and suitable conditions for performing the assay methods described herein. The components in the kits may be in unit doses, bulk packages (e.g., multi-dose packages), or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable. The label or package insert indicates that the kit is used for evaluating the level of immune system activation, selecting a treatment, and/or diagnostic purposes. Instructions may be provided for practicing any of the methods described herein.

The kits of this present disclosure are in suitable packaging. Suitable packaging includes, but is not limited to, vials, bottles, jars, flexible packaging (e.g., sealed Mylar or plastic bags), and the like. Kits may optionally provide additional components such as interpretive information, such as a control and/or standard or reference sample. Normally, the kit comprises a container and a label or package insert(s) on or associated with the container. In some embodiments, the present disclosure provides articles of manufacture comprising contents of the kits described above. Table 1 below provides sequence identifier numbers (SEQ ID NOs) used in the compositions of the experiments disclosed herein. The closest bacterial species to the indicated strain is presented by genus-species. The 16S rDNA sequence associated with each genus species identified as the closest related genus species is also provided. The percent alignment presents the percent identity between the sequence of the indicated strain with the sequence from the closest genus species and the length of the alignment. The GenBank Accession Number of the closest related species is provided in the last column.

TABLE 1

Strains and species with highest homology

| Strain # | SEQ ID NO | Strain ID | Species with highest homology | NCBI accession # of 16S locus | SEQ ID of NCBI 16S locus |
|---|---|---|---|---|---|
| 1 | 1 | 2G5 | *Phascolarctobacterium faecium* | LN998073 | 27 |
| 2 | 2 | 1A6 | *Fusobacterium ulcerans* | KR822463 | 28 |
| 3 | 3 | 1B11 | *Bacteroides dorei* | CP011531 | 29 |
| 4 | 4 | 2G1 | *Bacteroides uniformis* | NR112945 | 30 |
| 5 | 5 | 2B1 | *Subdoligranulum* sp. | KM098109 | 31 |
| 6 | 6 | 2A6 | *Paraprevotella xylaniphila* | NR113078 | 32 |
| 7 | 7 | 2F11 | *Parabacteroides johnsonii* | NR041464 | 33 |
| 8 | 8 | 1E7 | *Alistipes* sp. | LT223566 | 34 |
| 9 | 9 | 1H9 | *Parabacteroides gordonii* | NR112835 | 35 |
| 10 | 10 | 1C1 | *Eubacterum limosum* | NR113248 | 36 |
| 11 | 11 | 2G9 | *Parabacteroides distasonis* | NR041342 | 37 |
| 12 | 12 | 2B7 | *Bacteroides cellulosilyticus* | NR112933 | 38 |
| 13 | 13 | 2C1 | *Bacteroides clarus* | NR112893 | 39 |
| 14 | 14 | 1B4 | *Anaerostipes caccae* | HE974918 | 40 |
| 15 | 15 | 2A3 | *Bacteroides salyersiae* | NR043016 | 41 |
| 16 | 16 | 2A12 | *Bacteroides fragilis* | AB618791 | 42 |
| 17 | 17 | 1A2 | *Bacteroides uniformis* | AB215083 | 43 |
| 18 | 18 | 2B11 | *Bacteroides eggerthii* | NR112935 | 44 |
| 19 | 19 | 2D2 | *Clostridium* sp. | AB249652 | 45 |
| 20 | 20 | 2E8 | *Parabacteroides goldsteinii* | NR113076 | 46 |
| 21 | 21 | 1H8 | *Bacteroides* sp. | NR112944 | 47 |
| 22 | 22 | 3F2 | *Lachnospiraceae bacterium* HGA0140 | JX519760 | 48 |
| 23 | 23 | 1G1 | *Hungatella hathewayi* | AJ311620 | 49 |
| 24 | 24 | 1E6 | *Clostridium lavalense* | EF564278 | 50 |
| 25 | 25 | 1F3 | *Ruminococcus* sp. | KT156811 | 51 |
| 26 | 26 | 1A1 | *Clostridium innocuum* | HM008265 | 52 |

The nucleic acid sequences of the 16S rDNA, or portion thereof, for the bacterial strains described herein are provided below:

```
strain 1 2G5_Phascolarctobacterium faecium_LN998073
                                                                        SEQ ID NO: 1
GACGAACGCTGGCGGCGTGCCTAACACATGCAAGTCGAACGGAGAATTTTATTTCGGTAGAATTCTTAGTGGCGAACGGGTGAGTAA CGCGTAGGCAACCTACCCTTTAGACGGGGACAACATTCCGAAAGGAGTGCTAATACCGGATGTGATCATCTTGCCGCATGGCAGGAT GAAGAAAGATGGCCTCTACAAGTAAGCTATCGCTAAAGGATGGGCCTGCGTCTGATTAGCTAGTTGGTAGTGTAACGGACTACCAAG GCGATGATCAGTAGCCGGTCTGAGAGGATGAACGGCCACATTGGGACTGAGACACGGCCCAAACTCCTACGGGAGGCAGCAGTGGGG AATCTTCCGCAATGGACGAAAGTCTGACGGAGCAACGCCGCGTGAGTGATGAAGGATTTCGGTCTGTAAAGCTCTGTTGTTTATGAC GAACGTGCAGTGTGTGAACAATGCATTGCAATGACGGTAGTAAACGAGGAAGCCACGGCTAACTACGTGCCAGCAGCCGCGGTAATA CGTAGGTGGCGAGCGTTGTCCGGAATTATTGGGCGTAAAGAGCATGTAGGCGGCTTAATAAGTCGAGCGTGAAATGCGGGCTCAA CCCCGTATGGCGCTGGAAACTGTTAGGCTTGAGTGCAGGAGAGGAAAGGGGAATTCCCAGTGTAGCGGTGAAATGCGTAGATATTGG GAGGAACACCAGTGGCGAAGGCGCCTTTCTGGACTGTGTCTGACGCTGAGATGCGAAAGCCAGGGTAGCGAACGGGATTAGATACCC CGGTAGTCCTGGCCGTAAACGATGGGTACTAGGTGTAGGAGGTATCGACCCCTTCTGTGCCGGAGTTAACGCAATAAGTACCCCGCC TGGGGAGTACGGCCGCAAGGTTGAAACTCAAAGGAATTGACGGGGCCCGCACAAGCGGTGGAGTATGTGGTTTAATTCGACGCAAC GCGAAGAACCTTACCAAGGCTTGACATTGATTGAACGCTCTAGAGATAGAGATTTCCCTTCGGGGACAAGAAAACAGGTGGTGCATG GCTGTCGTCAGCTCGTGTCGTGAGATGTTGGGTTAAGTCCCGCAACGAGCGCAACCCCTATCCTATGTTACCAGCAAGTAAAGTTGG GGACTCATGGGAGACTGCCAGGGACAACCTGGAGGAAGGCGGGGATGACGTCAAGTCATCATGCCCCTTATGTCTTGGGCTACACAC GTACTACAATGGTCGGAAACAGAGGGAAGCGAAGCCGCGAGGCAGAGCAAACCCCAGAAACCCGATCTCAGTTCGGATCGCAGGCTG CAACCCGCCTGCGTGAAGTCGGAATCGCTAGTAATCGCAGGTCAGCATACTGCGGTGAATACGTTCCCGGGCCTTGTACACACCGCC

CGTCACACCACGAAAGTTGGTAACACCCGAAGCCGGTGAGGTAACCTA
```

-continued strain 2 1A6_ *Fusobacterium ulcerans*_KR822463

SEQ ID NO: 2

GATGAACGCTGACAGAATGCTTAACACATGCAAGTCTACTTGATCCTTCGGGTGAAGGTGGCGGACGGGTGAGTAACGCGTAAAGAA
CTTGCCTTACAGACTGGGACAACATTTGGAAACGAATGCTAATACCGGATATTATGATTGGGTCGCATGATCTGATTATGAAAGCTA
TATGCGCTGTGAGAGAGCTTTGCGTCCCATTAGTTAGTTGGTGAGGTAACGGCTCACCAAGACGATGATGGGTAGCCGGCCTGAGAG
GGTGAACGGCCACAAGGGGACTGAGACACGGCCCTTACTCCTACGGGAGGCAGCAGTGGGGAATATTGGACAATGGACCAAAAGTCT
GATCCAGCAATTCTGTGTGCACGAAGAAGTTTTTCGGAATGTAAAGTGCTTTCAGTTGGGAAGAAGTCAGTGACGGTACCAACAGAA
GAAGCGACGGCTAAATACGTGCCAGCAGCCGCGGTAATACGTATGTCGCAAGCGTTATCCGGATTTATTGGGCGTAAAGCGCGTCTA
GGCGGCTTAGTAAGTCTGATGTGAAAATGCGGGGCTCAACCCCGTATTGCGTTGGAAACTGCTAAACTAGAGTACTGGAGAGGTAGG
CGGAACTACAAGTGTAGAGGTGAAATTCGTAGATATTTGTAGGAATGCCGATGGGGAAGCCAGCCTACTGGACAGATACTGACGCTA
AAGCGCGAAAGCGTGGGTAGCAAACAGGATTAGATACCCTGGTAGTCCACGCCGTAAACGATGATTACTAGGTGTTGGGGGTCGAAC
CTCAGCGCCCAAGCTAACGCGATAAGTAATCCGCCTGGGGAGTACGTACGCAAGTATGAAACTCAAAGGAATTGACGGGGACCCGCA
CAAGCGGTGGAGCATGTGGTTTAATTCGACGCAACGCGAGGAACCTTACCAGCGTTTGACATCCCAAGAAGTTAACAGAGATGTTTT
CGTGCCTCTTCGGAGGAACTTGGTGACAGGTGGTGCATGGCTGTCGTCAGCTCGTGTCGTGAGATGTTGGGTTAAGTCCCGCAACGA
GCGCAACCCCTTTCGTATGTTACCATCATTAAGTTGGGGACTCATGCGAGACTGCCTGCGATGAGCAGGAGGAAGGTGGGGATGACG
TCAAGTCATCATGCCCCTTATACGCTGGGCTACACACGTGCTACAATGGGTAGTACAGAGAGCTGCAAACCTGCGAGGGTAAGCTAA
TCTCATAAAACTATTCTTAGTTCGGATTGTACTCTGCAACTCGAGTACATGAAGTTGGAATCGCTAGTAATCGCAAATCAGCTATGT
TGCGGTGAATACGTTCTCGGGTCTTGTACACACCGCCCGTCACACCACGAGAGTTGGTTGCACCTGAAGTAACAGGCCTAACCGTAA strain 3 1B11_*Bacteroides dorei*_CP011531

SEQ ID NO: 3

AGTTTGNNNTATGGCTCAGGATGAACGCTAGCTACAGGCTTAACACATGCAAGTCGAGGGGCAGCATGGTCTTAGCTTGCTAAGGCT
GATGGCGACCGGCGCACGGGTGAGTAACACGTATCCAACCTGCCGTCTACTCTTGGCCAGCCTTCTGAAAGGAAGATTAATCCAGGA
TGGGATCATGAGTTCACATGTCCGCATGATTAAAGGTATTTTCCGGTAGACGATGGGGATGCGTTCCATTAGATAGTAGGCGGGGTA
ACGGCCCACCTAGTCAACGATGGATAGGGGTTCTGAGAGGAAGGTCCCCCACATTGGAACTGAGACACGGTCCAAACTCCTACGGGA
GGCAGCAGTGAGGAATATTGGTCAATGGGCGATGGCCTGAACCAGCCAAGTAGCGTGAAGGATGACTGCCCTATGGGTTGTAAACTT
CTTTTATAAAGGAATAAAGTCGGGTATGCATACCCGTTTGCATGTACTTTATGAATAAGGATCGGCTAACTCCGTGCCAGCAGCCGC
GGTAATACGGAGGATCCGAGCGTTATCCGGATTTATTGGGTTTAAAGGGAGCGTAGATGGATGTTTAAGTCAGTTGTGAAAGTTTGC
GGCTCAACCGTAAAATTGCAGTTGATACTGGATGTCTTGAGTGCAGTTGAGGCAGGCGGAATTCGTGGTGTAGCGGTGAAATGCTTA
GATATCACGAAGAACTCCGATTGCGAAGGCAGCCTGCTAAGCTGCAACTGACATTGAGGCTCGAAAGTGTGGGTATCAAACAGGATT
AGATACCCTGGTAGTCCACACGGTAAACGATGAATACTCGCTGTTTGCGATATACGGCAAGCGGCCAAGCGAAAGCGTTAAGTATTC
CACCTGGGGAGTACGCCGGCAACGGTGAAACTCAAAGGAATTGACGGGGGCCCGCACAAGCGGAGGAACATGTGGTTTAATTCGATG
ATACGCGAGGAACCTTACCCGGGCTTAAATTGCACTCGAATGATCCGGAAACGGTTCAGCTAGCAATAGCGAGTGTGAAGGTGCTGC
ATGGTTGTCGTCAGCTCGTGCCGTGAGGTGTCGGCTTAAGTGCCATAACGAGCGCAACCCTTGTTGTCAGTTACTAACAGGTGATGC
TGAGGACTCTGACAAGACTGCCATCGTAAGATGTGAGGAAGGTGGGGATGACGTCAAATCAGCACGGCCCTTACGTCCGGGCTACA
CACGTGTTACAATGGGGGGTACAGAGGGCCGCTACCACGCGAGTGGATGCCAATCCCTAAAACCCTCTCAGTTCGGACTGGAGTCT
GCAACCCGACTCCACGAAGCTGGATTCGCTAGTAATCGCGCATCAGCCACGGCGCGGTGAATACGTTCCCGGGCCTTGTACACACCG
CCCGTCAAGCCATGGGAGCCGGGGGTACCTGAAGTGCGTAACCGCGAGGAT strain 4 2G1_*Bacteroides uniformis*_NR_112945

SEQ ID NO: 4

GATGAACGCTAGCTACAGGCTTAACACATGCAAGTCGAGGGGCAGCATGAACTTAGCTTGCTAAGTTTGATGGCGACCGGCGCACGG
GTGAGTAACACGTATCCAACCTGCCGATGACTCGGGGATAGCCTTTCGAAAGAAAGATTAATACCCGATGGCATAGTTCTTCCGCAT
GGTAGAACTATTAAAGAATTTCGGTCATCGATGGGGATGCGTTCCATTAGGTTGTTGGCGGGGTAACGGCCCACCAAGCCTTCGATG
GATAGGGGTTCTGAGAGGAAGGTCCCCCACATTGGAACTGAGACACGGTCCAAACTCCTACGGGAGGCAGCAGTGAGGAATATTGGT
CAATGGACGAGAGTCTGAACCAGCCAAGTAGCGTGAAGGATGACTGCCCTATGGGTTGTAAACTTCTTTTATACGGGAATAAAGTGA

-continued

```
GGCACGTGTGCCTTTTTGTATGTACCGTATGAATAAGGATCGGCTAACTCCGTGCCAGCAGCCGCGGTAATACGGAGGATCCGAGCG
TTATCCGGATTTATTGGGTTTAAAGGGAGCGTAGGCGGACGCTTAAGTCAGTTGTGAAAGTTTGCGGCTCAACCGTAAAATTGCAGT
TGATACTGGGTGTCTTGAGTACAGTAGAGGCAGGCGGAATTCGTGGTGTAGCGGTGAAATGCTTAGATATCACGAAGAACTCCGATT
GCGAAGGCAGCCTGCTGGACTGTAACTGACGCTGATGCTCGAAAGTGTGGGTATCAAACAGGATTAGATACCCTGGTAGTCCACACC
AGTAAACGATGAATACTCGCTGTTTGCGATATACAGTAAGCGGCCAAGCGAAAGCGTTAAGTATTCCACCTGGGGAGTACGCCGGCA
ACGGTGAAACTCAAAGGAATTGACGGGGGCCCGCACAAGCGGAGGAACATGTGGTTTAATTCGATGATACGCGAGGAACCTTACCCG
GGCTTGAATTGCAACTGAATGATGTGGAGACATGTCAGCCGCAAGGCAGTTGTGAAGGTGCTGCATGGTTGTCGTCAGCTCGTGCCG
TGAGGTGTCGGCTTAAGTGCCATAACGAGCGCAACCCTTATCGATAGTTACCATCAGGTGATGCTGGGGACTCTGTCGAGACTGCCG
TCGTAAGATGTGAGGAAGGTGGGGATGACGTCAAATCAGCACGGCCCTTACGTCCGGGGCTACACACGTGTTACAATGGGGGGTACA
GAAGGCAGCTACACGGCGACGTGATGCTAATCCCGAAAGCCTCTCTCAGTTCGGATTGGAGTCTGCAACCCGACTCCATGAAGCTGG
ATTCGCTAGTAATCGCGCATCAGCCACGGCGCGGTGAATACGTTCCCGGGCCTTGTACACACCGCCCGTCAAGCCATGAAAGCCGGG
GGTACCTGAAGTGCGTAACCGCAAGGAG
``` strain 5 2B1_ *Subdoligranulum* sp. 4_3_54A2FAA_NZ-ACWW00000000
SEQ ID NO: 5

```
GACGAACGCTGGCGGCGCGCCTAACACATGCAAGTCGAACGGAGCTGTTTTCTCTGAAGTTTTCGGATGGAAGAGAGTTCAGCTTAG
TGGCGAACGGGTGAGTAACACGTGAGCAACCTGCCTTTCAGTGGGGGACAACATTTGGAAACGAATGCTAATACCGCATAAGACCAC
AGTGTCGCATGGCACAGGGGTCAAAGGATTTATCCGCTGAAAGATGGGCTCGCGTCCGATTAGCTAGATGGTGAGGTAACGGCCCAC
CATGGCGACGATCGGTAGCCGGACTGAGAGGTTGAACGGCCACATTGGGACTGAGACACGGCCCAGACTCCTACGGGAGGCAGCAGT
GGGGAATATTGCACAATGGGGGAAACCCTGATGCAGCGACGCCGCGTGGAGGAAGAAGGTCTTCGGATTGTAAACTCCTGTCCCAGG
GGACGATAATGACGGTACCCTGGGAGGAAGCACCGGCTAACTACGTGCCAGCAGCCGCGGTAAAACGTAGGGTGCAAGCGTTGTCCG
GAATTACTGGGTGTAAAGGGAGCGCAGGCGGATTGGCAAGTTGGGAGTGAAATCTATGGGCTCAACCCATAAATTGCTTTCAAAACT
GTCAGTCTTGAGTGGTGTAGAGGTAGGCGGAATTCCCGGTGTAGCGGTGGAATGCGTAGATATCGGGAGGAACACCAGTGGCGAAGG
CGGCCTACTGGGCACTAACTGACGCTGAGGCTCGAAAGCATGGGTAGCAAACAGGATTAGATACCCTGGTAGTCCATGCCGTAAACG
ATGATTACTAGGTGTGGGAGGATTGACCCCTTCCGTGCCGCAGTTAACACAATAAGTAATCCACCTGGGGAGTACGACCGCAAGGTT
GAAACTCAAAGGAATTGACGGGGGCCCGCACAAGCAGTGGAGTATGTGGTTTAATTCGAAGCAACGCGAAGAACCTTACCAGGTCTT
GACATCGGATGCATACCTAAGAGATTAGGGAAGTCCTTCGGGACATCCAGACAGGTGGTGCATGGTTGTCGTCAGCTCGTGTCGTGA
GATGTTGGGTTAAGTCCCGCAACGAGCGCAACCCTTATCGTTAGTTACTACGCAAGAGGACTCTAGCGAGACTGCCGTTGACAAAAC
GGAGGAAGGTGGGGATGACGTCAAATCATCATGCCCTTTATGACCTGGGCTACACACGTACTACAATGGCTATTAACAGAGAGAAGC
GATACCGCGAGGTGGAGCAAACCTCACAAAAATAGTCTCAGTTCGGATCGCAGGCTGCAACCCGCCTGCGTGAAGCCGGAATTGCTA
GTAATCGCGGATCAGCATGCCGCGGTGAATACGTTCCCGGGCCTTGTACACACCGCCCGTCACACCATGAGAGCCGGGGGGACCCGA
AGTCGGTAGTCTAACCGC
``` strain 6 2A6_*Paraprevotella xylaniphila*_AB 331897
SEQ ID NO: 6

```
GATGAACGCTAGCTACAGGCTTAACACATGCAAGTCGAGGGGCAGCATGAACTTAGCTTGCTAAGTTTGATGGCGACCGGCGCACGG
GTGAGTAACGCGTATCCAACCTGCCCTTTACCCGGGGATAGCCTTCTGAAAAGGAAGTTTAATACCCGATGAATTCGTTTAGTCGCA
TGGCTNGATGAATAAAGATTAATTGGTAAAGGATGGGGATGCGTCCCATTAGCTTGTTGGCGGGGTAACGGCCCACCAAGGCGACGA
TGGGTAGGGGTTCTGAGAGGAAGGTCCCCCACATTGGAACTGAGACACGGTCCAAACTCCTACGGGAGGCAGCAGTGAGGAATATTG
GTCAATGGGCGCGAGCCTGAACCAGCCAAGTAGCGTGGAGGACGACGGCCCTACGGGTTGTAAACTCCTTTTATAAGGGGATAAAGT
TGGCCATGTATGGCCATTTGCAGGTACCTTATGAATAAGCATCGGCTAATTCCGTGCCAGCAGCCGCGGTAATACGAAGATGCGAG
CGTTATCCGGATTTATTGGGTTTAAAGGGAGCGTAGGCGGGCTGTCAAGTCAGCGGTCAAATGGCGCGGCTCAACCGCGTTCCGCCG
TTGAAACTGGCAGCCTTGAGTATGCACAGGGTACATGGAATTCGTGGTGTAGCGGTGAAATGCTTAGATATCACGAGGAACTCCGAT
CGCGCAGGCATTGTACCGGGGCATTACTGACGCTGAGGCTCGAAGGTGCGGGTATCAAACAGGATTAGATACCCTGGTAGTCCGCAC
```

```
AGTAAACGATGAATGCCCGCTGTCGGCGACATAGTGTCGGCGGCCAAGCGAAAGCGTTAAGCATTCCACCTGGGGAGTACGCCGGCA

ACGGTGAAACTCAAAGGAATTGACGGGGGCCCGCACAAGCGGAGGAACATGTGGTTTAATTCGATGATACGCGAGGAACCTTACCCG

GCCTTGAATCGCAGGTGCATGGGCCGGAGACGGCCCTTTCCTTCGGGACTCCTGCGAAGGTGCTGCATGGTTGTCGTCAGCTCGTGC

CGTGAGGTGTCGGCTTAAGTGCCATAACGAGCGCAACCCCCTCCCCAGTTGCCACCGGGTAATGCCGGGCACTTTGGGGACACTGC

CACCGCAAGGTGCGAGGAAGGTGGGGATGACGTCAAATCAGCACGGCCCTTACGTCCGGGGCGACACACGTGTTACAATGGGGGGTA

CAGAGGGCCGCTGCCCGGTGACGGTTGGCCAATCCCTAAAACCCCTCTCAGTTCGGACTGGAGTCTGCAACCCGACTCCACGAAGCT

GGATTCGCTAGTAATCGCGCATCAGCCATGGCGCGGTGAATACGTTCCCGGGCCTTGTACACACCGCCCGTCAAGCCATGAAAGCCG

GGGGTGCCTGAAGTCCGTNNCCGCGA strain 7 2F11_Parabacteroides johnsonii_AB261128
                                                                                    SEQ ID NO: 7
GATGAACGCTAGCGACAGGCTTAACACATGCAAGTCGAGGGGCAGCATGGTAAGTAGCAATACTTATTGATGGCGACCGGCGCACGG GTGAGTAACGCGTATGCAACTTACCTATCAGAGGGGGATAGCCCGGCGAAAGTCGGATTAATACTCCATAAAACAGGGGTTCCGCAT GGGACTATTTGTTAAAGATTCATCGCTGATAGATAGGCATGCGTTCCATTAGGCAGTTGGCGGGGTAACGGCCCACCAAACCGACGA TGGATAGGGGTTCTGAGAGGAAGGTCCCCCACATTGGTACTGAGACACGGACCAAACTCCTACGGGAGGCAGCAGTGAGGAATATTG GTCAATGGCCGAGAGGCTGAACCAGCCAAGTCGCGTGAAGGATGAAGGATCTATGGTTTGTAAACTTCTTTTATAGGGGAATAAAGT GTGGGACGTGTTCCATTTTGTATGTACCCTATGAATAAGCATCGGCTAACTCCGTGCCAGCAGCCGCGGTAATACGGAGGATGCGAG CGTTATCCGGATTTATTGGGTTTAAAGGGTGCGTAGGTGGTAATTTAAGTCAGCGGTGAAAGTTTGTGGCTCAACCATAAAATTGCC GTTGAAACTGGGTTACTTGAGTGTGTTTGAGGTAGGCGGAATGCGTGGTGTAGCGGTGAAATGCATAGATATCACGCAGAACTCCAA TTGCGAAGGCAGCTTACTAAACCATAACTGACACTGAAGCACGAAAGCGTGGGTATCAAACAGGATTAGATACCCTGGTAGTCCACG CAGTAAACGATGATTACTAGGAGTTTGCGATACACAGTAAGCTCTACAGCGAAAGCGTTAAGTAATCCACCTGGGGAGTACGCCGGC AACGGTGAAACTCAAAGGAATTGACGGGGGCCCGCACAAGCGGAGGAACATGTGGTTTAATTCGATGATACGCGAGGAACCTTACCC GGGTTTGAACGTAGTCAGACCGACCTTGAAAGAGGTTTTCTAGCAATAGCTGATTACGAGGTGCTGCATGGTTGTCGTCAGCTCGTG CCGTGAGGTGTCGGCTTAAGTGCCATAACGAGCGCAACCCTTATCACTAGTTACTAACAGGTTAAGCTGAGGACTCTGGTGAGACTG CCAGCGTAAGCTGTGAGGAAGGTGGGGATGACGTCAAATCAGCACGCCCTTACATCCGGGGCGACACACGTGTTACAATGGCATGG ACAAAGGGCAGCTACCTGGCGACAGGATGCTAATCTCTAAACCATGTCTCAGTTCGGATCGGAGTCTGCAACTCGACTCCGTGAAGC TGGATTCGCTAGTAATCGCGCATCAGCCATGGCGCGGTGAATACGTTCCCGGGCCTTGTACACACCGCCCGTCAAGCCATGGGAGCC

GGGGGTACCTGAAGTCCGTAACCGCAA strain 8 1E7_Alistipes sp. JC136_NZ-CAEG00000000
                                                                                    SEQ ID NO: 8
GATGAACGCTAGCGGCAGGCCTAACACATGCAAGTCGAGGGGCAGCGGGATTGAAGCTTGCTTCAGTTGCCGGCGACCGGCGCACGG GTGCGTAACGCGTATGCAACCTACCCATAACAGGGGGATAACACTGAGAAATCGGTACTAATATCCCATAACATCAAGAGGGGCATC CCTTTTGGTTGAAAACTCCGGTGGTTATGGATGGGCATGCGTTGTATTAGCTAGTTGGTGAGGTAACGGCTCACCAAGGCGACGATA CATAGGGGACTGAGAGGTTAACCCCCCACATTGGTACTGAGACACGGACCAAACTCCTACGGGAGGCAGCAGTGAGGAATATTGGT CAATGGACGCAAGTCTGAACCAGCCATGCCGCGTGCAGGATGACGGCTCTATGAGTTGTAAACTGCTTTTGTACGAGGGTAAACCCG GATACGTGTATCCGGCTGAAAGTATCGTACGAATAAGGATCGGCTAACTCCGTGCCAGCAGCCGCGGTAATACGGAGGATTCAAGCG TTATCCGGATTTATTGGGTTTAAAGGGTGCGTAGGCGGTTTGATAAGTTAGAGGTGAAATACCGGTGCTTAACACCGGAACTGCCTC TAATACTGTTGAGCTAGAGAGTAGTTGCGGTAGGCGGAATGTATGGTGTAGCGGTGAAATGCTTAGAGATCATACAGAACACCGATT GCNGAAGGCAGCTTACCAAACTATATCTGACGTTNGAGGCACGAAAGCGTGGGGAGCAAACAGGATTAGATACCCTGGTAGTCCAC GCAGTAAACGATGATAACTCGCTGTCGGCGATACACAGTCGGTGGCTAAGCGAAAGCGATAAGTTATCCACCTGGGGAGTACGTTCG CAAGAATGAAACTCAAAGGAATTGACGGGGGCCCGCACAAGCGGAGGAACATGTGGTTTAATTCGATGATACGCGAGGAACCTTACC CGGGCTTGAAAGTTACTGACGATTCTGGAAACAGGATTTCCCTTCGGGGCAGGAAACTAGGTGCTGCATGGTTGTCGTCAGCTCGTG CCGTGAGGTGTCGGGTTAAGTCCCATAACGAGCGCAACCCCTACCGTTAGTTGCCATCAGGTCAAGCTGGGCACTCTGGCGGGACTG CCGGTGTAAGCCGAGAGGAAGGTGGGGATGACGTCAAATCAGCACGGCCCTTACGTCCGGGCTACACACGTGTTACAATGGTAGGT
```

-continued

ACAGAGGGCAGCTACCCAGTGATGGGATGCGAATCTCGAAAGCCTATCTCAGTTCGGATTGGAGGCTGAAACCCGCCTCCATGAAGT

TGGATTCGCTAGTAATCGCGCATCAGCCATGGCGCGGTGAATACGTTCCCGGGCCTTGTACACACCGCCCGTCAAGCCATGGAAGCT

GGGGGTGCCTGAAGTTCGTGAC strain 9 1H9_Parabacteroides gordonii_AB470343

SEQ ID NO: 9

GATGAACGCTAGCGACAGGCTTAACACATGCAAGTCGAGGGGCAGCAGGAAGTAGCAATACTTTGCTGGCGACCGGCGCACGGGTGA

GTAACGCGTATGCAACCTACCTATCAGAGGGGGATAACCCGGCGAAAGTCGGACTAATACCGCATAAAACAGGGGTCCCGCATGGGA

ATATTTGTTAAAGATTTATTGCTGATAGATGGGCATGCGTTCCATTAGATAGTTGGTGAGGTAACGGCTCACCAAGTCTTCGATGGA

TAGGGGTTCTGAGAGGAAGGTCCCCCACACTGGTACTGAGACACGGACCAGACTCCTACGGGAGGCAGCAGTGAGGAATATTGGTCA

ATGGGCGAGAGCCTGAACCAGCCAAGTCGCGTGAAGGATGAAGGATCTATGGTTCGTAAACTTCTTTTATAGGGGAATAAAGTGCAG

GACGTGTCCTGTTTTGTATGTACCCTATGAATAAGGATCGGCTAACTCCGTGCCAGCAGCCGCGGTAATACGGAGGATCCGAGCGTT

ATCCGGATTTATTGGGTTTAAAGGGTGCGTAGGTGGCTTTTTAAGTCAGCGGTGAAAGTTTGTGGCTCAACCATAAAATTGCCGTTG

AAACTGGAGGGCTTGAGTATATTTGAGGTAGGCGGAATGCGTGGTGTAGCGGTGAAATGCATAGATATCACGCAGAACTCCAATTGC

GAAGGCAGCTTACTAAACTATAACTGACACTGAAGCACGAAAGCGTGGGATCAAACAGGATTAGATACCCTGGTAGTCCACGCAGT

AAACGATGATTACTAGGAGTTTGCGATACACAGTAAGCTCTACAGCGAAAGCGTTAAGTAATCCACCTGGGGAGTACGCCGGCAACG

GTGAAACTCAAAGGAATTGACGGGGGCCCGCACAAGCGGAGGAACATGTGGTTTAATTCGATGATACGCGAGGAACCTTACCCGGGT

TTGAACGTAAGTTGACCGGAGTGGAAACACTCTTTCTAGCAATAGCAATTTACGAGGTGCTGCATGGTTGTCGTCAGCTCGTGCCGT

GAGGTGTCGGCTTAAGTGCCATAACGAGCGCAACCCTTATCTTTAGTTACTAACAGGTCGAGCTGAGGACTCTAAAGAGACTGCCAG

CGTAAGCTGTGAGGAAGGTGGGGATGACGTCAAATCAGCACGGCCCTTACATCCGGGGCGACACACGTGTTACAATGGTGGGGACAA

AGGGCAGCTACCTGGCGACAGGATGCTAATCTCCAAACCCCATCTCAGTTCGGATCGAAGTCTGCAACCCGACTTCGTGAAGCTGGA

TTCGCTAGTAATCGCGCATCAGCCATGGCGCGGTGAATACGTTCCCGGGCCTTGTACACACCGCCCGTCAAGCCATGGGAGTTGGGG

GTACCTAAAGTCCGTNACCGCAAG strain 10 1C1_Eubacterium limosum_AB595134

SEQ ID NO: 10

GACGAACGCTGGCGGTATGCTTAACACATGCAAGTCGAACGAGAAGGTTTTGATGGATCCTTCGGGTGACATTAGAACTGGAAAGTG

GCGAACGGGTGAGTAACGCGTGGGTAACCTGCCCTATGGAAAGGAATAGCCTCGGGAAACTGGGAGTAAAGCCTTATATTATGGTTT

TGTCGCATGGCAAGATCATGAAAACTCCGGTGCCATAGGATGGACCCGCGTCCCATTAGCTAGTTGGTGAGATAACAGCCCACCAAG

GCGACGATGGGTAACCGGTCTGAGAGGGCGAACGGTCACACTGGAACTGAGACACGGTCCAGACTCCTACGGGAGGCAGCAGTGGGG

AATATTGCGCAATGGGGGCAACCCTGACGCAGCAATACCGCGTGAGTGAAGAAGGTTTTCGGATCGTAAAGCTCTGTTATTGGGGAA

GAAGAATGACGGTACCCAATGAGGAAGTCCCGGCTAACTACGTGCCAGCAGCCGCGGTAATACGTAGGGGACAAGCGTTGTCCGGAA

TGACTGGGCGTAAAGGGCGCGTAGGCGGTCTATTAAGTCTGATGTGAAAGGTACCGGCTCAACCGGTGAAGTGCATTGGAAACTGGT

AGACTTGAGTATTGGAGAGGCAAGTGGAATTCCTAGTGTAGCGGTGAAATGCGTAGATATTAGGAGGAACACCAGTGGCGAAGGCGG

CTTGCTGGACAAATACTGACGCTGAGGTGCGAAAGCGTGGGGAGCGAACAGGATTAGATACCCTGGTAGTCCACGCCGTAAACGATG

AATGCTAGGTGTTGGGGAAACTCAGTGCCGCAGTTAACACAATAAGCATTCCGCCTGGGGAGTACGACCGCAAGGTTGAAACTCAAA

GGAATTGACGGGGACCCGCACAAGCAGCGGAGCATGTGGTTTAATTCGAAGCAACGCGAAGAACCTTACCAGGTCTTGACATCCTCT

GACGAGCCTAGAGATAGGAAGTTTCCTTCGGGAACAGAGAGACAGGTGGTGCATGGTTGTCGTCAGCTCGTGTCGTGAGATGTTGGG

TTAAGTCCCGCAACGAGCGCAACCCCTGCCTTTAGTTGCCAGCATTAAGTTGGGCACTCTAGAGGGACTGCCGTAGACAATACGGAG

GAAGGTGGGGACGACGTCAAATCATCATGCCCCTTATGACCTGGGCTACACACGTGCTACAATGGTCTGAACAGAGGGCCGCGAAGC

CGCGAGGTGAAGCAAATCCCTTAAAACAGATCCCAGTTCGGATTGCAGGCTGCAACTCGCCTGCATGAAGTTGGAGTTGCTAGTAAT

CGCGGATCAGAATGCCGCGGTGAATGCGTTCCCGGGTCTTGTACACACCGCCCGTCACACCACGAGAGTTGGCAACACCCGAAGCCT

GTGAGAGAACCGTAAGGACTCAGCAGT strain 11 2G9_*Parabacteroides distasonis*_HE974920

SEQ ID NO: 11

GATGAACGCTAGCGACAGGCTTAACACATGCAAGTCGAGGGGCAGCACAGGTAGCAATACCGGGTGGCGACCGGCGCACGGGTGAGT
AACGCGTATGCAACTTGCCTATCAGAGGGGGATAACCCGGCGAAAGTCGGACTAATACCGCATGAAGCAGGGGCCCCGCATGGGGAT
ATTTGCTAAAGATTCATCGCTGATAGATAGGCATGCGTTCCATTAGGCAGTTGGCGGGGTAACGGCCCACCAAACCGACGATGGATA
GGGGTTCTGAGAGGAAGGTCCCCCACATTGGTACTGAGACACGGACCAAACTCCTACGGGAGGCAGCAGTGAGGAATATTGGTCAAT
GGCCGAGAGGCTGAACCAGCCAAGTCGCGTGAGGGATGAAGGTTCTATGGATCGTAAACCTCTTTTATAAGGGAATAAAGTGCGGGA
CGTGTCCCGTTTTGTATGTACCTTATGAATAAGGATCGGCTAACTCCGTGCCAGCAGCCGCGGTAATACGGAGGATCCGAGCGTTAT
CCGGATTTATTGGGTTTAAAGGGTGCGTAGGCGGCCTTTTAAGTCAGCGGTGAAAGTCTGTGGCTCAACCATAGAATTGCCGTTGAA
ACTGGGGGGCTTGAGTATGTTTGAGGCAGGCGGAATGCGTGGTGTAGCGGTGAAATGCATAGATATCACGCAGAACCCCGATTGCGA
AGGCAGCCTGCCAAGCCATTACTGACGCTGATGCACGAAAGCGTGGGGATCAAACAGGATTAGATACCCTGGTAGTCCACGCAGTAA
ACGATGATCACTAGCTGTTTGCGATACACTGTAAGCGGCACAGCGAAAGCGTTAAGTGATCCACCTGGGGAGTACGCCGGCAACGGT
GAAACTCAAAGGAATTGACGGGGGCCCGCACAAGCGGAGGAACATGTGGTTTAATTCGATGATACGCGAGGAACCTTACCCGGGTTT
GAACGCATTCGGACCGAGGTGGAAACACCTTTTCTAGCAATAGCCGTTTGCGAGGTGCTGCATGGTTGTCGTCAGCTCGTGCCGTGA
GGTGTCGGCTTAAGTGCCATAACGAGCGCAACCCTTGCCACTAGTTACTAACAGGTAAAGCTGAGGACTCTGGTGGGACTGCCAGCG
TAAGCTGCGAGGAAGGCGGGGATGACGTCAAATCAGCACGGCCCTTACATCCGGGGCGACACACGTGTTACAATGGCGTGGACAAAG
GGAAGCCACCTGGCGACAGGGAGCGAATCCCCAAACCACGTCTCAGTTCGGATCGGAGTCTGCAACCCGACTCCGTGAAGCTGGATT
CGCTAGTAATCGCGCATCAGCCATGGCGCGGTGAATACGTTCCCGGGCCTTGTACACACCGCCCGTCAAGCCATGGGAGCCNGGGGT
ACCTGAAGTCCGTAACCGCGA strain 12 2B7_*Bacteroides cellulosilyticus*_NR_112933

SEQ ID NO: 12

GATGAACGCTAGCTACAGGCTTAACACATGCAAGTCGAGGGGCAGCATGACCTAGCAATAGGTTGATGGCGACCGGCGCACGGGTGA
GTAACACGTATCCAACCTACCGGTTATTCCGGGATAGCCTTTCGAAAGAAAGATTAATACCGGATAGTATAACGAGAAGGCATCTTT
TTGTTATTAAAGAATTTCGATAACCGATGGGGATGCGTTCCATTAGTTTGTTGGCGGGGTAACGGCCCACCAAGACATCGATGGATA
GGGGTTCTGAGAGGAAGGTCCCCCACATTGGAACTGAGACACGGTCCAAACTCCTACGGGAGGCAGCAGTGAGGAATATTGGTCAAT
GGACGAGAGTCTGAACCAGCCAAGTAGCGTGAAGGATGACTGCCCTATGGGTTGTAAACTTCTTTTATATGGGAATAAAGTGAGCCA
CGTGTGGCTTTTTGTATGTACCATACGAATAAGGATCGGCTAACTCCGTGCCAGCAGCCGCGGTAATACGGAGGATCCGAGCGTTAT
CCGGATTTATTGGGTTTAAAGGGAGCGTAGGCGGACTATTAAGTCAGCTGTGAAAGTTTGCGGCTCAACCGTAAAATTGCAGTTGAT
ACTGGTCGTCTTGAGTGCAGTAGAGGTAGGCGGAATTCGTGGTGTAGCGGTGAAATGCTTAGATATCACGAAGAACTCCGATTGCGA
AGGCAGCTTACTGGACTGTAACTGACGCTGATGCTCGAAAGTGTGGGTATCAAACAGGATTAGATACCCTGGTAGTCCACACAGTAA
ACGATGAATACTCGCTGTTTGCGATATACAGCAAGCGGCCAAGCGAAAGCATTAAGTATTCCACCTGGGGAGTACGCCGGCAACGGT
GAAACTCAAAGGAATTGACGGGGGCCCGCACAAGCGGAGGAACATGTGGTTTAATTCGATGATACGCGAGGAACCTTACCCGGGCTT
AAATTGCATCTGAATAATTTGGAAACAGATTAGCCGTAAGGCAGATGTGAAGGTGCTGCATGGTTGTCGTCAGCTCGTGCCGTGAGG
TGTCGGCTTAAGTGCCATAACGAGCGCAACCCTTATCTTTAGTTACTAACAGGTCATGCTGAGGACTCTAGAGAGACTGCCGTCGTA
AGATGTGAGGAAGGTGGGGATGACGTCAAATCAGCACGGCCCTTACGTCCGGGGCTACACACGTGTTACAATGGGGGTACAGAAGG
CAGCTACACAGCGATGTGATGCTAATCCCAAAAGCCTCTCTCAGTTCGGATTGGAGTCTGCAACCCGACTCCATGAAGCTGGATTCG
CTAGTAATCGCGCATCAGCCACGGCGCGGTGAATACGTTCCCGGGCCTTGTACACACCGCCCGTCAAGCCATGAAAGCCGGGGTAC
CTGAAGTCCGTAAC strain 13 2C1_*Bacteroides clarus*_AB490801

SEQ ID NO: 13

GATGAACGCTAGCTACAGGCTTAACACATGCAAGTCGAGGGGCAGCGGGGTTGAAGCTTGCTTCAACCGCCGGCGACCGGCGCACGG
GTGAGTAACACGTATCCAACCTGCCGATAACTCCGGGATAGCCTTTCGAAAGAAAGATTAATACCGGATGGCATAGTTTTCCCGCAT
GGAATAACTATTAAAGAATTTCGGTTATCGATGGGGATGCGTTCCATTAGGCAGTTGGCGGGGTAACGGCCCACCAAACCGACGATG
GATAGGGGTTCTGAGAGGAAGGTCCCCCACATTGGAACTGAGACACGGTCCAAACTCCTACGGGAGGCAGCAGTGAGGAATATTGGT

-continued

```
CAATGGACGAGAGTCTGAACCAGCCAAGTAGCGTGAAGGATGACTGCCCTATGGGTTGTAAACTTCTTTTATACGGGAATAAAGTTG
GCCACGTGTGGTTTTTTGCATGTACCGTATGAATAAGGATCGGCTAACTCCGTGCCAGCAGCCGCGGTAATACGGAGGATCCGAGCG
TTATCCGGATTTATTGGGTTTAAAGGGAGCGTAGGCGGGTATTAAGTCAGTTGTGAAAGTTTGCGGCTCAACCGTAAAATTGCAGT
TGATACTGGTATCCTTGAGTGCAGCAGAGGTGGGCGGAATTCGTGGTGTAGCGGTGAAATGCTTAGATATCACGAAGAACTCCGATT
GCGAAGGCAGCTCACTGGAGTGTAACTGACGCTGATGCTCGAAAGTGTGGGTATCAAACAGGATTAGATACCCTGGTAGTCCACACA
GTAAACGATGAATACTCGCTGTTGGCGATACAATGTCAGCGGCCAAGCGAAAGCATTAAGTATTCCACCTGGGGAGTACGCCGGCAA
CGGTGAAACTCAAAGGAATTGACGGGGGCCCGCACAAGCGGAGGAACATGTGGTTTAATTCGATGATACGCGAGGAACCTTACCCGG
GCTTGAATTGCAACTGACTGAGCTGGAAACAGTTCTTTCTTCGGACAGTTGTGAAGGTGCTGCATGGTTGTCGTCAGCTCGTGCCGT
GAGGTGTCGGCTTAAGTGCCATAACGAGCGCAACCCTTATCTATAGTTACCATCAGGTCATGCTGGGGACTCTATGGAGACTGCCGT
CGTAAGATGTGAGGAAGGTGGGGATGACGTCAAATCAGCACGGCCCTTACGTCCGGGGCTACACACGTGTTACAATGGGGGGTACAG
AAGGCAGCTACACGGCGACGTGATGCTAATCCCAAAAACCTCTCTCAGTTCGGATTGGAGTCTGCAACCCGACTCCATGAAGCTGGA
TTCGCTAGTAATCGCGCATCAGCCACGGCGCGGTGAATACGTTCCCGGGCCTTGTACACACCGCCCGTCAAGCCATGAAAGCCGGGG
GTACCTGAAGTACGTAACCGCAA
``` strain 14 1B4_*Anaerostipes* sp. 3_2_56FAA_NZ-ACWB00000000

SEQ ID NO: 14

```
GATGAACGCTGGCGGCGTGCTTAACACATGCAAGTCGAACGAAGCATTTAGGATTGAAGTTTTCGGATGGATTTCCTATATGACTGA
GTGGCGGACGGGTGAGTAACGCGTGGGGAACCTGCCCTATACAGGGGGATAACAGCTGGAAACGGCTGCTAATACCGCATAAGCGCA
CAGAATCGCATGATTCAGTGTGAAAAGCCCTGGCAGTATAGGATGGTCCCGCGTCTGATTAGCTGGTTGGTGAGGTAACGGCTCACC
AAGGCGACGATCAGTAGCCGGCTTGAGAGAGTGAACGGCCACATTGGGACTGAGACACGGCCCAAACTCCTACGGGAGGCAGCAGTG
GGGAATATTGCACAATGGGGGAAACCCTGATGCAGCGACGCCGCGTGAGTGAAGAAGTATTTCGGTATGTAAAGCTCTATCAGCAGG
GAAGAAAACAGACGGTACCTGACTAAGAAGCCCCGGCTAACTACGTGCCAGCAGCCGCGGTAATACGTAGGGGGCAAGCGTTATCCG
GAATTACTGGGTGTAAAGGGTGCGTAGGTGGCATGGTAAGTCAGAAGTGAAAGCCCGGGGCTTAACCCCGGGACTGCTTTTGAAACT
GTCATGCTGGAGTGCAGGAGAGGTAAGCGGAATTCCTAGTGTAGCGGTGAAATGCGTAGATATTAGGAGGAACACCAGTGGCGAAGG
CGGCTTACTGGACTGTCACTGACACTGATGCACGAAAGCGTGGGGAGCAAACAGGATTAGATACCCTGGTAGTCCACGCCGTAAACG
ATGAATACTAGGTGTCGGGGCCGTAGAGGCTTCGGTGCCGCAGCAAACGCAGTAAGTATTCCACCTGGGGAGTACGTTCGCAAGAAT
GAAACTCAAAGGANTTGACGGGGACCGCNNNAGCGGTGGAGCATGTGGTTAATTCGAAGCACGCGAAG
``` strain 15 2A3_*Bacteroides salyersiae*_AY608696

SEQ ID NO: 15

```
GATGAACGCTAGCTACAGGCTTAACACATGCAAGTCGAGGGGCATCAGGGTGTAGCAATACACCGCTGGCGACCGGCGCACGGGTGA
GTAACACGTATCCAACCTGCCCTTTACTCGGGGATAGCCTTTCGAAAGAAAGATTAATACCCGATGGTATAACATGACCTCCTGGTT
TTGTTATTAAAGAATTTCGGTAGAGGATGGGGATGCGTTCCATTAGGCAGTTGGCGGGGTAACGGCCCACCAAACCTTCGATGGATA
GGGGTTCTGAGAGGAAGGTCCCCCACATTGGAACTGAGACACGGTCCAAACTCCTACGGGAGGCAGCAGTGAGGAATATTGGTCAAT
GGGCGAGAGCCTGAACCAGCCAAGTAGCGTGAAGGATGACCGCCCTATGGGTTGTAAACTTCTTTTATATGGGAATAAAGTCTGCCA
CGTGTGGCATTTTGTATGTACCATATGAATAAGGATCGGCTAACTCCGTGCCAGCAGCCGCGGTAATACGGAGGATCCGAGCGTTAT
CCGGATTTATTGGGTTTAAAGGGAGCGTAGGTGGACATGTAAGTCAGTTGTGAAAGTTTGCGGCTCAACCGTAAAATTGCAGTTGAA
ACTGCGTGTCTTGAGTACAGTAGAGGTGGGCGGAATTCGTGGTGTAGCGGTGAAATGCTTAGATATCACGAAGAACTCCGATTGCGA
AGGCAGCTCACTGGACTGCAACTGACACTGATGCTCGAAAGTGTGGGTATCAAACAGGATTAGATACCCTGGTAGTCCACACAGTAA
ACGATGAATACTCGCTGTTTGCGATATACAGTAAGCGGCCAAGCGAAAGCATTAAGTATTCCACCTGGGGAGTACGCCGGCAACGGT
GAAACTCAAAGGAATTGACGGGGGCCCGCACAAGCGGAGGAACATGTGGTTTAATTCGATGATACGCGAGGAACCTTACCCGGGCTT
AAATTGCAAATGAATATGCCGGAAACGGCATAGCCGCAAGGCATTTGTGAAGGTGCTGCATGGTTGTCGTCAGCTCGTGCCGTGAGG
TGTCGGCTTAAGTGCCATAACGAGCGCAACCCTTATCTTCAGTTACTAACAGGTCATGCTGAGGACTCTGGAGACTGCCGTCGTA
AGATGTGAGGAAGGTGGGGATGACGTCAAATCAGCACGGCCCTTACGTCCGGGGCTACACACGTGTTACAATGGGGGGTACAGAAGG
``` strain 16 2A12_Bacteroides fragilis_CR626927

SEQ ID NO: 16

GATGAACGCTAGCTACAGGCTTAACACATGCAAGTCGAGGGGCATCAGGAAGAAAGCTTGCTTTCTTTGCTGGCGACCGGCGCACGG

GTGAGTAACACGTATCCAACCTGCCCTTTACTCGGGGATAGCCTTTCGAAAGAAAGATTAATACCCGATAGCATAATGATTCCGCAT

GGTTTCATTATTAAAGGATTCCGGTAAAGGATGGGGATGCGTTCCATTAGGTTGTTGGTGAGGTAACGGCTCACCAAGCCTTCGATG

GATAGGGGTTCTGAGAGGAAGGTCCCCCACATTGGAACTGAGACACGGTCCAAACTCCTACGGGAGGCAGCAGTGAGGAATATTGGT

CAATGGGCGCTAGCCTGAACCAGCCAAGTAGCGTGAAGGATGAAGGCTCTATGGGTCGTAAACTTCTTTTATATAAGAATAAAGTGC

AGTATGTATACTGTTTTGTATGTATTATATGAATAAGGATCGGCTAACTCCGTGCCAGCAGCCGCGGTAATACGGAGGATCCGAGCG

TTATCCGGATTTATTGGGTTTAAAGGGAGCGTAGGTGGACTGGTAAGTCAGTTGTGAAAGTTTGCGGCTCAACCGTAAAATTGCAGT

TGATACTGTCAGTCTTGAGTACAGTAGAGGTGGGCGGAATTCGTGGTGTAGCGGTGAAATGCTTAGATATCACGAAGAACTCCGATT

GCGAAGGCAGCTCACTGGACTGCAACTGACACTGATGCTCGAAAGTGTGGGTATCAAACAGGATTAGATACCCTGGTAGTCCACACA

GTAAACGATGAATACTCGCTGTTTGCGATATACAGTAAGCGGCCAAGCGAAAGCATTAAGTATTCCACCTGGGGAGTACGCCGGCAA

CGGTGAAACTCAAAGGAATTGACGGGGGCCCGCACAAGCGGAGGAACATGTGGTTTAATTCGATGATACGCGAGGAACCTTACCCGG

GCTTAAATTGCAGTGGAATGATGTGGAAACATGTCAGTGAGCAATCACCGCTGTGAAGGTGCTGCATGGTTGTCGTCAGCTCGTGCC

GTGAGGTGTCGGCTTAAGTGCCATAACGAGCGCAACCCTTATCTTTAGTTACTAACAGGTTATGCTGAGGACTCTAGAGAGACTGCC

GTCGTAAGATGTGAGGAAGGTGGGGATGACGTCAAATCAGCACGGCCCTTACGTCCGGGCTACACACGTGTTACAATGGGGGGTAC

AGAAGGCAGCTAACGGGTGACCGTATGCTAATCCCAAAAGCCTCTCTCAGTTCGGATCGAAGTCTGCAACCCGACTTCGTGAAGCTG

GATTCGCTAGTAATCGCGCATCAGCCACGGCGCGGTGAATACGTTCCCGGGCCTTGTACACACCGCCCGTCAAGCCATGGGAGCCGG

GGGTACCTGAAGTACGTAACCGCAA strain 17 1A2_Bacteroides uniformis_AB247141

SEQ ID NO: 17

GATGAACGCTAGCTACAGGCTTAACACATGCAAGTCGAGGGGCATCAGGAAGAAAGCTTGCTTTCTTTGCTGGCGACCGGCGCACGG

GTGAGTAACACGTATCCAACCTGCCGATGACTCGGGGATAGCCTTTCGAAAGAAAGATTAATACCCGATGGTATATCTGAAAGGCAT

CTTTCAGCTATTAAAGAATTTCGGTCATTGATGGGGATGCGTTCCATTAGGTTGTTGGCGGGGTAACGGCCCACCAAGCCATCGATG

GATAGGGGTTCTGAGAGGAAGGTCCCCCACATTGGAACTGAGACACGGTCCAAACTCCTACGGGAGGCAGCAGTGAGGAATATTGGT

CAATGGACGAGAGTCTGAACCAGCCAAGTAGCGTGAAGGATGACTGCCCTATGGGTTGTAAACTTCTTTTATACGGGAATAAAGTTA

GGCACGTGTGCCTTTTTGTATGTACCGTATGAATAAGGATCGGCTAACTCCGTGCCAGCAGCCGCGGTAATACGGAGGATCCGAGCG

TTATCCGGATTTATTGGGTTTAAAGGGAGCGTAGGCGGATGCTTAAGTCAGTTGTGAAAGTTTGCGGCTCAACCGTAAAATTGCAGT

TGATACTGGGTGTCTTGAGTACAGTAGAGGCAGGCGGAATTCGTGGTGTAGCGGTGAAATGCTTAGATATCACGAAGAACTCCGATT

GCGAAGGCAGCTTGCTGGACTGTAACTGACGCTGATGCTCGAAAGTGTGGGTATCAAACAGGATTAGATACCCTGGTAGTCCACACA

GTAAACGATGAATACTCGCTGTTTGCGATATACAGTAAGCGGCCAAGCGAAAGCGTTAAGTATTCCACCTGGGGAGTACGCCGGCAA

CGGTGAAACTCAAAGGAATTGACGGGGGCCCGCACAAGCGGAGGAACATGTGGTTTAATTCGATGATACGCGAGGAACCTTACCCGG

GCTTAAATTGCAAATGAATGTTCTGGAAACAGATCAGCCGCAAGGCATTTGTGAAGGTGCTGCATGGTTGTCGTCAGCTCGTGCCGT

GAGGTGTCGGCTTAAGTGCCATAACGAGCGCAACCCTTATCGATAGTTACCATCAGGTTATGCTGGGGACTCTGTCGAGACTGCCGT

CGTAAGATGTGAGGAAGGTGGGGATGACGTCAAATCAGCACGGCCCTTACGTCCGGGCTACACACGTGTTACAATGGGGGGTACAG

AAGGCAGCTACACGGCGACGTGATGCTAATCCCTAAAACCTCTCTCAGTTCGGATTGGAGTCTGCAACCCGACTCCATGAAGCTGGA

TTCGCTAGTAATCGCGCATCAGCCACGGCGCGGTGAATACGTTCCCGGGCCTTGTACACACCGCCCGTCAAGCCATGAAAGCCGGGG

GTACCTGAAGTGCGT

-continued strain 18 2B11_Bacteroides eggerthii_NR_112935

SEQ ID NO: 18

GATGAACGCTAGCTACAGGCTTAACACATGCAAGTCGAGGGGCAGCATGATTGAAGCTTGCTTCAATCGATGGCGACCGGCGCACGG
GTGAGTAACACGTATCCAACCTGCCGATAACTCGGGGATAGCCTTTCGAAAGAAAGATTAATACCCGATAGCATAGTATTTCCGCAT
GGTTTCACTATTAAAGAATTTCGGTTATCGATGGGGATGCGTTCCNTTAGATAGTTGGCGGGGTAACGGCCCACCAAGTCAACGATG
GATAGGGGTTCTGAGAGGAAGGTCCCCCACATTGGAACTGAGACACGGTCCAAACTCCTACGGGAGGCAGCAGTGAGGAATATTGGT
CAATGGACGAGAGTCTGAACCAGCCAAGTAGCGTGAAGGATGACTGCCCTATGGGTTGTAAACTTCTTTTATACGGGAATAAAGTGG
AGTATGCATACTCCTTTGTATGTACCGTATGAATAAGGATCGGCTAACTCCGTGCCAGCAGCCGCGGTAATACGGAGGATCCGAGCG
TTATCCGGATTTATTGGGTTTAAAGGGAGCGTAGGCGGGTGCTTAAGTCAGTTGTGAAAGTTTGCGGCTCAACCGTAAAATTGCAGT
TGATACTGGGCGCCTTGAGTGCAGCATAGGTAGGCGGAATTCGTGGTGTAGCGGTGAAATGCTTAGATATCACGAAGAACTCCGATT
GCGAAGGCAGCTTACTGGACTGTAACTGACGCTGATGCTCGAAAGTGTGGGTATCAAACAGGATTAGATACCCTGGTAGTCCACACA
GTAAACGATGAATACTCGCTGTTGGCGATACACAGTCAGCGGCCAAGCGAAAGCATTAAGTATTCCACCTGGGGAGTACGCCGGCAA
CGGTGAAACTCAAAGGAATTGACGGGGGCCCGCACAAGCGGAGGAACATGTGGTTTAATTCGATGATACGCGAGGAACCTTACCCGG
GCTTAAATTGCAGCGGAATGTAGTGGAAACATTACAGCCTTCGGGCCGCTGTGAAGGTGCTGCATGGTTGTCGTCAGCTCGTGCCGT
GAGGTGTCGGCTTAAGTGCCATAACGAGCGCAACCCTTATCTATAGTTACTATCAGGTCATGCTGAGGACTCTATGGAGACTGCCGT
CGTAAGATGTGAGGAAGGTGGGGATGACGTCAAATCAGCACGGCCCTTACGTCCGGGGCTACACACGTGTTACAATGGGGGGTACAG
AAGGCAGCTACCTGGCGACAGGATGCTAATCCCTAAAACCTCTCTCAGTTCGGATTGGAGTCTGCAACCCGACTCCATGAAGCTGGA
TTCGCTAGTAATCGCGCATCAGCCACGGCGCGGTGAATACGTTCCCGGGCCTTGTACACACCGCCCGTCAAGCCATGAAAGCCGGGG
GTACCTGAAGTACGTAACCGCAAGGAGC strain 19 2D2_Clostridium sp. TM-40_AB249652

SEQ ID NO: 19

GATGAACGCTGGCGGCGTGCCTAATACATGCAAGTCGGACGCAATGCTTCGGCATTGAGTGGCGAACGGGTGAGTAATACATAAGCA
ACCTGCCCCTGTGAGGGGATAACTGCTGGAAACGGCAGCTAAGACCGCATATGCATACATGACGCATGTCGAGTATGTTAAATATC
CCACGGGATAGCACAGGGATGGGCTTATGACGCATTAGCTAGCTGGTGAGGTAGAGGCTCACCAGGGCGACGATGCGTAGCCGGCCT
GAGAGGGTGGACGGCCACACTGGGACTGAGACACGGCCCAGACTCCTACGGGAGGCAGCAGTAGGGAATTTTCGGCAATGGGCGAAA
GCCTGACCGAGCAACGCCGCGTGAAGGAAGAAGTCATTCGTGATGTAAACTTCTGTTATAAAGGAAGAACGGCGCCTGTAGGGAATG
ACAGGCGAGTGACGGTACTTTATGAGGAAGCCACGGCTAACTACGTGCCAGCAGCCGCGGTAATACGTAGGTGGCGAGCGTTATCCG
GAATCATTGGGCGTAAAGAGGGAGCAGGCGGCAGTGCAGGTCTGCGGTGAAAGCCCGAAGCTAAACTTCGGTAAGCCGTGGAAACCG
CACAGCTAGAGAGCATCAGAGGATCGCGGAATTCCATGTGTAGCGGTGAAATGCGTAGATATATGGAGGAACACCAGTGGCGAAGGC
GGCGGTCTGGGGTGCAGCTGACGCTCAGTCCCGAAAGCGTGGGGAGCAAATAGGATTAGATACCCTAGTAGTCCACGCCGTAAACGA
TGAGTGCTAAGTGTTGGGGGTCAGACCTCAGTGCTGCAGTTAACGCAATAAGCACTCCGCCTGAGTAGTACGTTCGCAAGAATGAAA
CTCAAAGGAATTGACGGGGGCCCGCACAAGCGGTGGAGCATGTGGTTTAATTCGAAGCAACGCGAAGAACCTTACCAGGTCTTGACA
TGGAGATAAAGGCTCTGGAGACAGAGAGATAGGTATATCTCACACAGGTGGTGCATGGTTGTCGTCAGCTCGTGTCGTGAGATGTTG
GGTTAAGTCCCGCAACGAGCGCAACCCCTGTTGCCAGTTGCCAGCATTAGGTTGGGACTCTGGCGAGACTGCCTCTGCAAGGAGGA
GGAAGGCGGGGATGACGTCAAATCATCATGCCCCTTATGACCTGGGCTACACACGTGCTACAATGGACGGATCAGAGGGAGGCAAG
CCGCGAGGTGGAGCGAAACCCAGAAACCCGTTCACAGTTCGGACTGCAGTCTGCAACTCGACTGCACGAAGCTGGAATCGCTAGTAA
TCGCGAATCAGCATGTCGCGGTGAATACGTTCTCGGGCCTTGTACACACCGCCCGTCACACCATGAGAGTTGGTAACACCCGAAGCC
GGTGGCCCAACCGCAA strain 20 2E8_Parabacteroides goldsteinii_NR_113076

SEQ ID NO: 20

GATGAACGCTAGCGACAGGCTTAACACATGCAAGTCGAGGGGCAGCACGATGTAGCAATACATTGGTGGCGACCGGCGCACGGGTGA
GTAACGCGTATGCAACCTACCTATCAGAGGGGAATAACCCGGCGAAAGTCGGACTAATACCGCATAAAACAGGGGTTCCACATGGAA
ATATTTGTTAAAGAATTATCGCTGATAGATGGGCATGCGTTCCATTAGATAGTTGGTGAGGTAACGGCTCACCAAGTCCACGATGGA
TAGGGGTTCTGAGAGGAAGGTCCCCCACACTGGTACTGAGACACGGACCAGACTCCTACGGGAGGCAGCAGTGAGGAATATTGGTCA

```
ATGGGCGAGAGCCTGAACCAGCCAAGTCGCGTGAAGGATGAAGGATCTATGGTTTGTAAACTTCTTTTATATGGGAATAAAGTGAGG
AACGTGTTCCTTTTTGTATGTACCATATGAATAAGCATCGGCTAACTCCGTGCCAGCAGCCGCGGTAATACGGAGGATGCGAGCGTT
ATCCGGATTTATTGGGTTTAAAGGGTGCGTAGGTGGTTAATTAAGTCAGCGGTGAAAGTTTGTGGCTCAACCATAAAATTGCCGTTG
AAACTGGTTGACTTGAGTATATTTGAGGTAGGCGGAATGCGTGGTGTAGCGGTGAAATGCATAGATATCACGCAGAACTCCGATTGC
GAAGGCAGCTTACTAAACTATAACTGACACTGAAGCACGAAAGCGTGGGGATCAAACAGGATTAGATACCCTGGTAGTCCACGCAGT
AAACGATGATTACTAGCTGTTTGCGATACACAGTAAGCGGCACAGCGAAAGCGTTAAGTAATCCACCTGGGGAGTACGCCGGCAACG
GTGAAACTCAAAGGAATTGACGGGGGCCCGCACAAGCGGAGGAACATGTGGTTTAATTCGATGATACGCGAGGAACCTTACCCGGGT
TTGAACGCATATTGACAGCTCTGGAAACAGAGTCTCTAGTAATAGCAATTTGCGAGGTGCTGCATGGTTGTCGTCAGCTCGTGCCGT
GAGGTGTCGGCTTAAGTGCCATAACGAGCGCAACCCTTATCACTAGTTACTAACAGGTCATGCTGAGGACTCTAGTGAGACTGCCAG
CGTAAGCTGTGAGGAAGGTGGGGATGACGTCAAATCAGCACGGCCCTTACATCCGGGGCGACACACGTGTTACAATGGTGGGGACAA
AGGGCAGCTACCGTGTGAGCGGATGCAAATCTCCAAACCCCATCTCAGTTCGGATCGAAGTCTGCAACCCGACTTCGTGAAGCTGGA
TTCGCTAGTAATCGCGCATCAGCCATGGCGCGGTGAATACGTTCCCGGGCCTTGTACACACCGCCCGTCAAGCCATGGGAGTTGGGG
GTACCTAAAGTCCGTAACCGC
```
strain 21 1H8_Bacteroides sp. AR29_AF139525

SEQ ID NO: 21
```
GATGAACGCTAGCTACAGGCTTAACACATGCAAGTCGAGGGGCAGCATTTCAGTTTGCTTGCAAACTGGAGATGGCGACCGGCGCAC
GGGTGAGTAACACGTATCCAACCTGCCGATAACTCGGGGATAGCCTTTCGAAAGAAAGATTAATACCCGATGGTATAATNAGACCGC
ATGGTCTTGTTATTAAAGAATTTCGGTTATCGATGGGGATGCGTTCCATTAGGCAGTTGGTGAGGTAACGGCTCACCAAACCTTCGA
TGGATAGGGGTTCTGAGAGGAAGGTCCCCCACATTGGAACTGAGACACGGTCCAAACTCCTACGGGAGGCAGCAGTGAGGAATATTG
GTCAATGGGCGCAGGCCTGAACCAGCCAAGTAGCGTGAAGGATGACTGCCCTATGGGTTGTAAACTTCTTTTATATGGGAATAAAGT
TTTCCACGTGTGGAATTTTGTATGTACCATATGAATAAGGATCGGCTAACTCCGTGCCAGCAGCCGCGGTAATACGGAGGATCCGAG
CGTTATCCGGATTTATTGGGTTTAAAGGGAGCGTAGGTGGACAGTTAAGTCAGTTGTGAAAGTTTGCGGCTCAACCGTAAAATTGCA
GTTGATACTGGCTGTCTTGAGTACAGTAGAGGTGGGCGGAATTCGTGGTGTAGCGGTGAAATGCTTAGATATCACGAAGAACTCCGA
TTGCGAAGGCAGCTCACTGGACTGCAACTGACACTGATGCTCGAAAGTGTGGGTATCAAACAGGATTAGATACCCTGGTAGTCCACA
CAGTAAACGATGAATACTCGCTGTTTGCGATATACAGTAAGCGGCCAAGCGAAAGCATTAAGTATTCCACCTGGGGAGTACGCCGGC
AACGGTGAAACTCAAAGGAATTGACGGGGGCCCGCACAAGCGGAGGAACATGTGGTTTAATTCGATGATACGCGAGGAACCTTACCC
GGGCTTAAATTGCATTTGAATATATTGGAAACAGTATAGCCGTAAGGCAAATGTGAAGGTGCTGCATGGTTGTCGTCAGCTCGTGCC
GTGAGGTGTCGGCTTAAGTGCCATAACGAGCGCAACCCTTATCTTTAGTTACTAACAGGTCATGCTGAGGACTCTAGAGAGACTGCC
GTCGTAAGATGTGA
```
strain 22 >3F2-PREMIX.fasta SEQ ID NO: 22
```
NNNNNNNNNTGCAGTCGAACGAAGCGATTTGAATGAAGTTTTCGGATGGATTTCAANTTGACTGAGTGGCGGACGGGTGAGTAACGC
GTGGGTAACCTGCCCCATACAGGGGGATAACAGTTAGAAATGACTGCTAATACCGCATAAGACCACAGNNCCGCATGGTGCAGGGGT
AAAAACTCCGGTGGTATGGGATGGACCCGCGTCTGATTAGCTTGTTGGCGGGTAACGGCCCACCAAGGCGACGATCAGTAGCCGAC
CTGAGAGGGTGACCGGCCACATTGGGACTGAGACACGGCCCAAACTCCTACGGGAGGCAGCAGTGGGGAATATTGCACAATGGGGGA
AACCCTGATGCAGCGACGCCGCGTGAGTGATGAAGTATTTCGGTATGTAAAGCTCTATCAGCAGGGAAGAAAATGACGGTACCTGAC
TAAGAAGCCCCGGCTAACTACGTGCCAGCAGCCGCGGTAATACGTAGGGGGCAAGCGTTATCCGGATTTACTGGGTGTAAAGGGAGC
GTAGACGGCTGTGCAAGTCTGGAGTGAAAGCCCGGGGCTCAACCCCGGGACTGCTTTGGAAACTGTACGGCTGGAGTGCTGGAGAGG
CAAGCGGAATTCCTAGTGTAGCGGTGAAATGCGTAGATATTAGGAGGAACACCAGTGGCGAAGGCGGCTTGCTGGACAGTAACTGAC
GTTGAGGCTCGAAAGCGTGGGGAGCAAACAGGATTAGATACCCTGGTAGTCCACGCCGTAAACGATGAATGCTAGGTGTCGGGGAGC
AAAGCTCTTCGGTGCCGCCGCAAACGCAATAAGCATTCCACCTGGGGAGTACGTTCGCAAGAATGAAACTCAAAGGANTTGACGGGG
ACCGCACANNGGTGGAGCATGTGGTTATTCGAGCACGCGAAANCTTACCAGTCTTGNNCCCCTGANGNNNNGTATGTCGCTNCTNN
```

GNNNNGGN strain 23 >1G1_3-PREMIX.fasta

SEQ ID NO: 23

AGTTTGATTATGGCTCAGGATGAACGCTGGCGGCGTGCTTAACACATGCAAGTCGAGCGAAGCGGTTTCAATGAAGTTTTCGGATGG
ATTTGAAATTGACTTAGCGGCGGACGGGTGAGTAACGCGTGGGTAACCTGCCTTACACTGGGGGATAACAGTTAGAAATGACTGCTA
ATACCGCATAAGCGCACAGGGCCGCATGGTCCGGTGTGAAAAACTCCGGTGGTGTAAGATGGACCCGCGTCTGATTAGGTAGTTGGC
GGGGTAACGGCCCACCAAGCCGACGATCAGTAGCCGACCTGAGAGGGTGACCGGCCACATTGGGACTGAGACACGGCCCAAACTCCT
ACGGGAGGCAGCAGTGGGGAATATTGGACAATGGGCGAAAGCCTGATCCAGCGACGCCGCGTGAGTGAAGAAGTATTTCGGTATGTA
AAGCTCTATCAGCAGGGAAGAAAATGACGGTACCTGACTAAGAAGCCCCGGCTAACTACGTGCCAGCAGCCGCGGTAATACGTAGGG
GGCAAGCGTTATCCGGATTTACTGGGTGTAAAGGGAGCGTAGACGGTTTAGCAAGTCTGAAGTGAAAGCCCGGGGCTCAACCCCGGT
ACTGCTTTGGAAACTGTTAGACTTGAGTGCAGGAGAGGTAAGTGGAATTCCTAGTGTAGCGGTGAAATGCGTAGATATTAGGAGGAA
CACCAGTGGCGAAGGCGGCTTACTGGACTGTAACTGACGTTGAGGCTCGAAAGCGTGGGGAGCAAACAGGATTAGATACCCTGGTAG
TCCACGCCGTAAACGATGAATACTAGGTGTCGGGGGGCAAAGCCCTTCGGTGCCGCCGCAAACGCAATAAGTATTCCACCTGGGGAG
TACGTTCGCAAGAATGAAACTCAAAGGAATTGACGGGGACCCGCACAAGCGGTGGAGCATGTGGTTTAATTCGAAGCAACGCGAAGA
ACCTTACCAAGTCTTGACATCCCACTGAAAACACTTTAACCGGTGTCCCTCTTCGGAGCAGTGGAGACAGGTGGTGCATGGTTGTCG
TCAGCTCGTGTCGTGAGATGTTGGGTTAAGTCCCGCAACGAGCGCAACCCTTATCCTTAGTAGCCAGCGAGTAGAGTCGGGCACTCT
GGGGAGACTGCCAGGGATAACCTGGAGGAAGGTGGGGATGACGTCAAATCATCATGCCCCTTATGATTTGGGCTACACACGTGCTAC
AATGGCGTAAACAAAGGGAGGCAAAGGAGCGATCTGGAGCAAACCCCAAAAATAACGTCTCAGTTCGGATTGCAGGCTGCAACTCGC
CTGCATGAAGCTGGAATCGCTAGTAATCGCGAATCAGAATGTCGCGGTGAATACGTTCCCGGGTCTTGTACACACCGCCCGTCACAC
CATGGGAGTTGGTAACGCCCGAAGTCAGTGACCCAACCGCAAGGAGGNAGCTGCCGAANNNNNNN strain 24 >1E6_27Fmod-PREMIX_Length_957

SEQ ID NO: 24

AGTTTGNNNNNNGCTCAGGATGAACGCTGGCGGCGTGCCTAACACATGCAAGTCGAACGAAGCATTTCAGATGAAGTTTTCGGATGGA
TTCTGAGATGACTGAGTGGCGGACGGGTGAGTAACACGTGGATAACCTGCCTCACACTGGGGGACAACAGTTAGAAATGACTGCTAA
TACCGCATAAGCGCACAGTACCGCATGGTACAGTGTGAAAAACTCCGGTGGTGTGAGATGGATCCGCGTCTGATTAGCCAGTTGGCG
GGGTAACGGCCCACCAAAGCGACGATCAGTAGCCGACCTGAGAGGGTGACCGGCCACATTGGGACTGAGACACGGCCCAAACTCCTA
CGGGAGGCAGCAGTGGGGAATATTGCACAATGGGCGAAAGCCTGATGCAGCGACGCCGCGTGAGTGAAGAAGTATTTCGGTATGTAA
AGCTCTATCAGCAGGGAAGATAATGACGGTACCTGACTAAGAAGCCCCGGCTAACTACGTGCCAGCAGCCGCGGTAATACGTAGGGG
GCAAGCGTTATCCGGATTTACTGGGTGTAAAGGGAGCGTAGACGGCATGGCAAGTCTGAAGTGAAAACCCAGGGCTCAACCCTGGGA
CTGCTTTGGAAACTGTCAAGCTAGAGTGCAGGAGAGGTAAGTGGAATTCCTAGTGTAGCGGTGAAATGCGTAGATATTAGGAGGAAC
ACCAGTGGCGAAGGCGGCTTACTGGACTGTAACTGACGTTGAGGCTCGAAAGCGTGGGGAGCAAACAGGATTAGATACCCTGGTAGT
CCACGCCGTAAACGATGAGTGCTAGGTGTTGGGGGGCAAAGCCCTTCGGTGCCGTCGCAAACGCAATAAGCACTCCACCTGGGGAGT
ACGTTCGCAAGAATGAAACTCAAAGGAATTGACGGGGACCCGCACAAGCGGTGGAGCATGTGGTTTAATTCGAAGCAACGCGAAGAA
CCTTACCAAGTCTTGACATCCTCTTGACCGGCGTGTAACGGCGCCTTTCCTTCGGGACAAGAGAGACAGGTGGTGCATGGTTGTCGT
CAGCTCGTGTCGTGAGATGTTGGGTTAAGTCCCGCAACGAGCGCAACCCTTATCCTTAGTAGCCAGCATTAAGATGGGCACTCTAGG
GAGACTGCCAGGGACAACCTGGAGGAAGGTGGGGATGACGTCAAATCATCATGCCCCTTATGATTTGGGCTACACACGTGCTACAAT
GGCGTAAACAAAGGGAAGCGACCCTGCGAAGGTGAGCAAATCTCAAAAATAACGTCCCAGTTCGGACTGTAGTCTGCAACCCGACTA
CACGAAGCNNGAATCGCTAGTAATCGCGAATCAGAATGTCGCGGTGAATACGNTCCCGGGTCTTGTACACACCGCCCGTCACACCAT
GGGAGTCAGCAACGNCCGAAGTCAGTGACCCAACCGAAAGGAGGGAGNTGCNGAAGNNGNNNNN strain 25 >1F3_27Fmod-PREMIX.fasta

SEQ ID NO: 25

AGTTTGANNTTGGCTCAGGATGAACGCTGGCGGCGTGCCTAACACATGCAAGTCGAGCGAAGCGCTGTTTTCAGAATCTTCGGAGGA
AGAGGACAGTGACTGAGCGGCGGACGGGTGAGTAACGCGTGGGCAACCTGCCTCATACAGGGGGATAACAGTTAGAAATGACTGCTA
ATACCGCATAAGCGCACAGGACCGCATGGTGTAGTGTGAAAAACTCCGGTGGTATGAGATGGACCCGCGTCTGATTAGGTAGTTGGT

-continued

```
GGGGTAAAGGCCTACCAAGCCGACGATCAGTAGCCGACCTGAGAGGGTGACCGGCCACATTGGGACTGAGACACGGCCCAAACTCCT
ACGGGAGGCAGCAGTGGGGAATATTGCACAATGGGGGAAACCCTGATGCAGCGACGCCGCGTGAAGGAAGAAGTATTTCGGTATGTA
AACTTCTATCAGCAGGGAAGAAGATGACGGTACCTGAGTAAGAAGCACCGGCTAAATACGTGCCAGCAGCCGCGGTAATACGTATGG
TGCAAGCGTTATCCGGATTTACTGGGTGTAAAGGGAGCGTAGACGGATAGGCAAGTCTGGAGTGAAAACCCAGGGCTCAACTCTGGG
ACTGCTTTGGAAACTGCAGATCTGGAGTGCCGGAGAGGTAAGCGGAATTCCTAGTGTAGCGGTGAAATGCGTAGATATTAGGAGGAA
CACCAGTGGCGAAGGCGGCTTACTGGACGGTGACTGACGTTGAGGCTCGAAAGCGTGGGGAGCAAACAGGATTAGATACCCTGGTAG
TCCACGCCGTAAACGATGACTACTAGGTGTCGGTGTGCAAAGCACATCGGTGCCGCAGCAAACGCAATAAGTAGTCCACCTGGGGAG
TACGTTCGCAAGAATGAAACTCAAAGGAATTGACGGGGACCCGCACAAGCGGTGGAGCATGTGGTTTAATTCGAAGCAACGCGAAGA
ACCTTACCTGGTCTTGACATCCGGATGACGGGCGAGTAATGTCGCCGTCCCTTCGGGGCATCCGAGACAGGTGGTGCATGGTTGTCG
TCAGCTCGTGTCGTGAGATGTTGGGTTAAGTCCCGCAACGAGCGCAACCCTTATCTTCAGTAGCCAGCATATAAGGTGGGCACTCTG
GAGAGACTGCCAGGGAGAACCTGGAGGAAGGTGGGGATGACGTCAAATCATCATGCCCCTTATGGCCAGGGCTACACACGTGCTACA
ATGGCGTAAACAAAGGGAAGCGAGAGGGTGACCTGAAGCGAATCCCAAAAATAACGTCTCAGTTCGGATTGTAGTCTGCAACTCGAC
TACATGAAGCTGGAATCGCTAGTAATCGCGGATCAGCATGCCGCGGTGAATACGTTCCCGGGTCTTGTACACACCGCCCGTCACACC
ATGGGAGTCAGTAACGCCCGAAGCCANTGACCCAACCTTAGAGGAGGGAGNNNNNNNNNNNNNN
strain 26 1A1_27Fmod-PREMIX_Length_998
                                                                       SEQ ID NO: 26
AGTTTGATTATGGCTCAGGATGAACGCTGGCGGCATGCCTAATACATGCAAGTCGAACGAAGTTTCGAGGAAGCTTGCTTCCAAAGA
GACTTAGTGGCGAACGGGTGAGTAACACGTAGGTAACCTGCCCATGTGTCCGGGATAACTGCTGGAAACGGTAGCTAAAACCGGATA
GGTATACAGAGCGCATGCTCAGTATATTAAAAGCGCCCATCAAGGCGTGAACATGGATGGACCTGCGCGCATTAGCTAGTTGGTGAG
GTAACGGCCCACCAAGGCGATGATGCGTAGCCGGCCTGAGAGGGTAAACGGCCACATTGGGACTGAGACACGGCCCAAACTCCTACG
GGAGGCAGCAGTAGGGAATTTTCGTCAATGGGGGAAACCCTGAACGAGCAATGCCGCGTGAGTGAAGAAGGTCTTCGGATCGTAAAG
CTCTGTTGTAAGTGAAGAACGGCTCATAGAGGAAATGCTATGGGAGTGACGGTAGCTTACCAGAAAGCCACGGCTAACTACGTGCCA
GCAGCCGCGGTAATACGTAGGTGGCAAGCGTTATCCGGAATCATTGGGCGTAAAGGGTGCGTAGGTGGCGTACTAAGTCTGTAGTAA
AAGGCAATGGCTCAACCATTGTAAGCTATGGAAACTGGTATGCTGGAGTGCAGAAGAGGGCGATGGAATTCCATGTGTAGCGGTAAA
ATGCGTAGATATATGGAGGAACACCAGTGGCGAAGGCGGTCGCCTGGTCTGTAACTGACACTGAGGCACGAAAGCGTGGGGAGCAAA
TAGGATTAGATACCCTAGTAGTCCACGCCGTAAACGATGAGAACTAAGTGTTGGAGGAATTCAGTGCTGCAGTTAACGCAATAAGTT
CTCCGCCTGGGGAGTATGCACGCAAGTGTGAAACTCAAAGGAATTGACGGGGCCCGCACAAGCGGTGGAGTATGTGGTTTAATTCG
AAGCAACGCGAAGAACCTTACCAGGCCTTGACATGGAAACAAATACCCTAGAGATAGGGGGATAATTATGGATCACACAGGTGGTGC
ATGGTTGTCGTCAGCTCGTGTCGTGAGATGTTGGGTTAAGTCCCGCAACGAGCGCAACCCTTGTCGCATGTTACCAGCATCAAGTTG
GGGACTCATGCGAGACTGCCGGTGACAAACCGGAGGAAGGTGGGGATGACGTCAAATCATCATGCCCCTTATGGCCTGGGCTACACA
CGTACTACAATGGCGACCACAAAGAGCAGCGACACAGTGATGTGAAGCGAATCTCATAAAGGTCGTCTCAGTTCGGATTGAAGTCTG
CAACTCGACTTCATGAAGTCGGAATCGCTAGTAATCGCAGATCAGCATGCTGCGGTGAATACGTTCTCGGGCCTTGTACACACCGCC
CGTCAAACCATGGGAGTCAGTAATACCCGAAGCCGGTGGCATAACCNTAAGGNNNNNCCNNNNNNA
```

SEQ ID NO: 27
16S RNA sequence corresponding to LN998073

SEQ ID NO: 28
16S RNA sequence corresponding to KR822463

SEQ ID NO: 29
16S RNA sequence corresponding to CP011531

SEQ ID NO: 30
16S RNA sequence corresponding to NR112945

SEQ ID NO: 31
16S RNA sequence corresponding to KM098109

-continued

| Description | SEQ ID NO |
|---|---|
| 16S RNA sequence corresponding to NR113078 | SEQ ID NO: 32 |
| 16S RNA sequence corresponding to NR041464 | SEQ ID NO: 33 |
| 16S RNA sequence corresponding to LT223566 | SEQ ID NO: 34 |
| 16S RNA sequence corresponding to NR112835 | SEQ ID NO: 35 |
| 16S RNA sequence corresponding to NR113248 | SEQ ID NO: 36 |
| 16S RNA sequence corresponding to NR041342 | SEQ ID NO: 37 |
| 16S RNA sequence corresponding to NR112933 | SEQ ID NO: 38 |
| 16S RNA sequence corresponding to NR112893 | SEQ ID NO: 39 |
| 16S RNA sequence corresponding to HE974918 | SEQ ID NO: 40 |
| 16S RNA sequence corresponding to NR043016 | SEQ ID NO: 41 |
| 16S RNA sequence corresponding to AB618791 | SEQ ID NO: 42 |
| 16S RNA sequence corresponding to AB215083 | SEQ ID NO: 43 |
| 16S RNA sequence corresponding to NR112935 | SEQ ID NO: 44 |
| 16S RNA sequence corresponding to AB249652 | SEQ ID NO: 45 |
| 16S RNA sequence corresponding to NR113076 | SEQ ID NO: 46 |
| 16S RNA sequence corresponding to NR112944 | SEQ ID NO: 47 |
| 16S RNA sequence corresponding to JX519760 | SEQ ID NO: 48 |
| 16S RNA sequence corresponding to AJ311620 | SEQ ID NO: 49 |
| 16S RNA sequence corresponding to EF564278 | SEQ ID NO: 50 |
| 16S RNA sequence corresponding to KT156811 | SEQ ID NO: 51 |
| 16S RNA sequence corresponding to HM008265 | SEQ ID NO: 52 |

Additional sequences of interest are provided below:

H81A6_16S_ribosomal_RNA

SEQ ID NO: 54

```
CGAAGAGTTTGATCCTGGCTCAGGATGAACGCTGACAGAATGCTTAACACATGCAAGTCTACTTGATCCTTCGGGTGAAGGTGGCGG
ACGGGTGAGTAACGCGTAAAGAACTTGCCTTACAGACTGGGACAACATTTGGAAACGAATGCTAATACCGGATATTATGATTGGGTC
GCATGATCTGATTATGAAAGCTATATGCGCTGTGAGAGAGCTTTGCGTCCCATTAGTTAGTTGGTGAGGTAACGGCTCACCAAGACG
ATGATGGGTAGCCGGCCTGAGAGGGTGAACGGCCACAAGGGGACTGAGACACGGCCCTTACTCCTACGGGAGGCAGCAGTGGGGAAT
ATTGGACAATGGACCAAAAGTCTGATCCAGCAATTCTGTGTGCACGAAGAAGTTTTTCGGAATGTAAAGTGCTTTCAGTTGGGAAGA
AGTCAGTGACGGTACCAACAGAAGAAGCGACGGCTAAATACGTGCCAGCAGCCGCGGTAATACGTATGTCGCAAGCGTTATCCGGAT
```

-continued

TTATTGGGCGTAAAGCGCGTCTAGGCGGCTTAGTAAGTCTGATGTGAAAATGCGGGGCTCAACCCCGTATTGCGTTGGAAACTGCTA
AACTAGAGTACTGGAGAGGTAGGCGGAACTACAAGTGTAGAGGTGAAATTCGTAGATATTTGTAGGAATGCCGATGGGGAAGCCAGC
CTACTGGACAGATACTGACGCTAAAGCGCGAAAGCGTGGGTAGCAAACAGGATTAGATACCCTGGTAGTCCACGCCGTAAACGATGA
TTACTAGGTGTTGGGGGTCGAACCTCAGCGCCCAAGCTAACGCGATAAGTAATCCGCCTGGGGAGTACGTACGCAAGTATGAAACTC
AAAGGAATTGACGGGGACCCGCACAAGCGGTGGAGCATGTGGTTTAATTCGACGCAACGCGAGGAACCTTACCAGCGTTTGACATCC
CAAGAAGTTAACAGAGATGTTTTCGTGCCTCTTCGGAGGAACTTGGTGACAGGTGGTGCATGGCTGTCGTCAGCTCGTGTCGTGAGA
TGTTGGGTTAAGTCCCGCAACGAGCGCAACCCCTTTCGTATGTTACCATCATTAAGTTGGGGACTCATGCGAGACTGCCTGCGATGA
GCAGGAGGAAGGTGGGGATGACGTCAAGTCATCATGCCCCTTATACGCTGGGCTACACACGTGCTACAATGGGTAGTACAGAGAGCT
GCAAACCTGCGAGGGTAAGCTAATCTCATAAAACTATTCTTAGTTCGGATTGTACTCTGCAACTCGAGTACATGAAGTTGGAATCGC
TAGTAATCGCAAATCAGCTATGTTGCGGTGAATACGTTCTCGGGTCTTGTACACACCGCCCGTCACACCACGAGAGTTGGTTGCACC
TGAAGTAACAGGCCTAACCGTAAGGAGGGATGTTCCGAGGGTGTGATTAGCGATTGGGGTGAAGTCGTAACAAGGTATCCGTACGGG
AACGTGCGGATGGATCACCTCCTT

H82F11_16S_ribosomal_RNA
SEQ ID NO: 55
CGAAGAGTTTGATCCTGGCTCAGGATGAACGCTAGCGACAGGCTTAACACATGCAAGTCGAGGGGCATCATGGTAAGTAGCAATACT
TATTGATGGCGACCGGCGCACGGGTGAGTAACGCGTATGCAACTTACCTATCAGAGGGGGATAGCCCGGCGAAAGTCGGATTAATAC
TCCATAAAACAGGGGTTCCGCATGGGACTATTTGTTAAAGATTCATCGCTGATAGATAGGCATGCGTTCCATTAGGCAGTTGGCGGG
GTAACGGCCCACCAAACCGACGATGGATAGGGGTTCTGAGAGGAAGGTCCCCCACATTGGTACTGAGACACGGACCAAACTCCTACG
GGAGGCAGCAGTGAGGAATATTGGTCAATGGCCGAGAGGCTGAACCAGCCAAGTCGCGTGAAGGATGAAGGATCTATGGTTTGTAAA
CTTCTTTTATAGGGGAATAAAGTGTGGGACGTGTTCCATTTTGTATGTACCCTATGAATAAGCATCGGCTAACTCCGTGCCAGCAGC
CGCGGTAATACGGAGGATGCGAGCGTTATCCGGATTTATTGGGTTTAAAGGGTGCGTAGGTGGTAATTTAAGTCAGCGGTGAAAGTT
TGTGGCTCAACCATAAAATTGCCGTTGAAACTGGGTTACTTGAGTGTGTTTGAGGTAGGCGGAATGCGTGGTGTAGCGGTGAAATGC
ATAGATATCACGCAGAACTCCAATTGCGAAGGCAGCTTACTAAACCATAACTGACACTGAAGCACGAAAGCGTGGGTATCAAACAGG
ATTAGATACCCTGGTAGTCCACGCAGTAAACGATGATTACTAGGAGTTTGCGATACACAGTAAGCTCTACAGCGAAAGCGTTAAGTA
ATCCACCTGGGGAGTACGCCGGCAACGGTGAAACTCAAAGGAATTGACGGGGGCCCGCACAAGCGGAGGAACATGTGGTTTAATTCG
ATGATACGCGAGGAACCTTACCCGGGTTTGAACGTAGTCAGACCGACCTTGAAAGAGGTTTTCTAGCAATAGCTGATTACGAGGTGC
TGCATGGTTGTCGTCAGCTCGTGCCGTGAGGTGTCGGCTTAAGTGCCATAACGAGCGCAACCCTTATCACTAGTTACTAACAGGTTA
AGCTGAGGACTCTGGTGAGACTGCCAGCGTAAGCTGTGAGGAAGGTGGGGATGACGTCAAATCAGCACGGCCCTTACATCCGGGCG
ACACACGTGTTACAATGGCATGGACAAAGGGCAGCTACCTGGCGACAGGATGCTAATCTCTAAACCATGTCTCAGTTCGGATCGGAG
TCTGCAACTCGACTCCGTGAAGCTGGATTCGCTAGTAATCGCGCATCAGCCATGGCGCGGTAATACGTTCCCGGGCCTTGTACACA
CCGCCCGTCAAGCCATGGGAGCCGGGGGTACCTGAAGTCCGTAACCGCAAGGATCGGCCTAGGGTAAAACTGGTGACTGGGGCTAAG
TCGTAACAAGGTAGCCGTACCGGAAGGTGCGGCTGGAACACCTCCTT H82A6_16S_ribosomal_RNA
SEQ ID NO: 56
AATAAAGATTAATTGGTAAAGGATGGGGATGCGTCCCATTAGCTTGTTGGCGGGGTAACGGCCCACCAAGGCGACGATGGGTAGGGG
TTCTGAGAGGAAGGTCCCCCACATTGGAACTGAGACACGGTCCAAACTCCTACGGGAGGCAGCAGTGAGGAATATTGGTCAATGGGC
GCGAGCCTGAACCAGCCAAGTAGCGTGGAGGACGACGGCCCTACGGGTTGTAAACTCCTTTTATAAGGGGATAAAGTTGGCCATGTA
TGGCCATTTGCAGGTACCTTATGAATAAGCATCGGCTAATTCCGTGCCAGCAGCCGCGGTAATACGGAAGATGCGAGCGTTATCCGG
ATTTATTGGGTTTAAAGGGAGCGTAGGCGGGCAGTCAAGTCAGCGGTCAAATGGCGCGGCTCAACCGCGTTCCGCCGTTGAAACTGG
CAGCCTTGAGTATGCACAGGGTACATGGAATTCGTGGTGTAGCGGTGAAATGCTTAGATATCACGAGGAACTCCGATCGCGCAGGCA
TTGTACCGGGGCATTACTGACGCTGAGGCTCGAAGGTGCGGGTATCAAACAGGATTAGATACCCTGGTAGTCCGCACAGTAAACGAT
GAATGCCCGCTGTCGGCGACATAGTGTCGGCGGCCAAGCGAAAGCGTTAAGCATTCCACCTGGGGAGTACGCCGGCAACGGTGAAAC
TCAAAGGAATTGACGGGGGCCCGCACAAGCGGAGGAACATGTGGTTTAATTCGATGATACGCGAGGAACCTTACCCGGGCTTGAATC GCAGGTGCATGGGCCGGAGACGGCCCTTTCCTTCGGGACTCCTGCGAAGGTGCTGCATGGTTGTCGTCAGCTCGTGCCGTGAGGTGT CGGCTTAAGTGCCATAACGAGCGCAACCCCCCTCCCCAGTTGCCACCGGGTAATGCCGGGCACTTTGGGACACTGCCACCGCAAGG TGCGAGGAAGGTGGGGATGACGTCAAATCAGCACGGCCCTTACGTCCGGGGCGACACACGTGTTACAATGGGGGGTACAGAGGGCCG CTGCCCGGTGACGGTTGGCCAATCCCTAAAACCCCTCTCAGTTCGGACTGGAGTCTGCAACCCGACTCCACGAAGCTGGATTCGCTA GTAATCGCGCATCAGCCATGGCGCGGTGAATACGTTCCCGGGCCTTGTACACACCGCCCGTCAAGCCATGAAAGCCGGGGGTGCCTG AAGTCCGTGACCGCGAGGGTCGGCCTAGGGTAAAACCGGTGATTGGGGCTAAGTCGTAACAAGGTAGCCGTACCGGAAGGTGCGGCT

GGAACACCTCCTTT

H82G9_16S_ribosomal_RNA

SEQ ID NO: 57

CGAAGAGTTTGATCCTGGCTCAGGATGAACGCTAGCGACAGGCTTAACACATGCAAGTCGAGGGGCAGCACAGGTAGCAATACCGGG

TGGCGACCGGCGCACGGGTGAGTAACGCGTATGCAACTTGCCTATCAGAGGGGGATAACCCGGCGAAAGTCGGACTAATACCGCATG

AAGCAGGGGCCCCGCATGGGGATATTTGCTAAAGATTCATCGCTGATAGATAGGCATGCGTTCCATTAGGCAGTTGGCGGGGTAACG

GCCCACCCAAACCGACGATGGATAGGGGTTCTGAGAGGAAGGTCCCCCACATTGGTACTGAGACACGGACCAAACTCCTACGGGAGGC

AGCAGTGAGGAATATTGGTCAATGGCCGAGAGGCTGAACCAGCCAAGTCGCGTGAGGGATGAAGGTTCTATGGATCGTAAACCTCTT

TTATAAGGGAATAAAGTGCGGGACGTGTCCCGTTTTGTATGTACCTTATGAATAAGGATCGGCTAACTCCGTGCCAGCAGCCGCGGT

AATACGGAGGATCCGAGCGTTATCCGGATTTATTGGGTTTAAAGGGTGCGTAGGCGGCCTTTTAAGTCAGCGGTGAAAGTCTGTGGC

TCAACCATAGAATTGCCGTTGAAACTGGGGGGCTTGAGTATGTTTGAGGCAGGCGGAATGCGTGGTGTAGCGGTGAAATGCATAGAT

ATCACGCAGAACCCCGATTGCGAAGGCAGCCTGCCAAGCCATTACTGACGCTGATGCACGAAAGCGTGGGATCAAACAGGATTAGA

TACCCTGGTAGTCCACGCAGTAAACGATGATCACTAGCTGTTTGCGATACACTGTAAGCGGCACAGCGAAAGCGTTAAGTGATCCAC

CTGGGGAGTACGCCGGCAACGGTGAAACTCAAAGGAATTGACGGGGGCCCGCACAAGCGGAGGAACATGTGGTTTAATTCGATGATA

CGCGAGGAACCTTACCCGGGTTTGAACGCATTCGGACCGAGGTGGAAACACCTTTTCTAGCAATAGCCGTTTGCGAGGTGCTGCATG

GTTGTCGTCAGCTCGTGCCGTGAGGTGTCGGCTTAAGTGCCATAACGAGCGCAACCCTTGCCACTAGTTACTAACAGGTAAAGCTGA

GGACTCTGGTGGGACTGCCAGCGTAAGCTGCGAGGAAGGCGGGGATGACGTCAAATCAGCACGGCCCTTACATCCGGGGCGACACAC

GTGTTACAATGGCGTGGACAAAGGGAAGCCACCTGGCGACAGGGAGCGAATCCCCAAACCACGTCTCAGTTCGGATCGGAGTCTGCA

ACCCGACTCCGTGAAGCTGGATTCGCTAGTAATCGCGCATCAGCCATGGCGCGGTGAATACGTTCCCGGGCCTTGTACACACCGCCC

GTCAAGCCATGGGAGCCGGGGGTACCTGAAGTCCGTAACCGCGAGGATCGGCCTAGGGTAAAACTGGTGACTGGGGCTAAGTCGTAA

CAAGGTAGCCGTACCGGAAGGTGCGGCTGGAACACCTCCTTT

H81E7_16S_ribosomal_RNA

SEQ ID NO: 58

ATGGAGAGTTTGATCCTGGCTCAGGATGAACGCTAGCGGCAGGCCTAACACATGCAAGTCGAGGGGCAGCGGGATTGAAGCTTGCTT

CAGTTGCCGGCGACCGGCGCACGGGTGCGTAACGCGTATGCAACCTACCCATAACAGGGGGATAACACTGAGAAATCGGTACTAATA

TCCCATAACATCAAGAGGGGCATCCCTTTTGGTTGAAAACTCCGGTGGTTATGGATGGGCATGCGTTGTATTAGCTAGTTGGTGAGG

TAACGGCTCACCAAGGCGACGATACATAGGGGACTGAGAGGTTAACCCCCCACATTGGTACTGAGACACGGACCAAACTCCTACGG

GAGGCAGCAGTGAGGAATATTGGTCAATGGACGCAAGTCTGAACCAGCCATGCCGCGTGCAGGATGACGGCTCTATGAGTTGTAAAC

TGCTTTTGTACGAGGGTAAACCCGGATACGTGTATCCGGCTGAAAGTATCGTACGAATAAGGATCGGCTAACTCCGTGCCAGCAGCC

GCGGTAATACGGAGGATTCAAGCGTTATCCGGATTTATTGGGTTTAAAGGGTGCGTAGGCGGTTTGATAAGTTAGAGGTGAAATACC

GGTGCTTAACACCGGAACTGCCTCTAATACTGTTGAGCTAGAGAGTAGTTGCGGTAGGCGGAATGTATGGTGTAGCGGTGAAATGCT

TAGAGATCATACAGAACACCGATTGCGAAGGCAGCTTACCAAACTATATCTGACGTTGAGGCACGAAAGCGTGGGGAGCAAACAGGA

TTAGATACCCTGGTAGTCCACGCAGTAAACGATGATAACTCGCTGTCGGCGATACACAGTCGGTGGCTAAGCGAAAGCGATAAGTTA

TCCACCTGGGGAGTACGTTCGCAAGAATGAAACTCAAAGGAATTGACGGGGGCCCGCACAAGCGGAGGAACATGTGGTTTAATTCGA

TGATACGCGAGGAACCTTACCCGGGCTTGAAAGTTACTGACGATTCTGGAAACAGGATTTCCCTTCGGGGCAGGAAACTAGGTGCTG

CATGGTTGTCGTCAGCTCGTGCCGTGAGGTGTCGGGTTAAGTCCCATAACGAGCGCAACCCCTACCGTTAGTTGCCATCAGGTCAAG

CTGGGCACTCTGGCGGGACTGCCGGTGTAAGCCGAGAGGAAGGTGGGGATGACGTCAAATCAGCACGGCCCTTACGTCCGGGCTAC

ACACGTGTTACAATGGTAGGTACAGAGGGCAGCTACCCAGTGATGGGATGCGAATCTCGAAAGCCTATCTCAGTTCGGATTGGAGGC

TGAAACCCGCCTCCATGAAGTTGGATTCGCTAGTAATCGCGCATCAGCCATGGCGCGGTGAATACGTTCCCGGGCCTTGTACACACC

GCCCGTCAAGCCATGGAAGCTGGGGGTGCCTGAAGTTCGTGACCGCAAGGAGCGACCTAGGGCAAAACCGGTGACTGGGGCTAAGTC

GTAACAAGGTAGCCGTACCGGAAGGTGCGGCTGGAACACCTCCTTT

H81C1_16S_ribosomal_RNA
SEQ ID NO: 59

TATTGAGAGTTTGATCCTGGCTCAGGACGAACGCTGGCGGTATGCTTAACACATGCAAGTCGAACGAGAAGGTTTTGATGGATCCTT

CGGGTGATATCAGAACTGGAAAGTGGCGAACGGGTGAGTAACGCGTGGGTAACCTGCCCTATGGAAAGGAATAGCCTCGGGAAACTG

GGAGTAAAGCCTTATATTATGGTTTTGTCGCATGGCAAGATCATGAAAACTCCGGTGCCATAGGATGGACCCGCGTCCCATTAGCTA

GTTGGTGAGATAACAGCCCACCAAGGCGACGATGGGTAACCGGTCTGAGAGGGCGAACGGTCACACTGGAACTGAGACACGGTCCAG

ACTCCTACGGGAGGCAGCAGTGGGGAATATTGCGCAATGGGGGCAACCCTGACGCAGCAATACCGCGTGAGTGAAGAAGGTTTTCGG

ATCGTAAAGCTCTGTTATTGGGGAAGAAGAATGACGGTACCCAATGAGGAAGTCCCGGCTAACTACGTGCCAGCAGCCGCGGTAATA

CGTAGGGGACAAGCGTTGTCCGGAATGACTGGGCGTAAAGGGCGCGTAGGCGGTCTATTAAGTCTGATGTGAAAGGTACCGGCTCAA

CCGGTGAAGTGCATTGGAAACTGGTAGACTTGAGTATTGGAGAGGCAAGTGGAATTCCTAGTGTAGCGGTGAAATGCGTAGATATTA

GGAGGAACACCAGTGGCGAAGGCGGCTTGCTGGACAAATACTGACGCTGAGGTGCGAAAGCGTGGGGAGCGAACAGGATTAGATACC

CTGGTAGTCCACGCCGTAAACGATGAATGCTAGGTGTTGGGAAACTCAGTGCCGCAGTTAACACAATAAGCATTCCGCCTGGGGAG

TACGACCGCAAGGTTGAAACTCAAAGGAATTGACGGGGACCCGCACAAGCAGCGGAGCATGTGGTTTAATTCGAAGCAACGCGAAGA

ACCTTACCAGGTCTTGACATCCTCTGACGAGCCTAGAGATAGGAAGTTTCCTTCGGGAACAGAGAGACAGGTGGTGCATGGTTGTCG

TCAGCTCGTGTCGTGAGATGTTGGGTTAAGTCCCGCAACGAGCGCAACCCCTGCCTTTAGTTGCCAGCATTAAGTTGGGCACTCTAG

AGGGACTGCCGTAGACAATACGGAGGAAGGTGGGGACGACGTCAAATCATCATGCCCCTTATGACCTGGGCTACACACGTGCTACAA

TGGTCTGAACAGAGGGCCGCGAAGCCGCGAGGTGAAGCAAATCCCTTAAAACAGATCCCAGTTCGGATTGCAGGCTGCAACTCGCCT

GCATGAAGTTGGAGTTGCTAGTAATCGCGGATCAGAATGCCGCGGTGAATGCGTTCCCGGGTCTTGTACACACCGCCCGTCACACCA

CGAGAGTTGGCAACACCCGAAGCCTGTGAGAGAACCGTAAGGACTCAGCAGTCGAAGGTGGGGCTAGTAATTGGGGTGAAGTCGTAA

CAAGGTAGCCGTATCGGAAGGTGCGGCTGGATCACCTCCTTT

H81B11_16S_ribosomal_RNA
SEQ ID NO: 60

ATGAAGAGTTTGATCCTGGCTCAGGATGAACGCTAGCTACAGGCTTAACACATGCAAGTCGAGGGGCAGCATGGTCTTAGCTTGCTA

AGGCTGATGGCGACCGGCGCACGGGTGAGTAACACGTATCCAACCTGCCGTCTACTCTTGGCCAGCCTTCTGAAAGGAAGATTAATC

CAGGATGGGATCATGAGTTCACATGTCCGCATGATTAAAGGTATTTTCCGGTAGACGATGGGGATGCGTTCCATTAGATAGTAGGCG

GGGTAACGGCCCACCTAGTCAACGATGGATAGGGGTTCTGAGAGGAAGGTCCCCCACATTGGAACTGAGACACGGTCCAAACTCCTA

CGGGAGGCAGCAGTGAGGAATATTGGTCAATGGGCGATGGCCTGAACCAGCCAAGTAGCGTGAAGGATGACTGCCCTATGGGTTGTA

AACTTCTTTTATAAAGGAATAAAGTCGGGTATGCATACCCGTTTGCATGTACTTTATGAATAAGGATCGGCTAACTCCGTGCCAGCA

GCCGCGGTAATACGGAGGATCCGAGCGTTATCCGGATTTATTGGGTTTAAAGGGAGCGTAGATGGATGTTTAAGTCAGTTGTGAAAG

TTTGCGGCTCAACCGTAAAATTGCAGTTGATACTGGATGTCTTGAGTGCAGTTGAGGCAGGCGGAATTCGTGGTGTAGCGGTGAAAT

GCTTAGATATCACGAAGAACTCCGATTGCGAAGGCAGCCTGCTAAGCTGCAACTGACATTGAGGCTCGAAAGTGTGGGTATCAAACA

GGATTAGATACCCTGGTAGTCCACACGGTAAACGATGAATACTCGCTGTTTGCGATATACGGCAAGCGGCCAAGCGAAAGCGTTAAG

TATTCCACCTGGGGAGTACGCCGGCAACGGTGAAACTCAAAGGAATTGACGGGGCCCGCACAAGCGGAGGAACATGTGGTTTAATT

CGATGATACGCGAGGAACCTTACCCGGGCTTAAATTGCACTCGAATGATCCGGAAACGGTTCAGCTAGCAATAGCGAGTGTGAAGGT

GCTGCATGGTTGTCGTCAGCTCGTGCCGTGAGGTGTCGGCTTAAGTGCCATAACGAGCGCAACCCTTGTTGTCAGTTACTAACAGGT

GATGCTGAGGACTCTGACAAGACTGCCATCGTAAGATGTGAGGAAGGTGGGGATGACGTCAAATCAGCACGGCCCTTACGTCCGGGG

CTACACACGTGTTACAATGGGGGGTACAGAGGGCCGCTACCACGCGAGTGGATGCCAATCCCTAAAACCCCTCTCAGTTCGGACTGG

AGTCTGCAACCCGACTCCACGAAGCTGGATTCGCTAGTAATCGCGCATCAGCCACGGCGCGGTGAATACGTTCCCGGGCCTTGTACA

-continued

CACCGCCCGTCAAGCCATGGGAGCCGGGGGTACCTGAAGTGCGTAACCGCGAGGATCGCCCTAGGGTAAAACTGGTGACTGGGGCTA

AGTCGTAACAAGGTAGCCGTACCGGAAGGTGCGGCTGGAACACCTCCTT

H81H9_16S_ribosomal_RNA
SEQ ID NO: 61

CGAAGAGTTTGATCCTGGCTCAGGATGAACGCTAGCGACAGGCTTAACACATGCAAGTCGAGGGGCAGCAGGAAGTAGCAATACTTT

GCTGGCGACCGGCGCACGGGTGAGTAACGCGTATGCAACCTACCTATCAGAGGGGGATAACCCGGCGAAAGTCGGACTAATACCGCA

TAAAACAGGGGTCCCGCATGGGAATATTTGTTAAAGATTTATTGCTGATAGATGGGCATGCGTTCCATTAGATAGTTGGTGAGGTAA

CGGCTCACCAAGTCTTCGATGGATAGGGGTTCTGAGAGGAAGGTCCCCCACACTGGTACTGAGACACGGACCAGACTCCTACGGGAG

GCAGCAGTGAGGAATATTGGTCAATGGGCGAGAGCCTGAACCAGCCAAGTCGCGTGAAGGATGAAGGATCTATGGTTCGTAAACTTC

TTTTATAGGGGAATAAAGTGCAGGACGTGTCCTGTTTTGTATGTACCCTATGAATAAGGATCGGCTAACTCCGTGCCAGCAGCCGCG

GTAATACGGAGGATCCGAGCGTTATCCGGATTTATTGGGTTTAAAGGGTGCGTAGGTGGCTTTTTAAGTCAGCGGTGAAAGTTTGTG

GCTCAACCATAAAATTGCCGTTGAAACTGGAGGGCTTGAGTATATTTGAGGTAGGCGGAATGCGTGGTGTAGCGGTGAAATGCATAG

ATATCACGCAGAACTCCAATTGCGAAGGCAGCTTACTAAACTATAACTGACACTGAAGCACGAAAGCGTGGGGATCAAACAGGATTA

GATACCCTGGTAGTCCACGCAGTAAACGATGATTACTAGGAGTTTGCGATACACAGTAAGCTCTACAGCGAAAGCGTTAAGTAATCC

ACCTGGGGAGTACGCCGGCAACGGTGAAACTCAAAGGAATTGACGGGGGCCCGCACAAGCGGAGGAACATGTGGTTTAATTCGATGA

TACGCGAGGAACCTTACCCGGGTTTGAACGTAAGTTGACCGGAGTGGAAACACTCTTTCTAGCAATAGCAATTTACGAGGTGCTGCA

TGGTTGTCGTCAGCTCGTGCCGTGAGGTGTCGGCTTAAGTGCCATAACGAGCGCAACCCTTATCTTTAGTTACTAACAGGTCGAGCT

GAGGACTCTAAAGAGACTGCCAGCGTAAGCTGTGAGGAAGGTGGGGATGACGTCAAATCAGCACGGCCCTTACATCCGGGCGACAC

ACGTGTTACAATGGTGGGGACAAAGGGCAGCTACCTGGCGACAGGATGCTAATCTCCAAACCCCATCTCAGTTCGGATCGAAGTCTG

CAACCCGACTTCGTGAAGCTGGATTCGCTAGTAATCGCGCATCAGCCATGGCGCGGTGAATACGTTCCCGGGCCTTGTACACACCGC

CCGTCAAGCCATGGGAGTTGGGGGTACCTAAAGTCCGTAACCGCAAGGATCGGCCTAGGGTAAAACCGATGACTGGGGCTAAGTCGT

AACAAGGTAGCCGTACCGGAAGGTGCGGCTGGAACACCTCCTTT

H82B1_16S_ribosomal_RNA
SEQ ID NO: 62

AATGAAGAGTTTGATCCTGGCTCAGGACGAACGCTGGCGGCGCGCCTAACACATGCAAGTCGAACGGAGCTGTTTTCTCTGAAGTTT

TCGGATGGAAGAGAGTTCAGCTTAGTGGCGAACGGGTGAGTAACACGTGAGCAACCTGCCTTTCAGTGGGGGACAACATTTGGAAAC

GAATGCTAATACCGCATAAGACCACAGTGTCGCATGGCACAGGGGTCAAAGGATTTATCCGCTGAAAGATGGGCTCGCGTCCGATTA

GCTAGATGGTGAGGTAACGGCCCACCATGGCGACGATCGGTAGCCGGACTGAGAGGTTGAACGGCCACATTGGGACTGAGACACGGC

CCAGACTCCTACGGGAGGCAGCAGTGGGGAATATTGCACAATGGGGGAAACCCTGATGCAGCGACGCCGCGTGGAGGAAGAAGGTCT

TCGGATTGTAAACTCCTGTCCCAGGGGACGATAATGACGGTACCCTGGGAGGAAGCACCGGCTAACTACGTGCCAGCAGCCGCGGTA

AAACGTAGGGTGCAAGCGTTGTCCGGAATTACTGGGTGTAAAGGGAGCGCAGGCGGATTGGCAAGTTGGGAGTGAAATCTATGGGCT

CAACCCATAAATTGCTTTCAAAACTGTCAGTCTTGAGTGGTGTAGAGGTAGGCGGAATTCCGGTGTAGCGGTGGAATGCGTAGATA

TCGGAGGAACACCAGTGGCGAAGGCGGCCTACTGGGCACTAACTGACGCTGAGGCTCGAAAGCATGGGTAGCAAACAGGATTAGAT

ACCCTGGTAGTCCATGCCGTAAACGATGATTACTAGGTGTGGGAGGATTGACCCCTTCCGTGCCGCAGTTAACACAATAAGTAATCC

ACCTGGGGAGTACGACCGCAAGGTTGAAACTCAAAGGAATTGACGGGGGCCCGCACAAGCAGTGGAGTATGTGGTTTAATTCGAAGC

AACGCGAAGAACCTTACCAGGTCTTGACATCGGATGCATACCTAAGAGATTAGGGAAGTCCTTCGGGACATCCAGACAGGTGGTGCA

TGGTTGTCGTCAGCTCGTGTCGTGAGATGTTGGGTTAAGTCCCGCAACGAGCGCAACCCTTATCGTTAGTTACTACGCAAGAGGACT

CTAGCGAGACTGCCGTTGACAAAACGGAGGAAGGTGGGGATGACGTCAAATCATCATGCCCTTTATGACCTGGGCTACACACGTACT

ACAATGGCTATTAACAGAGAGAAGCGATACCGCGAGGTGGAGCAAACCTCACAAAAATAGTCTCAGTTCGGATCGCAGGCTGCAACC

CGCCTGCGTGAAGCCGGAATTGCTAGTAATCGCGGATCAGCATGCCGCGGTGAATACGTTCCCGGGCCTTGTACACACCGCCCGTCA

CACCATGAGAGCCGGGGGACCCGAAGTCGGTAGTCTAACCGCAAGGAGGACGCCGCCGAAGGTAAAACTGGTGATTGGGGTGAAGT

CGTAACAAGGTAGCCGTATCGGAAGGTGCGGCTGGATCACCTCCTTT

H82G1_16S_ribosomal_RNA

SEQ ID NO: 63

ATGAAGAGTTTGATCCTGGCTCAGGATGAACGCTAGCTACAGGCTTAACACATGCAAGTCGAGGGGCAGCATGAACTTAGCTTGCTA
AGTTTGATGGCGACCGGCGCACGGGTGAGTAACACGTATCCAACCTGCCGATGACTCGGGGATAGCCTTTCGAAAGAAAGATTAATA
CCCGATGGCATAGTTCTTCCGCATGGTGGAACTATTAAAGAATTTCGGTCATCGATGGGGATGCGTTCCATTAGGTTGTTGGCGGGG
TAACGGCCCACCAAGCCTTCGATGGATAGGGGTTCTGAGAGGAAGGTCCCCCACATTGGAACTGAGACACGGTCCAAACTCCTACGG
GAGGCAGCAGTGAGGAATATTGGTCAATGGACGAGAGTCTGAACCAGCCAAGTAGCGTGAAGGATGACTGCCCTATGGGTTGTAAAC
TTCTTTTATACGGGAATAAAGTGAGGCACGTGTGCCTTTTTGTATGTACCGTATGAATAAGGATCGGCTAACTCCGTGCCAGCAGCC
GCGGTAATACGGAGGATCCGAGCGTTATCCGGATTTATTGGGTTTAAAGGGAGCGTAGGCGGACGCTTAAGTCAGTTGTGAAAGTTT
GCGGCTCAACCGTAAAATTGCAGTTGATACTGGGTGTCTTGAGTACAGTAGAGGCAGGCGGAATTCGTGGTGTAGCGGTGAAATGCT
TAGATATCACGAAGAACTCCGATTGCGAAGGCAGCCTGCTGGACTGTAACTGACGCTGATGCTCGAAAGTGTGGGTATCAAACAGGA
TTAGATACCCTGGTAGTCCACACAGTAAACGATGAATACTCGCTGTTTGCGATATACAGTAAGCGGCCAAGCGAAAGCGTTAAGTAT
TCCACCTGGGGAGTACGCCGGCAACGGTGAAACTCAAAGGAATTGACGGGGGCCCGCACAAGCGGAGGAACATGTGGTTTAATTCGA
TGATACGCGAGGAACCTTACCCGGGCTTGAATTGCAACTGAATGATGTGGAGACATGTCAGCCGCAAGGCAGTTGTGAAGGTGCTGC
ATGGTTGTCGTCAGCTCGTGCCGTGAGGTGTCGGCTTAAGTGCCATAACGAGCGCAACCCTTATCGATAGTTACCATCAGGTGATGC
TGGGGACTCTGTCGAGACTGCCGTCGTAAGATGTGAGGAAGGTGGGGATGACGTCAAATCAGCACGGCCCTTACGTCCGGGGCTACA
CACGTGTTACAATGGGGGGTACAGAAGGCAGCTACACGGCGACGTGATGCTAATCCCGAAAGCCTCTCTCAGTTCGGATTGGAGTCT
GCAACCCGACTCCATGAAGCTGGATTCGCTAGTAATCGCGCATCAGCCACGGCGCGGTGAATACGTTCCCGGGCCTTGTACACACCG
CCCGTCAAGCCATGAAAGCCGGGGGTACCTGAAGTGCGTAACCGCAAGGAGCGCCCTAGGGTAAAACTGGTGATTGGGGCTAAGTCG
TAACAAGGTAGCCGTACCGGAAGGTGCGGCTGGAACACCTCCTT

H82G5_16S_ribosomal_RNA

SEQ ID NO: 64

ATTGGAGAGTTTGATCCTGGCTCAGGACGAACGCTGGCGGCGTGCCTAACACATGCAAGTCGAACGGAGAATTTTATTTCGGTAGAA
TTCTTAGTGGCGAACGGGTGAGTAACGCGTAGGCAACCTACCCTTTAGACGGGGACAACATTCCGAAAGGAGTGCTAATACCGGATG
TGATCATCTTGCCGCATGGCAGGATGAAGAAAGATGGCCTCTACAAGTAAGCTATCGCTAAAGGATGGGCCTGCGTCTGATTAGCTA
GTTGGTAGTGTAACGGACTACCAAGGCGATGATCAGTAGCCGGTCTGAGAGGATGAACGGCCACATTGGGACTGAGACACGGCCCAA
ACTCCTACGGGAGGCAGCAGTGGGGAATCTTCCGCAATGGACGAAAGTCTGACGGAGCAACGCCGCGTGAGTGATGAAGGATTTCGG
TCTGTAAAGCTCTGTTGTTTATGACGAACGTGCAGTGTGTGAACAATGCATTGCAATGACGGTAGTAAACGAGGAAGCCACGGCTAA
CTACGTGCCAGCAGCCGCGGTAATACGTAGGTGGCGAGCGTTGTCCGGAATTATTGGGCGTAAAGAGCATGTAGGCGGCTTAATAAG
TCGAGCGTGAAAATGCGGGGCTCAACCCCGTATGGCGCTGGAAACTGTTAGGCTTGAGTGCAGGAGAGGAAAGGGGAATTCCCAGTG
TAGCGGTGAAATGCGTAGATATTGGGAGGAACACCAGTGGCGAAGGCGCCTTTCTGGACTGTGTCTGACGCTGAGATGCGAAAGCCA
GGGTAGCGAACGGGATTAGATACCCCGGTAGTCCTGGCCGTAAACGATGGGTACTAGGTGTAGGAGGTATCGACCCCTTCTGTGCCG
GAGTTAACGCAATAAGTACCCCGCCTGGGGAGTACGCCGCAAGGTTGAAACTCAAAGGAATTGACGGGGGCCCGCACAAGCGGTGG
AGTATGTGGTTTAATTCGACGCAACGCGAAGAACCTTACCAAGGCTTGACATTGATTGAACGCTCTAGAGATAGAGATTTCCCTTCG
GGGACAAGAAAACAGGTGGTGCATGGCTGTCGTCAGCTCGTGTCGTGAGATGTTGGGTTAAGTCCCGCAACGAGCGCAACCCCTATC
CTATGTTACCAGCAAGTAAAGTTGGGGACTCATGGGAGACTGCCAGGGACAACCTGGAGGAAGGCGGGGATGACGTCAAGTCATCAT
GCCCCTTATGTCTTGGGCTACACACGTACTACAATGGTCGGAAACAGAGGGAAGCGAAGCCGCGAGGCAGAGCAAACCCCAGAAACC
CGATCTCAGTTCGGATCGCAGGCTGCAACCCGCCTGCGTGAAGTCGGAATCGCTAGTAATCGCAGGTCAGCATACTGCGGTGAATAC
GTTCCCGGGCCTTGTACACACCGCCCGTCACACCACGAAAGTTGGTAACACCCGAAGCCGGTGAGGTAACCTATTAGGAGCCAGCCG
TCTAAGGTGGGGCCGATGATTGGGGTGAAGTCGTAACAAGGTAGCCGTATCGGAAGGTGCGGCTGGATCACCTCCTTT

The invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items. Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1: Identification of a CD8+ T-Cell Inducing Bacterial Cocktail

Figure 1B:
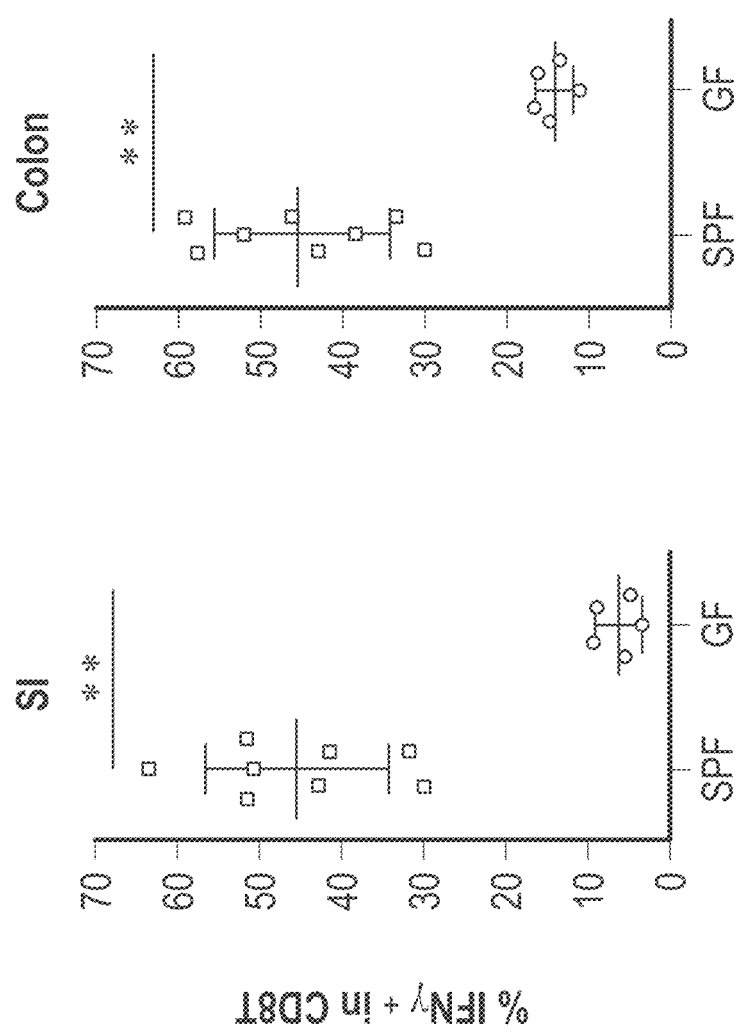
Figures 2A, 2B:
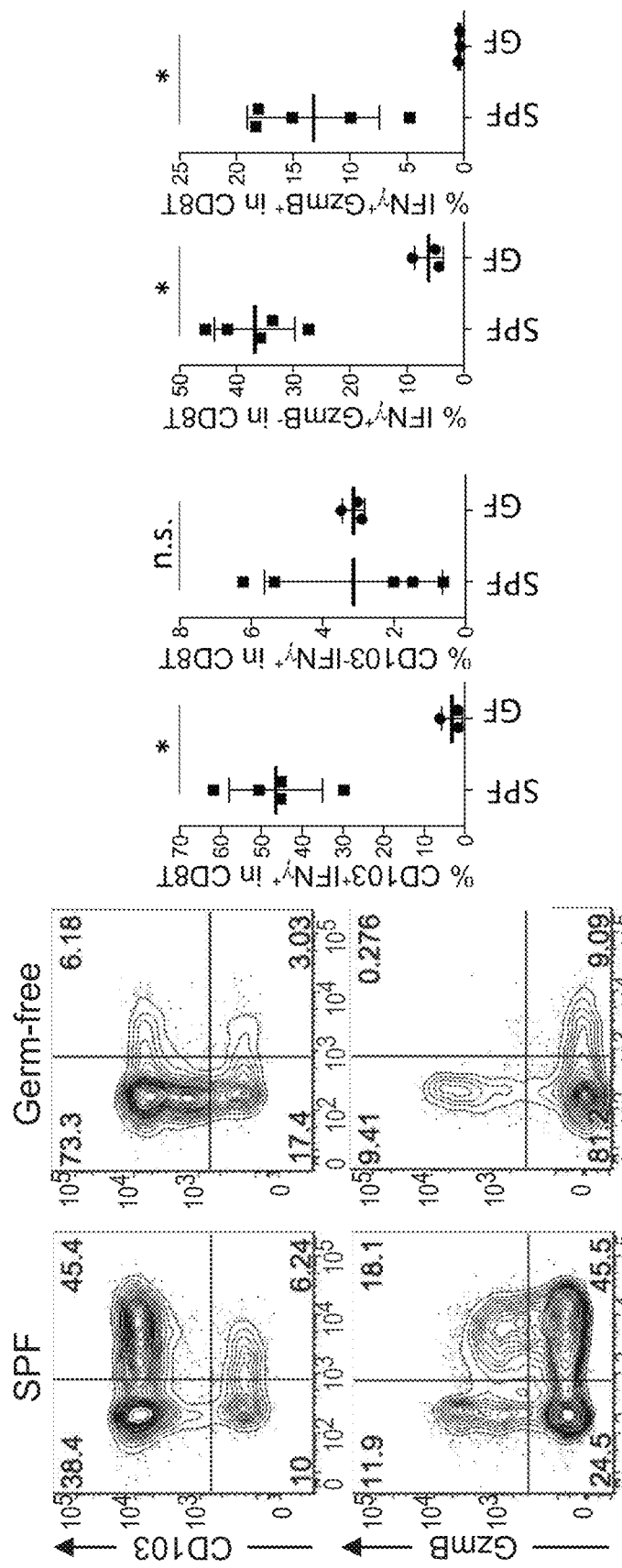
FIGS. 2A and 2B show data of experiments with lymphocytes that were isolated from the small intestinal mucosal lamina propria of SPF and germ-free mice and stimulated with PMA/ionomycin for 3.5 hours. CD3, TCRβ, CD8, CD103, IFNγ and GzmB were stained with antibodies and analyzed by flow cytometry.
Figure 3A:
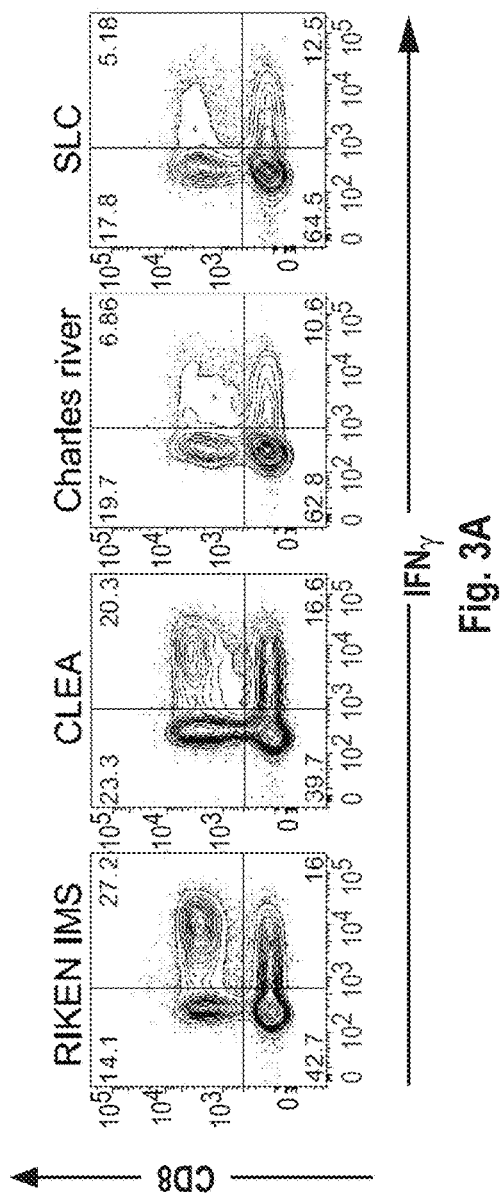
FIGS. 3A and 3B show data of experiments with lymphocytes that were isolated from small intestine (SI) and large intestine (Colon) mucosal lamina propria of SPF mice delivered from different laboratory animal facilities and stimulated with PMA/ionomycin for 3.5 hours. CD3, TCRβ, CD8 and IFNγ were stained with antibodies and analyzed by flow cytometry.
Figure 3B:
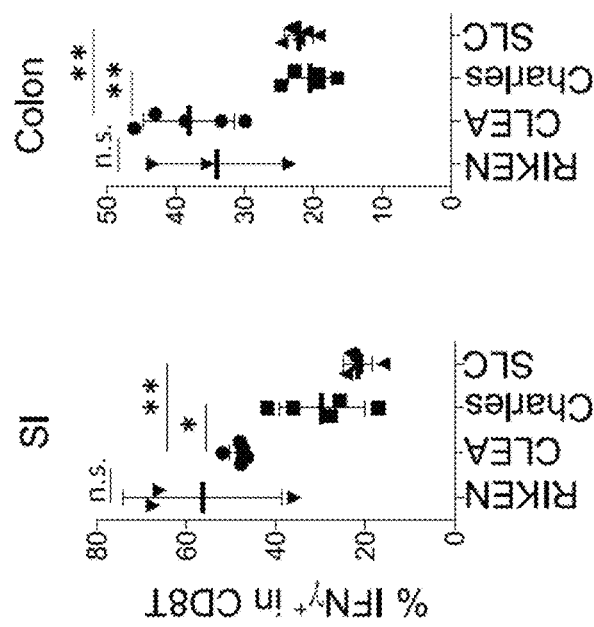
Figure 4A:
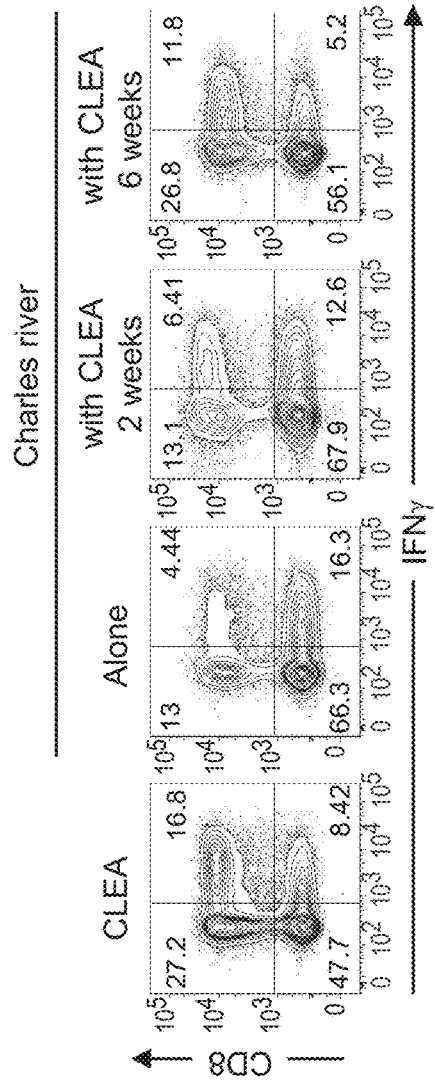
FIGS. 4A and 4B show data of experiments in which after co-housing of SPF mice from Charles River Laboratories with CLEA Japan for 2 or 6 weeks, lymphocytes were isolated from intestinal (SI) and colon mucosal lamina propria and stimulated with PMA/ionomycin for 3.5 h. CD3, TCRβ, CD8 and IFNγ were stained with antibodies and analyzed by flow cytometry.
Figure 4B:
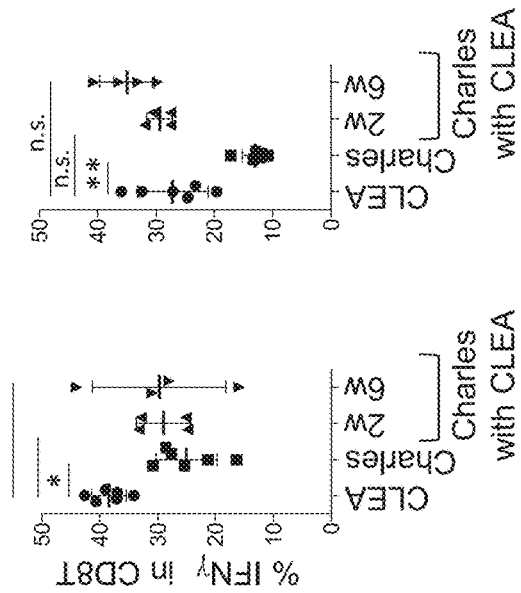

C57BL/6 mice kept under specific-pathogen free (SPF) conditions which possess resident microbiota have abundant IFNγ+CD8+ T-cells, whereas markedly few IFNγ+CD8+ T-cells were found in intestinal lamina propria of germ free mice (See FIG. 1). This indicates that gut microbiota induces the accumulation of IFNγ+CD8+ T-cells. A subset of IFNγ+CD8+ T cells also expressed CD103 as well as GranzymeB (see FIG. 2A), suggesting that the subset was tissue-resident memory T cells. FIG. 3A shows that remarkably small numbers of IFNγ+CD8+ T-cells were found in SPF C57BL/6 mice purchased from Charles River Laboratories Inc. and Japan SLC Inc. as compared to SPF C57BL/6 mice purchased from CLEA Japan Inc. and mice bred in RIKEN. When SPF C57BL/6 mice from Charles River Laboratories Inc. were co-housed together with CLEA mice in the same cage, an increase of IFNγ+CD8+ T-cells was observed in mice delivered from Charles River Laboratories Inc. (FIGS. 4A and 4B). This finding strongly supports a hypothesis that there are specific microbial species in the mouse microbiota which induce and accumulate IFNγ+CD8+ T cells in the intestine.

Figure 6A:
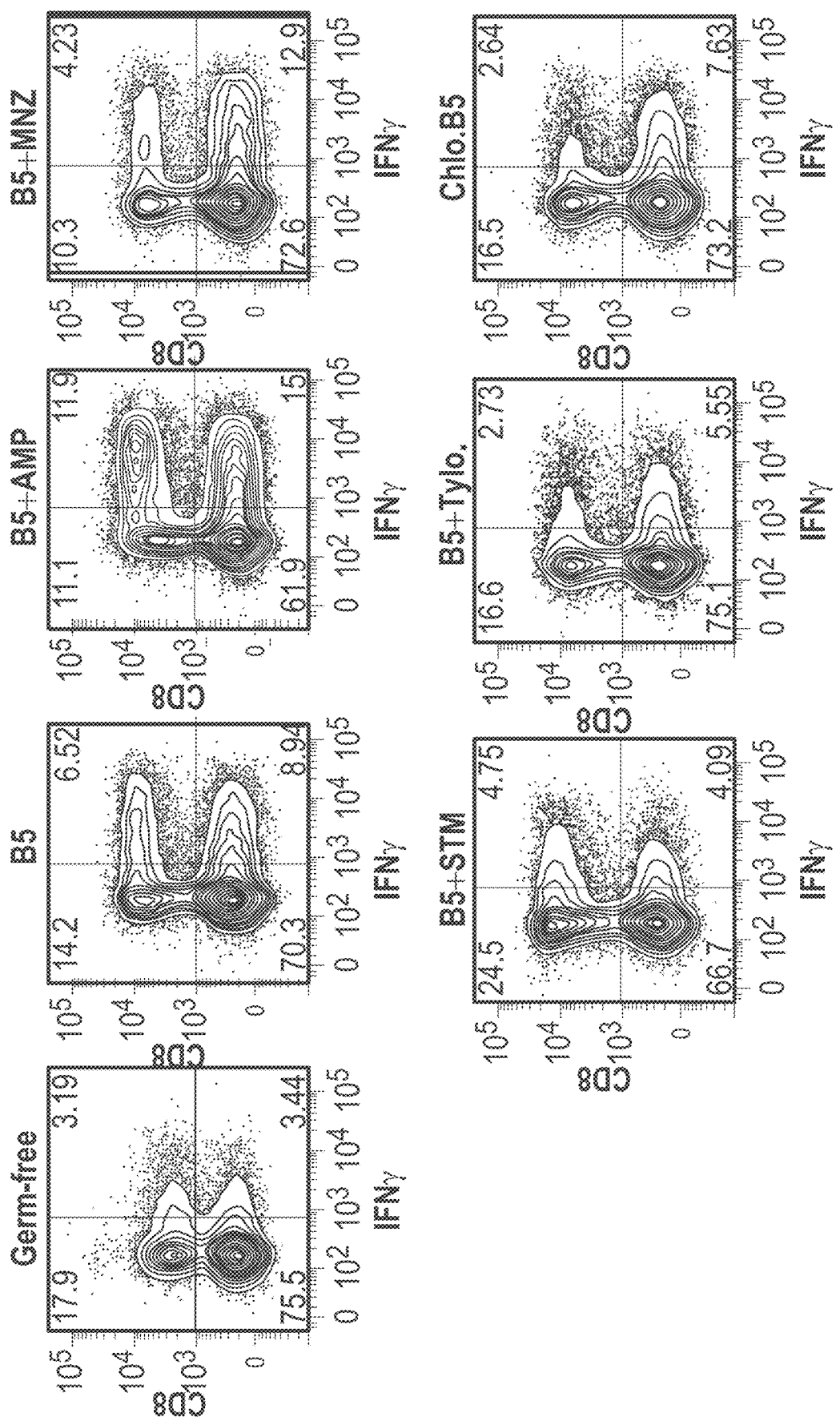
FIGS. 6A and 6B show data of experiments with the cecal contents of B #5 mouse, which was orally administered to germ free mice. One day later, their drinking waters were switched to ampicillin (AMP), metronidazole (MNZ), streptomycin (STM) or tylosin (Tylo.) until the end of experiment. The contents of the cecum of B #5 treated with 3% of chloroform were administered to germ free mice. Four weeks later, lymphocytes were isolated from the lamina propria of the large intestine and stimulated with PMA/ionomycin for 3.5 hours. CD3, TCRβ, CD8, IFNγ were stained with antibodies and analyzed by flow cytometry.
Figure 6B:
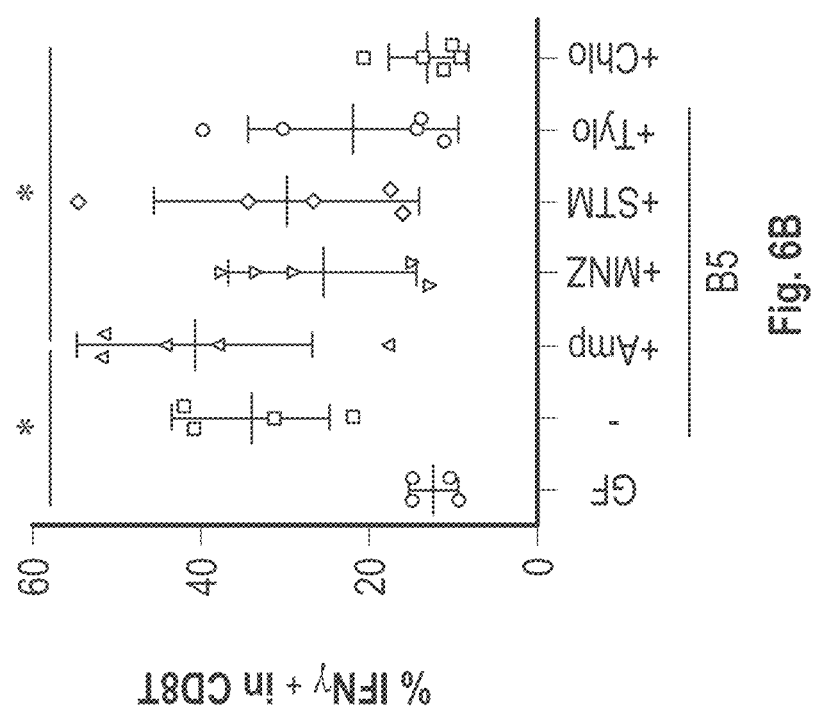

Next, it was investigated whether the human gut microbiota contained microbes which were able to induce IFNγ+CD8+ T cells. Stool samples were collected from six healthy human volunteers (A~F). The samples were individually administered orally into germ free C57BL/6 mice kept in sterile isolators (five or six mice per group). Four weeks after oral inoculation of stool samples, mice were sacrificed, and small intestine and colons were harvested and investigated for IFNγ+CD8+ T-cells by FACS. As shown in FIGS. 5A and 5B, colonic IFNγ+CD8+ T-cells were most remarkably induced in mice inoculated with a stool sample collected from donor B. Among mice inoculated with the donor B stool sample, we selected a mouse that exhibited the highest frequency of IFNγ+CD8+ T cells (called 'mouse B #5' hereafter). In order to concentrate microbes responsible for IFNγ+CD8+ T cell induction, cecal contents were collected from the mouse B #5 and inoculated into another germ-free mouse. The mice were then orally administrated drinking water with or without Ampicillin, Metronidazole, Streptomycin or Tylosin (five mice per group). Alternatively, cecal contents of mouse B #5 were treated with 3% chloroform and orally inoculated into another five germ-free mice ('B #5+Chrolo'). FIGS. 6A and 6B show that Ampicillin treatment enhanced induction of colonic lamina propria IFNγ+CD8+ T-cells by the mouse B #5 microbiota, whereas other antibiotics treatment or chloroform treatment reduced the induction capability of IFNγ+CD8+ T-Cells by the mouse B #5 microbiota.

Figure 7A:
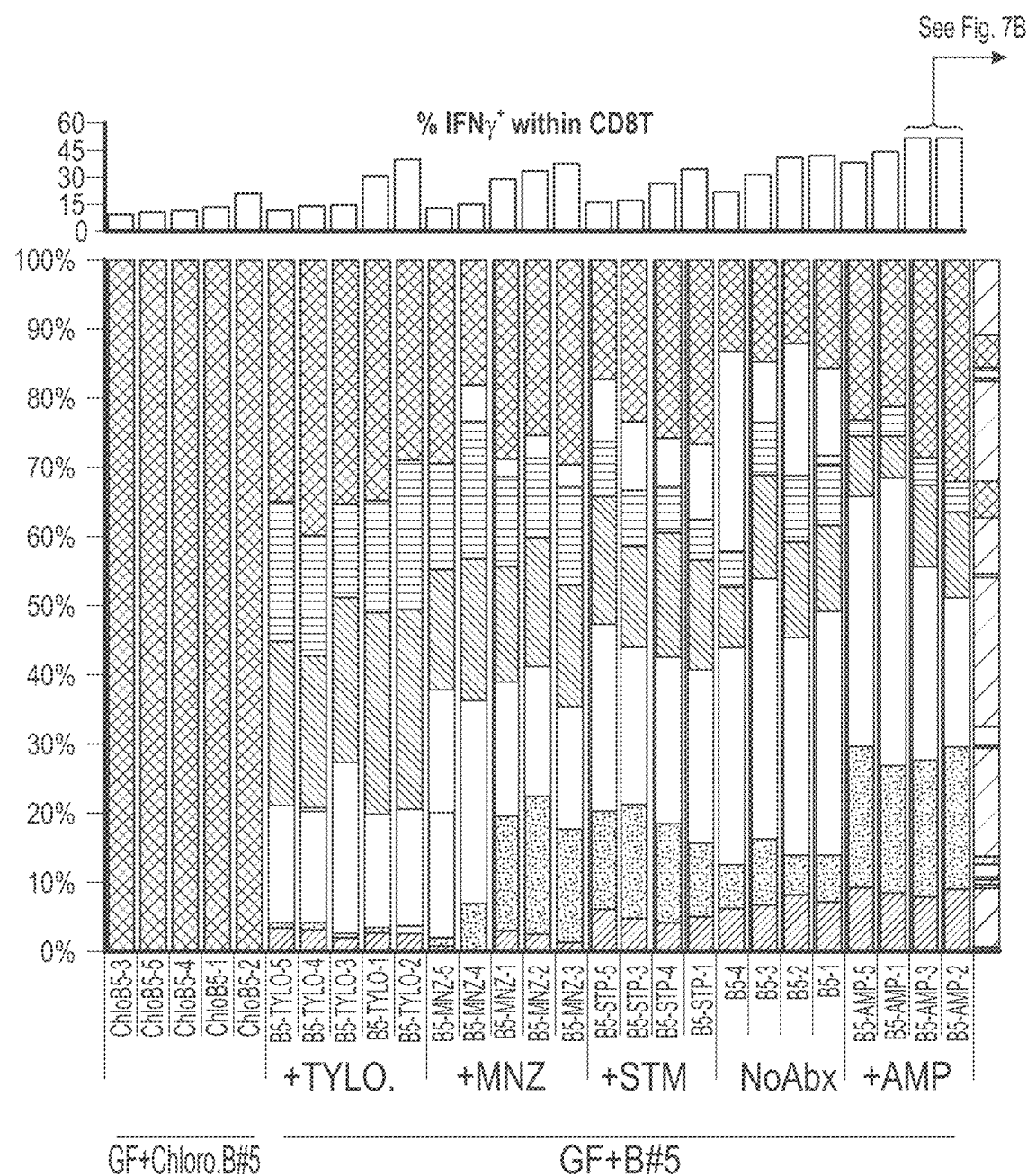
Figure 8A:
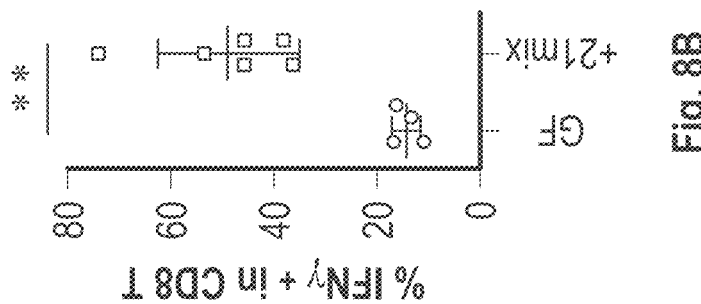
FIGS. 8A and 8B show data on the mixture of 21 isolated strains which was orally administered to germ free mice. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry.
Figure 8B:
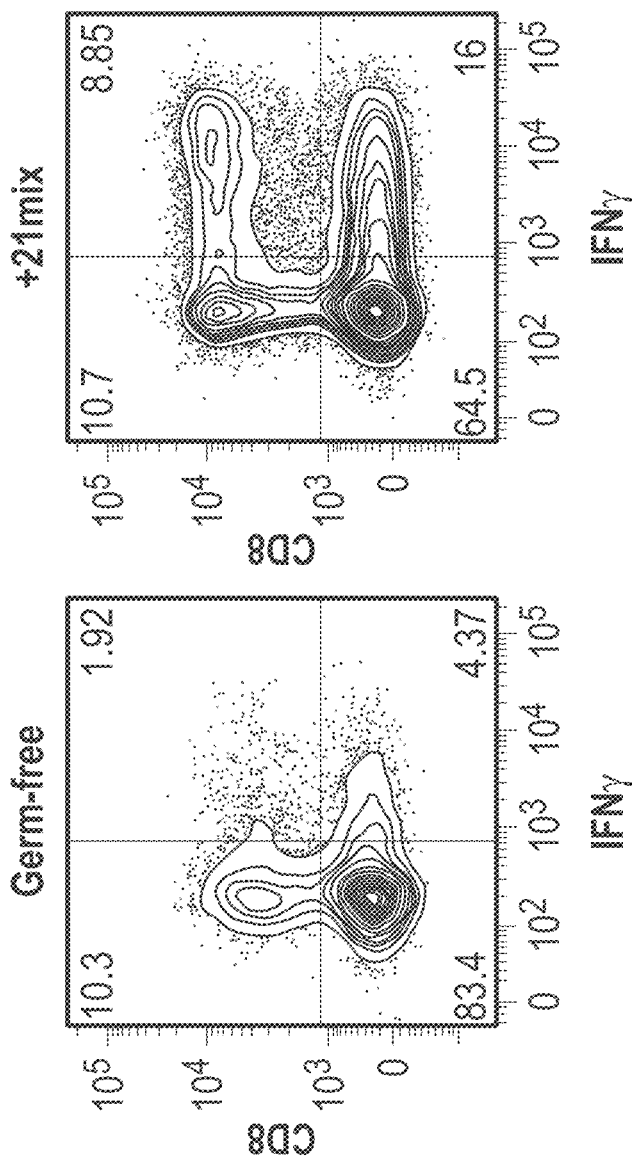

FIGS. 7A and 7B show the operational taxonomic unit (OTU) analysis of intestinal contents of mice inoculated with mouse B #5 microbiota and treated with/without antibiotics or chloroform. Cecal contents were collected from two B #5+AMP mice that exhibited the highest frequency of IFNγ+CD8+ T cells (mouse B #5+AMP-2 and mouse B #5+AMP-3) and cultured in an anaerobic chamber. 304 colonies were picked and sequencing of the 16S rRNA gene revealed that 26 strains were isolated. Twenty-one strains were selected from the 26 strains, excluding 5 strains which were included in the microbiota of B #5+Chrolo mice (therefore predicted to be unnecessary for induction of IFNγ+CD8+ T-cells). The mixture of 21 strains was orally inoculated into germ free mice and strong induction of IFNγ+CD8+ T-cells was observed (FIGS. 8A and 8B). IFNγ+CD8+ T cells induced by the 21 strains also expressed CD103 and a part of the IFNγ+CD8+ T-cells expressed Granzyme B as well (FIGS. 9A and 9B). A mixture of 11 strains with the highest correlation with IFNγ+CD8+ T-cells was inoculated into GF mice as well. The mixture of 11 strains (11 mix) was orally a strong induction of IFNγ+CD8+ T-cells, even when compared to the 21 strains mixture (21 mix) (FIGS. 10A and 10B). Identification of the bacterial species with the highest homology to each of the strains in the 11 mix is provided in Table 2, below.

TABLE 2

| | | | | NCBI | SEQ ID of |
| | | | | accession # | NCBI 16S |
| Strain # | SEQ ID NO | Strain ID | Species with highest homology | of 16S locus | locus |
|---|---|---|---|---|---|
| 1 | 1 | 2G5 | Phascolarctobacterium faecium | LN998073 | 27 |
| 2 | 2 | 1A6 | Fusobacterium ulcerans | KR822463 | 28 |
| 3 | 3 | 1B11 | Bacteroides dorei | CP011531 | 29 |
| 4 | 4 | 2G1 | Bacteroides uniformis | NR112945 | 30 |
| 5 | 5 | 2B1 | Subdoligranulum sp. | KM098109 | 31 |
| 6 | 6 | 2A6 | Paraprevotella xylaniphila | NR113078 | 32 |
| 7 | 7 | 2F11 | Parabacteroides johnsonii | NR041464 | 33 |
| 8 | 8 | 1E7 | Alistipes sp. | LT223566 | 34 |
| 9 | 9 | 1H9 | Parabacteroides gordonii | NR112835 | 35 |
| 10 | 10 | 1C1 | Eubacterum limosum | NR113248 | 36 |
| 11 | 11 | 2G9 | Parabacteroides distasonis | NR041342 | 37 |

Example 1A: Further Characterization of the Mixture of 11 Strains (Composition A)

The strains of Table 2 were characterized further by resequencing of the 16S sequences and by whole genome sequencing. The results of the further characterization are found in Table 3.

TABLE 3

[Further characterization of the 11-mix (the mixture of 11 strains)]

| Strain # | SEQ ID NO | Strain ID | species with highest homology based on original 16S analysis | NCBI accession ID | species with highest homology based on 16S resequencing |
|---|---|---|---|---|---|
| 2 | 2 | 1A6 | Fusobacterium ulcerans | K0052822463 | Fusobacterium varium |
| 7 | 7 | 2F11 | Parabacteroides johnsonii | NR041464 | Parabacteroides johnsonii |
| 6 | 6 | 2A6 | Paraprevotella xylaniphila | NR113078 | Paraprevotella xylaniphila |
| 11 | 11 | 2G9 | Parabacteroides distasonis | NR041342 | Parabacteroides distasonis |
| 8 | 8 | 1E7 | Alistipes sp. | LT223566 | Alistipes senegalensis |
| 10 | 10 | 1C1 | Eubacterium limosum | NR113248 | Eubacterium limosum |
| 3 | 3 | 1B11 | Bacteroides dorei | CP011531 | Bacteroides dorei |
| 9 | 9 | 1H9 | Parabacteroides gordonii | NR112835 | Parabacteroides gordonii |
| 5 | 5 | 2B1 | Subdolinogranulum sp. | KM098109 | Gemminger formicilis |
| 4 | 4 | 2G1 | Bacteroides uniformis | NR112945 | Bacteroides uniformis |
| 1 | 1 | 2G5 | Phascolarctobacterium faecium | LN998073 | Phascolarctobacterium faecium |

| Strain # | 16S Identity (%) of re-sequencing | species with highest homology based on whole genome sequencing (WGS) | WGS Identity (%) | WGS Coverage (%) | Alternative species with high(est) homology |
|---|---|---|---|---|---|
| 2 | 99 | Fusobacterium ulcerans | 93.2 | 78.6 | |
| 7 | 99 | Parabacteroides johnsonii | 99.9 | 90.5 | |
| 6 | 99 | Paraprevotella xylaniphila | 98.9 | 92.1 | |
| 11 | 99 | Parabacteroides sp. CAG:2 | 99.4 | 95.4 | |
| 8 | 99 | Alistipes senegalensis | 98.7 | 72.2 | Alistipes timonensis |
| 10 | 99 | Eubacterium limosum | 95 | 81 | |

TABLE 3-continued

[Further characterization of the 11-mix (the mixture of 11 strains)]

| 3 | 99 | *Bacteroides dorei* | 99.3 | 79.5 | *Bacteroides fluxus* |
| 9 | 97 | *Parabacteroides* sp. HGS0025 | 90 | 50 | |
| 5 | 99 | Ruminococcaceae bacterium cv2 | 99.2 | 73.9 | *Ruthenibacterium lactatiformans* |
| 4 | 99 | *Bacteroides* sp. D20 | 98.5 | 81 | |
| 1 | 99 | *Phascolarctobacterium* sp. CAG:207 | 99.2 | 87 | |

Figure 11:
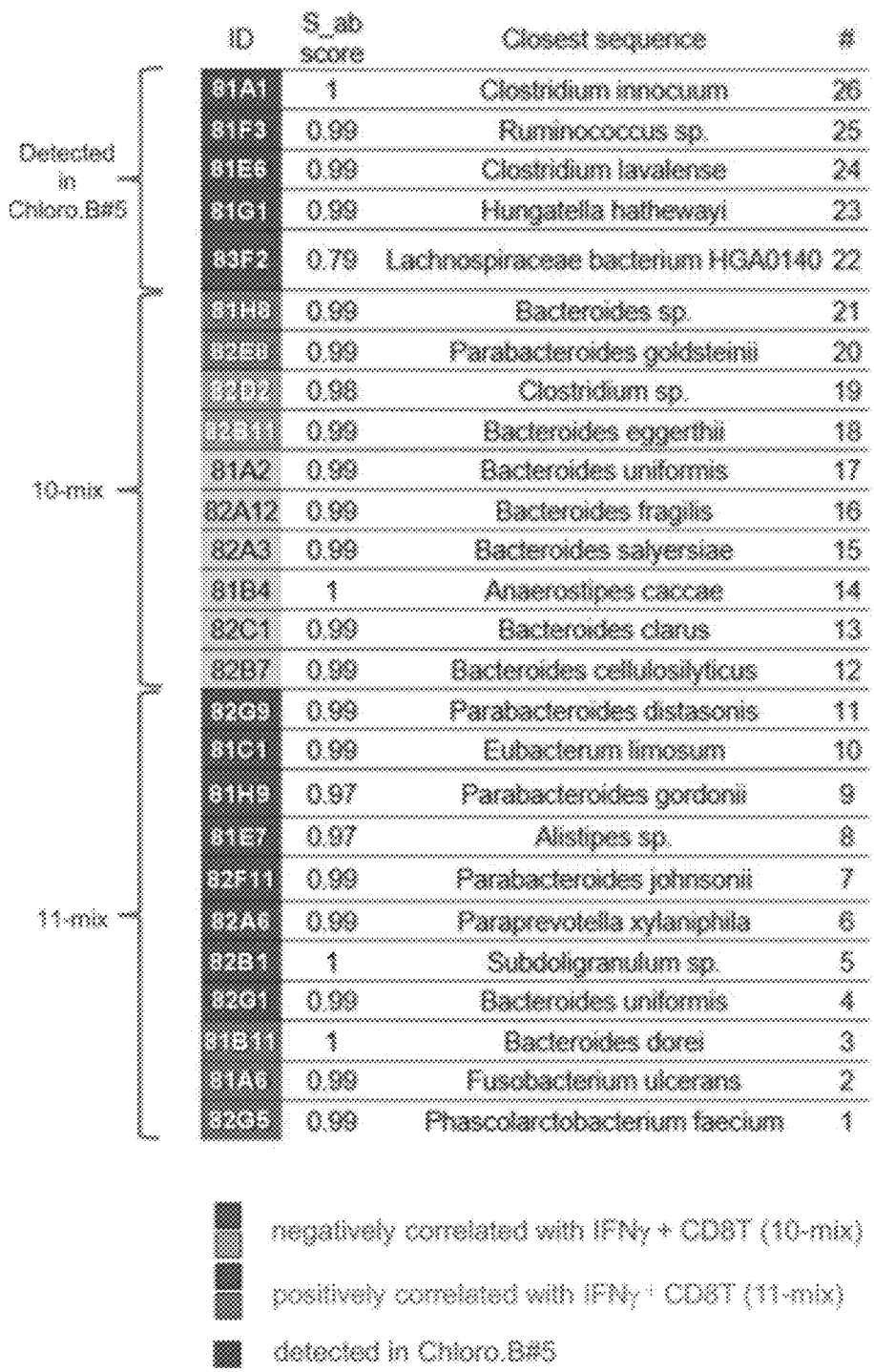
FIG. 11 shows the compositions of the 10-mix and 11-mix bacterial strains that were inoculated into GF mice (See FIGS. 12A and 12B).
Figure 12A:
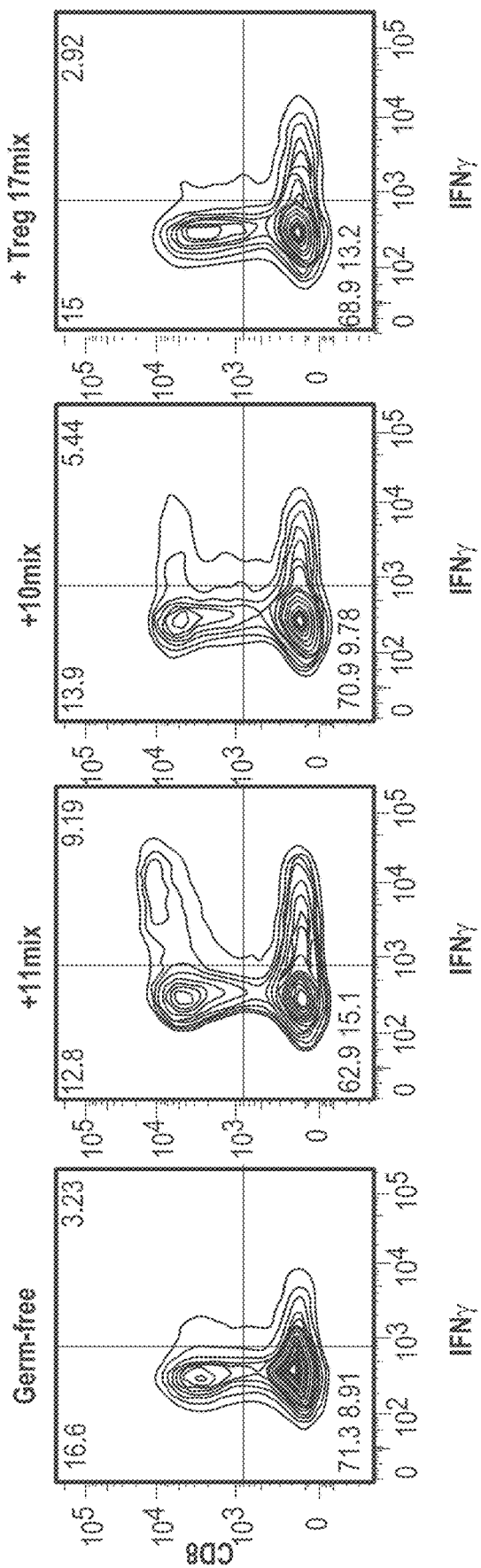
FIGS. 12A and 12B show data obtained from mixtures of 11 or 10 strains (see FIG. 11), or a mixture of 17 strains that are known Treg-inducers, which were orally administered to germ free mice. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry.
Figure 12B:
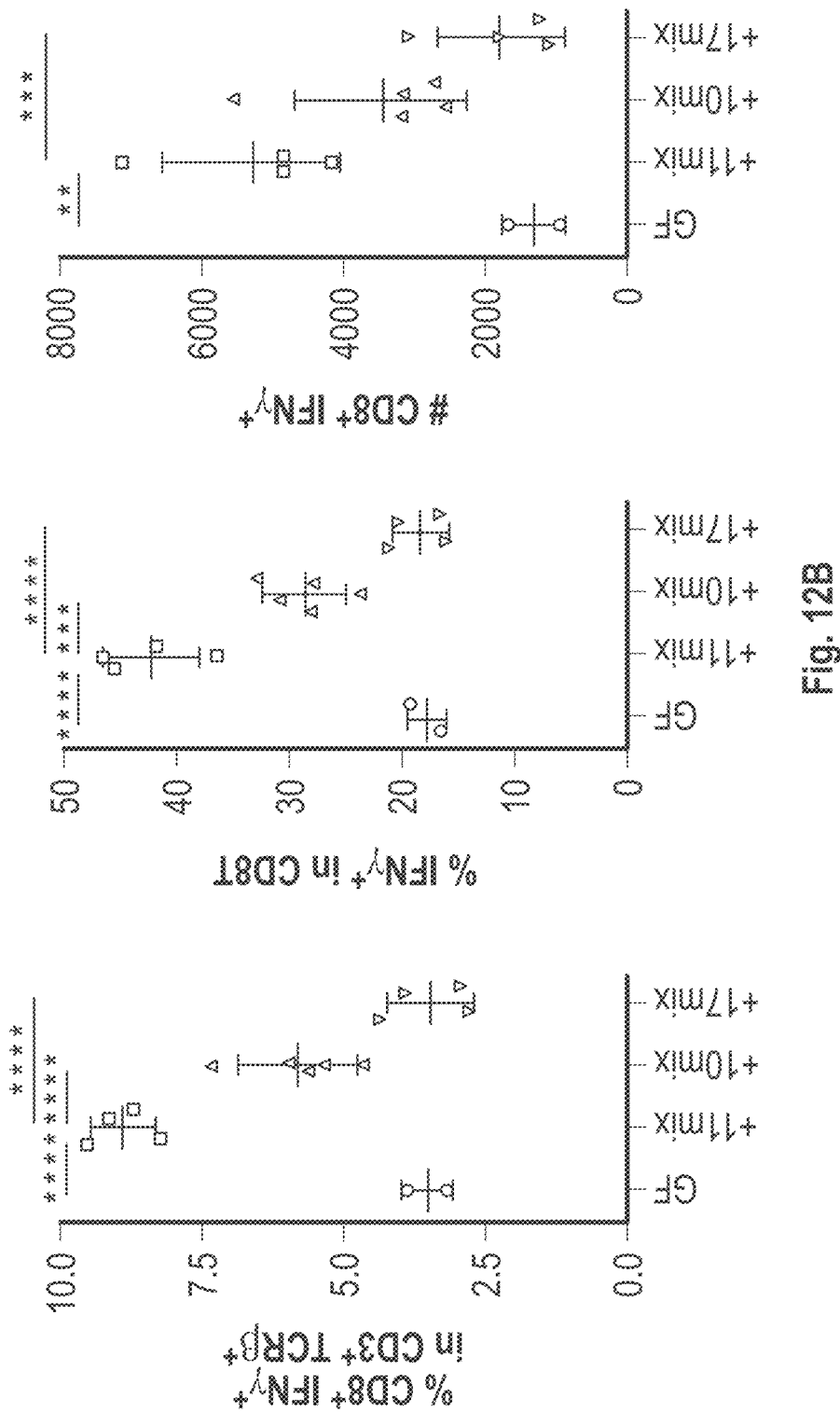
Figure 13:
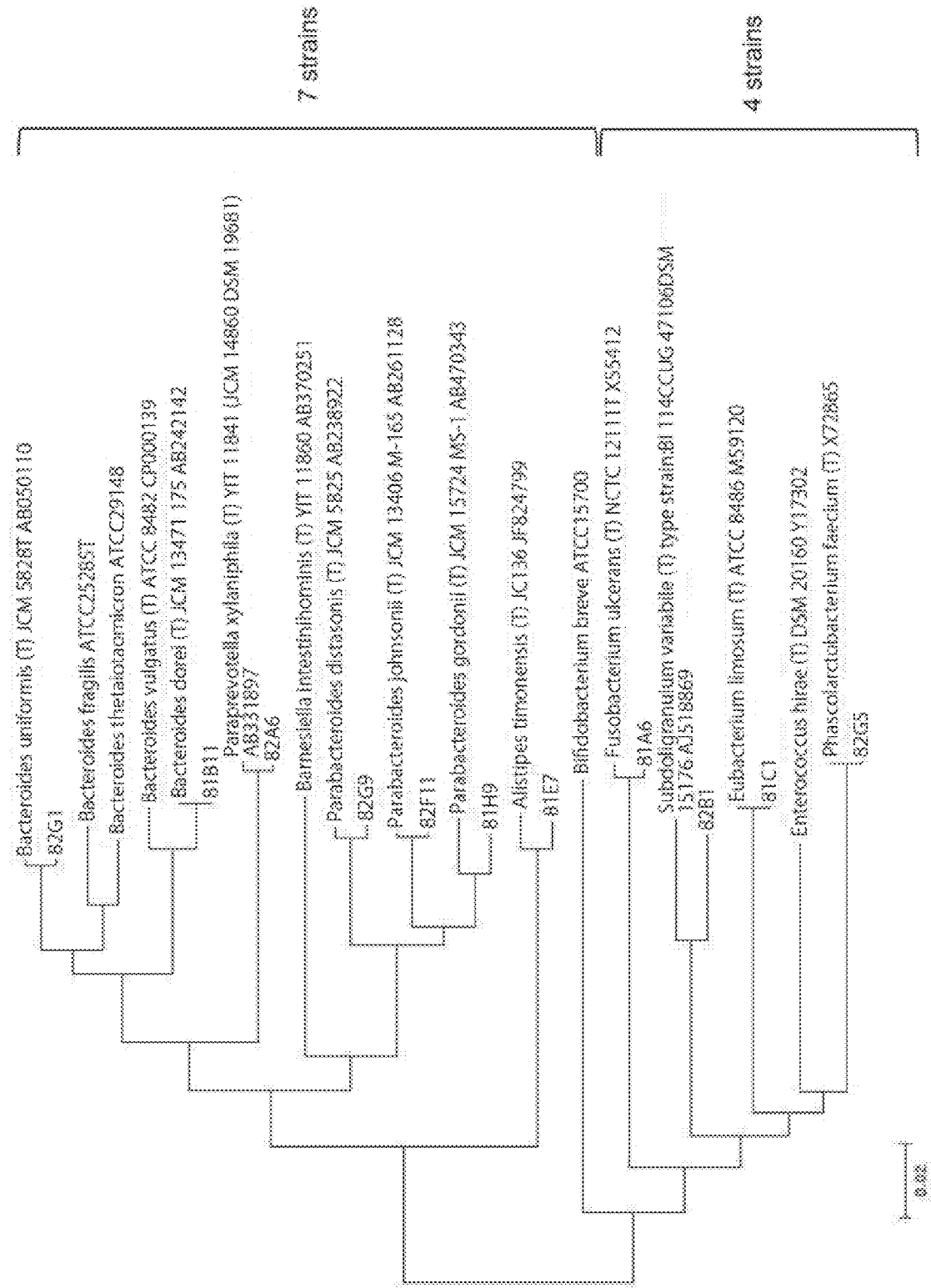
FIG. 13 shows a phylogenetic tree which was constructed from the 16S rRNA gene sequences of the 11 strains (See FIG. 11), their closest sequences and some type strains using the MEGA v5.0 package and the neighbor-joining method. The strains which were inoculated into GF mice as a 7 mix or 4 mix are shown as well (The results of the inoculation experiments are shown in FIGS. 14A and 14B).

Example 2: Further Characterization of a CD8+ T-Cell Inducing Bacterial Cocktail Twenty six strains isolated from cecal contents of B #5+AMP mice that exhibited high frequencies of IFNγ+ CD8+ T cells are shown in FIG. 11. Among the 26 strains, 11 strains ("11 mix") were positively correlated with the frequency of IFNγ+CD8+ T cells. Therefore, these 11 strains were selected for further experiments, and the mixture of 11 strains ("11-mix") was inoculated into germ-free mice (see also Table 2). Colonization with the 11-mix resulted in a strong induction of colonic IFNγ+CD8+ T cells (FIGS. 10A, 10B, 12A, and 12B), whereas the other 10 strains ("10-mix") weakly induced IFNγ+CD8+ T cells compared to the levels induced by the 11-mix (FIGS. 12A and 12B). Mice inoculated with a mixture of 17 Treg-inducing bacterial strains (See e.g., WO2013/080561; Atarashi et al., Nature (2013) 500 (7461): 232-236; Narushima et al. Gut Microbes (2014) 5(3): 333-339) did not accumulate IFNγ+CD8+ T cells (FIGS. 12A and 12B). A phylogenetic comparison using 16S rRNA gene sequences showed that the 11 strain mixture (also referred to as "the 11 mix") consists of 7 strains falling within Bacteroidales ("7 strains") and 4 strains of non-Bacteroidales: 2 Clostridiales, 1 Fusobacteriales and 1 Selenomonadales ("4 strains") (See FIG. 13 and Table 4).

Figure 14A:
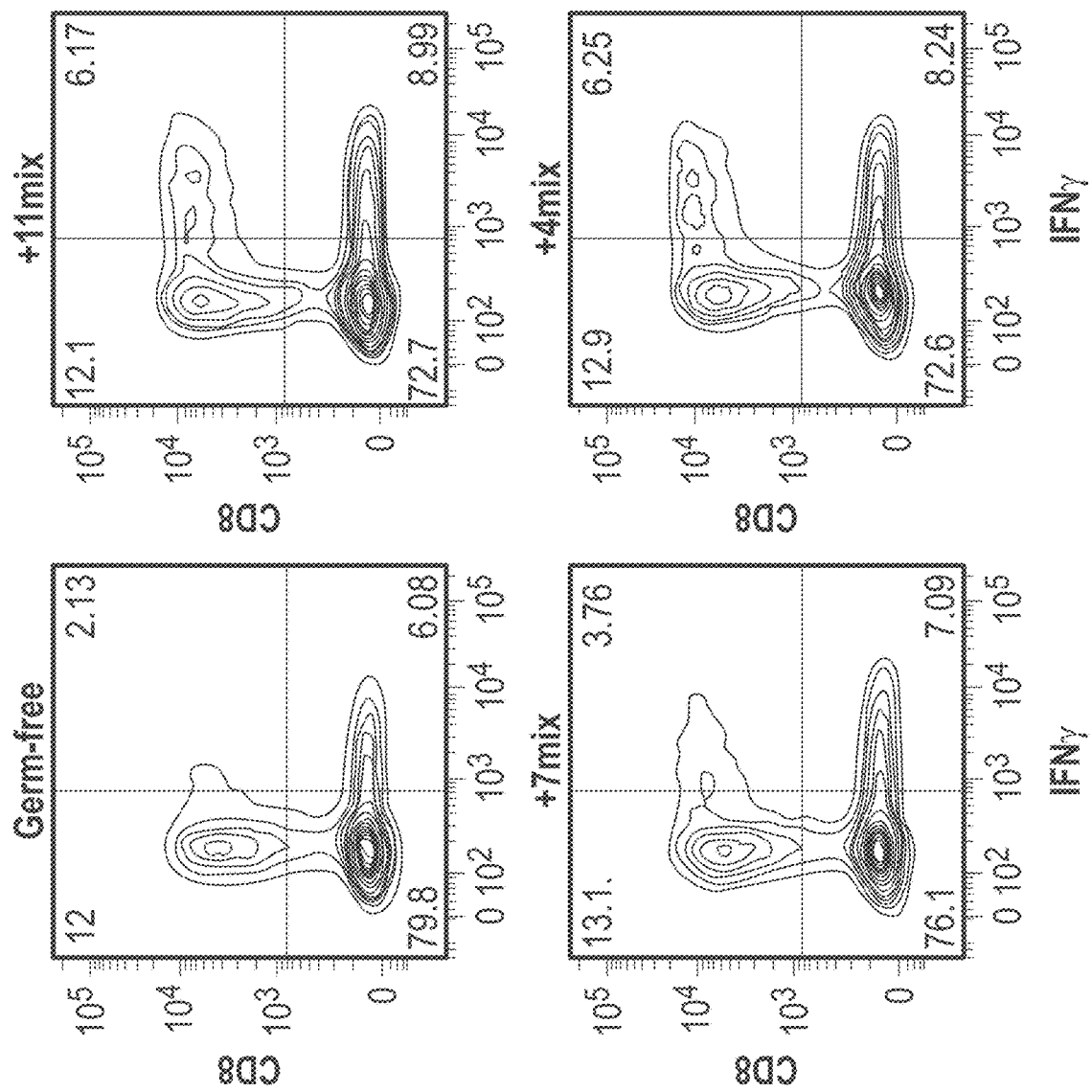
Figures 47A, 47B:
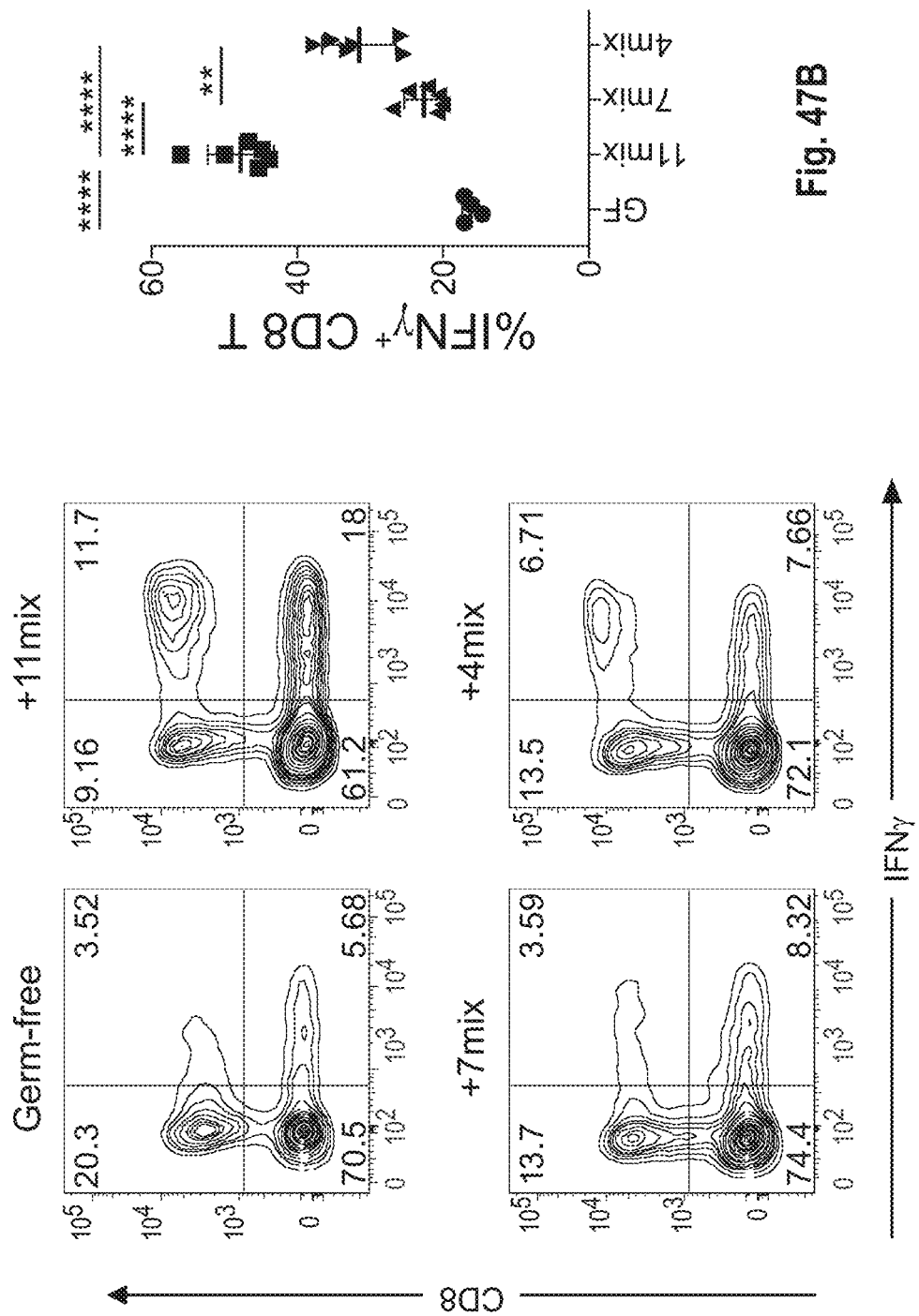
FIGS. 47A and 47B shows data relating to Example 2. The mixtures of the 11 strains, 7 or 4 strains mixtures listed in FIG. 13, were orally administered to germ free mice. Four weeks later, lymphocytes were isolated from the lamina propria of the large intestine and stimulated with PMA/ionomycin for 3.5 hours. CD3, TCRβ, CD8 and IFNγ were stained with antibodies and analyzed by flow cytometry (FIG. 47A). The expression of CD8 and IFNγ by the gated CD3 and TCRβ positive cells of representative mice is show in FIG. 47B, as indicated by the percentage of IFNγ+ cells in CD8T cells. Each plot represents individual mice. * $P<0.05$,  $P<0.01$, * $P<0.001$ (one-way ANOVA).

Inoculation with the mixture of 4 non-Bacteroidales strains ("4-mix") resulted in a strong accumulation of colonic IFNγ+CD8+ T cells, comparable to the level of colonic IFNγ+CD8+ T cells observed in mice colonized with the 11 mix. In contrast, colonization with 7 Bacteroidales strains ("7-mix") weakly induced IFNγ+CD8+ T cells (FIGS. 14A and 14B). A repeat of the experiment is shown in FIG. 47, which shows that the 11-mix is more effective than either the 7-mix or the 4-mix. The data of the experiment shown in FIG. 47 have strong statistical support. Identification of the bacterial species with the highest homology to each of the strains in the 4 mix is provided in Table 4, below.

Example 3: Anti-Cancer Characteristics of CD8+ T-Cell Inducing Bacterial Cocktail To investigate whether colonization with the 11 mix could enhance anticancer immune responses, a subcutaneous tumor model was used. SPF mice were treated with mixture of antibiotics (1 g/L ampicillin, 0.5 g/L vancomycin, 1 g/L metronidazole, and 1 g/L neomycin) via the drinking water from day −7 to day 2. A MC38 colon cancer cell line ($3 \times 10^5$ cells per mouse) was subcutaneously injected into the right flank of mice at day 0. Antibiotics treatment was stopped at day 2, and mice were gavaged with fecal microbiota from SPF mice mixed with or without 11-mix on day 3. For the 11-mix treatment groups, mice were gavaged with the 11 mix two or three times per week until the end of the experiment. For the anti-PD-1 antibody (Ab) treatment groups, mice were intraperitoneally injected with 200µg of anti-PD1 monoclonal Ab (clone J43) at days 3, 5 and 9. Tumor size was measured using a caliper and tumor volume was determined as length×width $2 \times 0.5$.

Figure 15:
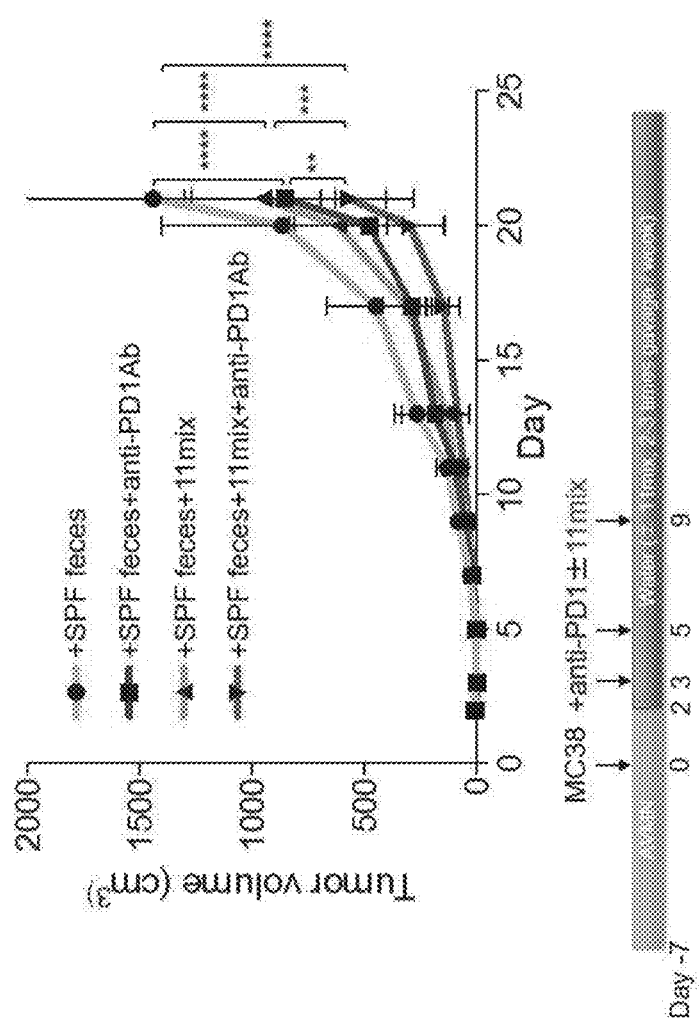
FIG. 15 shows data on experiments with six weeks-old SPF C57BL/6 mice, which were purchased from Japan SLC and treated with antibiotics (1 g/L Ampicillin, 0.5 g/L Vancomycin, 1 g/L Metronidazole and 1 g/L Neomycin; "AVMN") in their drinking water. Then, mice were subcutaneously injected into the right flank with 3×105 MC38 tumor cells line at day 0. When tumors appeared and were palpable, antibiotics treatment was stopped (day 2). Mice were injected intraperitoneally with 200 μg of anti-PD1 antibody (clone J43) at day 3, 5 and 9 ("+anti-PD1Ab"). Mice were gavaged with the 11 mix 2 or 3 times a week including day 3, 5 and 9 ("+11 mix"). Tumor size was measured using a caliper and tumor volume was determined as length×width2×0.5.  $P<0.01$, * $P<0.001$, **** $P<0.0001$ (two-way ANOVA).
Figure 16A:
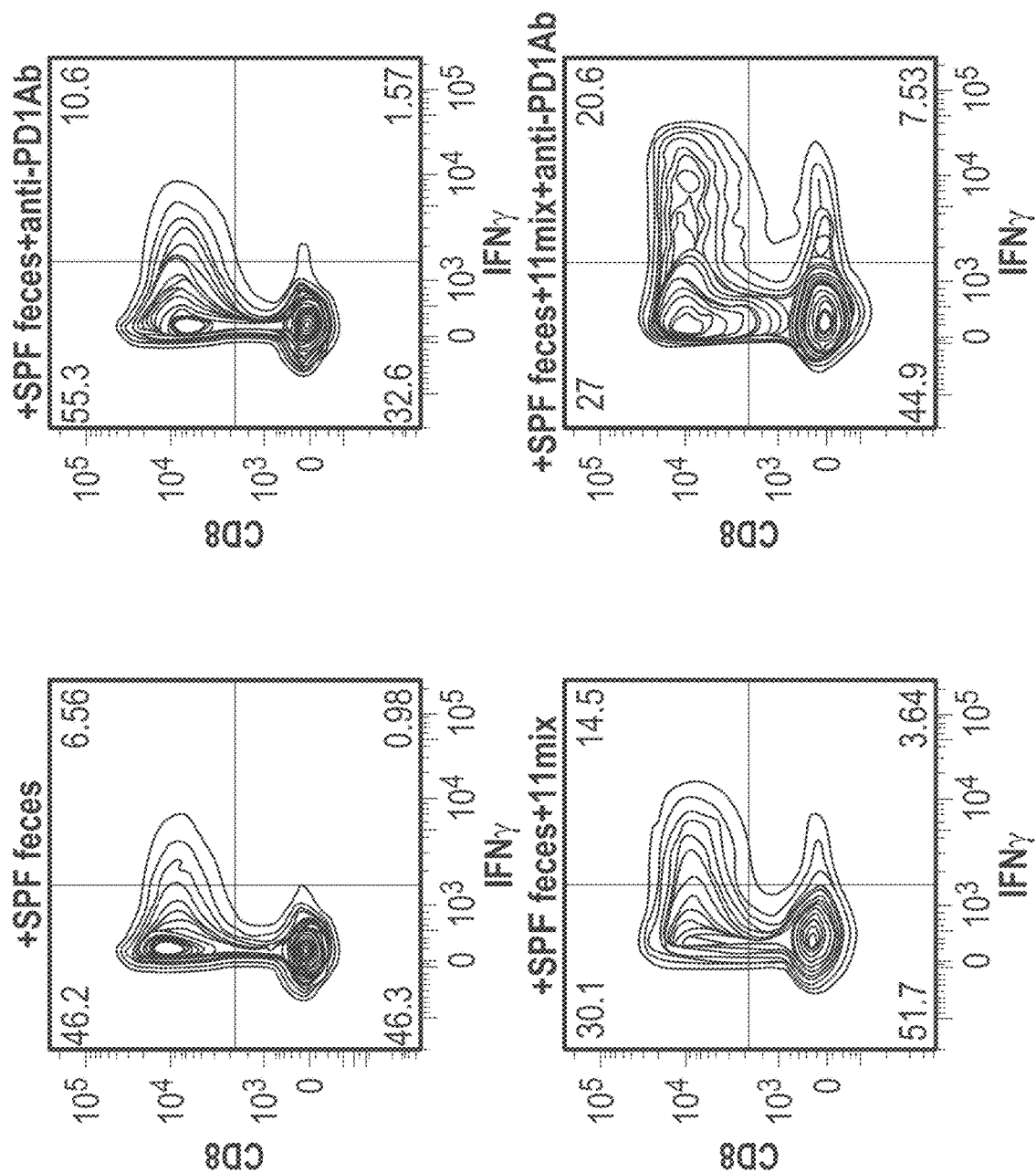
Figure 17A:
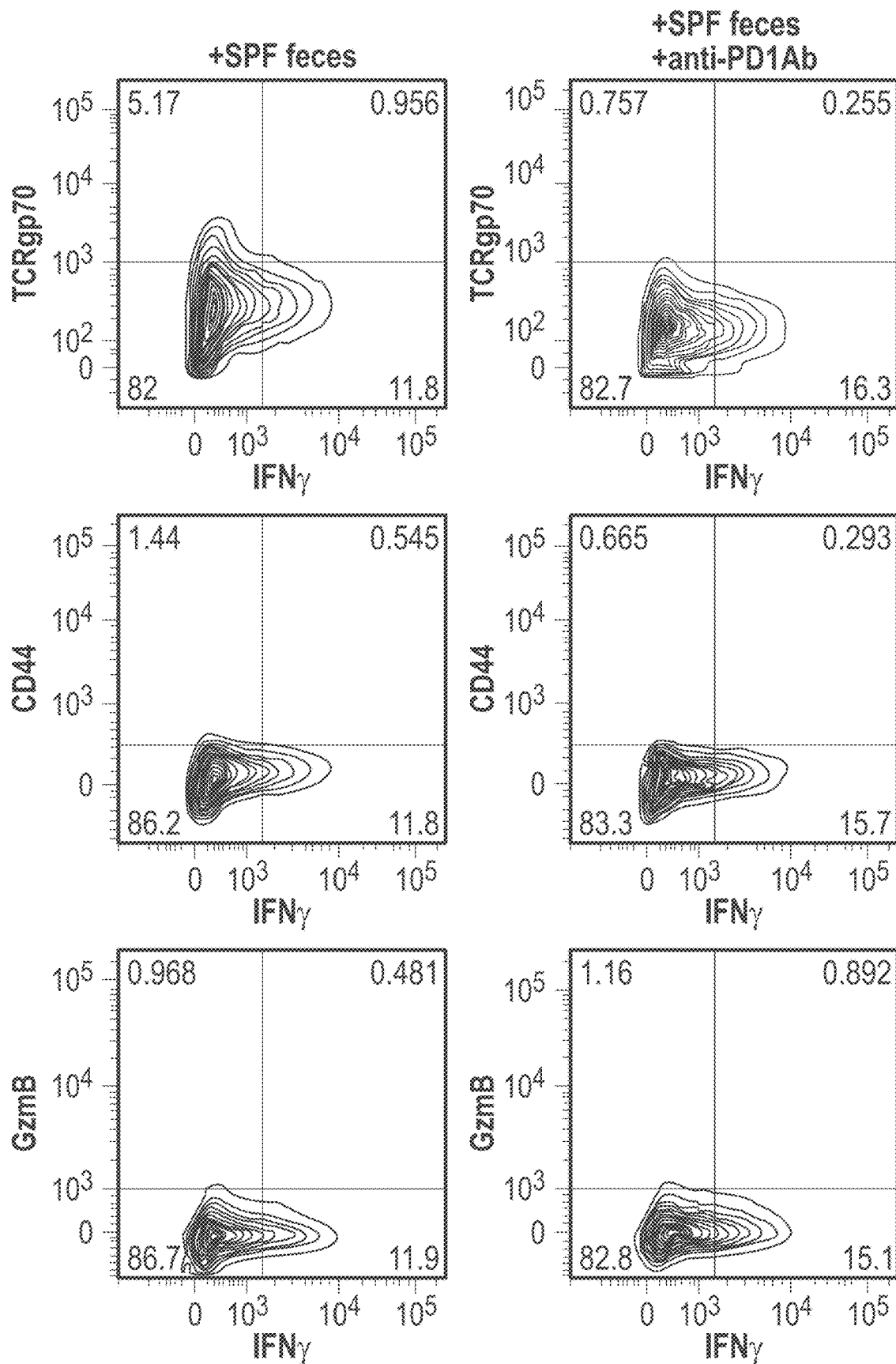
FIGS. 17A, 17B show data on lymphocytes isolated from tumor cells. At day 23 or 27, lymphocytes were isolated from tumors and stimulated with PMA/ionomycin for 4 hours. CD3, TCRβ, CD8, gp70 MC38 peptide (KSPWFTTL (SEQ ID NO: 53))-specific TCRβ, CD44, GzmB and IFNγ were stained with antibodies and peptide-H2Kb tetramer, and analyzed by flow cytometry.
Figure 17A:
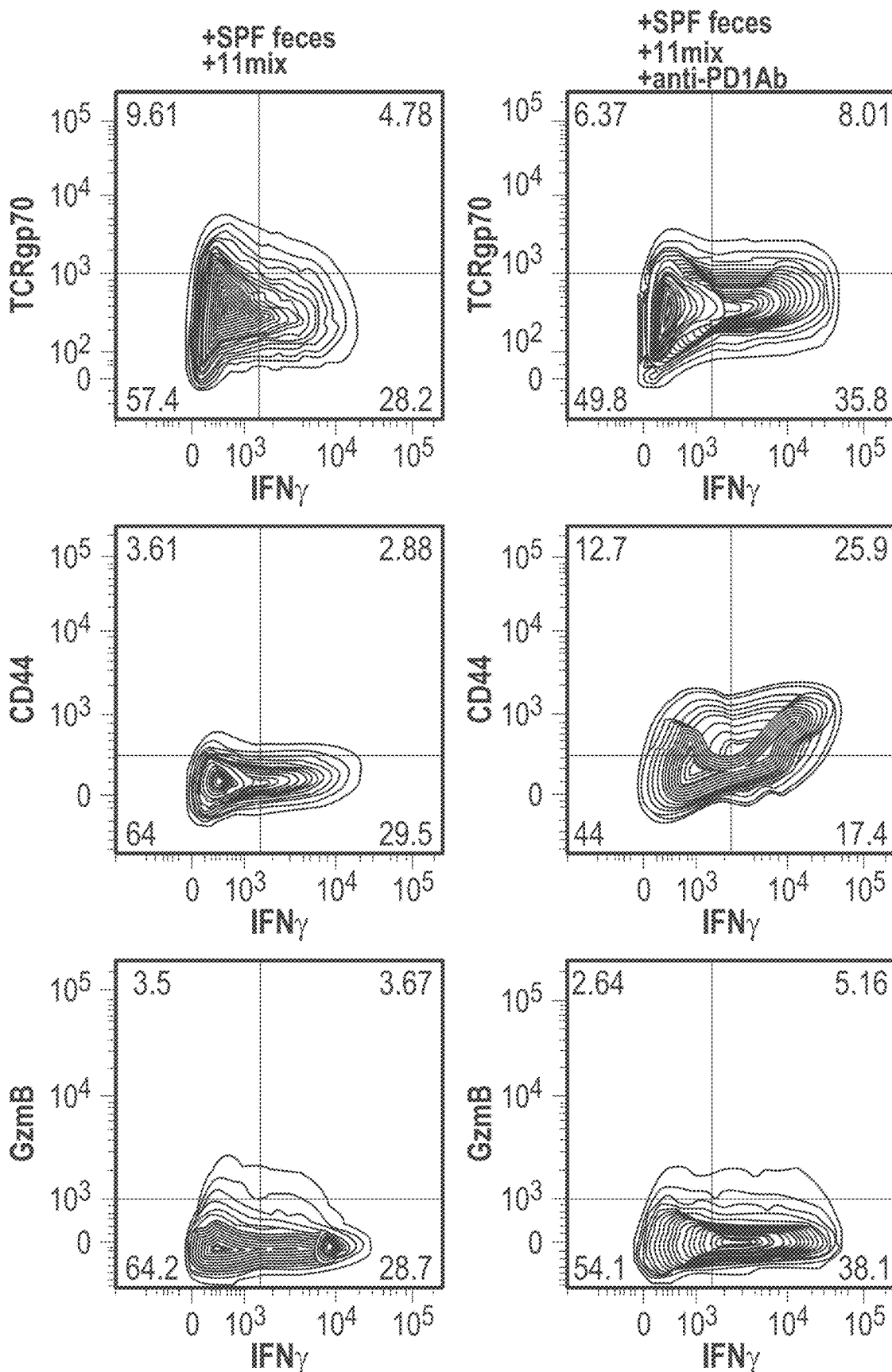
Figure 17B:
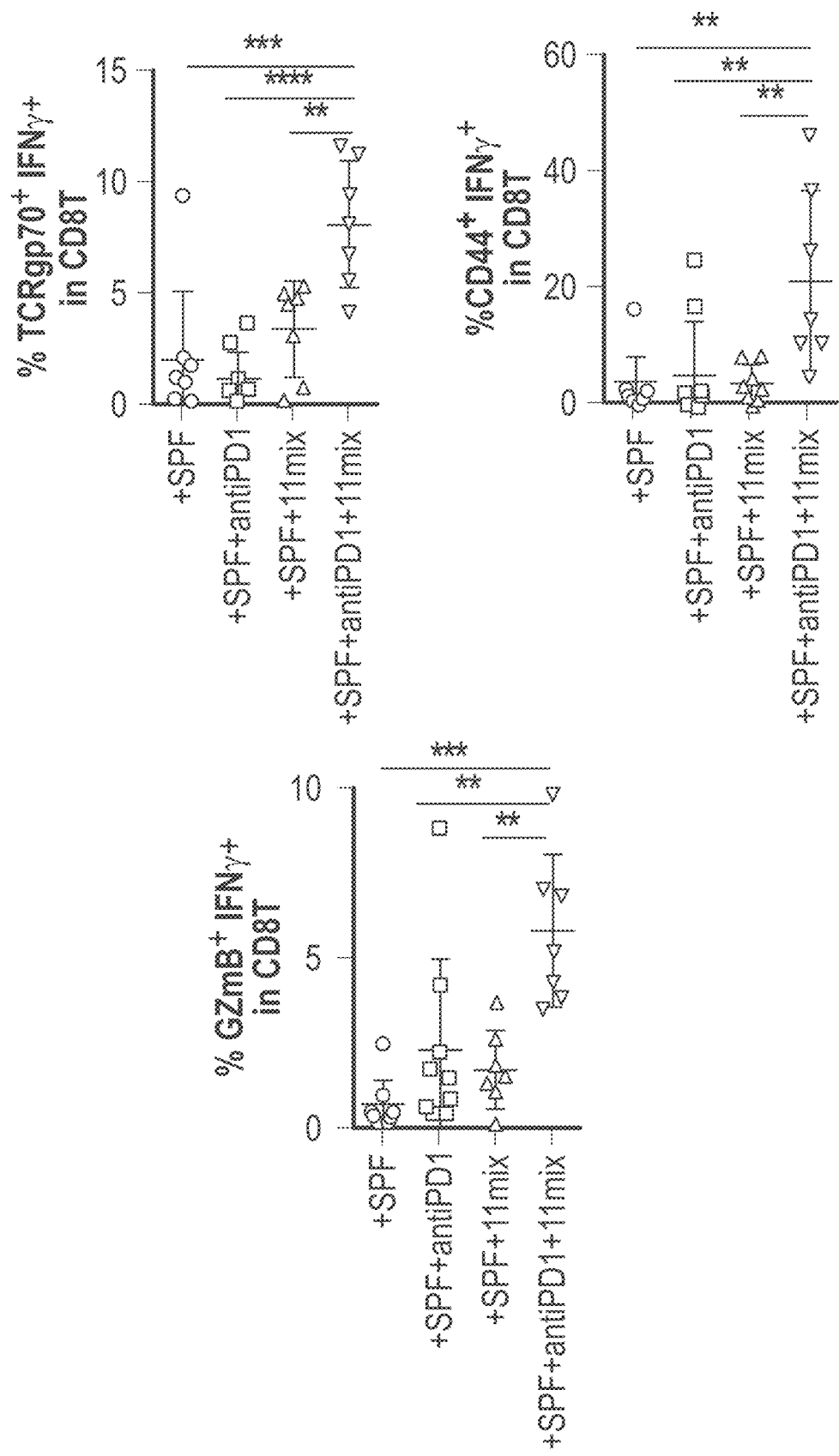
Figure 18:
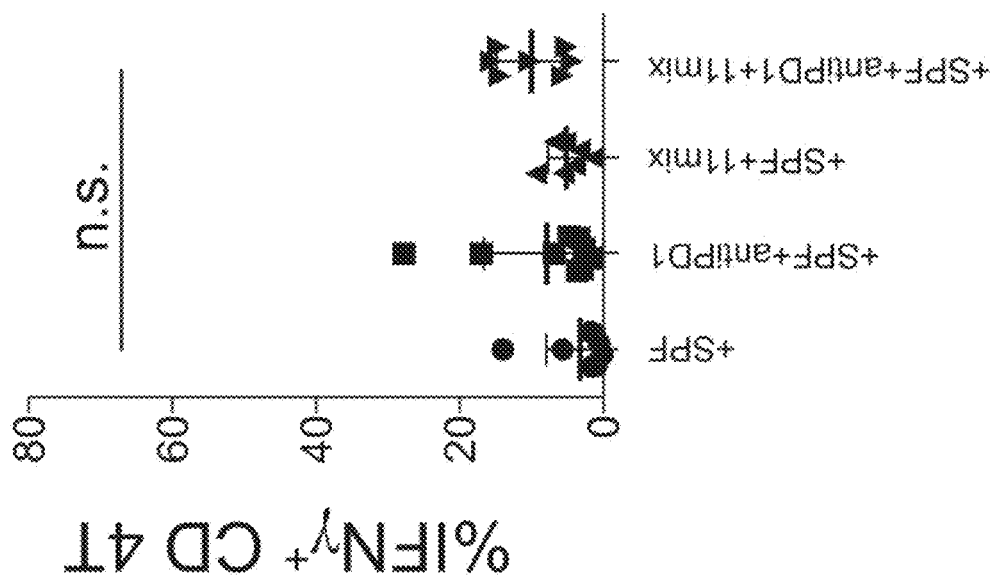
FIG. 18 shows data on lymphocytes isolated from tumor cells. The effect on IFNγ+CD4 T cells is shown in FIG. 18.
Figure 19:
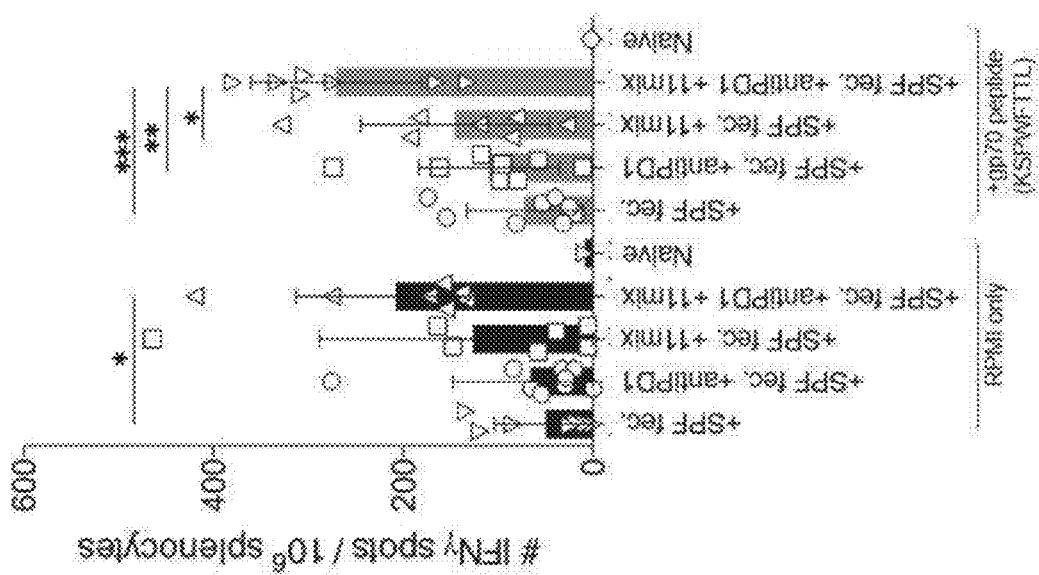
FIG. 19 shows data on lymphocytes isolated from tumor cells. At day 23 or 27, whole splenocytes were isolated and plated at 106 cells per well and stimulated with 0.5 μg/mL gp70 MC38 peptide (KSPWFTTL (SEQ ID NO: 53)) for 36 hours at 37° C. Spots were developed using the Mouse IFNγ ELISPOT Ready-SET Go!R kit (eBioscience), and the number of spots was measured using an Immunospot Series 4 Analyzer and analyzed using ImmunoSpot software (Cellular Technology). Each plot represents individual mice. "Naive" is a mouse which was not treated with antibiotics, not injected with MC38 cells and not treated with 11mix and anti-PD1 antibody. * $P<0.05$,  $P<0.01$, * $P<0.001$ (one-way ANOVA).
Figure 21:
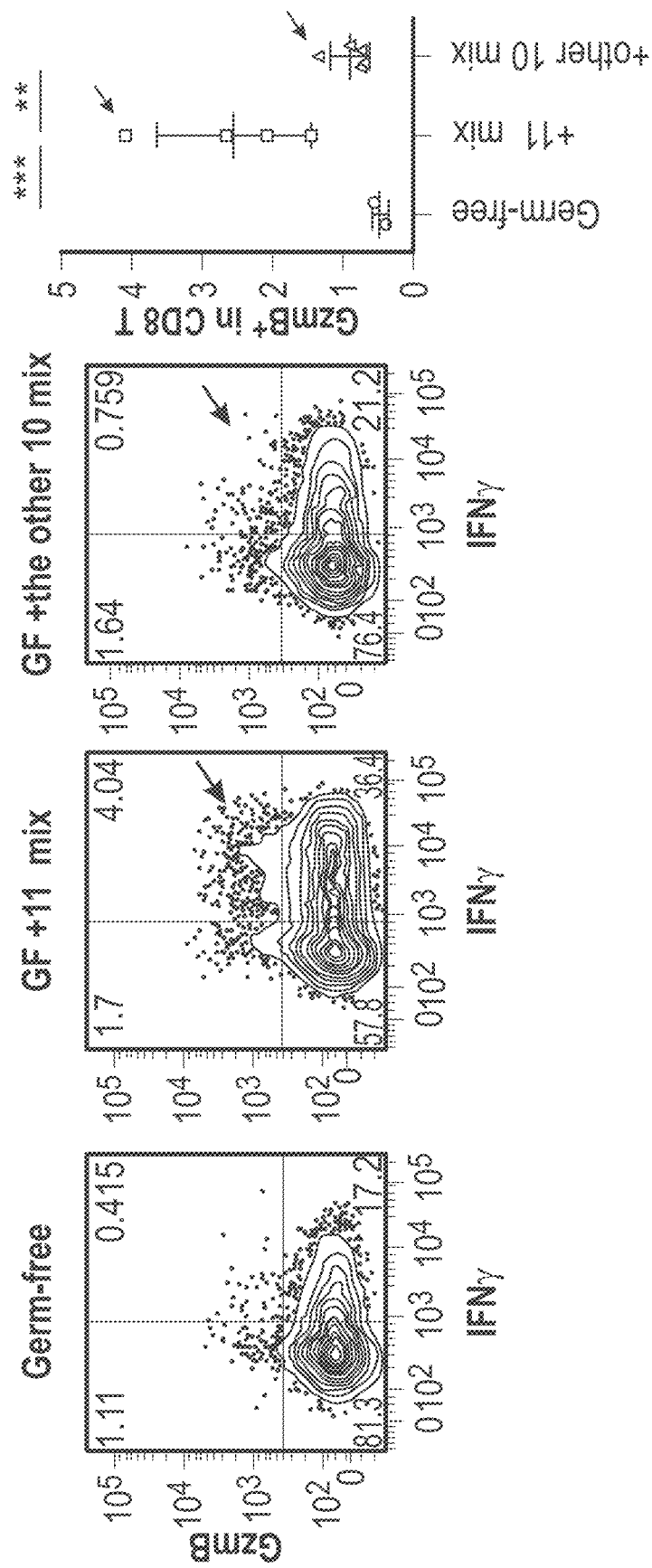
FIG. 21 shows data on induction of GzmB+ IFNγ+CD8 T cells by 11-mix bacterial strains.
Figure 22:
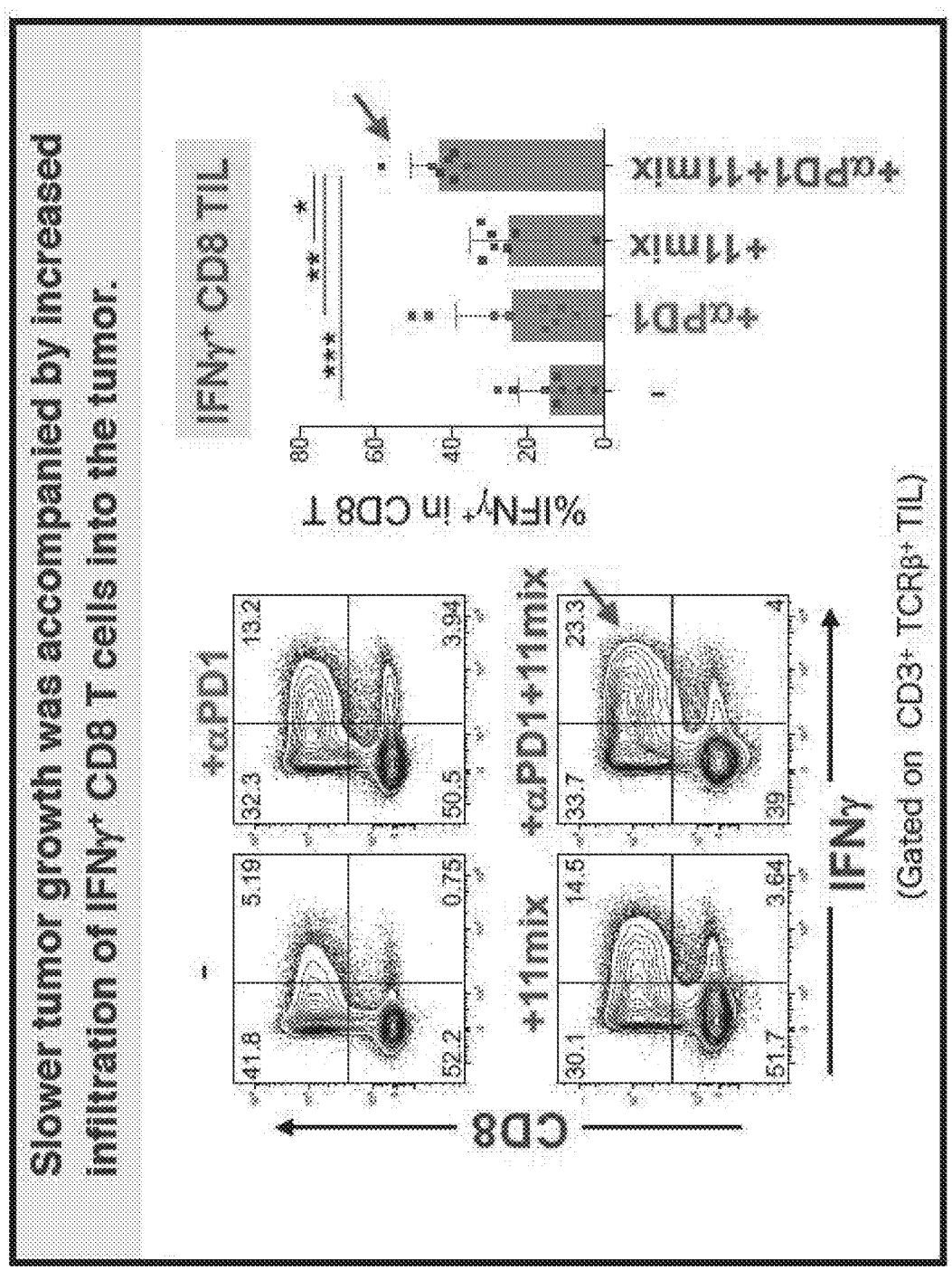
FIG. 22 shows that slower tumor growth was accompanied by increased infiltration of IFNγ+CD8 T cells into the tumor.
Figure 23:
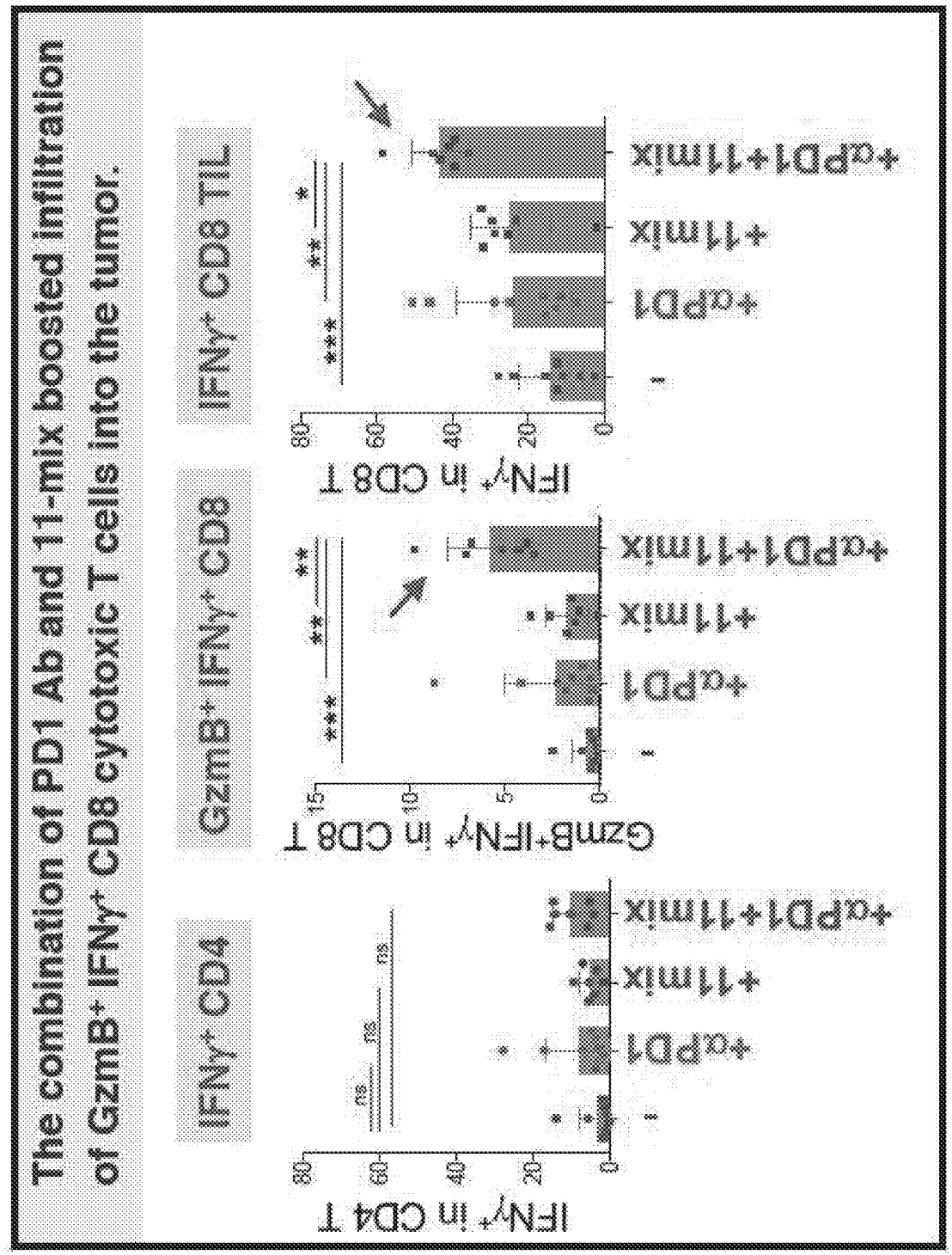
FIG. 23 shows that the combination of αPD1 Ab and 11-mix bacterial strains boosted infiltration of GzmB+ IFNγ+CD8 cytotoxic T cells into the tumor.

Treatment with the 11 mix alone (i.e., without anti-PD1 Ab) significantly suppressed MC38 tumor growth (see FIG. 15). The combination of the 11 mix and anti-PD1 Ab exhibited the strongest suppressive effect on the growth of tumor cells (see FIG. 15). Treatment with the 11 mix and anti-PD1 Ab resulted in elevated accumulation of IFNγ+ CD8+ T cells in the MC38 tumor mass (see FIGS. 16A and 16B). A subset of the IFNγ+CD8+ T cells in tumors expressed T-cell receptors specific for gp70p15E604-611 (KSPWFTTL; SEQ ID NO; 53), which is an immunodominant epitope of MC38 (FIG. 17A). Furthermore, a subset of IFNγ+CD8+ T cells expressed CD44 and Granzyme B, suggesting that the IFNγ+CD8+ T cells accumulated in the tumor included tumor-specific and memory-type cytotoxic CD8+ T cells (see FIGS. 17A and 17B). The effect on IFNγ+CD4 T cells is shown in FIG. 18. Oral inoculation with the 11 mix resulted in the increased numbers of IFNγ-producing splenocytes, even in the absence of tumor antigen stimulation (see FIG. 19).

TABLE 4

Mixture of 4 strains

| Strain # | SEQ ID NO | Strain ID | Species with highest homology | NCBI accession # of 16S locus | SEQ ID of NCBI 16S locus |
|---|---|---|---|---|---|
| 1 | 1 | 2G5 | *Phascolarctobacterium faecium* | LN998073 | 27 |
| 2 | 2 | 1A6 | *Fusobacterium ulcerans* | KR822463 | 28 |
| 5 | 5 | 2B1 | *Subdoligranulum* sp. | KM098109 | 31 |
| 10 | 10 | 1C1 | *Eubacterum limosum* | NR113248 | 36 |

These results show that treatment with 11 mix in combination with, or without, anti-PD1 Ab systemically activate CD8 T cells that respond to tumor cells.

Figure 24:
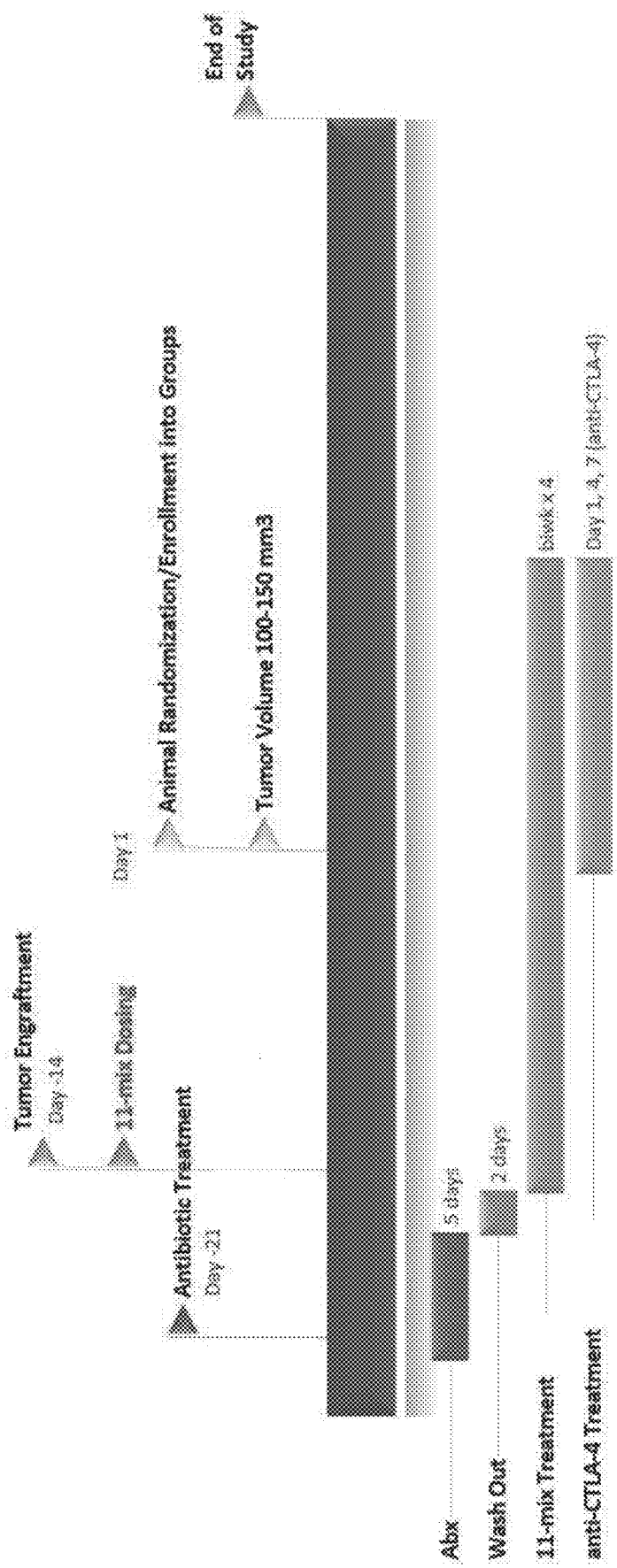
FIG. 24 shows a schematic of the experimental plan described in Example 4 relating to treatment with the 11-mix and/or an anti-CTLA-4 antibody.
Figure 25:
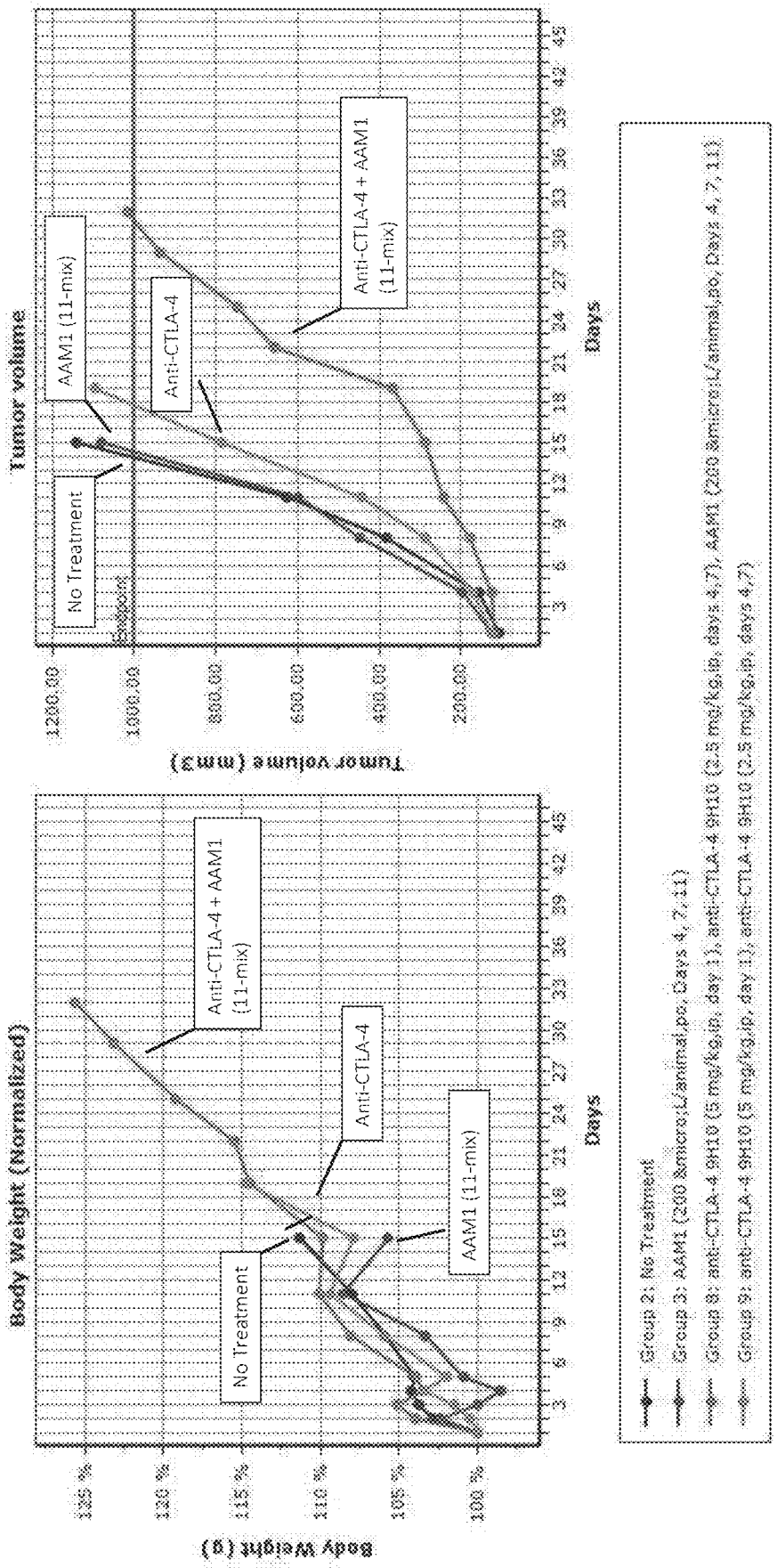
FIG. 25 shows body weight of mice that received the combination of α CTLA-4 Ab and the 11-mix of bacterial strains (left panel). Mice that received the combination of α CTLA-4 Ab and the 11-mix of bacterial strains had a significant reduction in tumor growth (right panel) in the experiment presented in FIG. 24 (Example 4).
Figure 26:
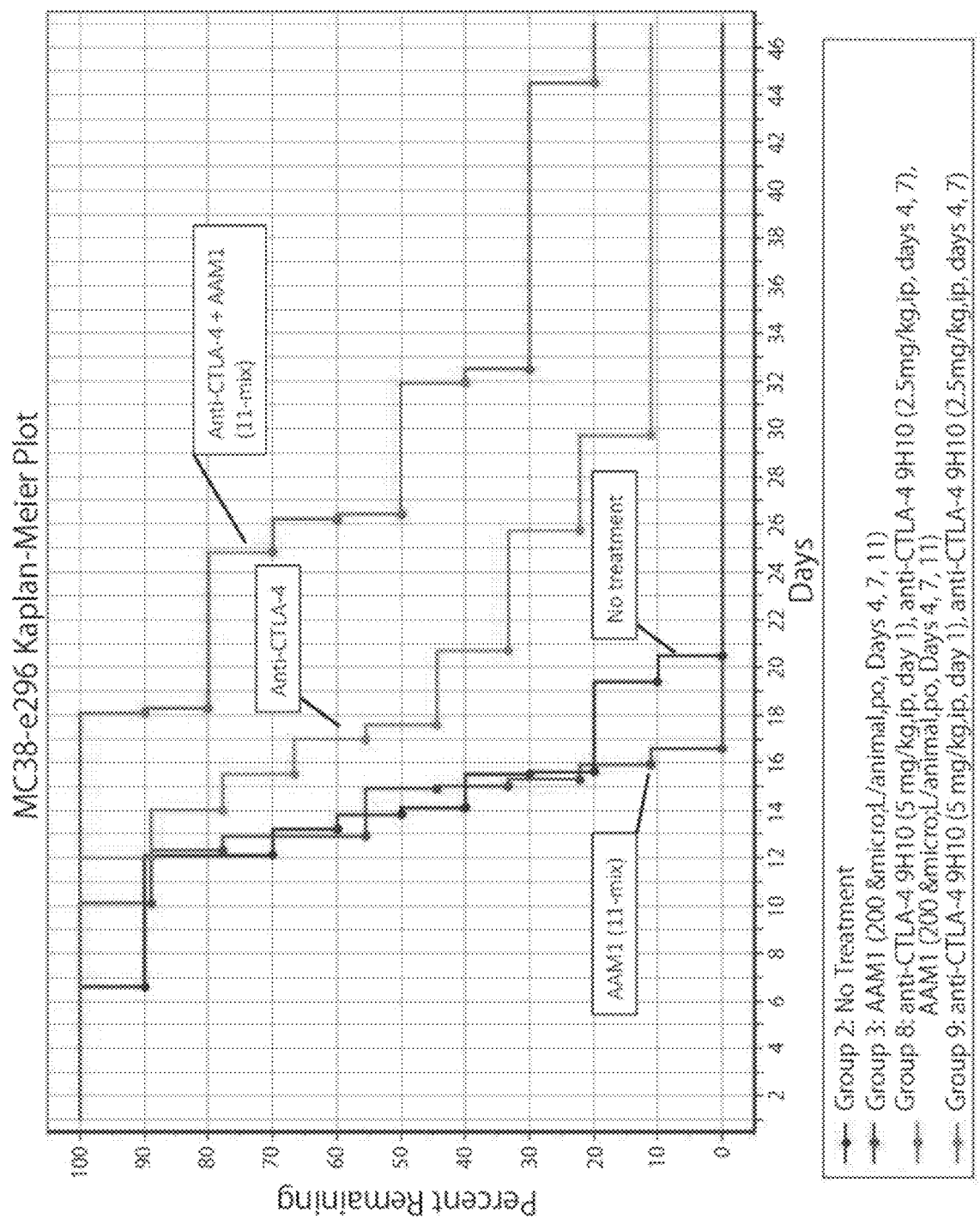
FIG. 26 shows that the combination of αCTLA-4 Ab and the 11-mix of bacterial strains had a significant effect on the survival of the mice in the experiment presented in FIG. 24 (Example 4).

Example 4: Anti-Cancer Characteristics of CD8+ T-Cell Inducing Bacterial Cocktail in Combination with CTLA-4 Immune Checkpoint Inhibitor To investigate whether colonization with the 11-mix in combination with immune checkpoint inhibitor CTLA4 could enhance anticancer immune response, a subcutaneous tumor model was used (FIG. 24). Mice were treated with mixture of antibiotics for 5 days (from day −21 to day −16), followed by a two-day period to wash out the antibiotics. A MC38 colon cancer cell line (3×105 cells per mouse) was subcutaneously injected into the right flank of mice at day −14. The animals were randomized into the following treatment groups:

Group 1: No antibiotics, no treatments (provides a reference for standard progression of MC38 tumor model);
Group 2: Antibiotic pre-treatment, no treatment (provides a reference for the progression of the MC38 tumor model with antibiotic pre-treatment);
Group 3: 11-mix monotherapy (referred to as AAM1 in FIGS. 25 and 26);
Group 8: anti-CTLA-4 antibody (9H10) and 11-mix (referred to as AAM1 in FIGS. 25 and 26) combination;
Group 9: anti-CTLA-4 antibody (9H10) monotherapy. Bacterial cocktail treatments were also begun on day −14 and administered biweekly 4 times. For groups receiving the CTLA-4 immune checkpoint inhibitor, the treatment was begun once the tumor volume reached approximately 100 mm3 (100-150 mm3). The anti-CTLA-4 antibody was administered on days 1, 4, and 7. The mice were assessed for weight and survival through the course of the experiment. Tumor size and volume were measured.

Tumor Measurements

Figure 27:
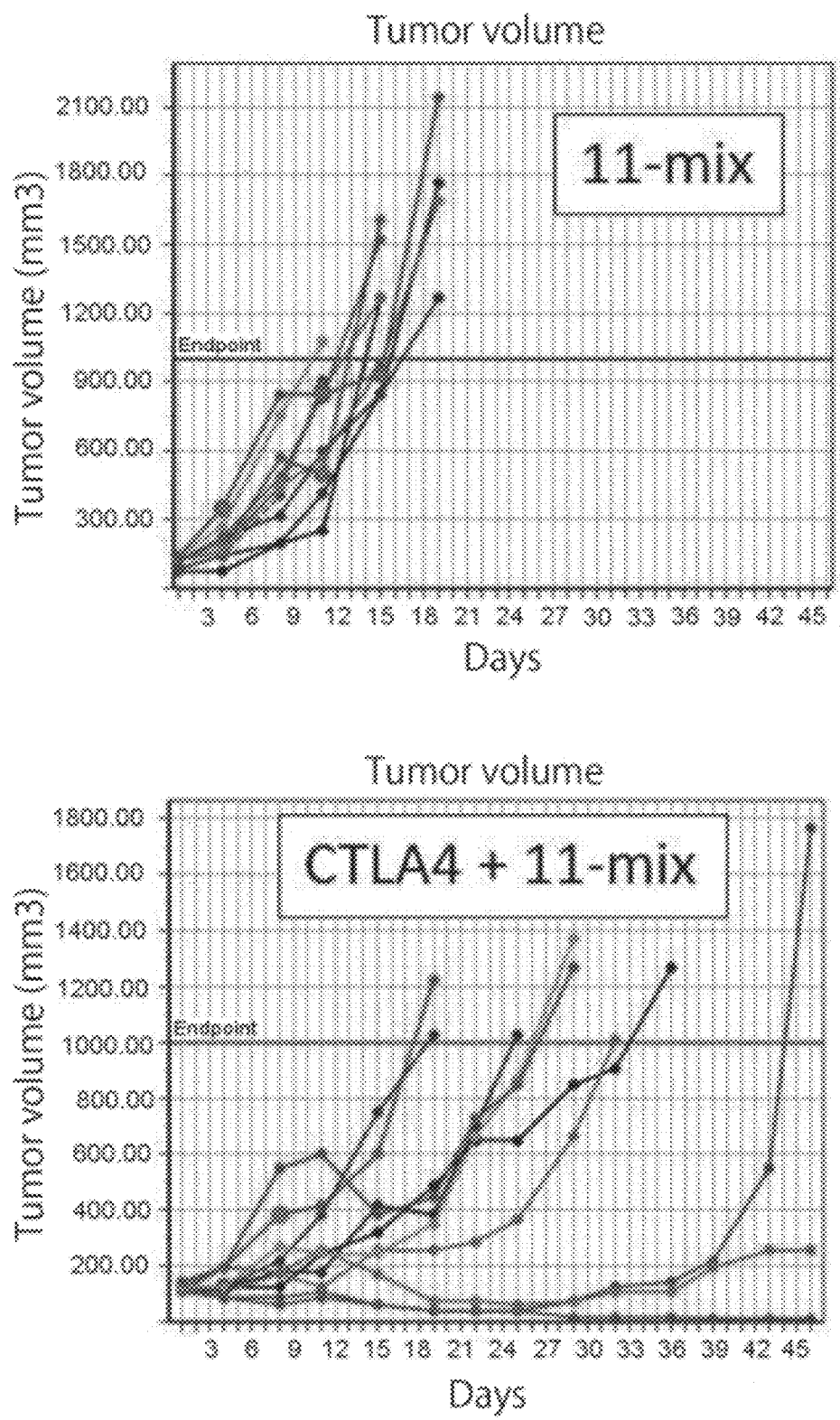
FIG. 27 shows tumor volume plots of individual mice treated in the experiments described in Example 4 (control, 11-mix; αCTLA-4 Ab; 11-mix+αCTLA-4 Ab).

The group of mice that received the anti-CTLA-4 antibody alone (Group 9) had slightly reduced tumor growth compared to control mice. The combination of the 11-mix (referred to as "AAM1" in FIG. 25) and the anti-CTLA-4 antibody (Group 8) significantly reduced the tumor growth as compared to the 11-mix on its own and as compared to the anti-CTLA-4 antibody on its own. See FIG. 25. Tumor volume plots of individual mice are shown in FIG. 27.

Survival

The group of mice that received the anti-CTLA-4 antibody alone had slightly increased survival compared to control mice. The 11-mix by itself had no impact on survival. The combination of the 11-mix (referred to as "AAM1" in FIG. 26) and the anti-CTLA-4 antibody significantly enhanced survival of the treated mice (Group 8). See FIG. 26.

Figure 28:
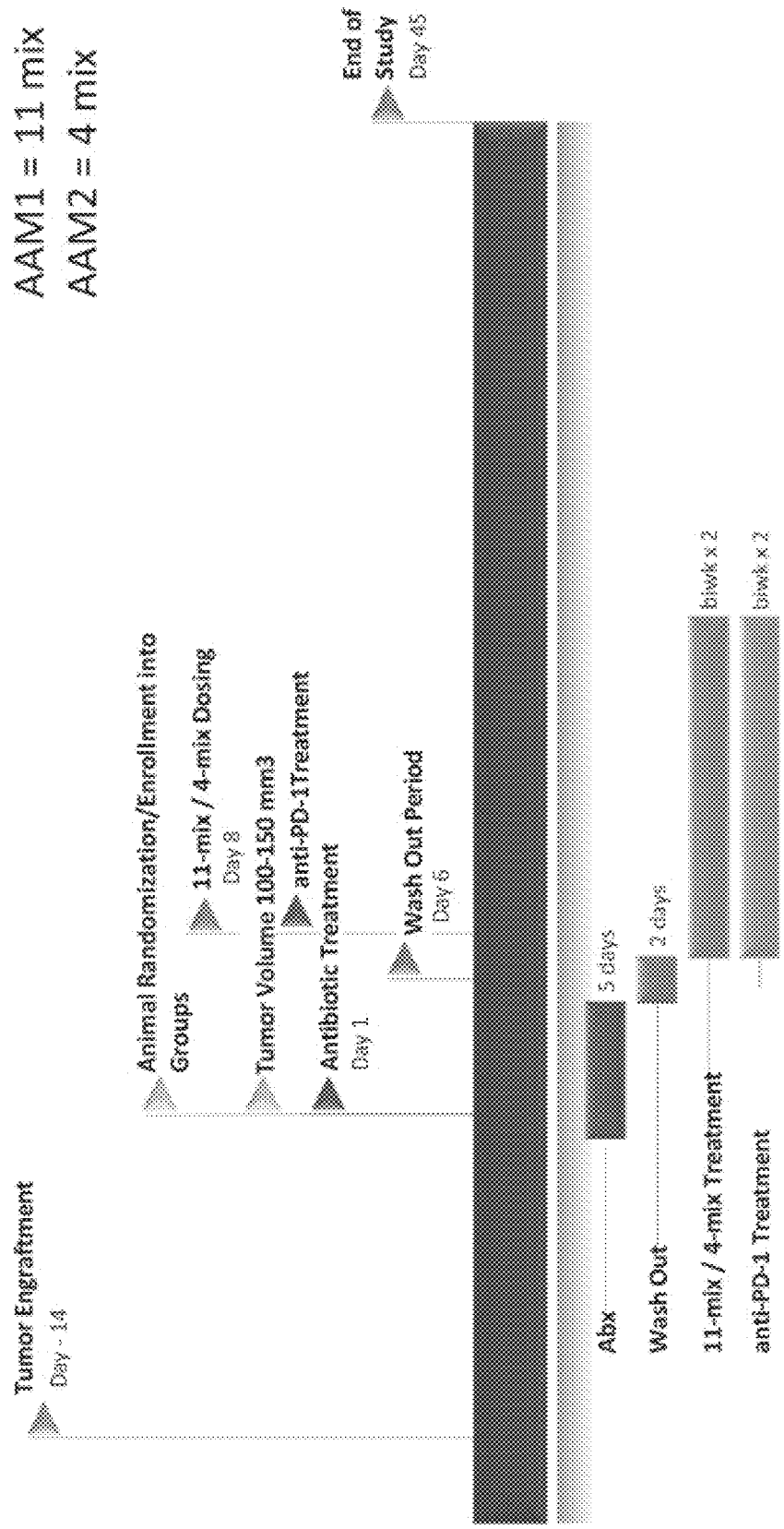
FIG. 28 shows a schematic of the experimental plan described in Example 5 relating to treatment with the 11-mix or 4-mix and/or an anti-PD-1 antibody.
Figure 29:
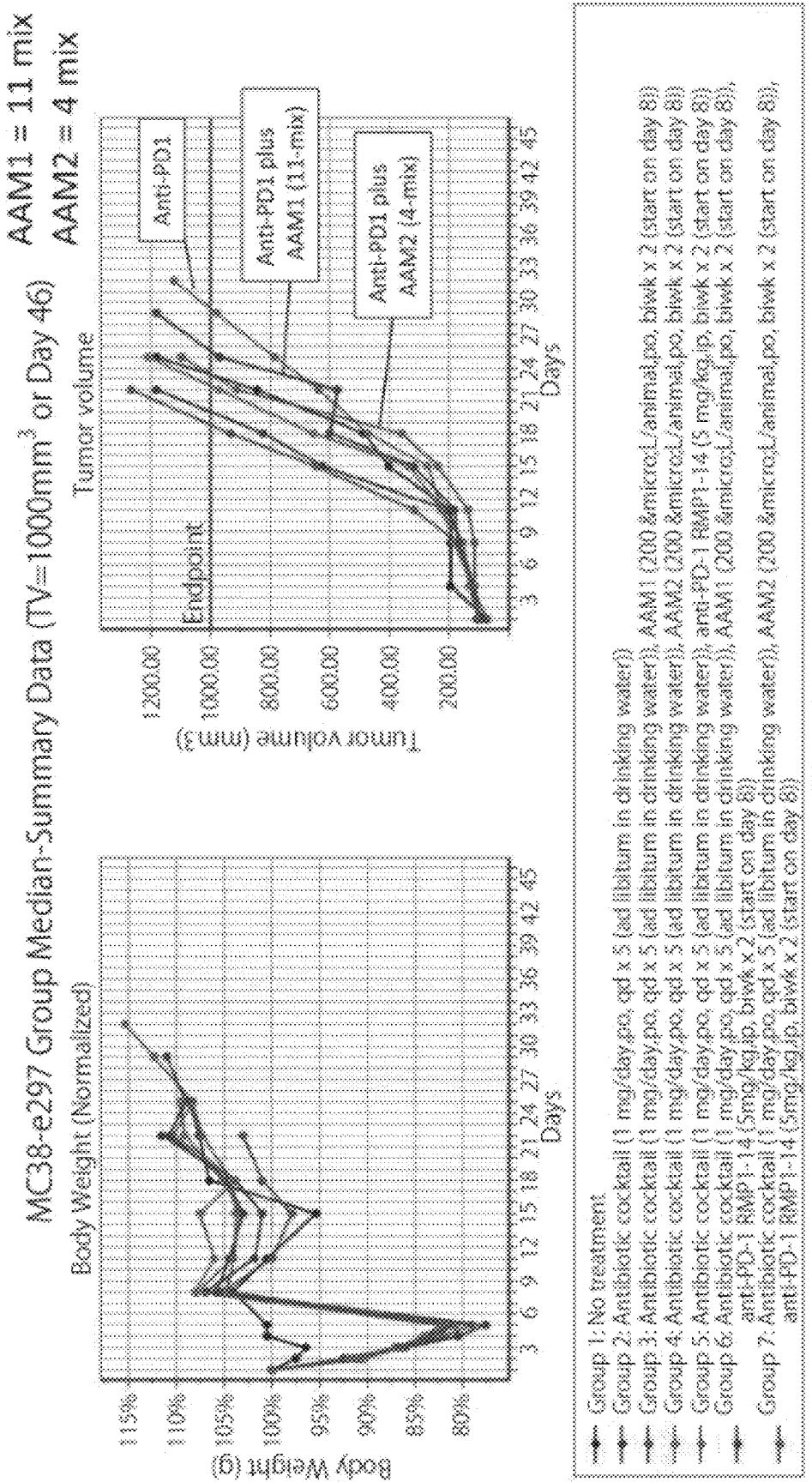
FIG. 29 shows body weight (left panel) and tumor volume (right panel) of mice that received the combination of α PD1 Ab and the 4-mix of bacterial strains or α PD1 Ab and the 11-mix of bacterial strains, and the various control groups.

Example 5: Anti-Cancer Characteristics of CD8+ T-Cell Inducing Bacterial Cocktails in Combination with an Anti-PD1 Antibody To investigate whether colonization with the 4-mix or 11-mix in combination with immune checkpoint inhibitor anti-PD1 could enhance anticancer immune responses in the absence of antibiotic pretreatment and prior engraftment, a MC38 colon cancer cell line (3×105 cells per mouse) was subcutaneously injected into the right flank of mice at day −14 (See FIG. 28). The animals were randomized into the following treatment groups:

Group 1: No treatment;
Group 3: 11-mix monotherapy (referred to as "AAM1" in FIGS. 28 and 29);
Group 4: 4-mix monotherapy (referred to as "AAM2" in FIGS. 28 and 29);
Group 5: anti-PD1 antibody (RMP1-14) monotherapy;
Group 6: anti-PD1 antibody (RMP1-14) and 11-mix (referred to as "AAM1" in FIGS. 28 and 29) combination; and
Group 7: anti-PD1 antibody (RMP1-14) and 4-mix (referred to as "AAM2" in FIGS. 28 and 29) combination.

The treatments were begun at day 1 (tumor volume approximately 100-150 mm3). Bacterial cocktail treatment and the anti-PD1 antibody were administered biweekly twice. The mice were assessed for weight and survival through the course of the experiment. Tumor size and volume were measured.

Tumor Measurement

Figure 30:
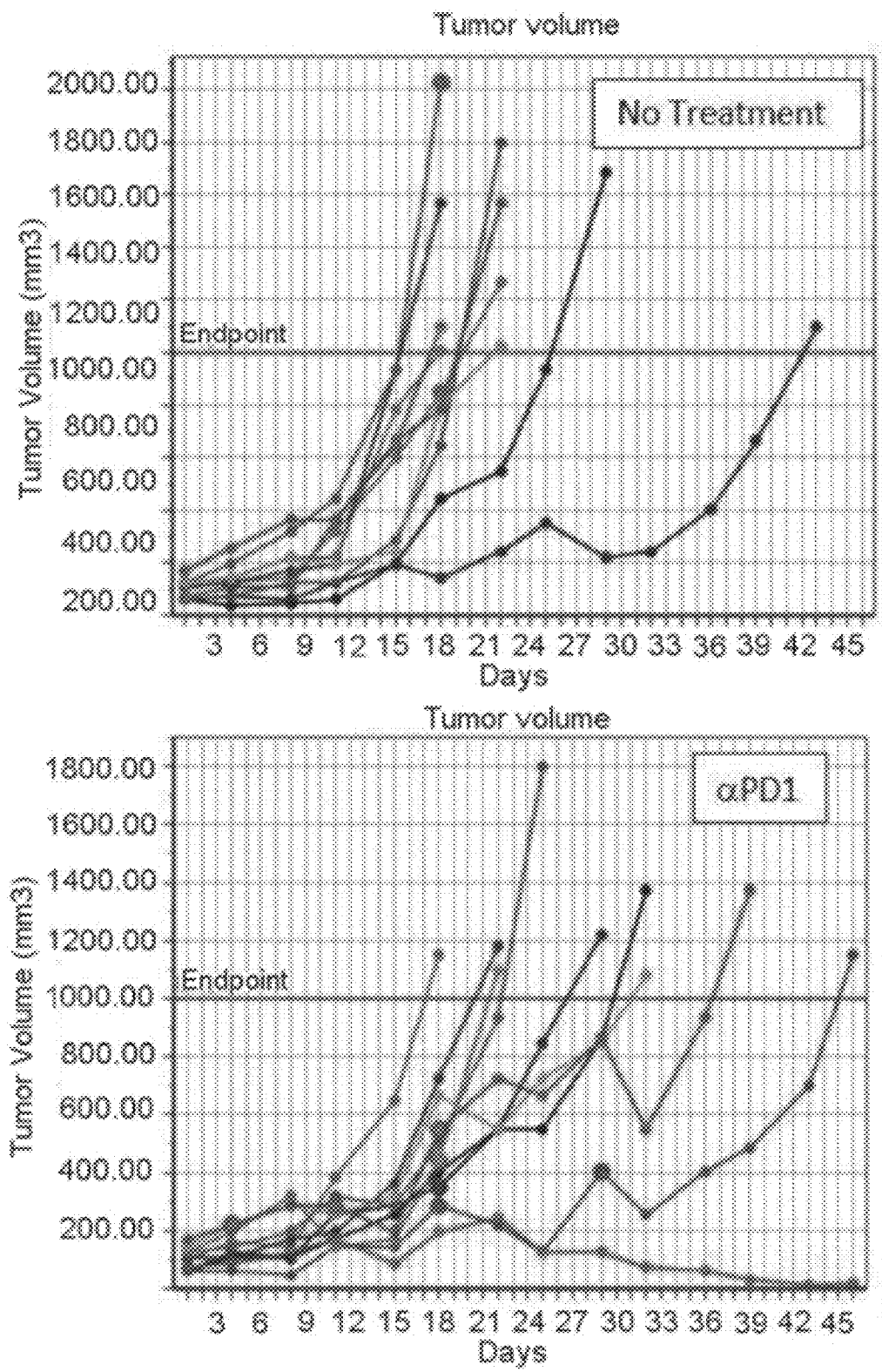
FIG. 30 shows tumor volume plots of individual mice treated in experiments of Example 5 (11-mix; α PD-1 Ab; 11-mix+α PD-1 Ab). The tumor volume did not increase in multiple animals in the 11-mix+αPD-1 Ab treatment group (bottom right panel).
Figure 30:
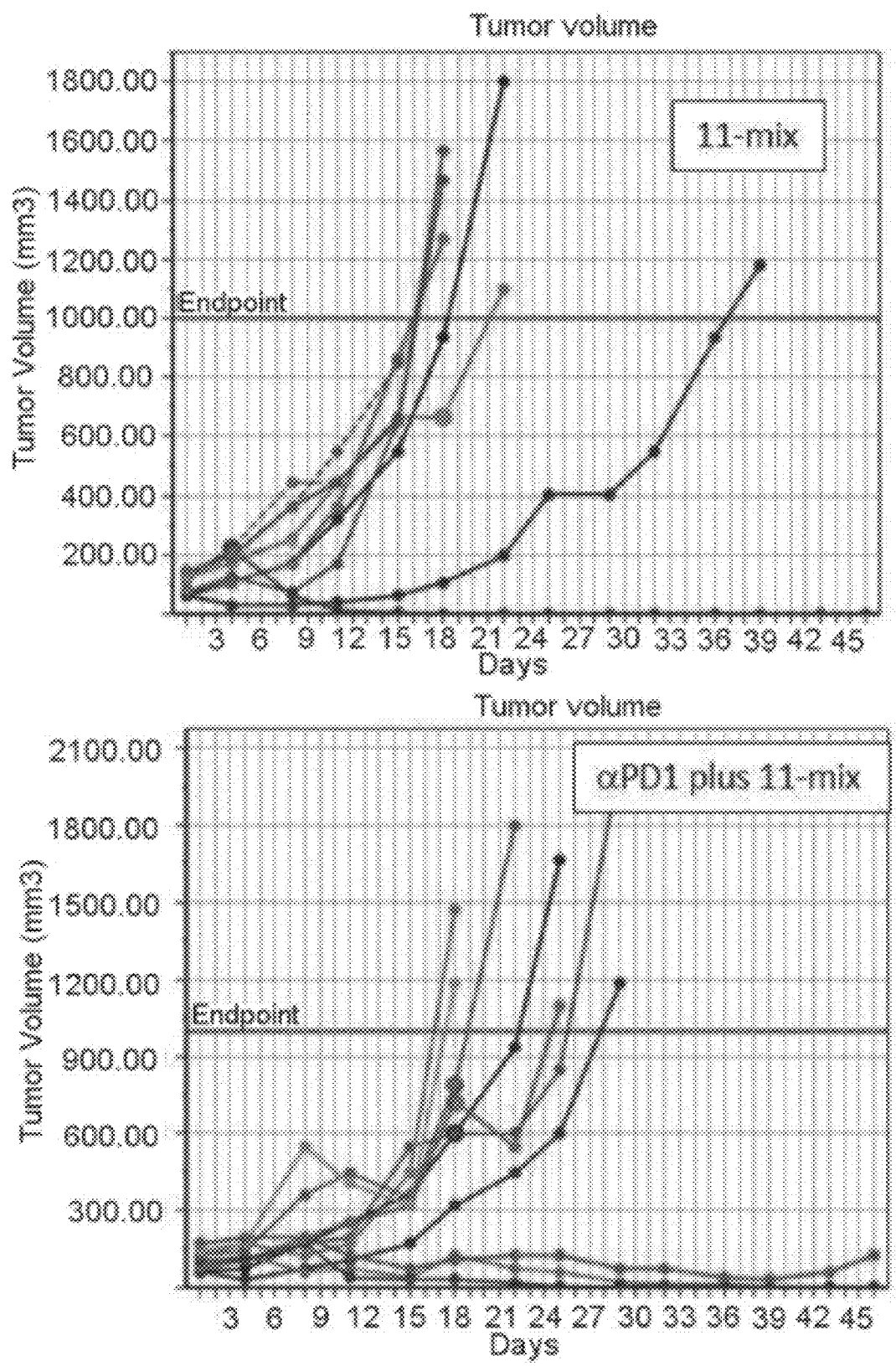
Figure 32:
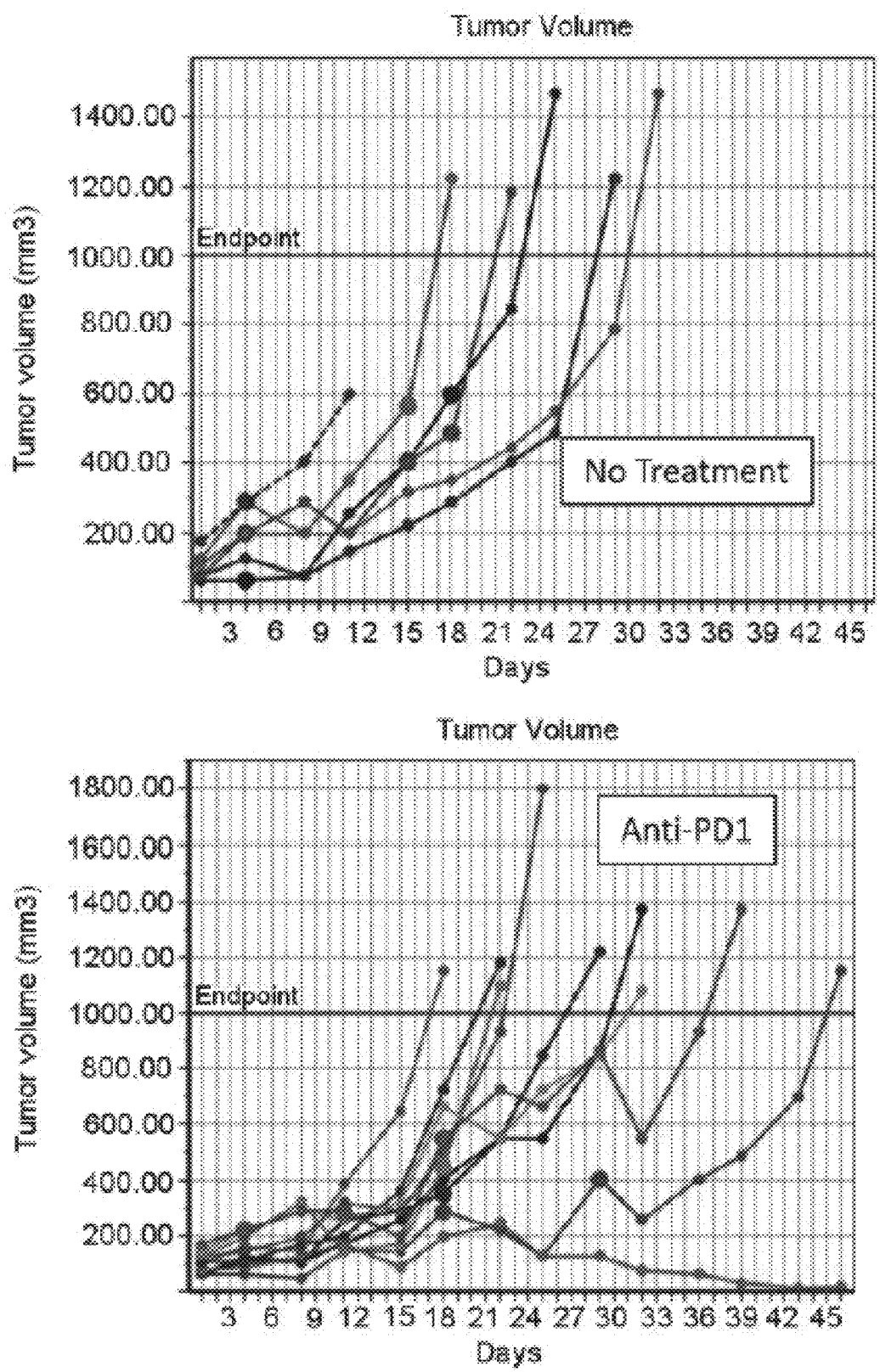
FIG. 32 shows tumor volume plots of individual mice treated in experiments of Example 5 (4-mix; αPD-1 Ab; 4-mix+αPD-1 Ab). The tumor volume did not increase in multiple animals in the 4-mix+αPD-1 Ab treatment (bottom right panel).

Treatment with the anti-PD1 antibody alone or in combination with either the 4-mix or the 11-mix resulted in a reduction in tumor growth as compared to no treatment. FIG. 30 shows tumor volume plots of the individual mice treated in experiments of Example 5 (control, 11-mix; αPD-1 Ab; 11-mix+αPD-1 Ab). The tumor volume did not increase in multiple animals in the 11-mix+αPD-1 Ab treatment group (bottom right panel). FIG. 32 shows tumor volume plots of individual mice treated in experiments of Example 5 (control, 4-mix; αPD-1 Ab; 4-mix+αPD-1 Ab). The tumor volume did not increase in multiple animals in the 4-mix+αPD-1 Ab treatment group (bottom right panel).

Survival

Figure 31:
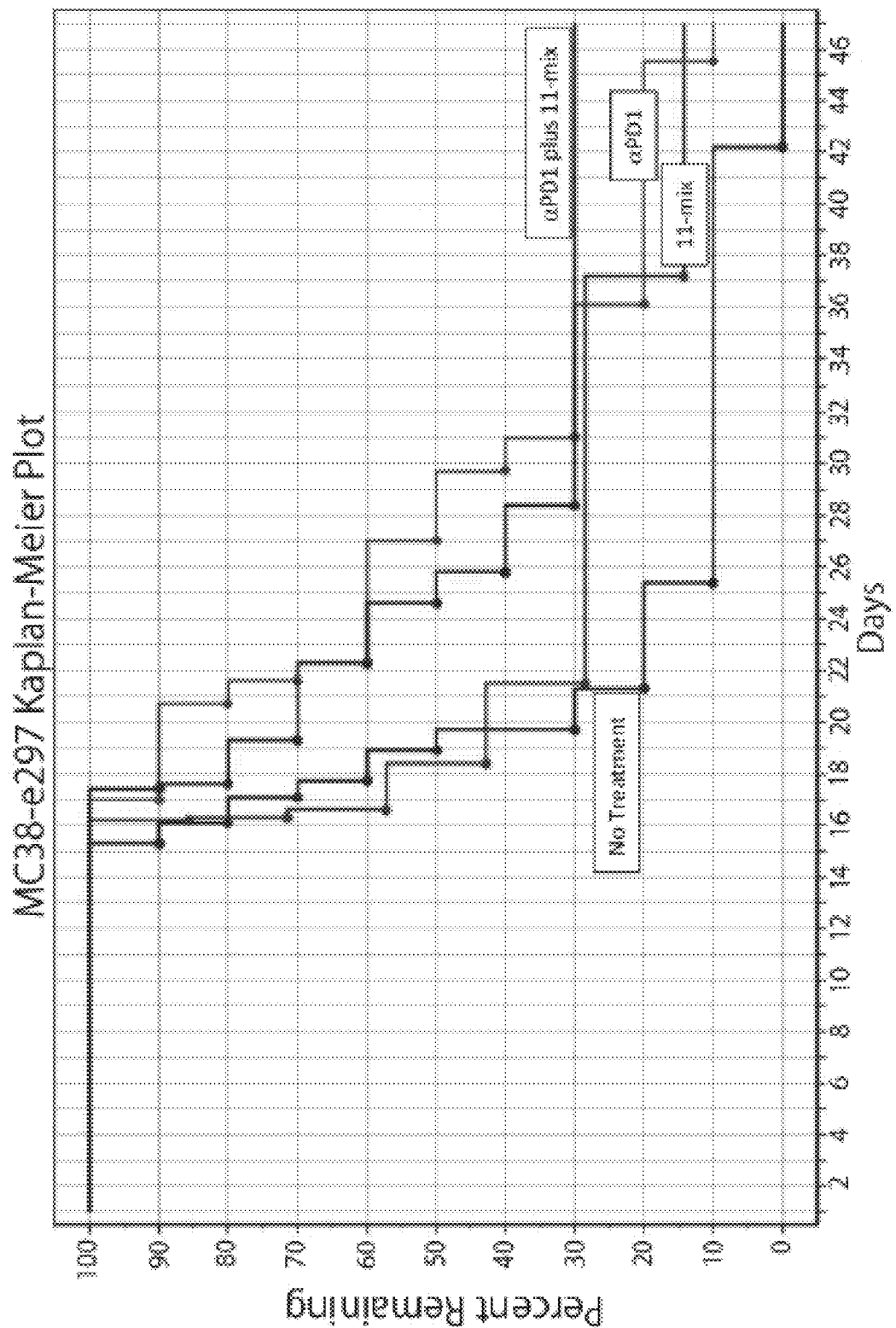
FIG. 31 shows survival plots of mice treated in experiments of Example 5 (11-mix; αPD-1 Ab; 11-mix+αPD-1 Ab).
Figure 33:
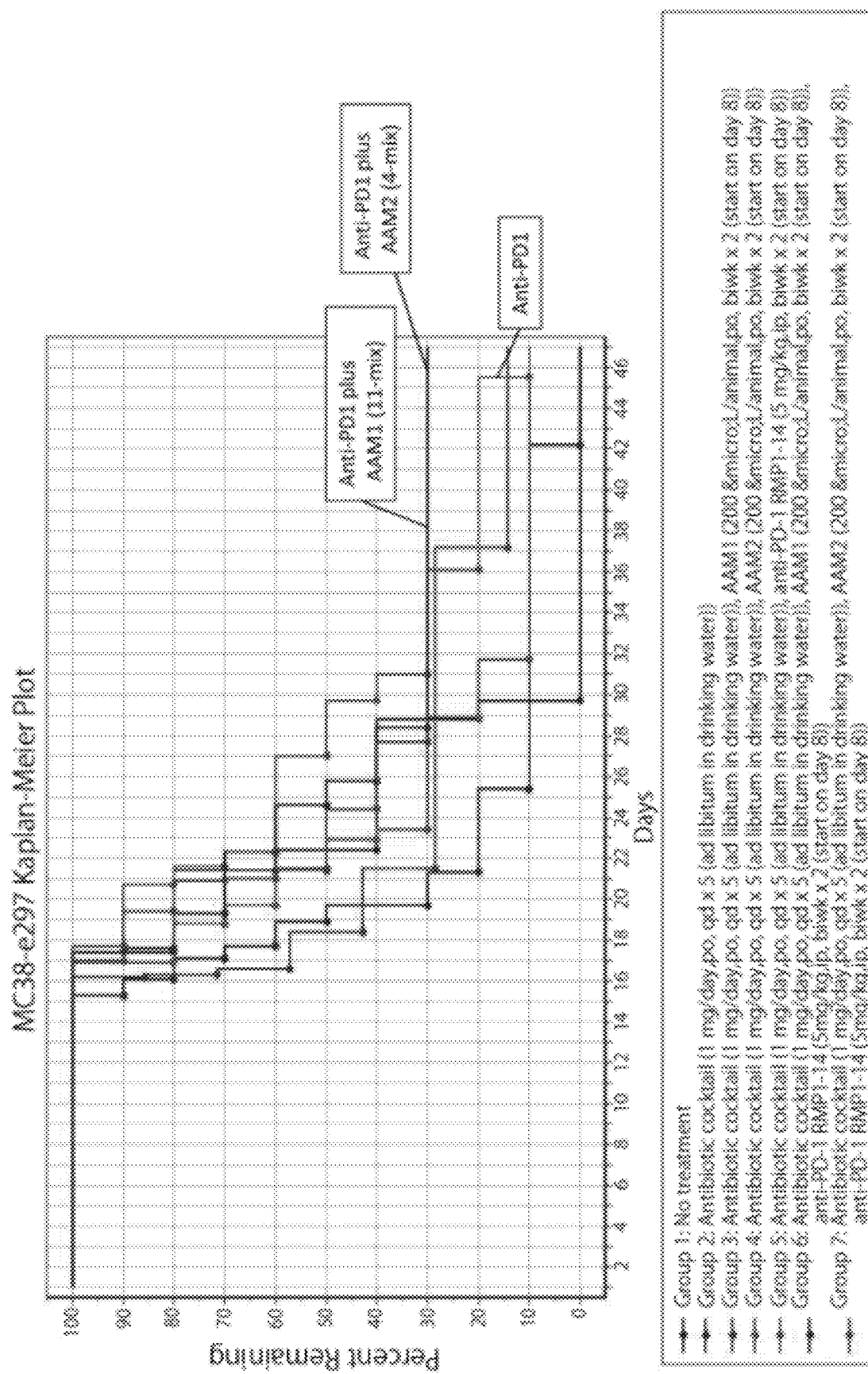
FIG. 33 shows plots of mice treated in experiments of Example 5. Highlighted are treatment with αPD-1 Ab, 11-mix+αPD-1 Ab, and 4-mix+αPD-1 Ab.

Survival data are shown in FIG. 31 for the control, 11-mix; PD-1 Ab; and 11-mix+PD-1 Ab groups. The combination of the 11-mix and the αPD-1 Ab showed increased survival when compared to either the 11-mix or the αPD-1 Ab on its own. The combined survival data of mice in the control, 4-mix; αPD-1 Ab; 4-mix+αPD-1 Ab, 11-mix, and 11-mix+αPD-1 Ab groups are shown in FIG. 33. Both the combination of the 4-mix and the αPD-1 Ab and the combination of the 11-mix and the αPD-1 antibody showed increased survival when compared to the αPD-1 Ab on its own.

Figure 34:
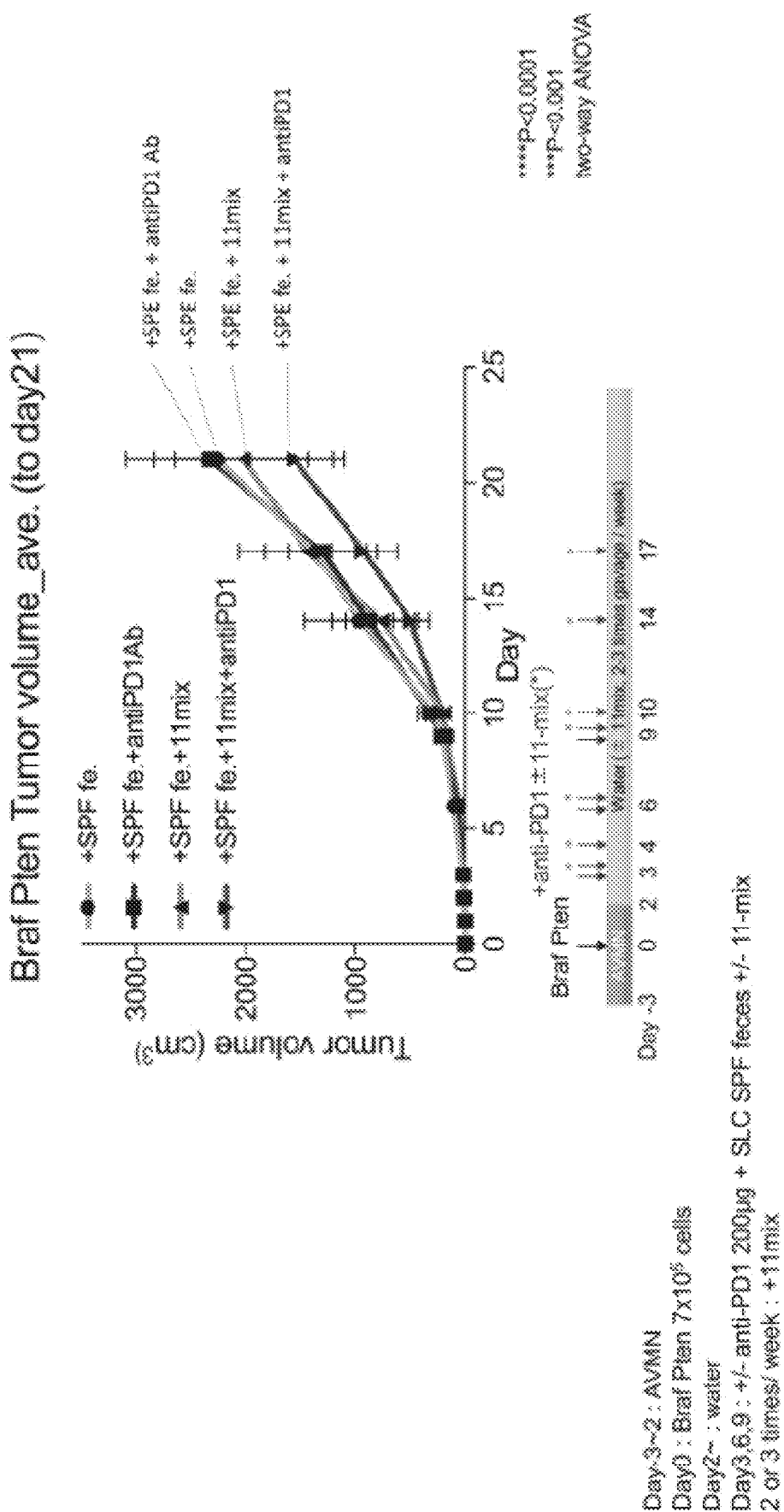
FIG. 34 shows data of experiments with the Braf Pten melanoma model (Example 6). Briefly, mice were administered antibiotics ("AVMN") from day −3 to day 2 and engrafted with 7×105 Braf Pten cells on day 0. On days 3, 6, and 9 the indicated groups of mice were administered an anti-PD1 antibody (arrows on the timeline) and SLC SPF feces from specific-pathogen free (SPF) mice obtained from Japan SLC (SLC SPF feces), with or without the 11-mix (arrows with asterisk on the timeline). The groups of mice indicated as having received the 11-mix were administered the 11-mix 2 or 3 times per week. The plot shows the average tumor volume at each of the timepoints for the groups of mice** $P<0.0001$, * $P<0.001$ (two-way ANOVA).
Figure 35:
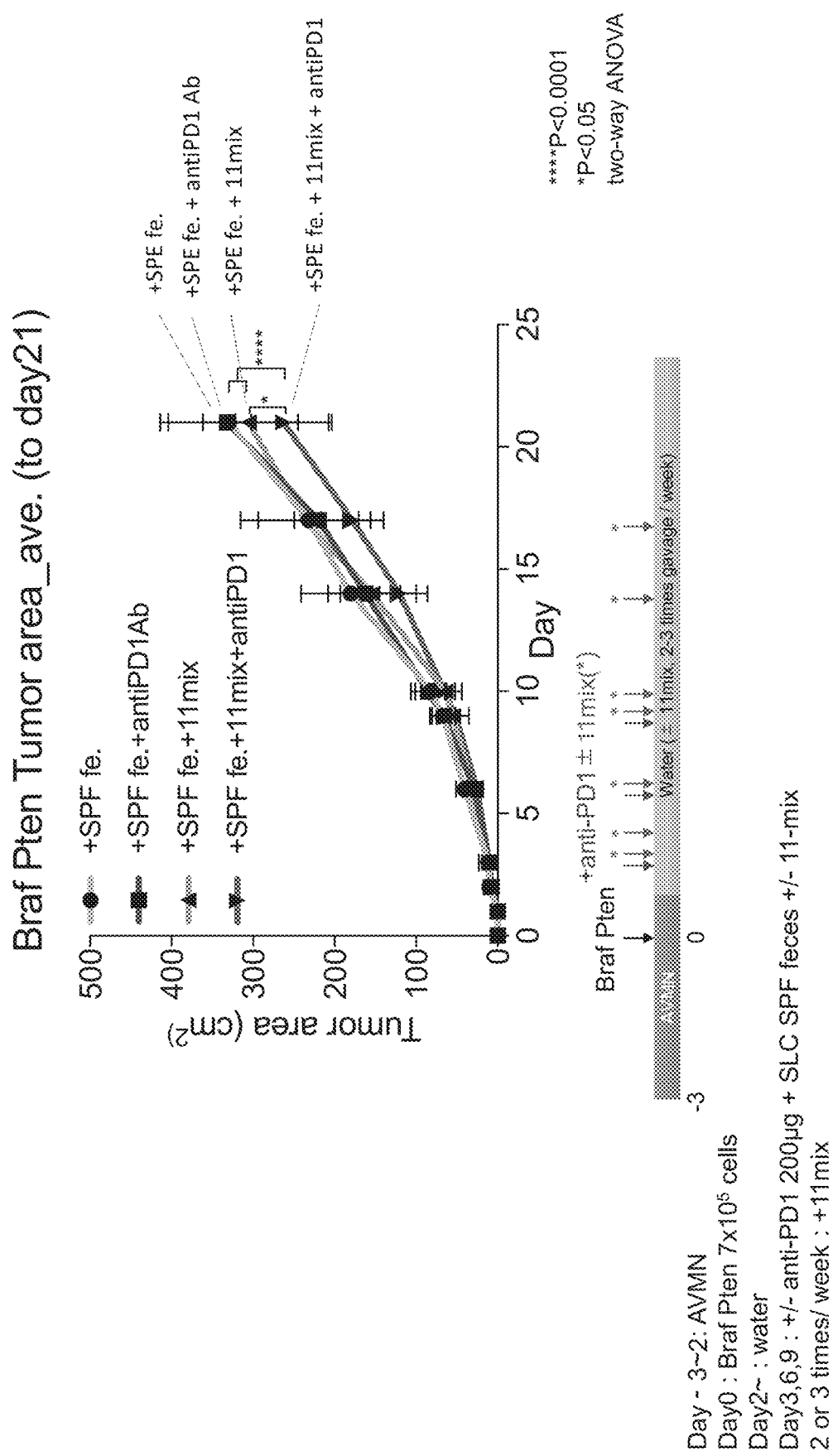
FIG. 35 shows data of experiments with the Braf Pten melanoma model (Example 6). Briefly, mice were administered antibiotics ("AVMN") from day −3 to day 2 and engrafted with 7×105 Braf Pten cells on day 0. On days 3, 6, and 9 the indicated groups of mice were administered an anti-PD1 antibody (arrows on the timeline) and SLC SPF feces from specific-pathogen free (SPF) mice obtained from Japan SLC (SLC SPF feces), with or without the 11-mix (arrows with asterisk on the timeline). The groups of mice indicated as having received the 11-mix were administered the 11-mix 2 or 3 times per week. The plot shows the average tumor area at each of the timepoints for the groups of mice. ** $P<0.0001$, * $P<0.001$ (two-way ANOVA).
Figure 36:
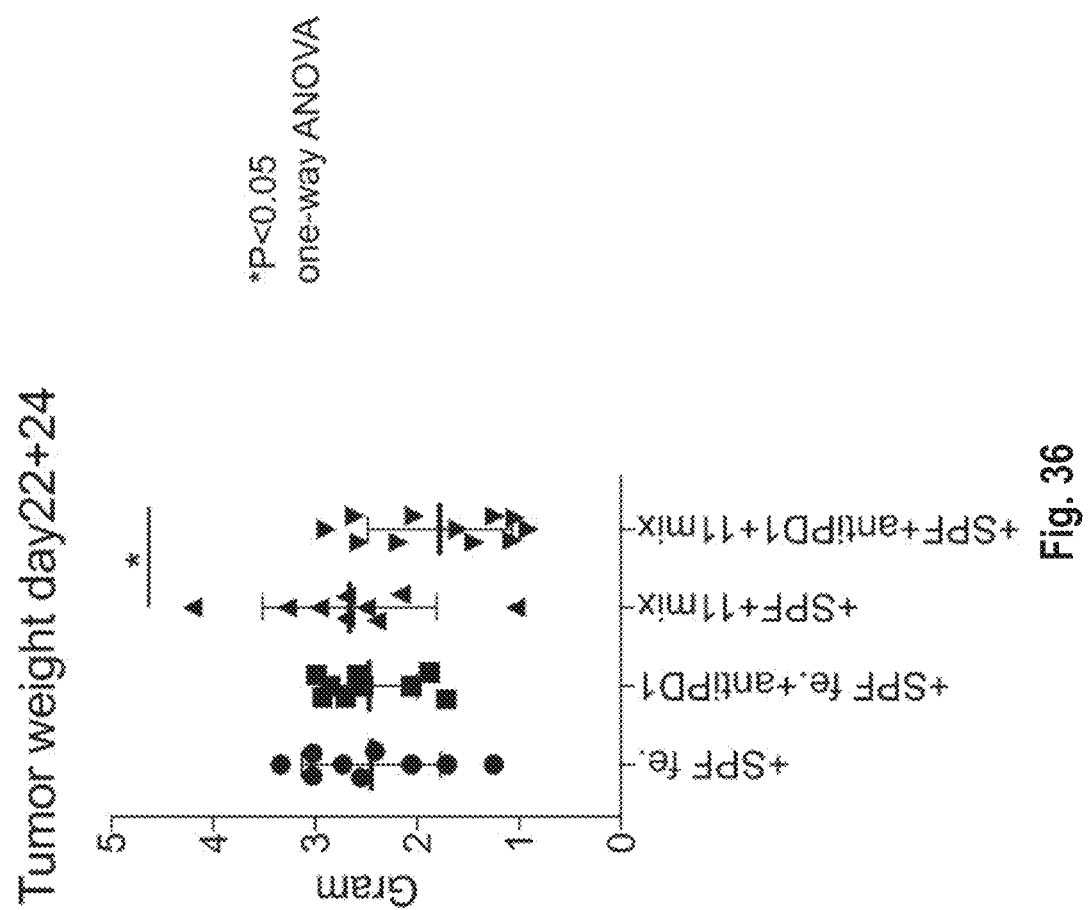
FIG. 36 shows data on the weight of tumors obtained on days 22 and 24 from the indicated groups of mice. * $P<0.05$ (one-way ANOVA).
Figure 37:
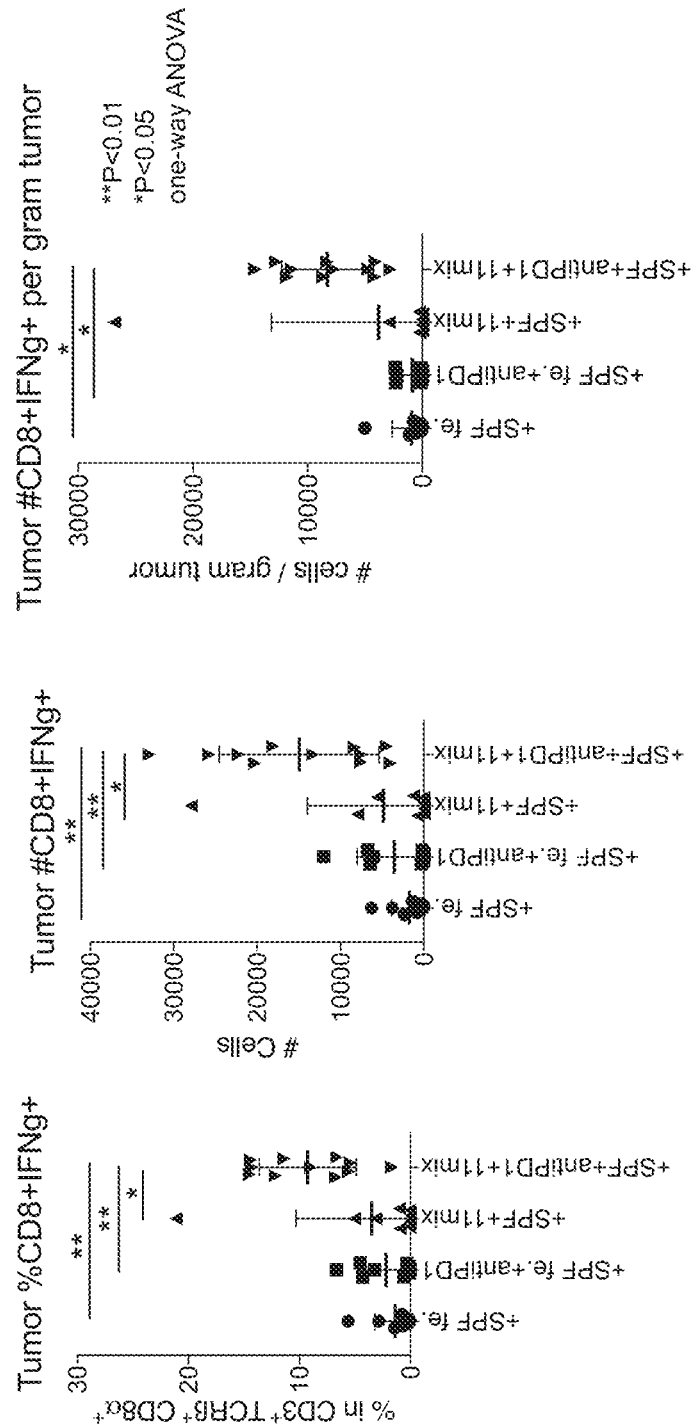
FIGS. 37A-37C show data on lymphocytes isolated from tumor cells. On days 22 and 24, lymphocytes were isolated from tumors. CD3, TCRβ, CD8, and IFNγ were stained with antibodies.
Figure 38:
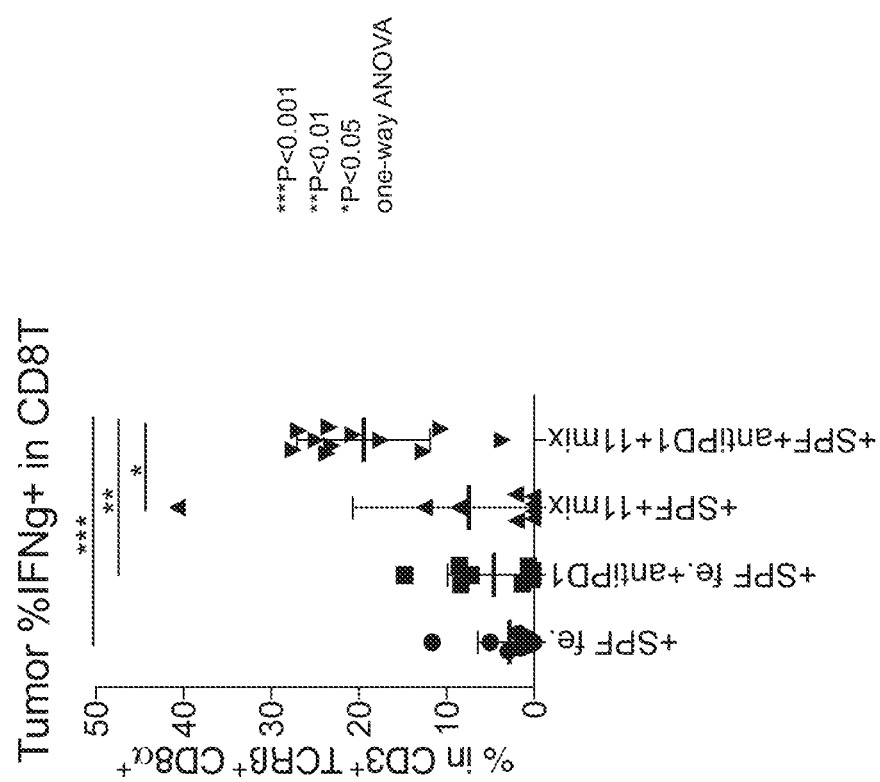
FIG. 38 shows the percentage of IFNγ+ cells in the population of CD8T cells isolated from the tumors. * $P<0.001$,  $P<0.01$, * $P<0.05$ (one-way ANOVA).
Figure 39D:
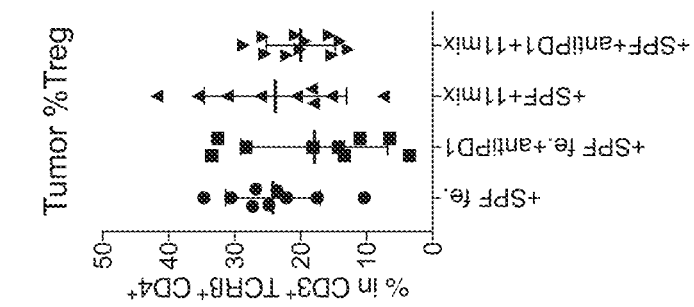
FIGS. 39A-39D show data on lymphocytes isolated from tumor cells. On days 22 and 24, lymphocytes were isolated from tumors. CD3, TCRβ, CD8, IFNγ, GzmB, IL-17, and CD4 were stained with antibodies.
Figure 39C:
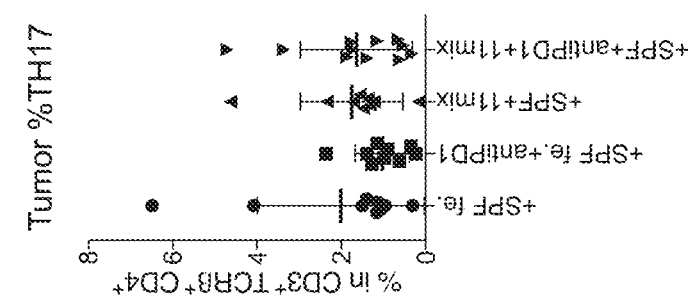
Figure 39B:
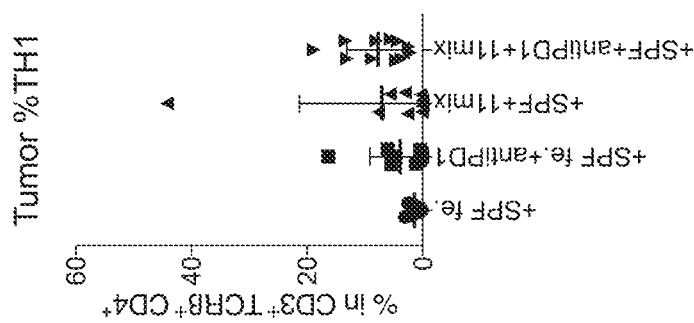
Figure 39A:
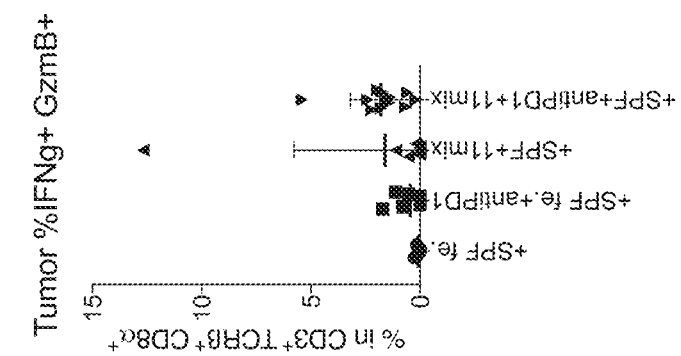

Example 6: Anti-Cancer Characteristics of CD8+ T-Cell Inducing Bacterial Cocktail Combination with an Anti-PD1 Antibody in a Melanoma Model A melanoma engraftment mouse model was used to evaluate the efficacy of the 11-mix in combination with a PD-1 antibody in the treatment of melanoma. As shown in the timelines in FIGS. 34 and 35, mice received antibiotics (Ampicillin, Vancomycin, Metronidazole, and Neomycin: "AVMN") from day −3 to day 2. On day 0, the mice were engrafted with 7×105 Braf Pten melanoma cells. The mice were grouped in the following treatment groups:

Specific Pathogen Free (SPF) feces;
SPF feces+anti-PD1 antibody;
SPF feces+11-mix; and
SPF feces+11-mix+anti-PD1 antibody. On days 3, 6, and 9, the mice were administered SLC SPF feces from specific-pathogen free (SPF) mice obtained from Japan SLC (SLC SPF feces), an anti-PD1 antibody (arrows on the timelines in FIGS. 34 and 35) and/or the 11-mix (arrows with asterisk on the timelines in FIGS. 34 and 35). The 11-mix was administered to the indicated groups of mice 2 or 3 times per week by gavage. Mice that received the combination of the anti-PD1 antibody and the 11-mix had reduced tumor volume (FIG. 34), tumor area (FIG. 35), and tumor weight (FIG. 36) as compared to the other groups of mice.

Lymphocytes were isolated from tumors obtained from the mice on days 22 and 24 and stained using antibodies to cell markers, including CD3, TCRβ, CD8, CD4, IFNγ, Granzyme, and IL-17. Treatment with the 11-mix and anti-PD1 antibody combination resulted in elevated accumulation of IFNγ+CD8+ T cells in the melanoma tumor. FIGS. 37A-37C and 38. In this experiment, there was no significant difference in the number of IFNγ+GzmB+ cells, Th1 cells, Th17 cells, or Treg cells between the groups of mice. FIGS. 39A-39D.

These results show that treatment with 11-mix in combination with the anti-PD1 antibody systemically activates CD8 T cells in the melanoma.

Example 7: CD8 T-Cell Induction in Specific-Pathogen Free (SPF) Mice

Experimental parameters were evaluated for the induction of CD8 T cells by the 11-mix bacterial cocktail. The animals used in this study were specific pathogen free mice (SPF mice) as compared to germ-free mice.

Figure 40:
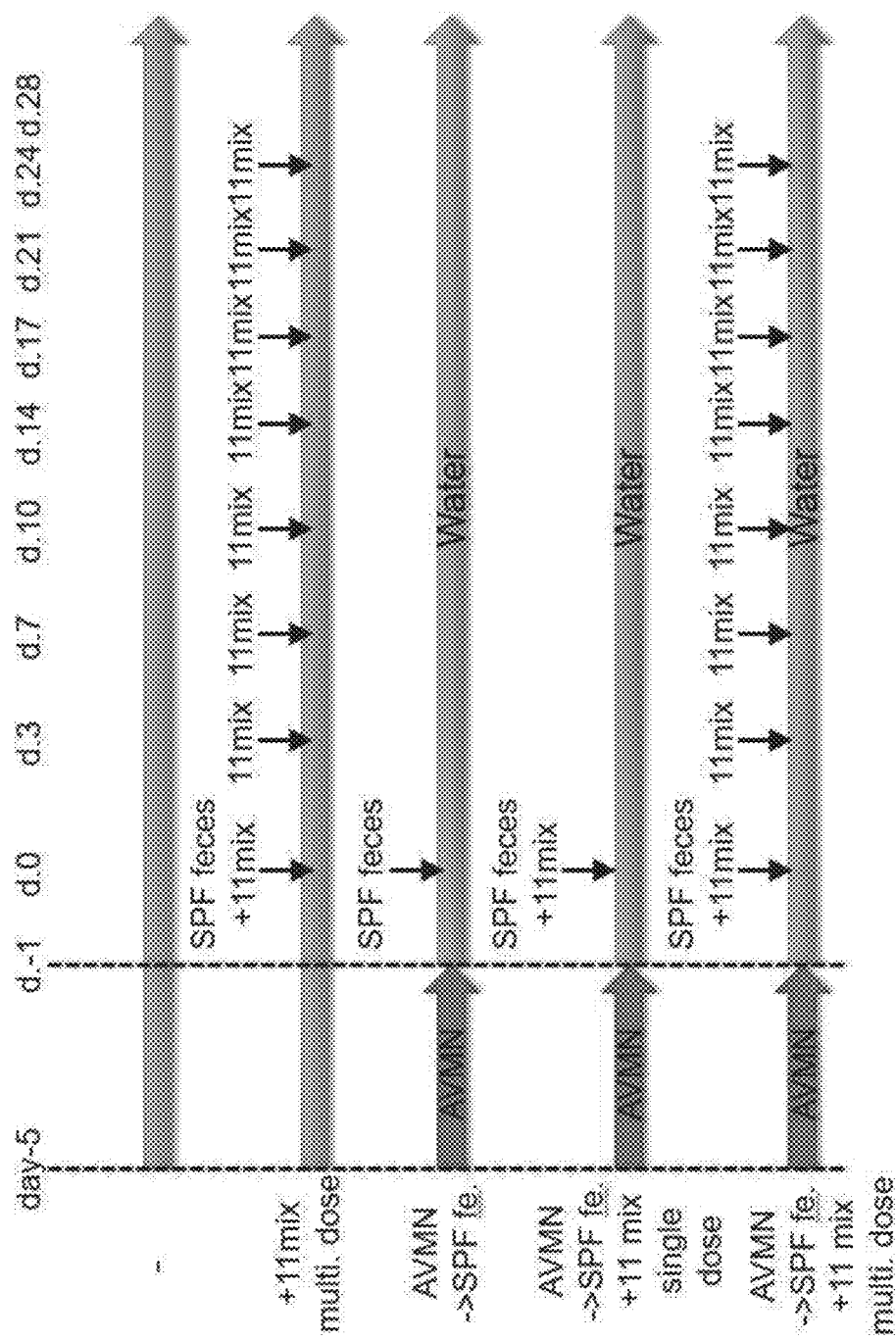
FIG. 40 shows a schematic of the experimental plan described in Example 7 (the dosing study).

As shown in FIG. 40, the mice were grouped in the following treatment groups:
11-mix multi-dose;
AVMN+SPF feces;
AVMN+SPF feces+11-mix single dose; and
AVMN+SPF feces+11-mix multi-dose. The indicated groups of mice received antibiotics (Ampicillin, Vancomycin, Metronidazole, and Neomycin: "AVMN") in their drinking water from day −5 to day −1. Mice were inoculated with SPF feces with or without the 11-mix on day 0. For groups that received multiple doses of the 11-mix, the bacterial cocktail was also administered in the water on days 3, 7, 10, 14, 17, 21, 24, and 28.

Figure 41C:
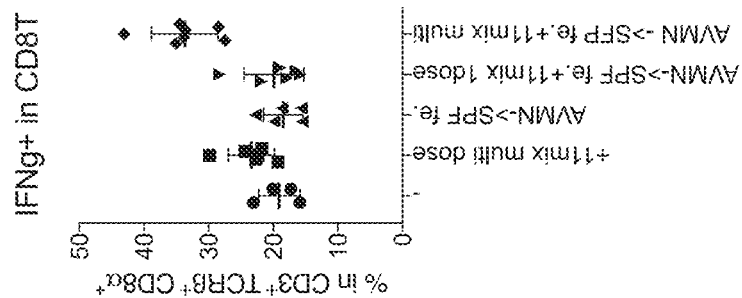
FIGS. 41A-41C show data on lymphocytes isolated from mice in the experiment shown in FIG. 40 (Example 7). CD3, TCRβ, CD8, and IFNγ were stained with antibodies.
Figure 41B:
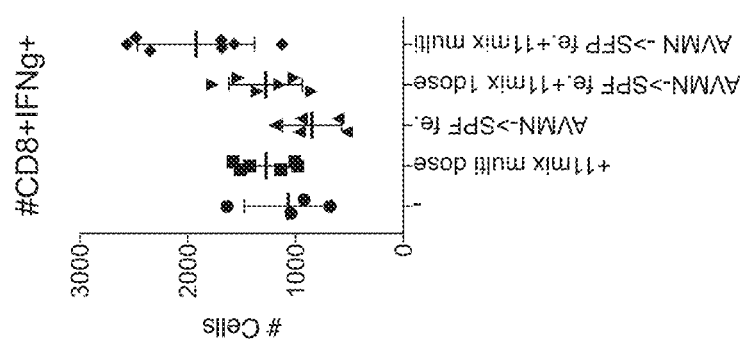
Figure 41A:
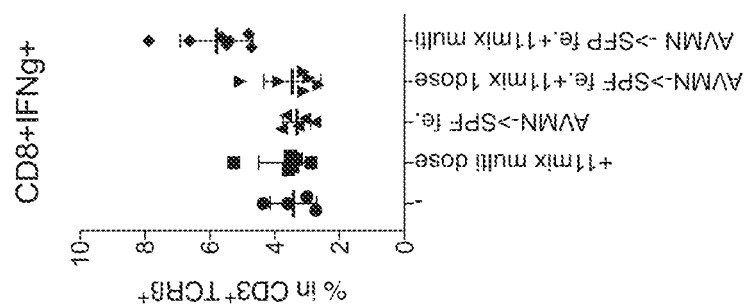
Figure 42C:
FIGS. 42A-42C show data on lymphocytes isolated from mice from the experiment shown in FIG. 40 (Example 7). CD3, TCRβ, CD8, IFNγ, CD103, IL-17, and CD4 were stained with antibodies.
Figure 42B:
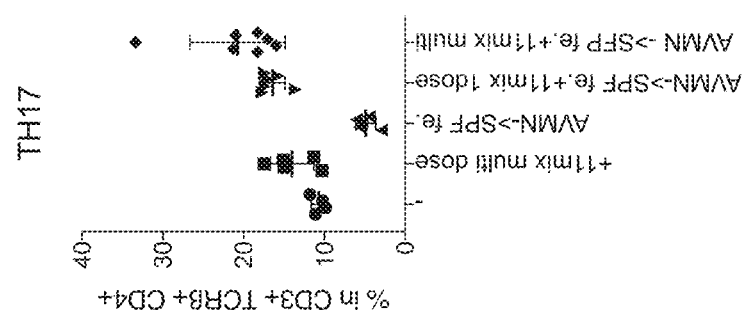
Figure 42A:
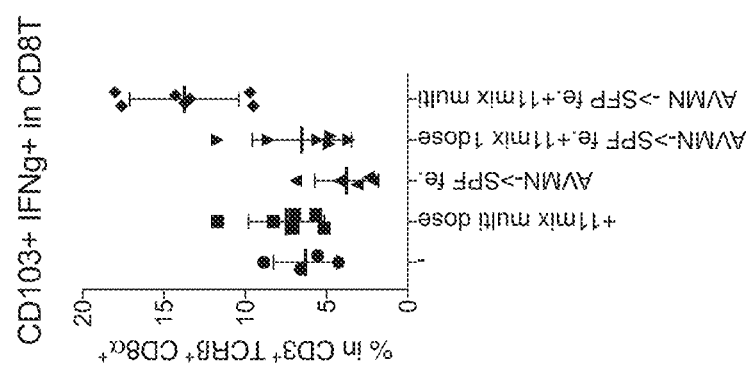

Lymphocytes were isolated from the mice on days 22 and 24 and stained using antibodies to cell markers, including CD3, TCRβ, CD8, CD4, IFNγ, Granzyme, and IL-17. Mice that received the antibiotic pretreatment and multiple doses of the 11-mixed showed enhanced levels of IFNγ+CD8+ T cells. FIGS. 41A-41C. The mice that received the antibiotic pretreatment and multiple doses of the 11-mixes also had enhanced levels of CD103+ IFNγ+ cells in the CD8T cell population of cells (FIG. 42A) and slightly enhanced levels of Th17 cells (FIG. 42B). There was no significant difference in the number of Th1 cells between the groups of mice. (FIG. 42C). These data show that the 11-mix can induce CD8+ T cells in a complex background: a specific pathogen free mouse (as compared to a germ free mouse).

Example 8: The Role of Transcription Factor BATF3

Figures 43A, 43B, 43C:
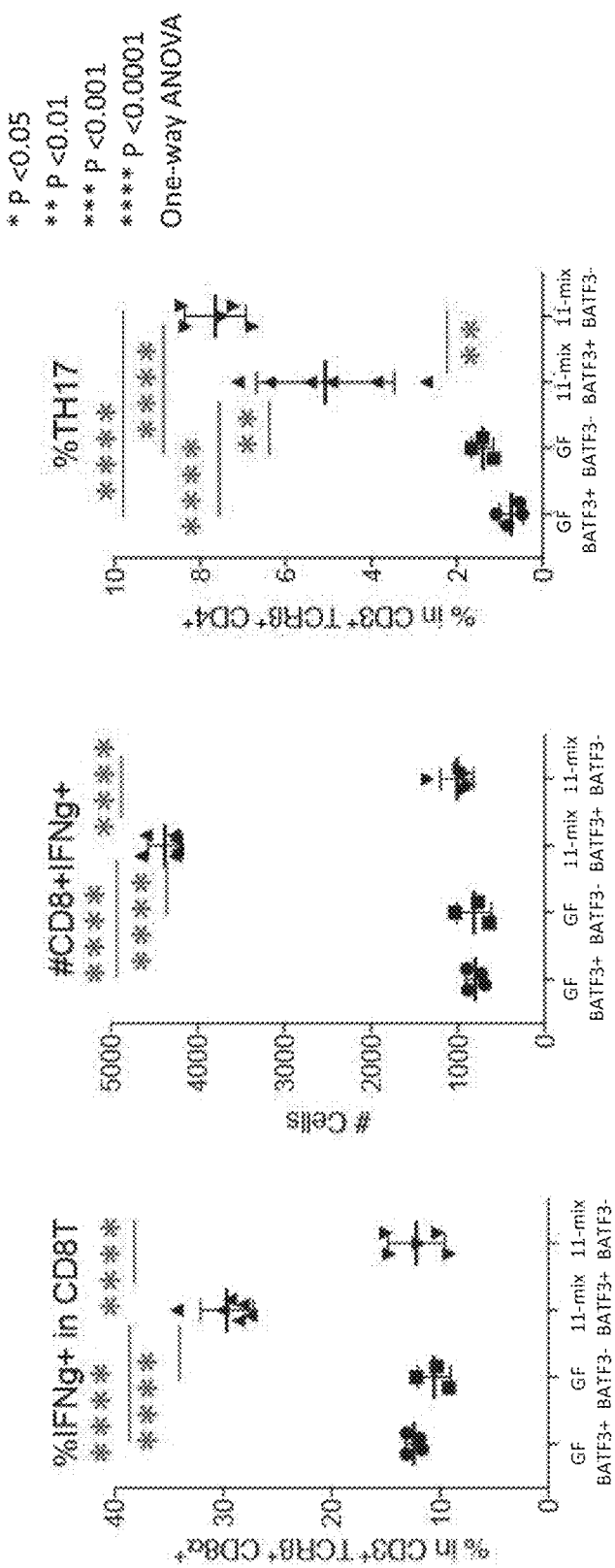
FIGS. 43A-43C and 44 show the results from the experiments of Example 8. The experiments show that BATF3 is required for the 11-mix to induce CD8-T cells. BATF3 is not required to induce Th17.
Figures 44A, 44B:
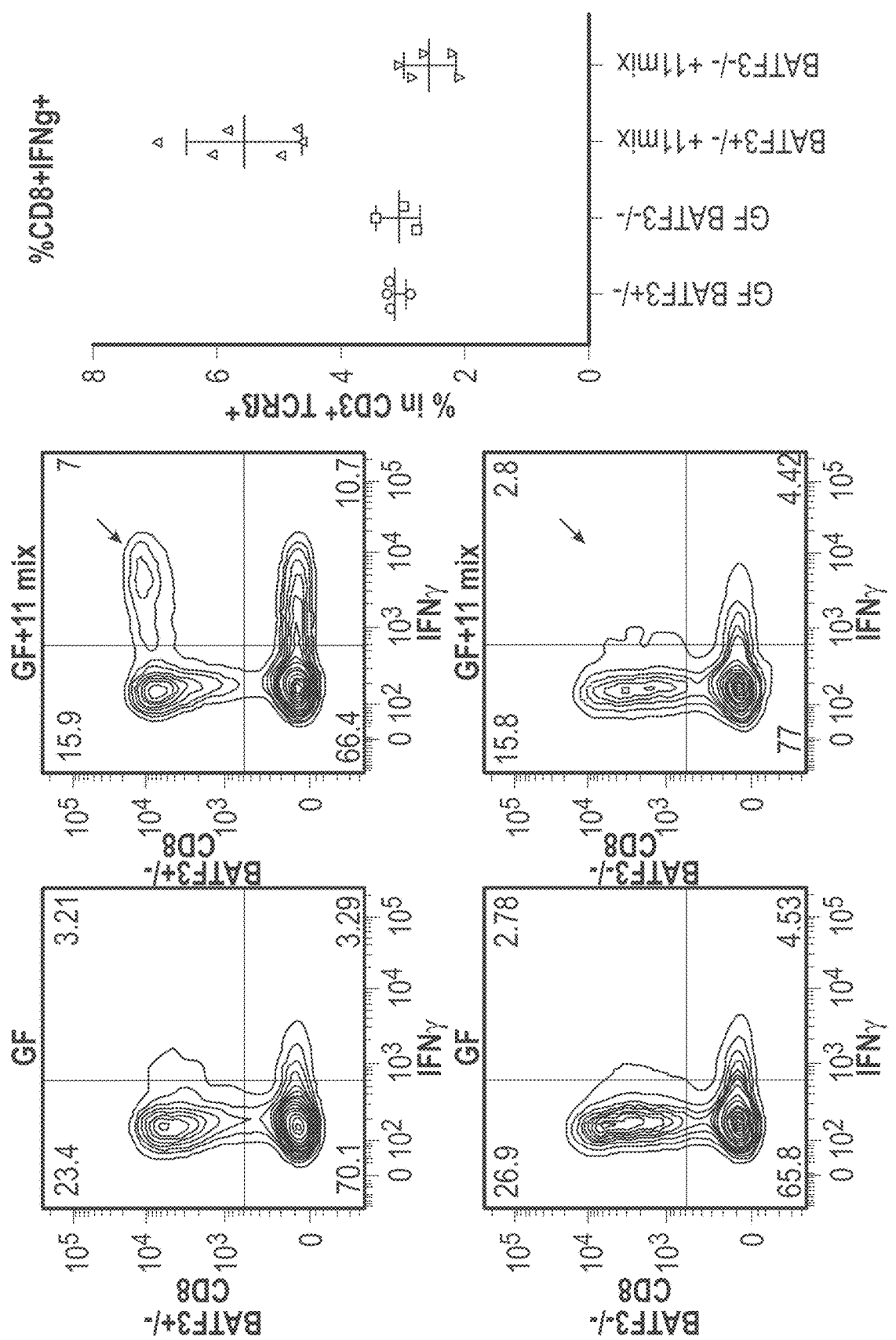

The 11-mix was administered to mice that have the BATF3 transcription factor and mice that do not have the BATF3 transcription factor. Mice that do not have the transcription factor BATF3 are not susceptible to CD8 T cell induction by the 11-mix. (FIGS. 43A and 43B). It is likely that CD103-CD11b dendritic cells are required for stimulation of IFNγ-producing CD8 and Th1 cells. The induction of Th17 cells by the 11-mix cocktail is independent of BAFT3 status. (FIG. 43C). FIGS. 43 and 44 show the results from the experiments of Example 8. The experiments show that BATF3 is required for the 11-mix to induce CD8−T cells. BATF3 is not required to induce Th17.

Example 9: Treatment of *Listeria* Infected Mice

Figure 45:
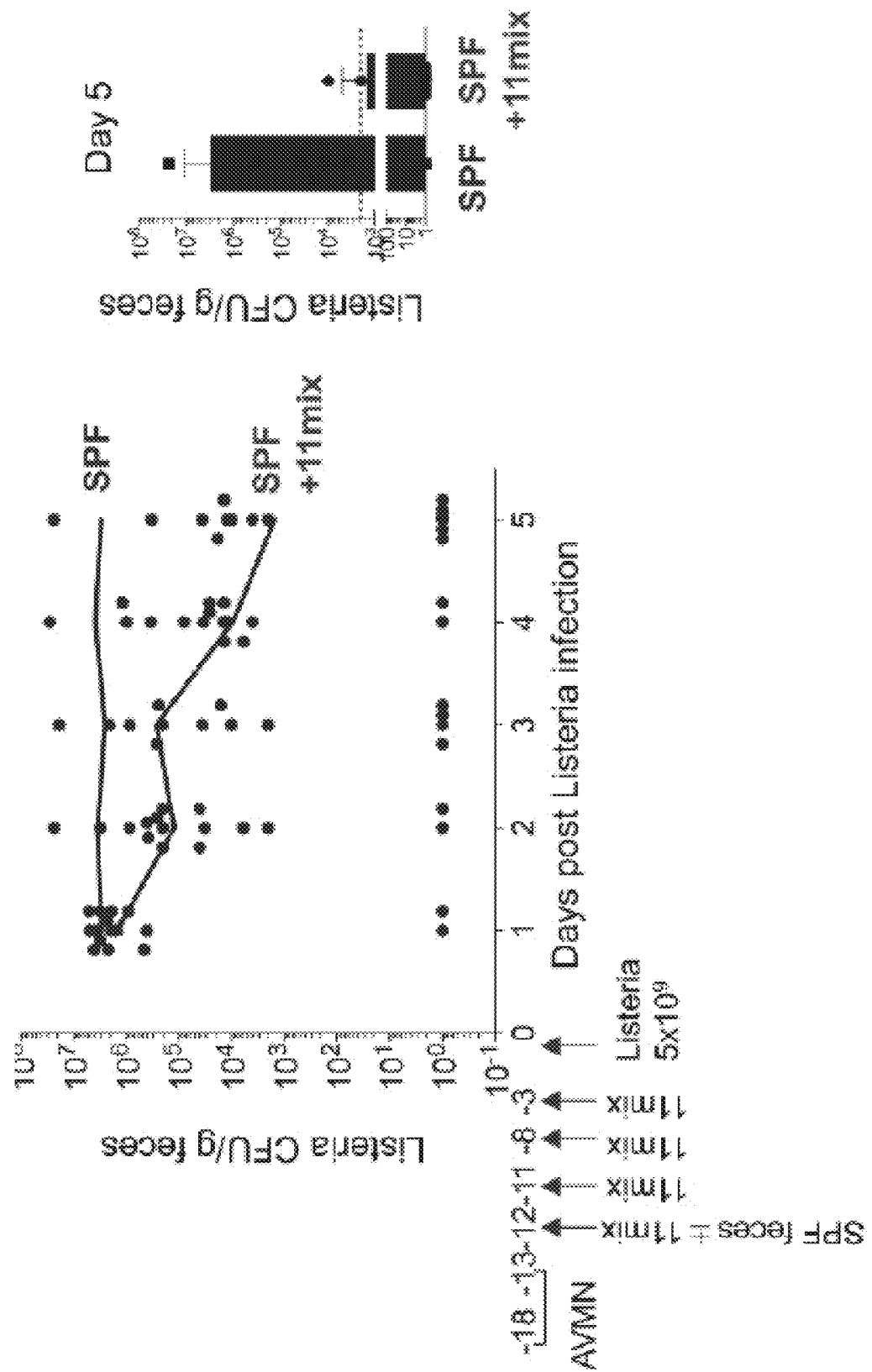
FIGS. 45-46 show the results from the experiments of Example 9. The experiments show that the 11-mix is effective in treating Listeria infections.
Figure 46:
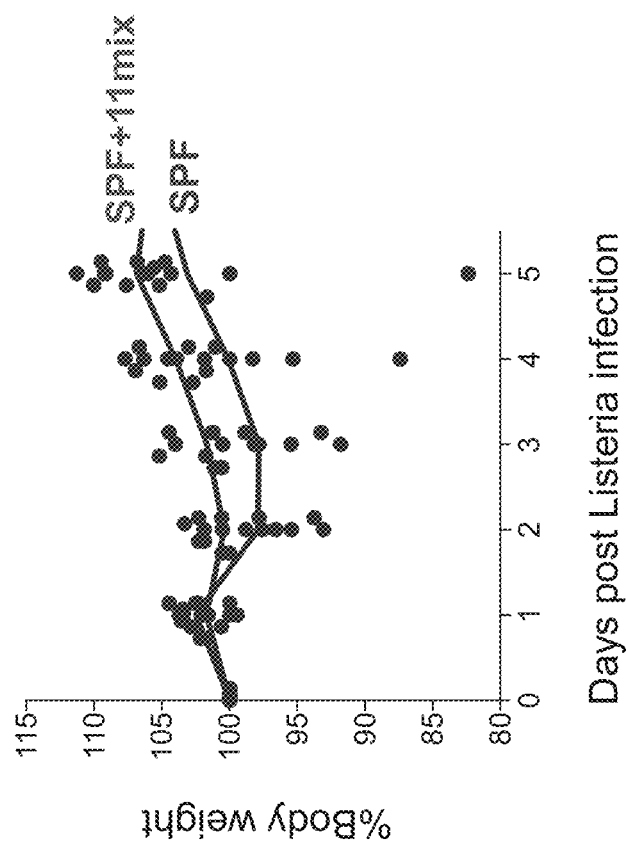

Since IFNγ+CD8+ T cells have been reported to play critical roles in controlling intracellular pathogens, it was evaluated whether oral supplementation with the 11 strain mixture in a multiple dosing regimen could augment host protective immunity against *Listeria monocytogenes* infection. SPF mice were treated with AVMN (ampicillin, vancomycin, metronidazole, neomycin) for 5 days via the drinking water. After one day washout of antibiotics, multiple oral administrations of the 11-mix (4 times) were performed. To reconstitute complex microbiota, fecal microbiota from SPF mice were introduced together with the first administration of 11-mix. The mice were then orally infected with *Listeria monocytogenes* on day 0. Fecal *Listeria* CFU and body weight of mice were determined. Treatment with 11-mix significantly reduced *Listeria monocytogenes* colonization of the gut lumen (FIG. 45) and maintained the body weight of the mice (FIG. 46). Thus, administration of the 11 strain-mixture can provide protective immunity against an intracellar, infectious pathogen.

Example 10: Localization of the CD8 T-Cells Induced by the 11-Mix

Figure 48:
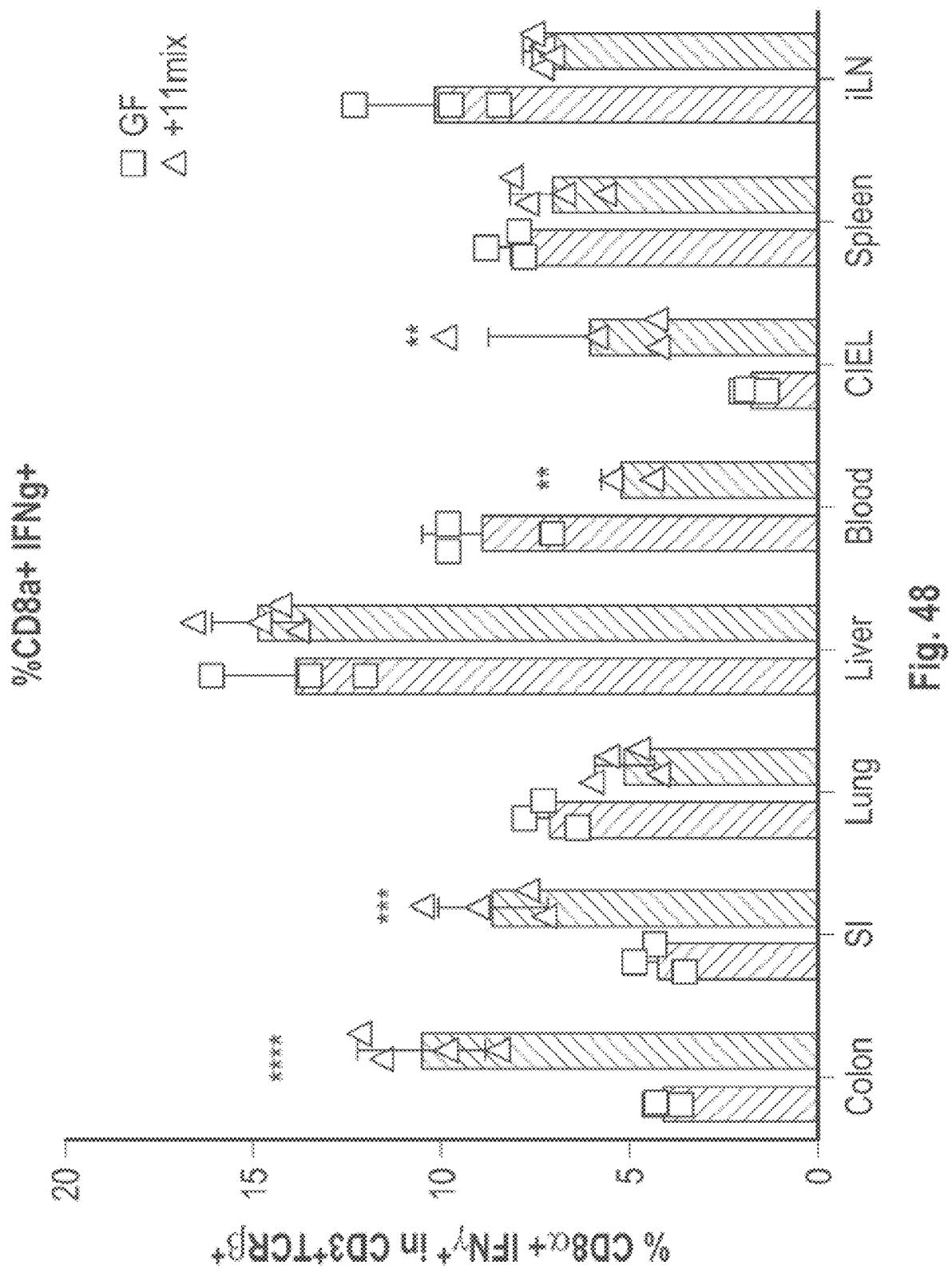
FIG. 48 relates to Example 10 and shows that the CD8 induction effect of the 11-mix in mice that are not otherwise challenged is limited to the intestine/gut compartment. (SI=short intestine, CIEL=colonic intraepithelial lymphocytes, LN=lymph nodes)

The 11-mix was administered to normal healthy mice (i.e., mice that were not otherwise stressed). Various organs and compartments in the mice were investigated for the presence of CD8 positive T-cells. As shown in FIG. 48, the CD8 positive T-cell induction effect of the 11-mix is limited to the intestine/gut (SI=small intestine, CIEL=colonic intra-epithelial lymphocytes, LN=lymph nodes).

Figure 49:
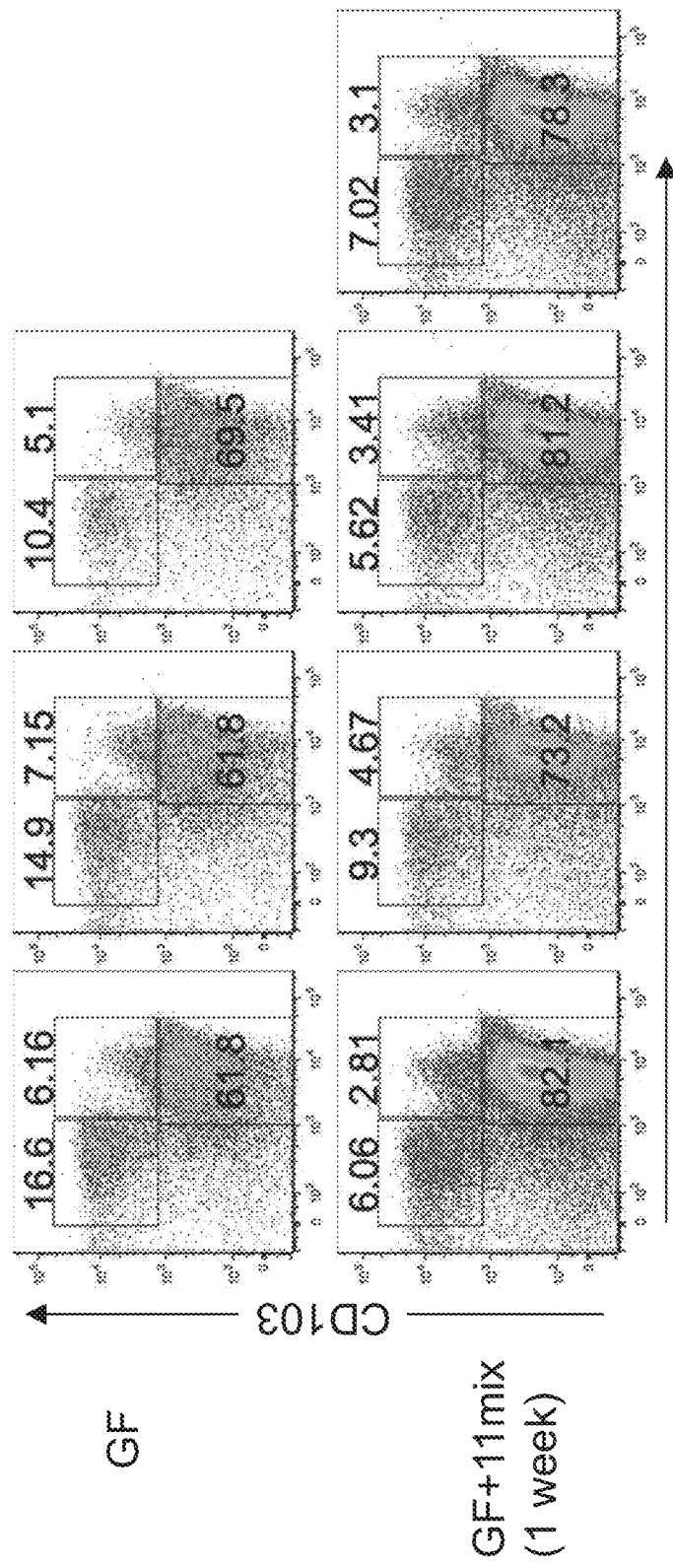
FIG. 49 shows that the frequencies of DC subsets in colonic LP were only slightly changed by the colonization with 11-mix.
Figure 50:
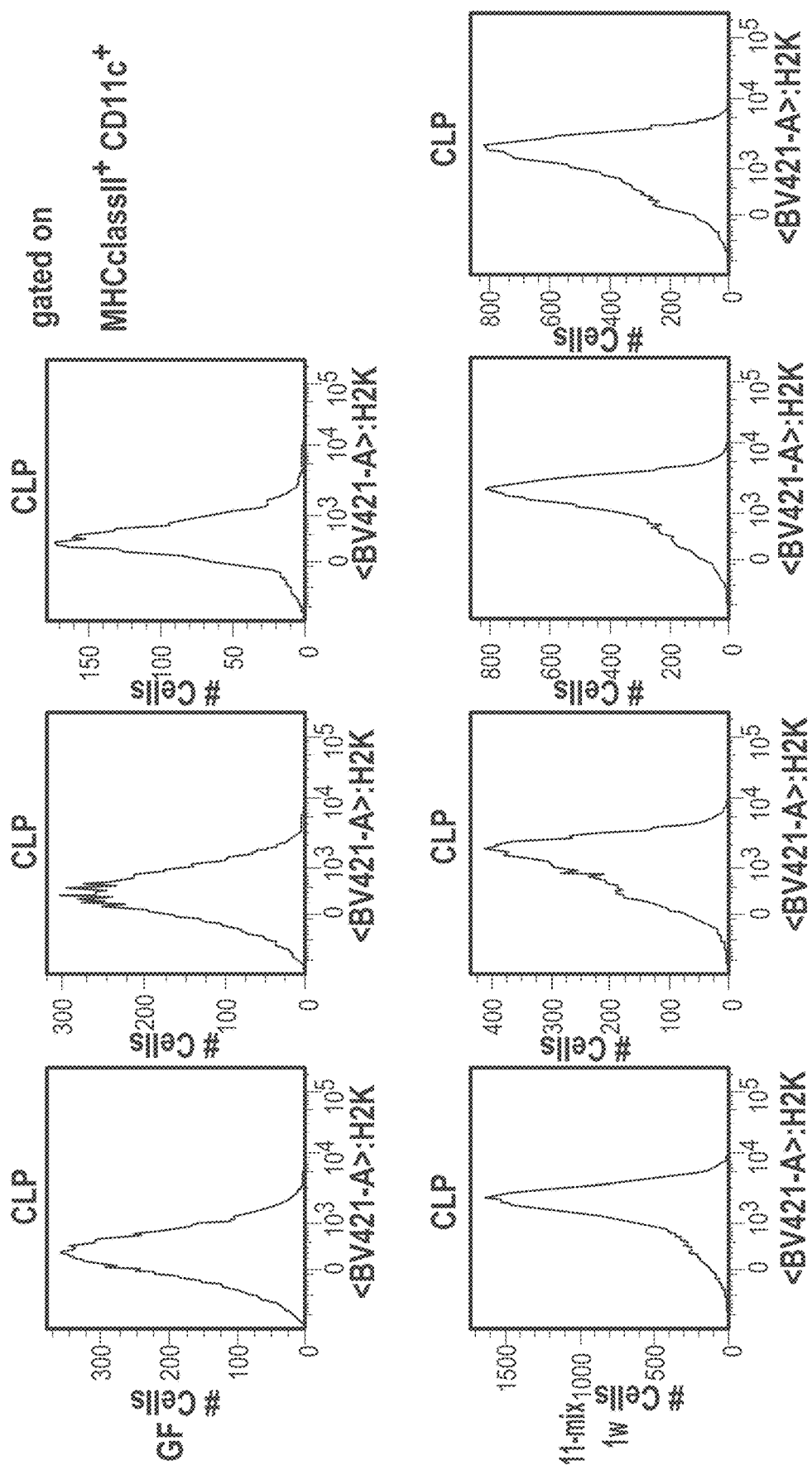
FIGS. 50-52 show that MHC CLP class cells are activated by the administration of the 11-mix, and that the activation is strongest within the first week of activation. There is no activation of the MHC MLN class cells. The individual measurements are shown in FIGS. 50 and 51, while the accumulated data are depicted in FIG. 52.
Figure 50:
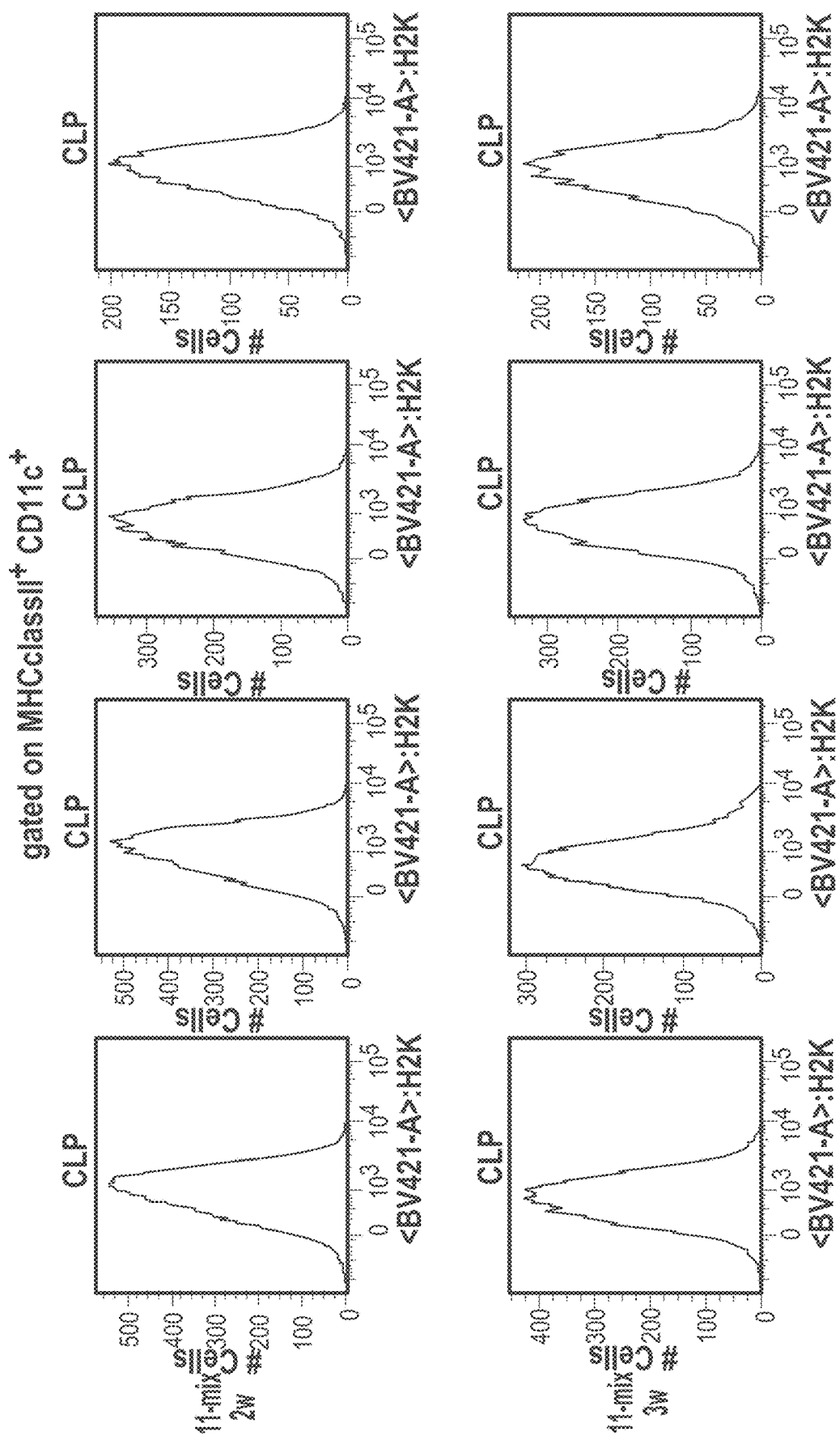
Figure 50:
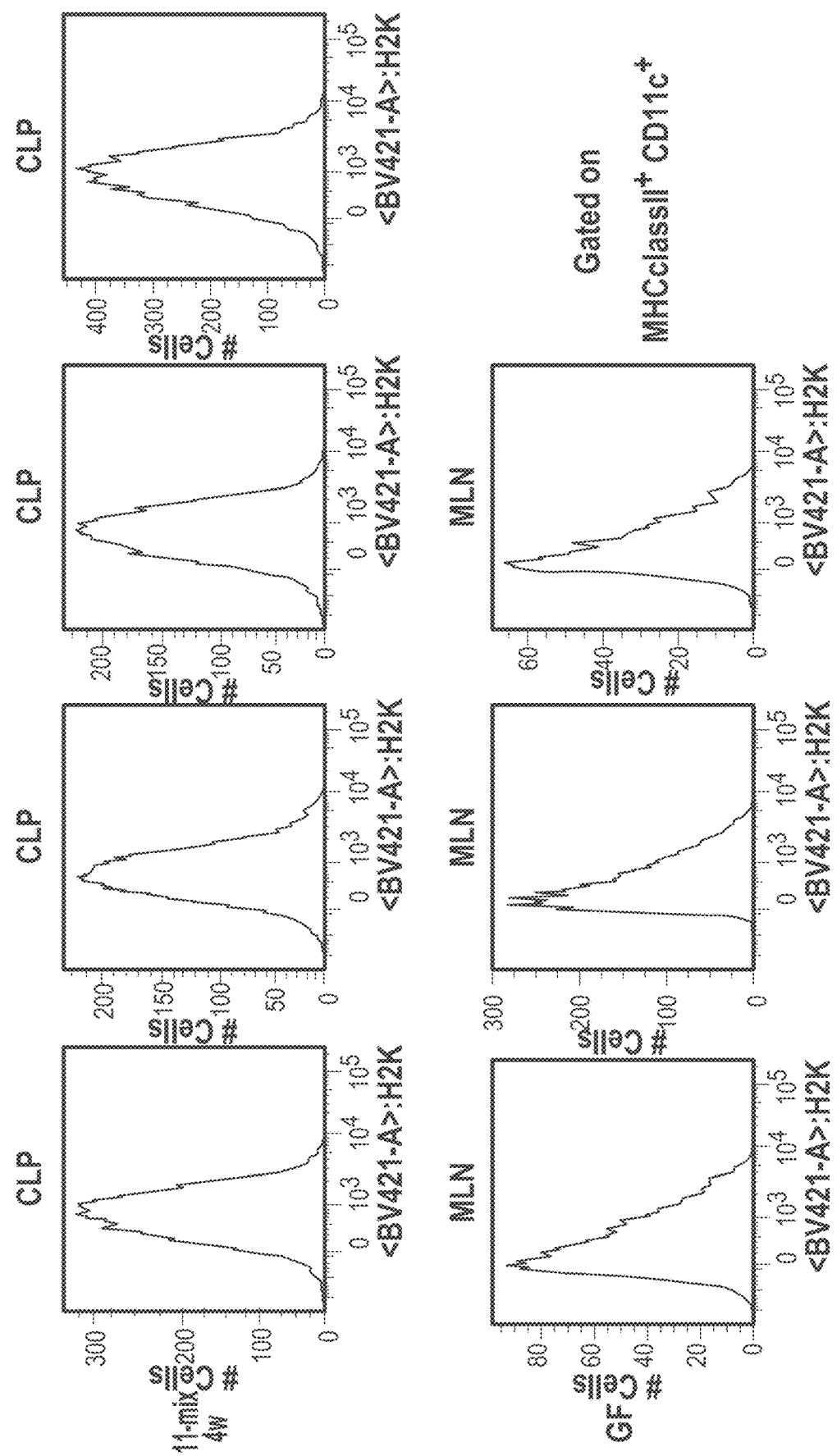
Figure 50:
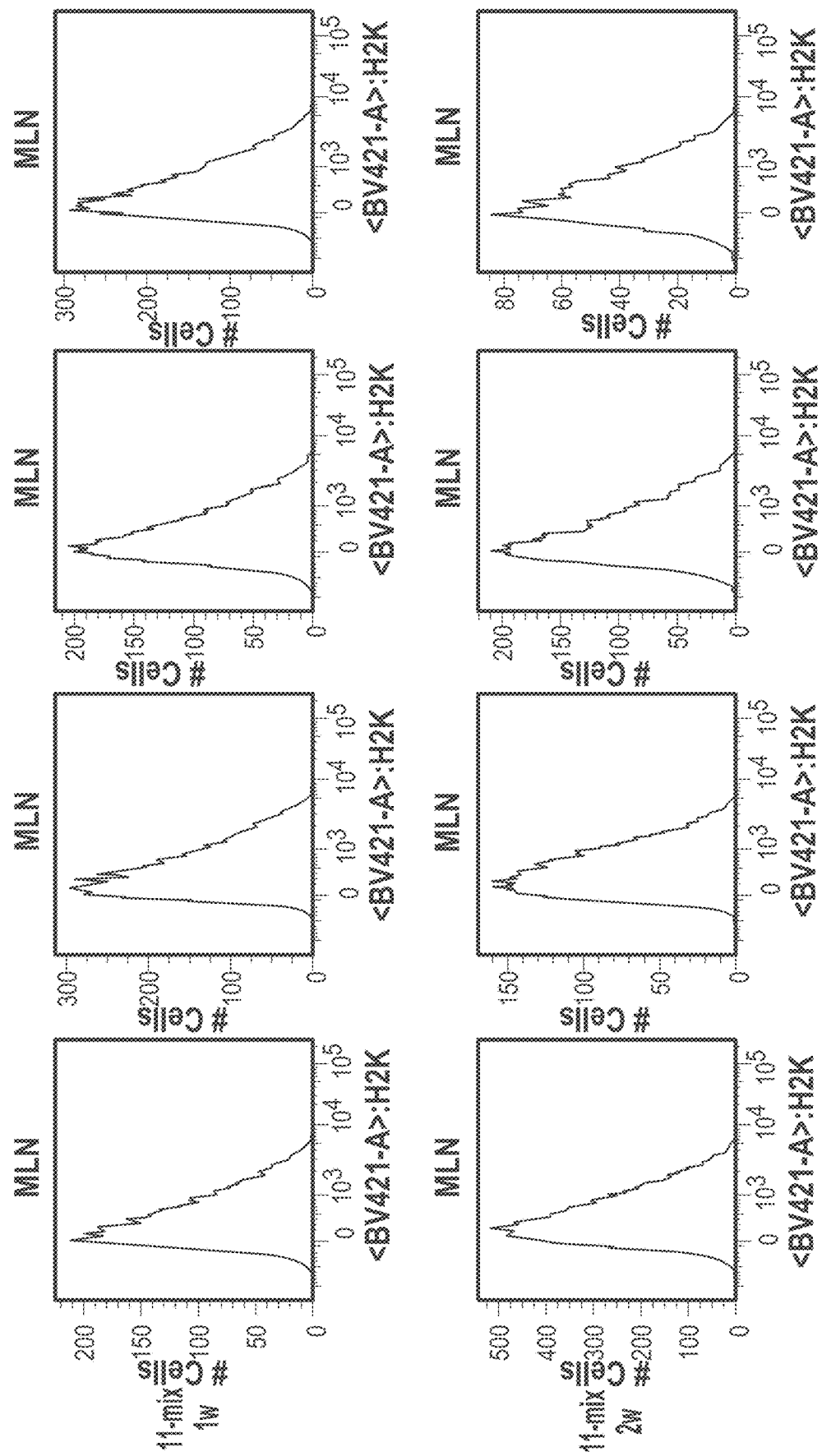
Figure 50:
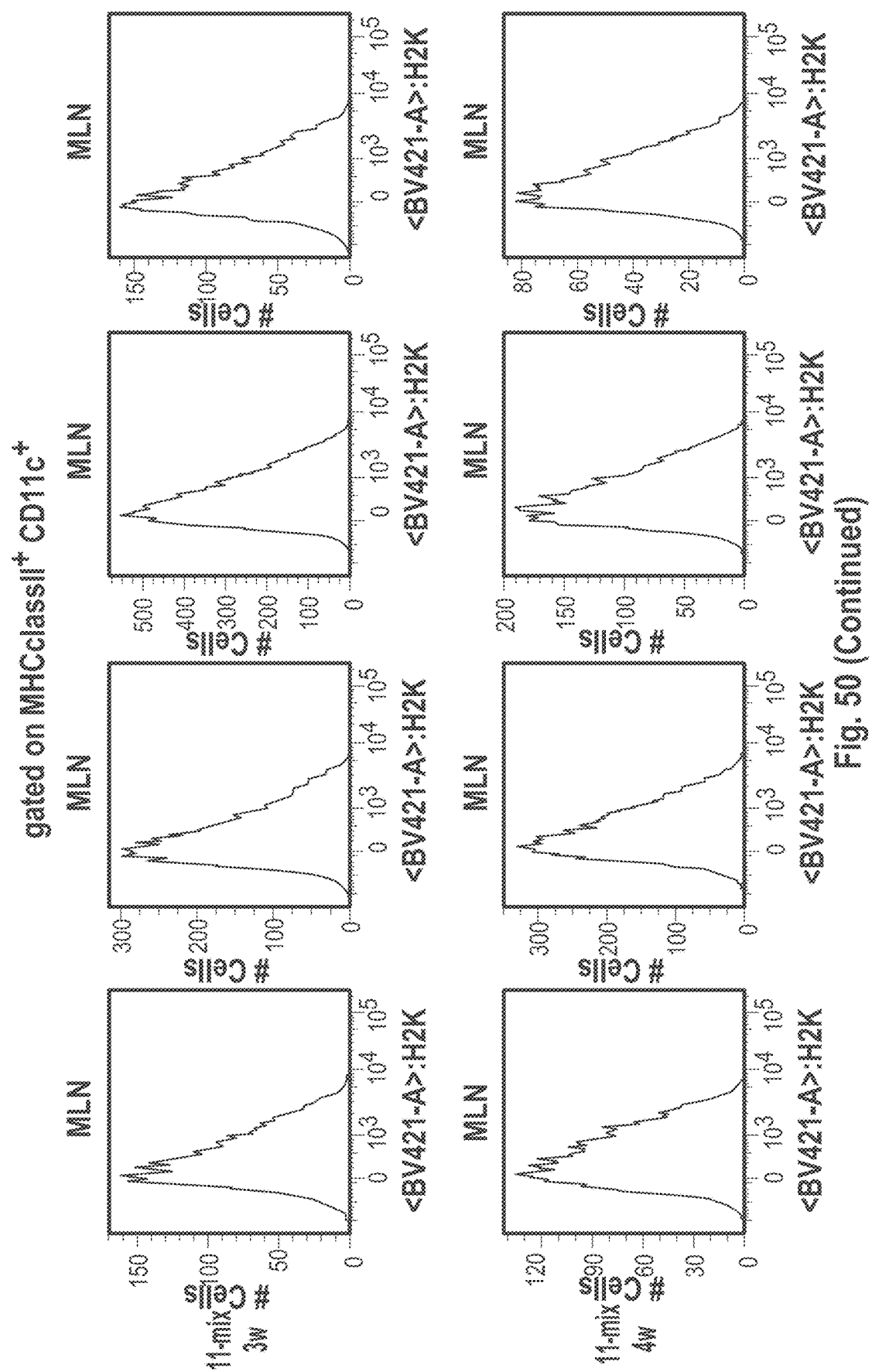
Figure 51:
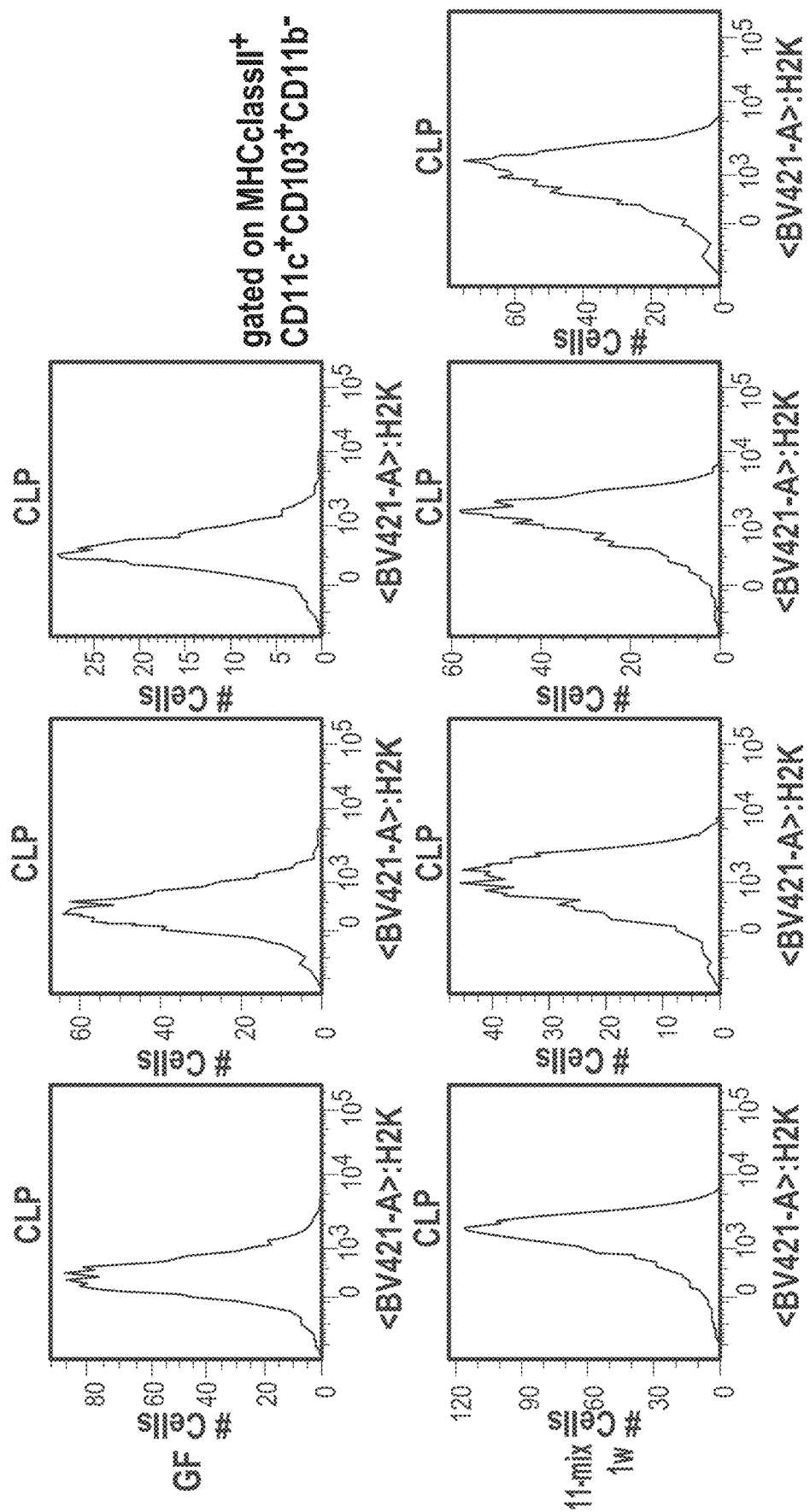
Figure 51:
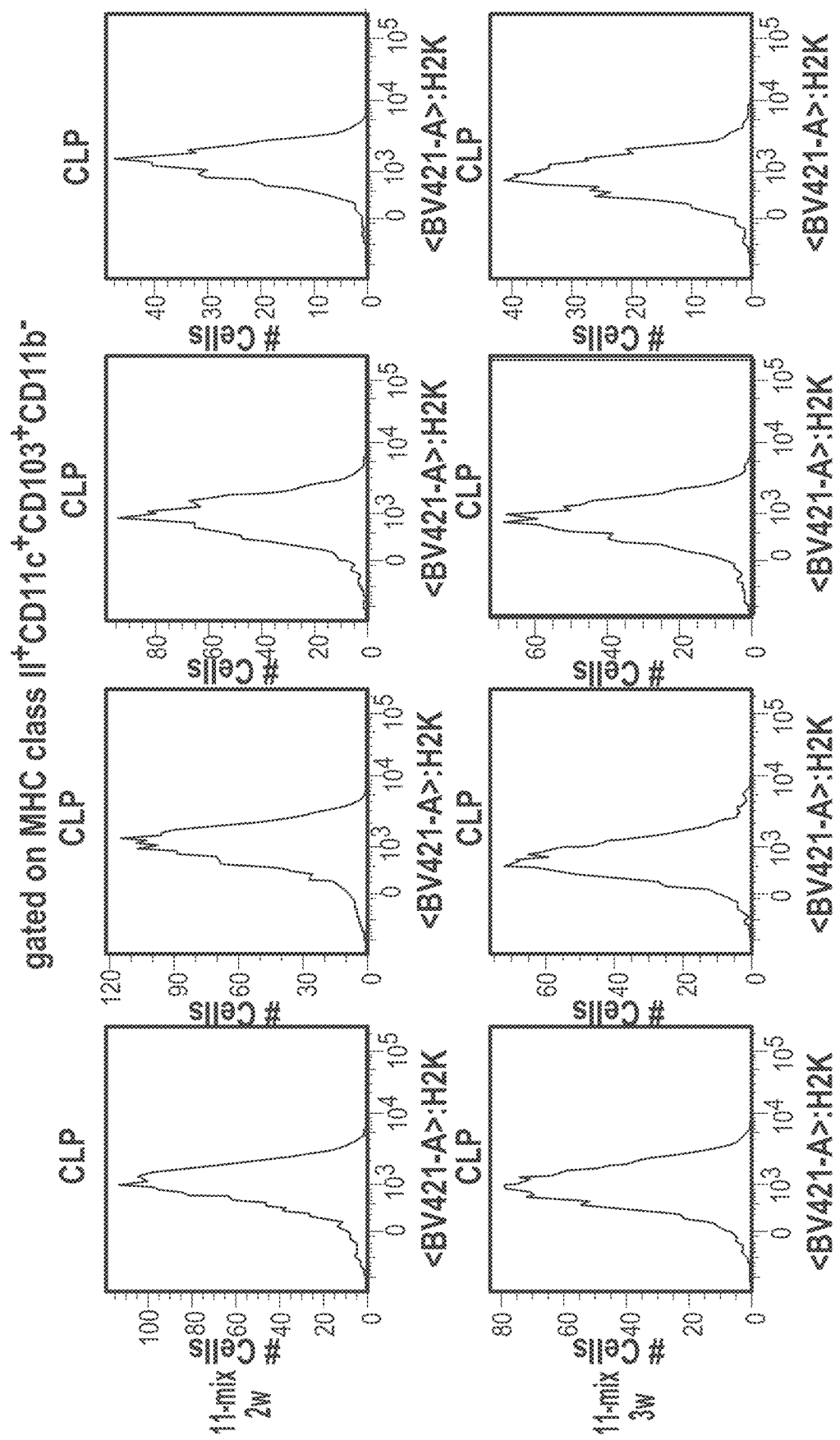
Figure 51:
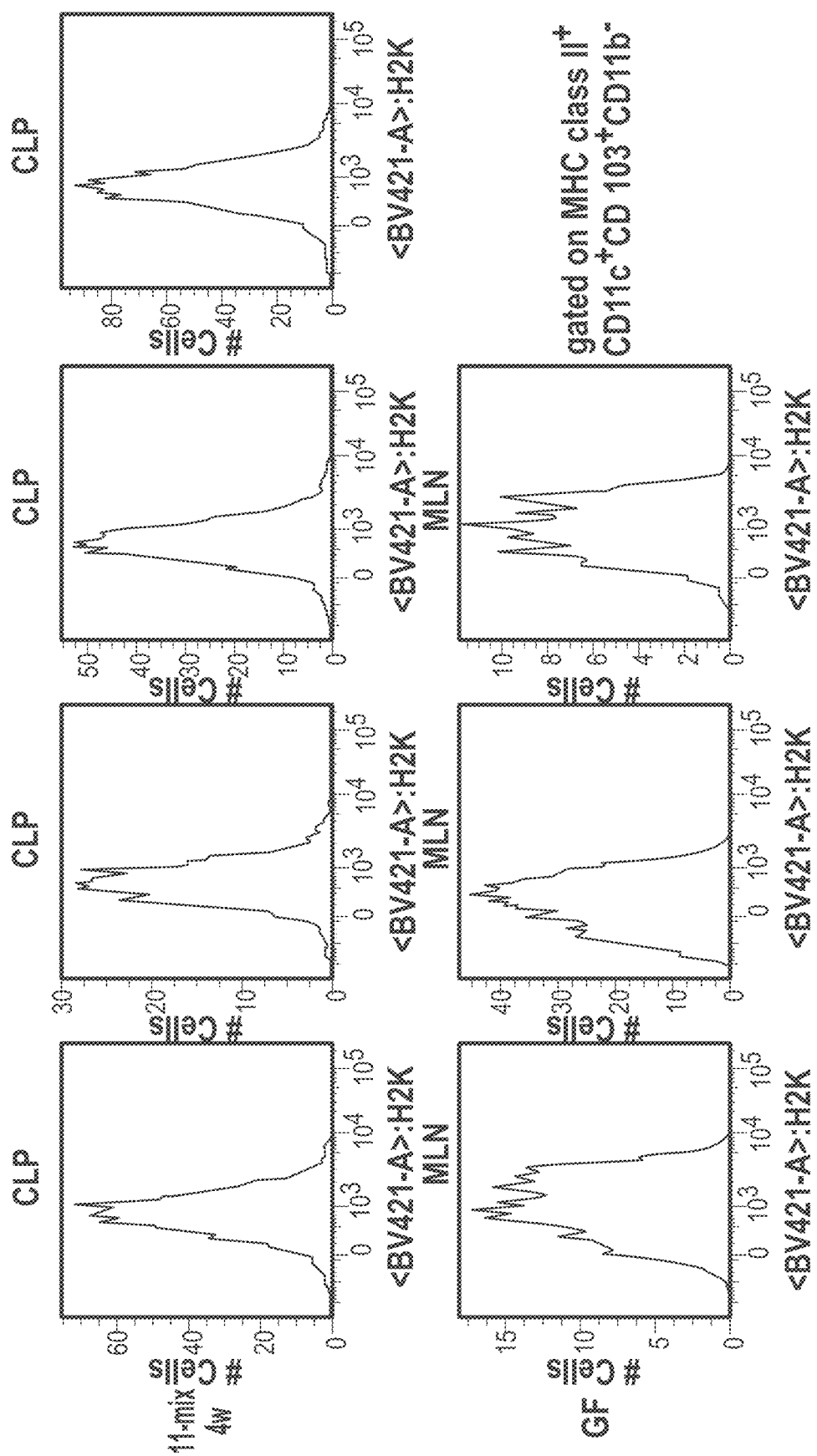
Figure 51:
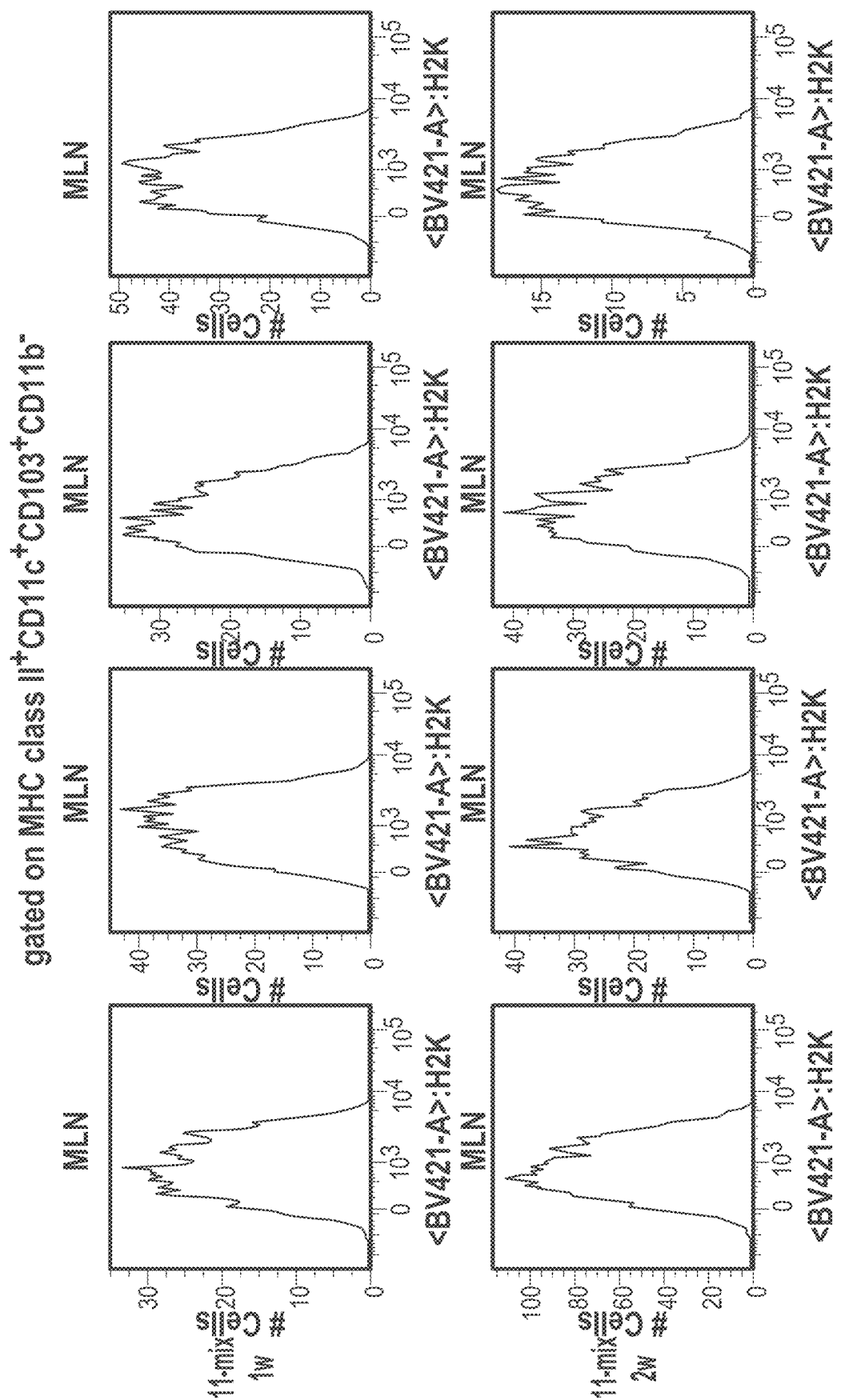
Figure 51:
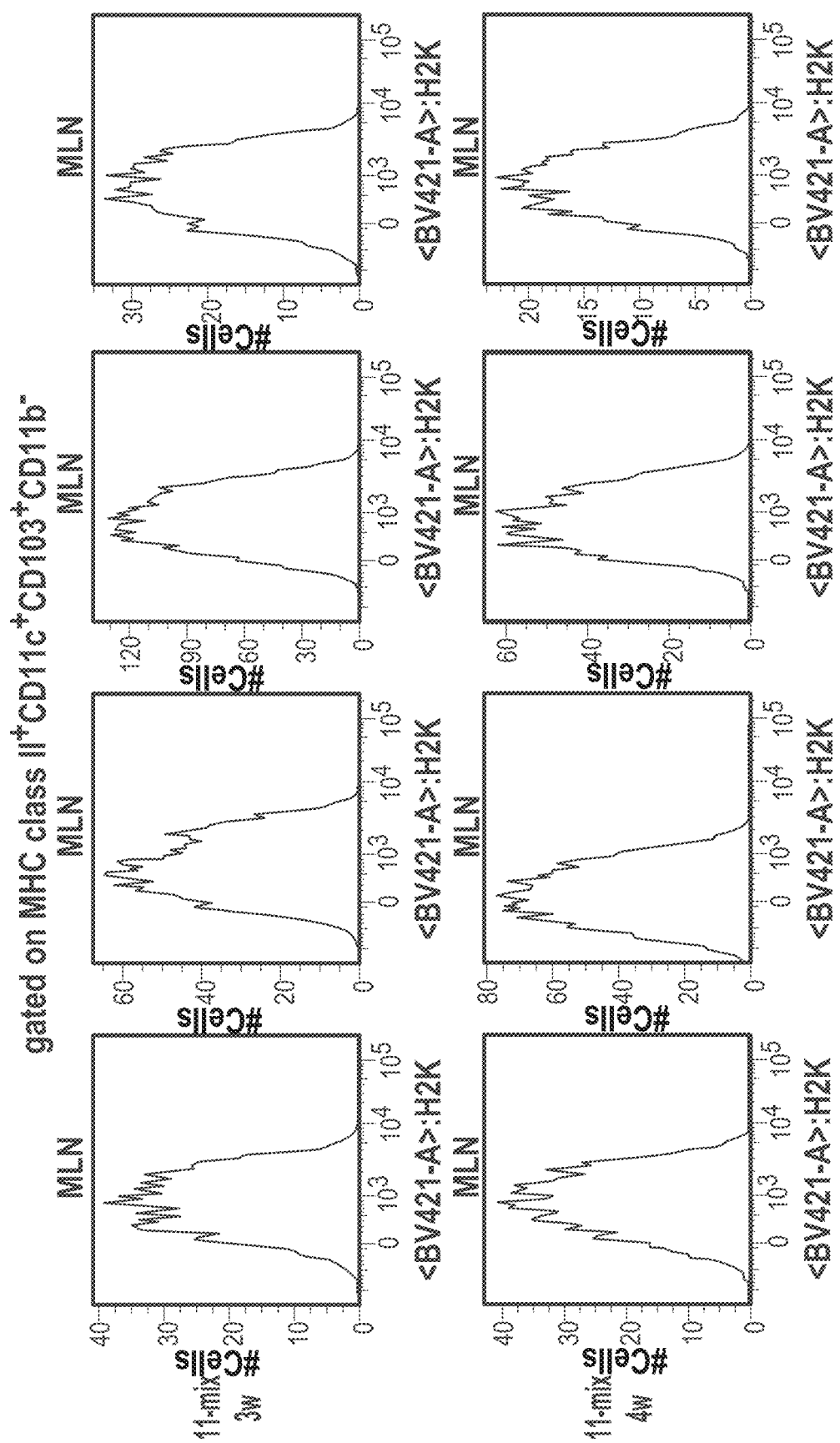
Figure 52:
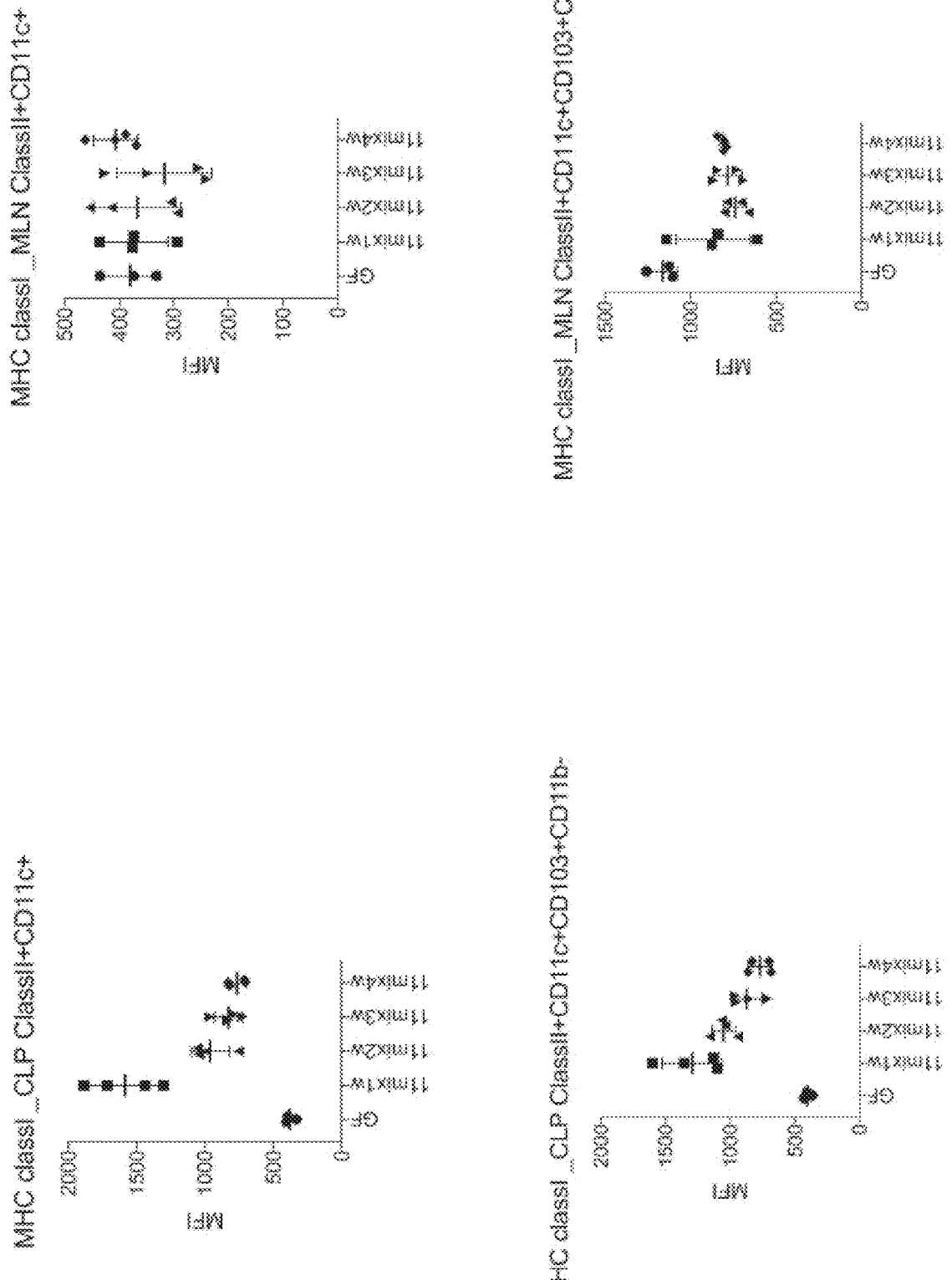
Figure 53:
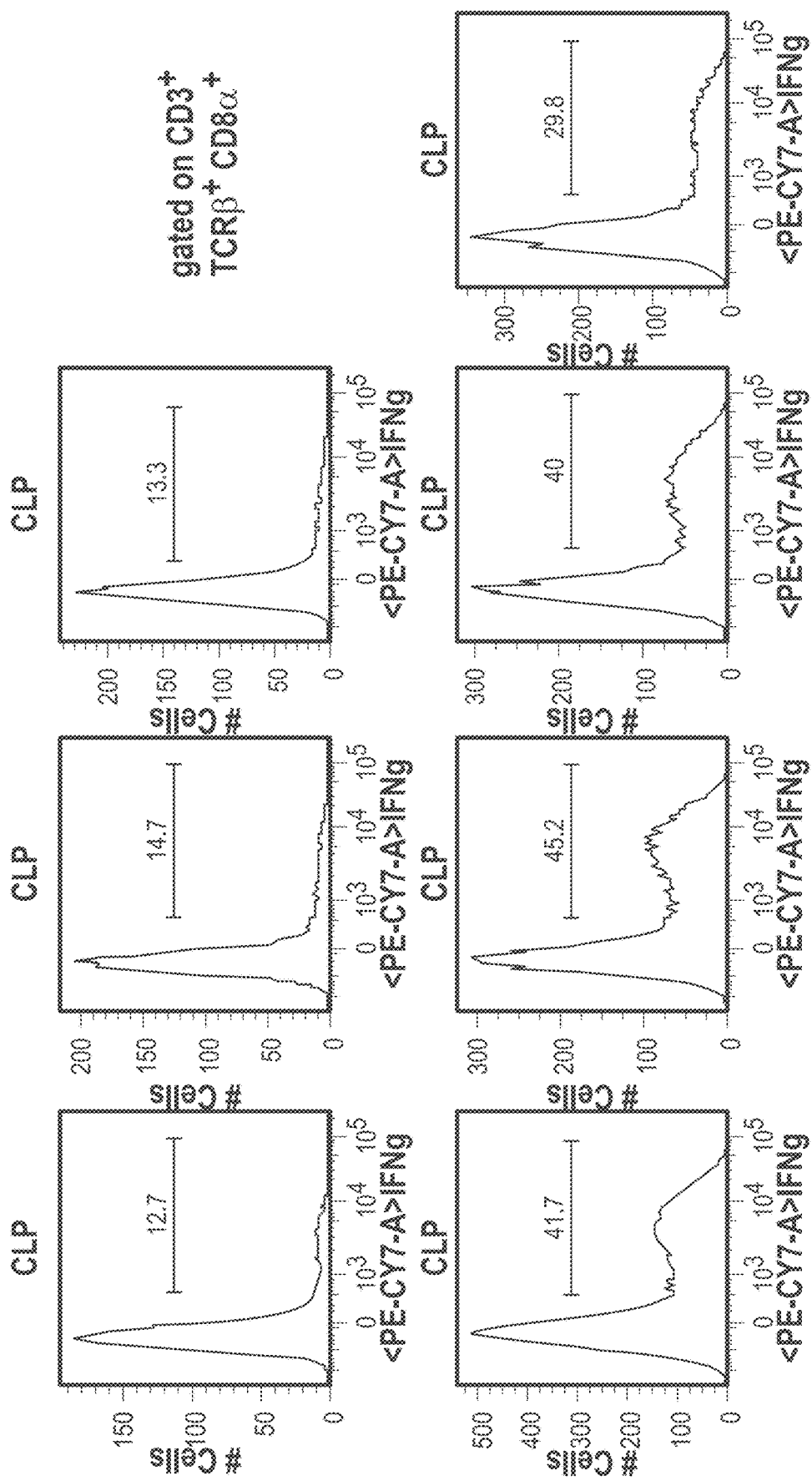
FIGS. 53 and 54 show that MHC CLP class cells are activated by the administration of the 11-mix, while there is no activation of the MHC MLN class cells. The individual measurements are shown in FIG. 53, while the accumulated data are depicted in FIG. 54 expressed as percentage of CD3+ TCDRbeta+CD8alpha+ cells.
Figure 53:
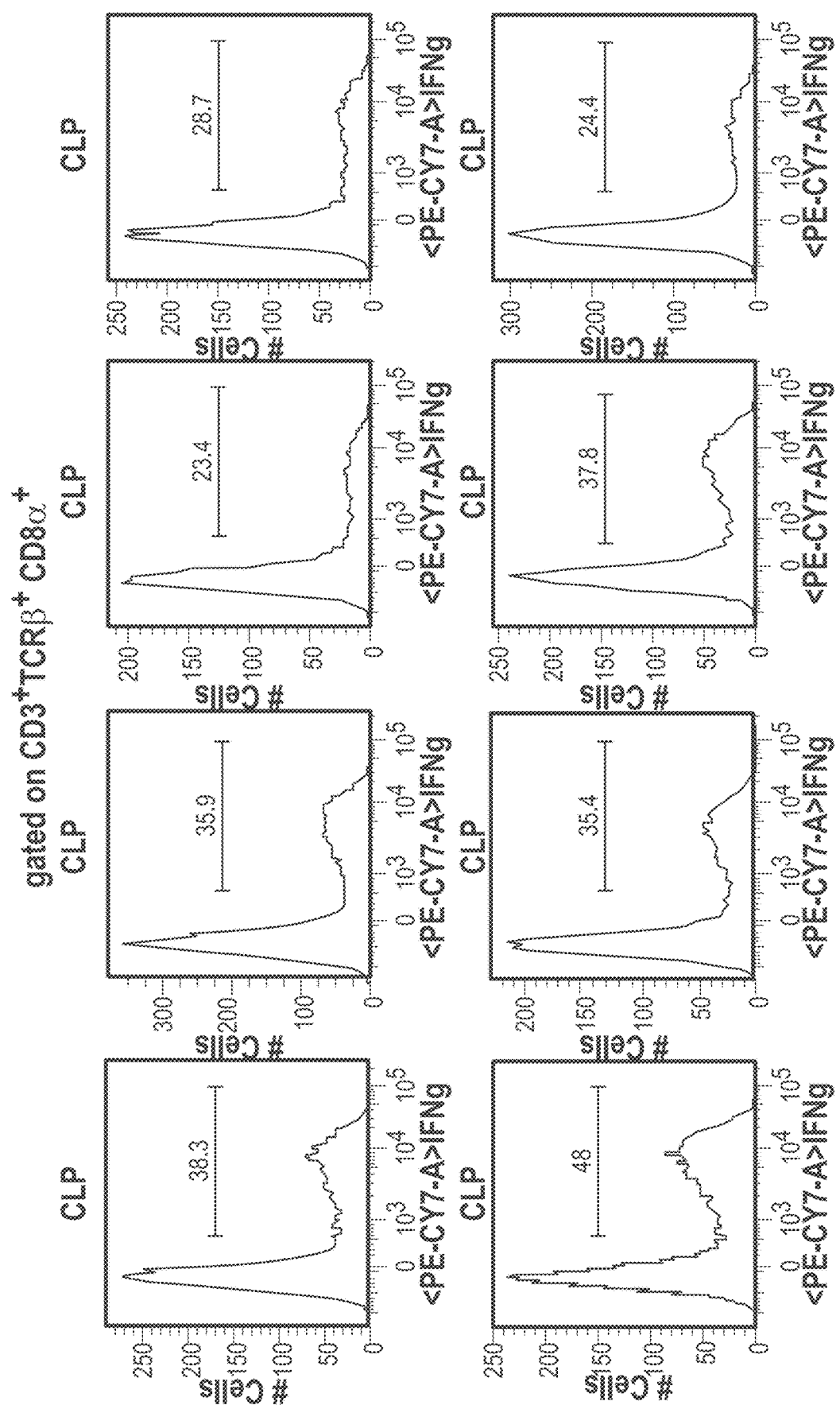
Figure 53:
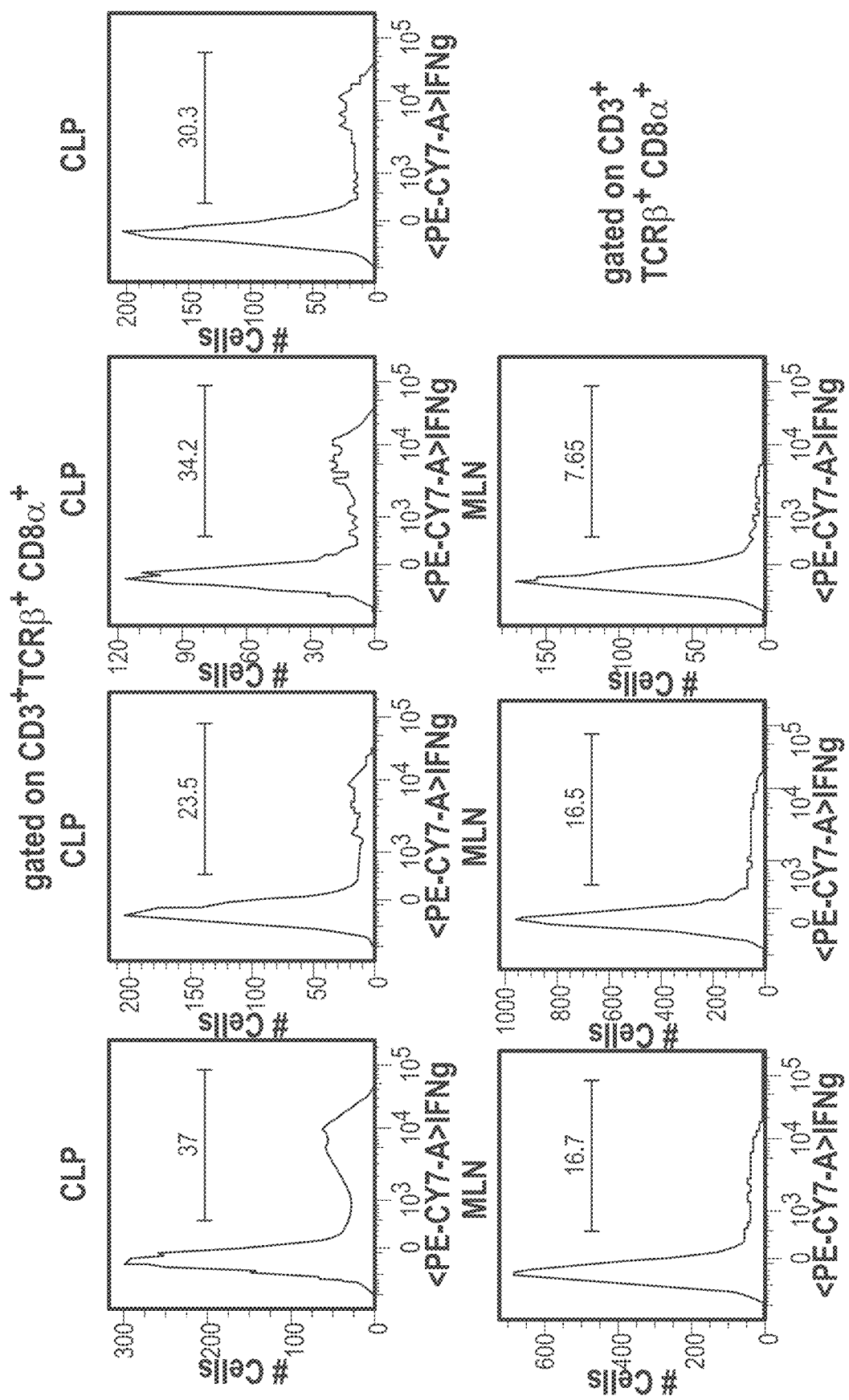
Figure 53:
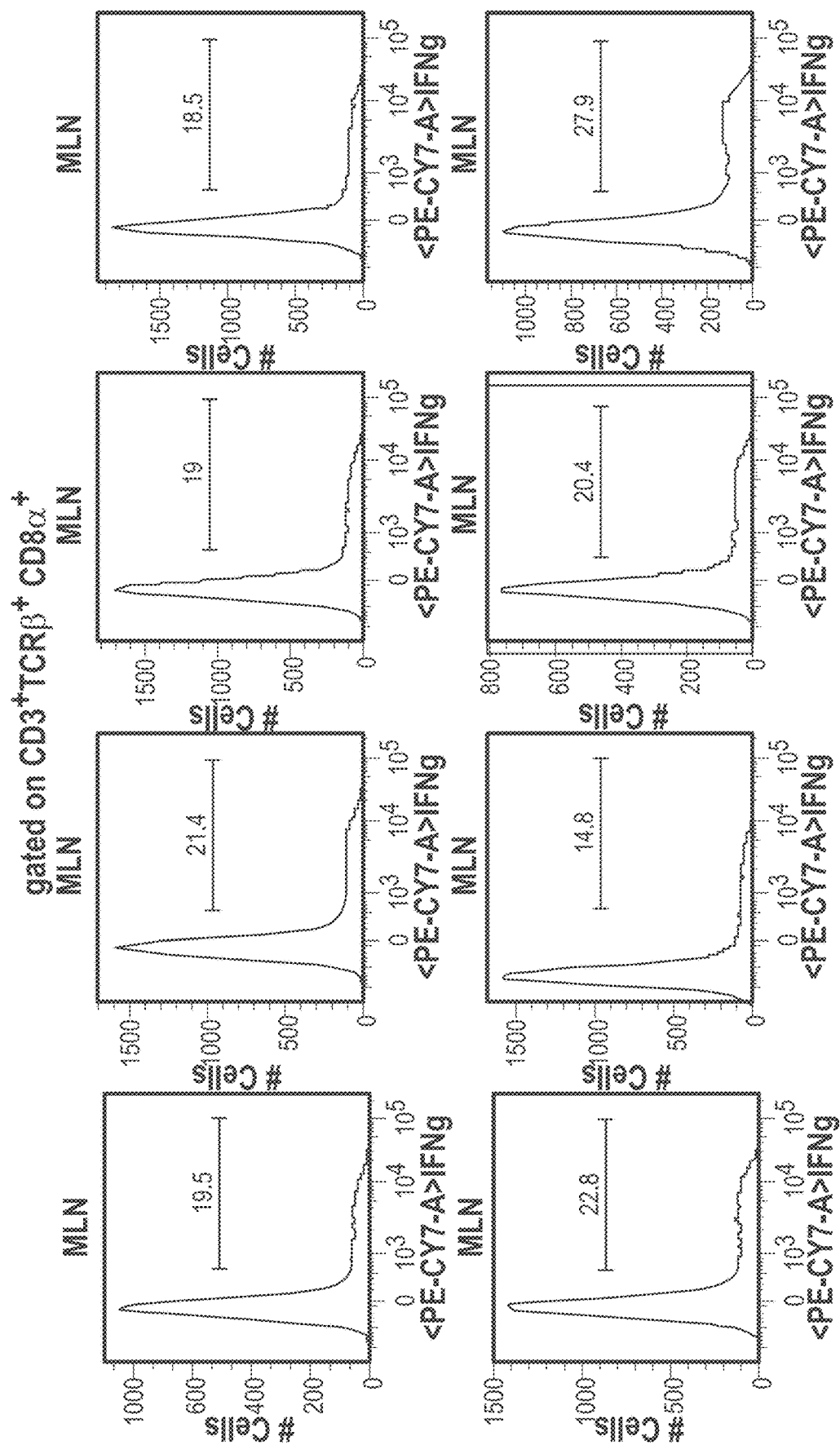
Figure 53:
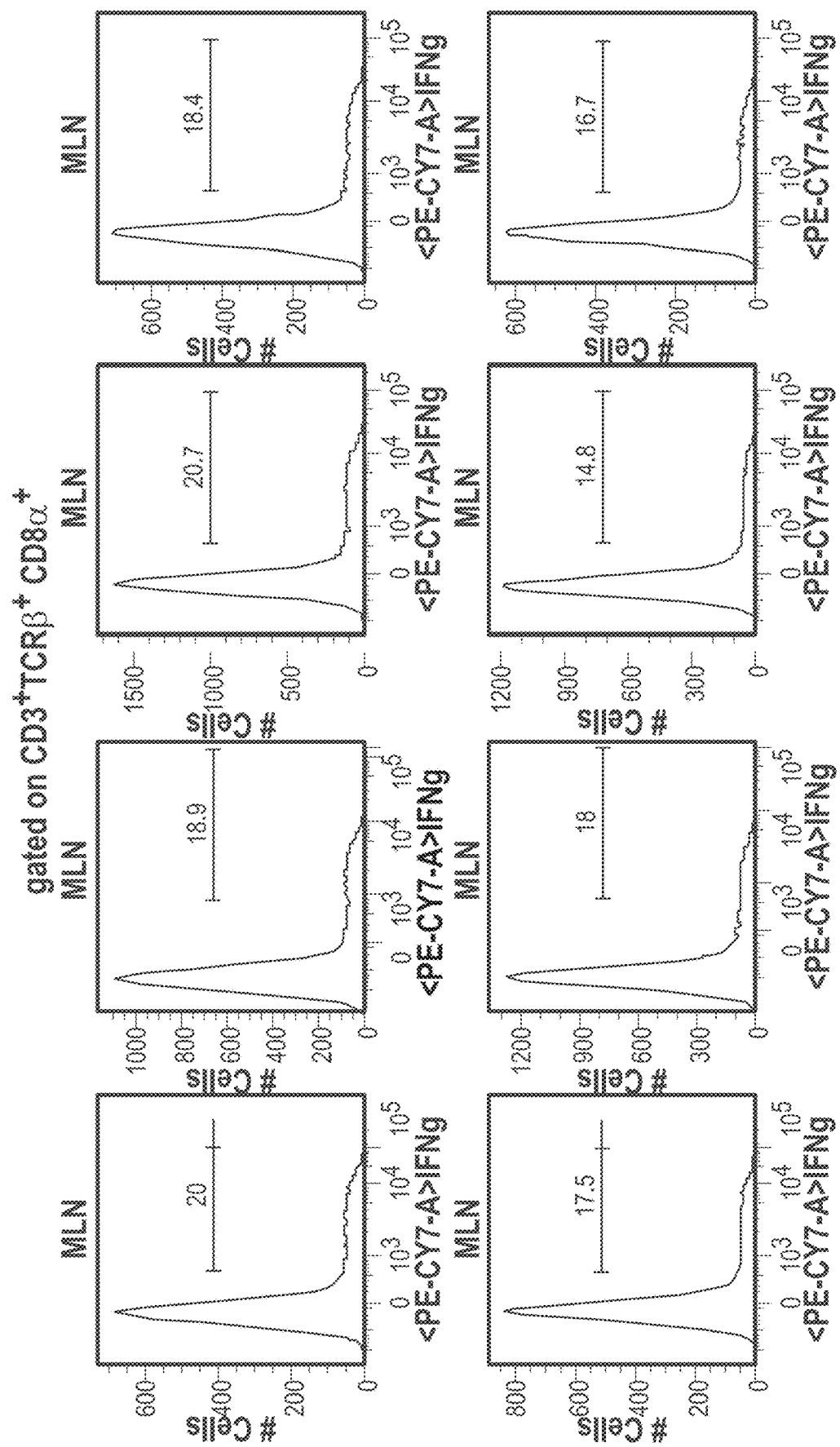
Figure 54:
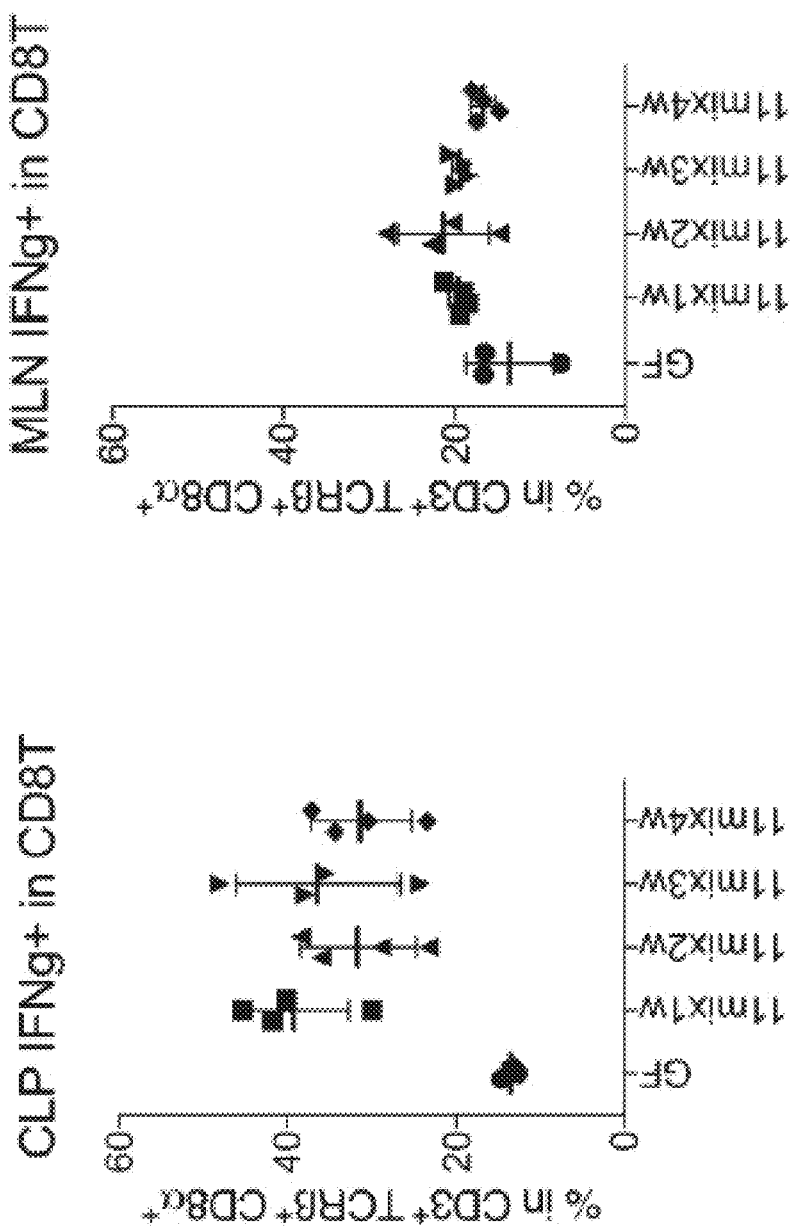
Figure 55:
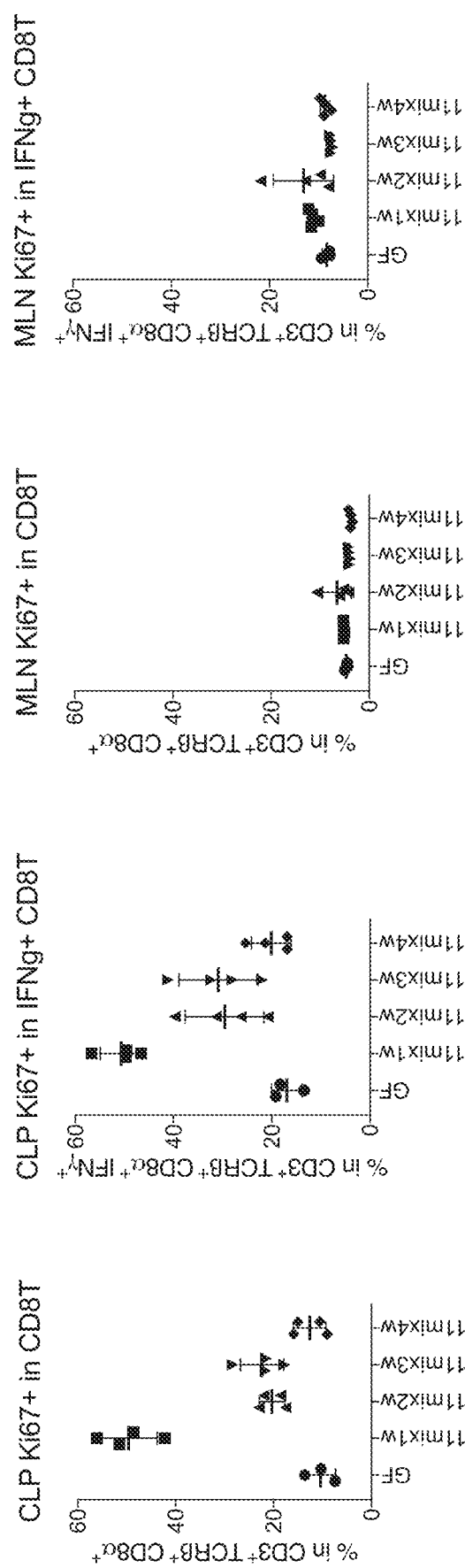
FIG. 55 shows that MHC CLP class cells are activated by the administration of the 11-mix, as evidenced by Ki67 status, while there is no activation of the MHC MLN class cells.
Figure 56:
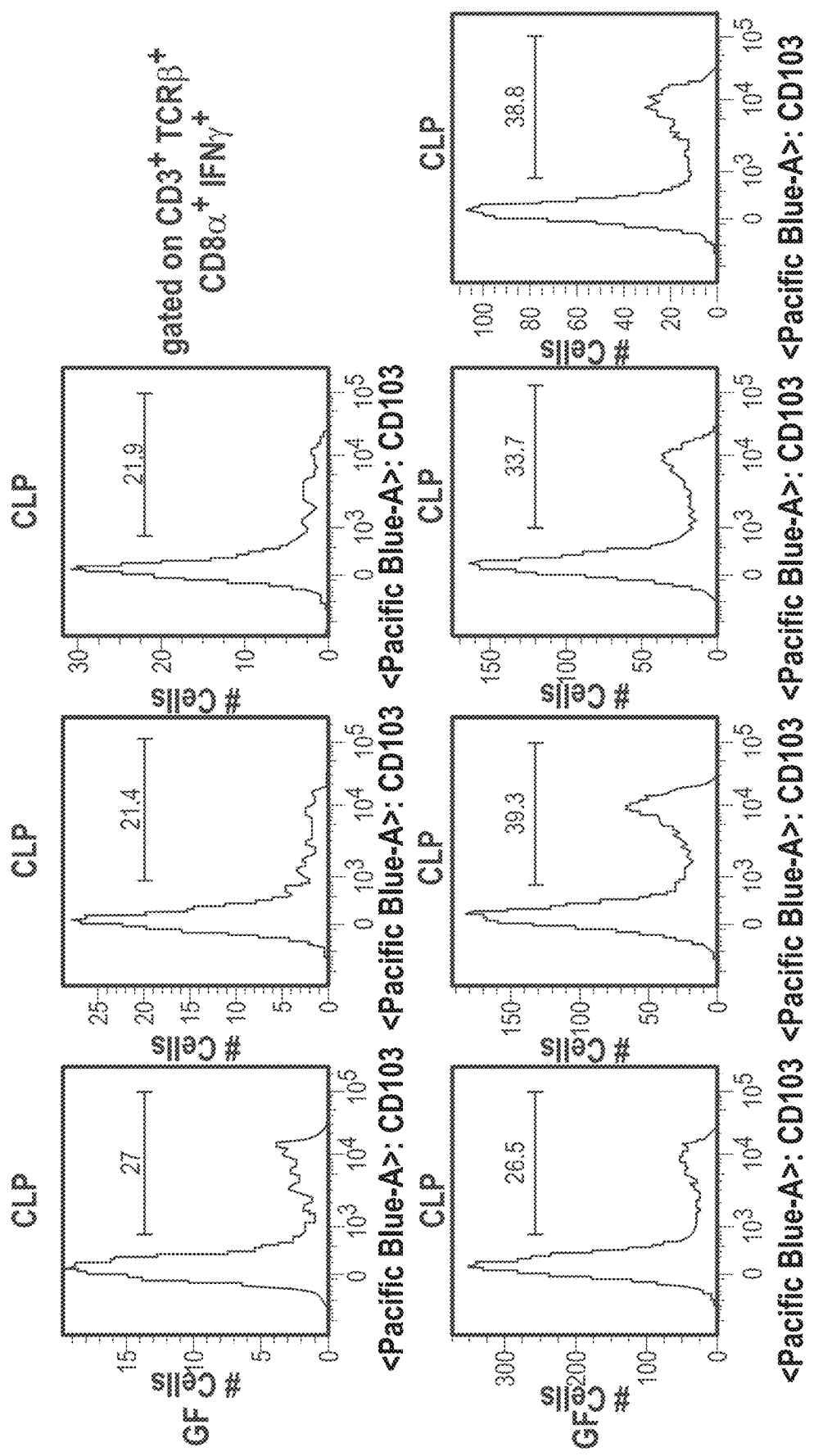
FIGS. 56 and 57 show that MHC CLP class cells are activated by the administration of the 11-mix, as evidenced by CD103+ status, while there is no activation of the MHC MLN class cells. The individual measurements are shown in FIG. 56, while the accumulated data are depicted in FIG. 57 expressed as percentage of CD3+ TCRβeta+ CD8alpha+ IFNγ+ cells.
Figure 56:
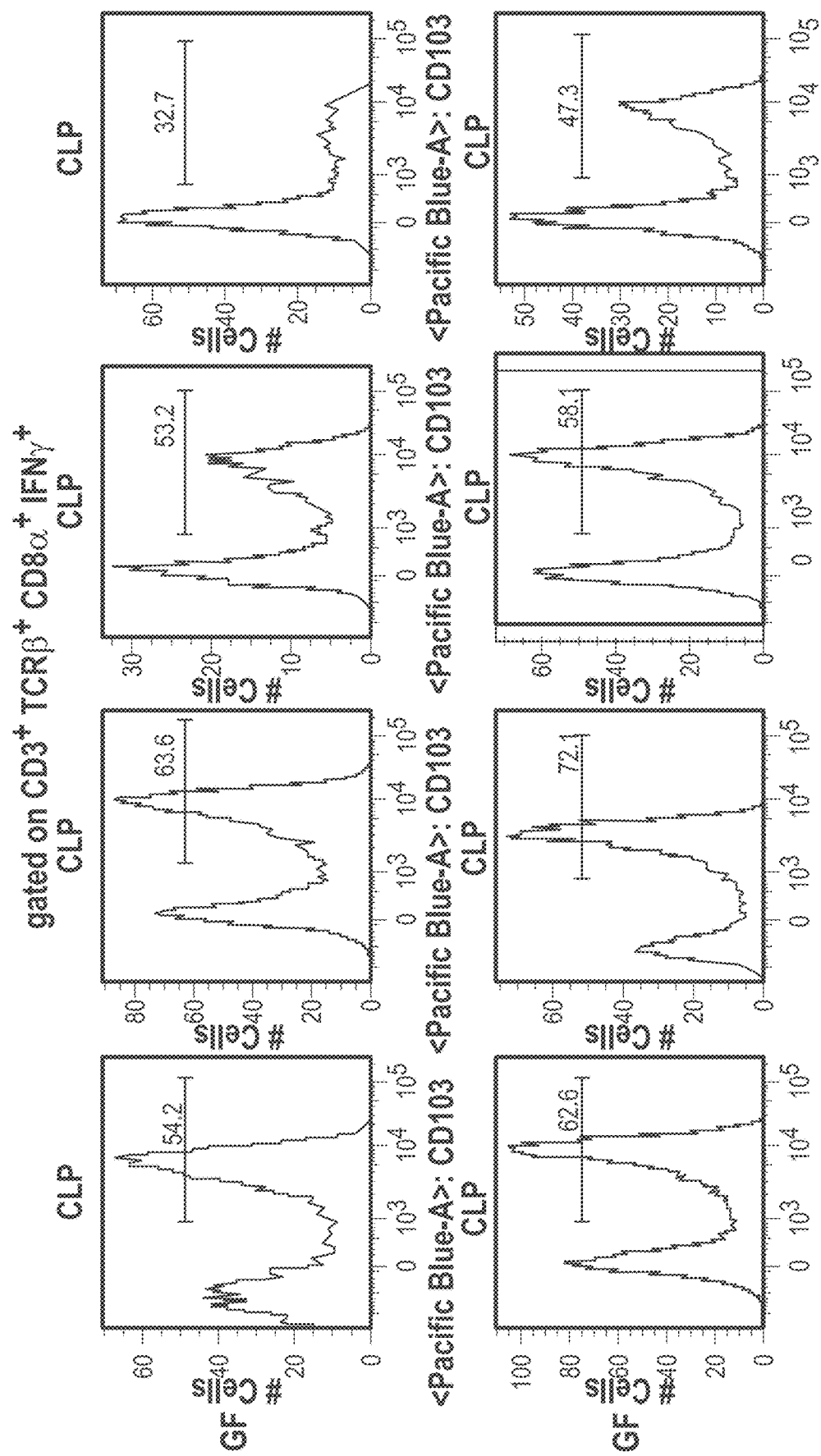
Figure 56:
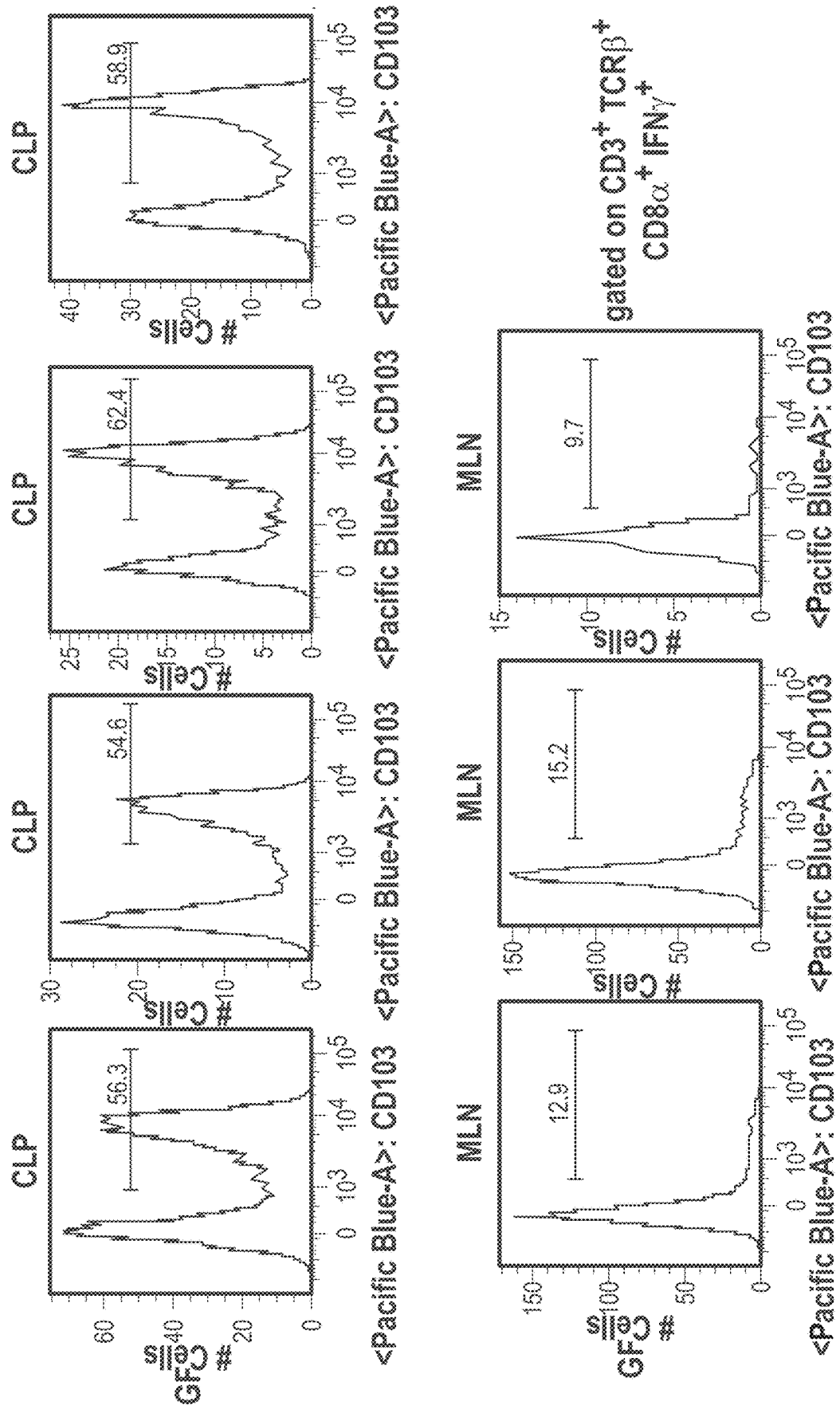
Figure 56:
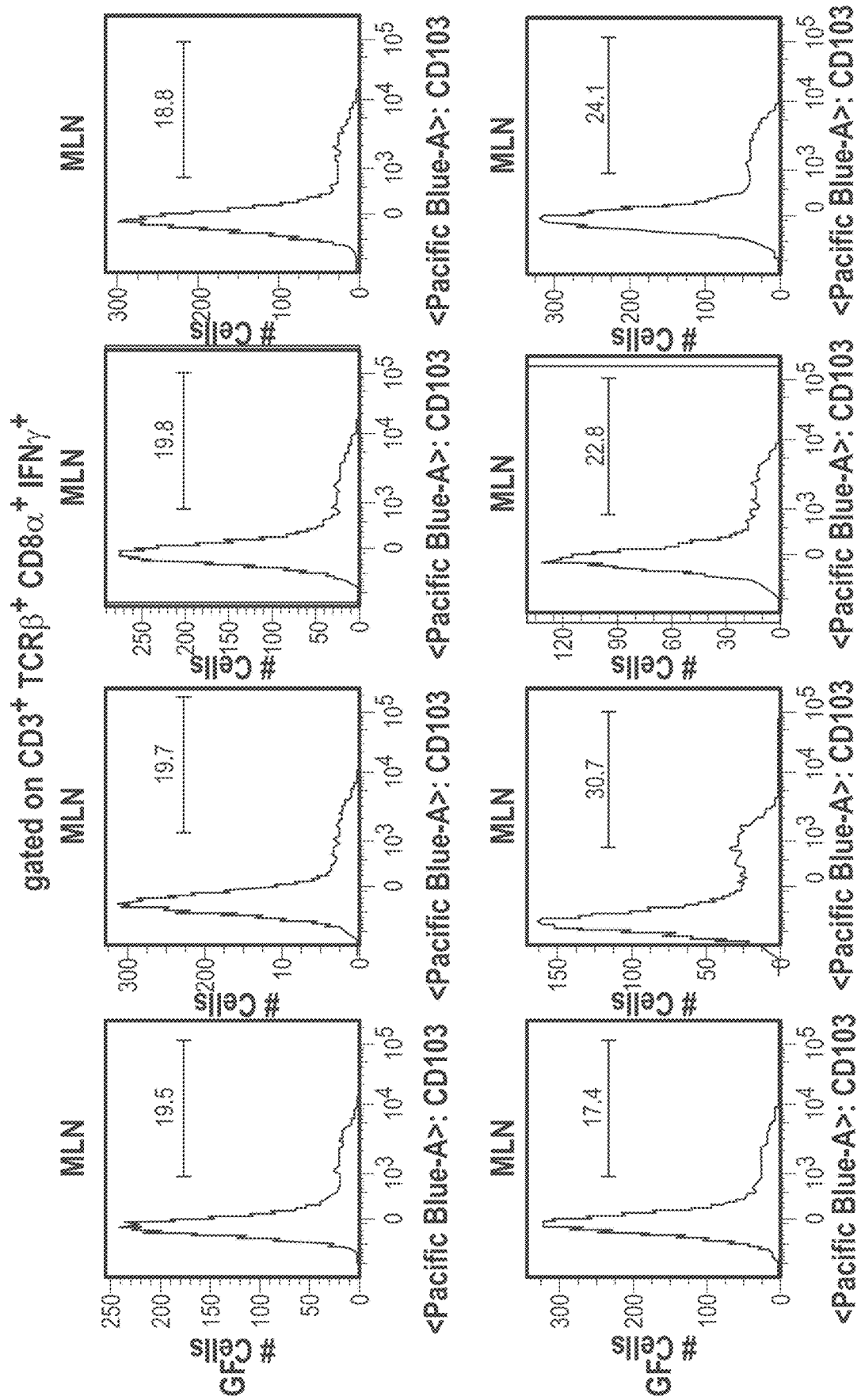
Figure 56:
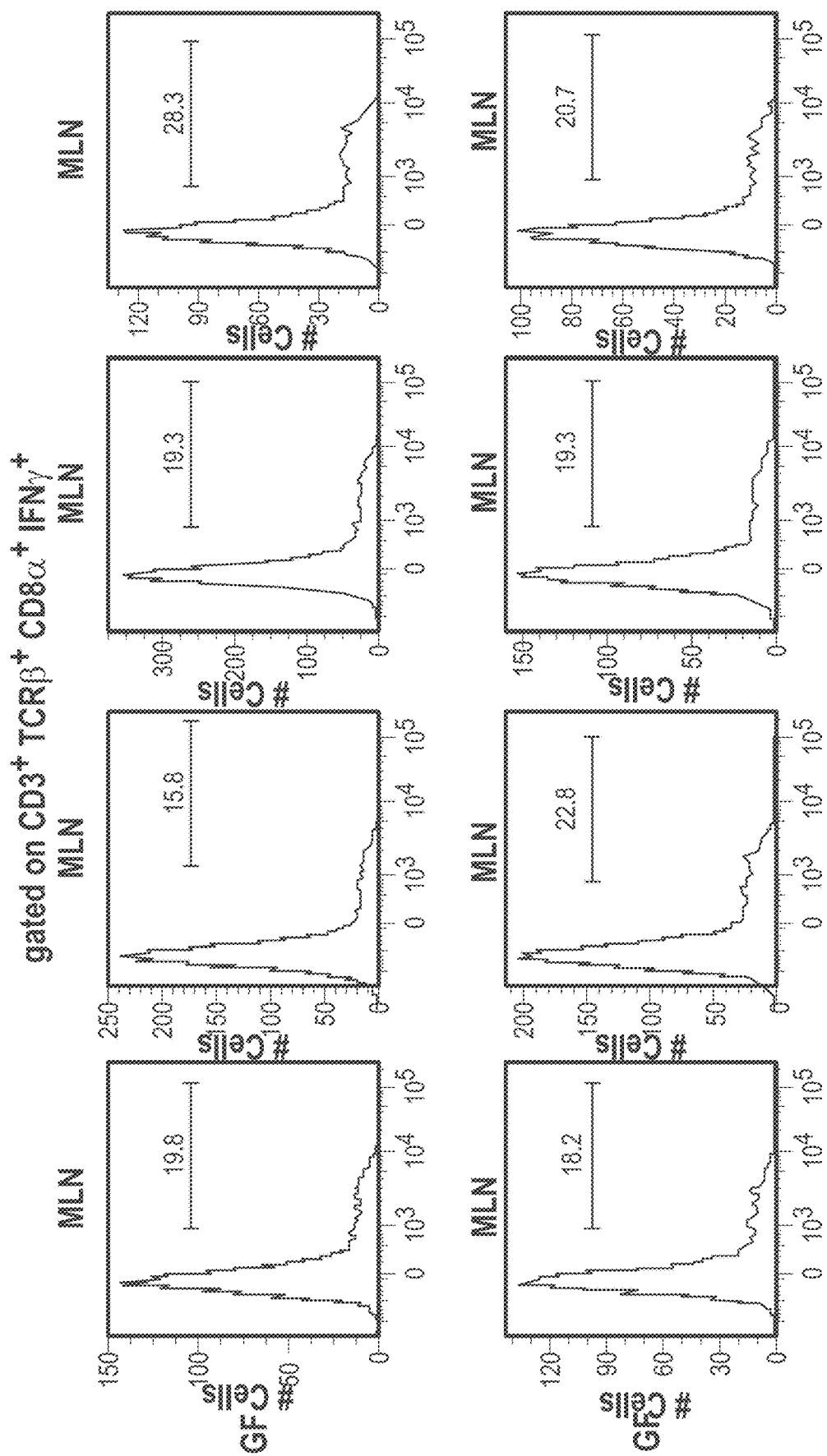
Figure 57:
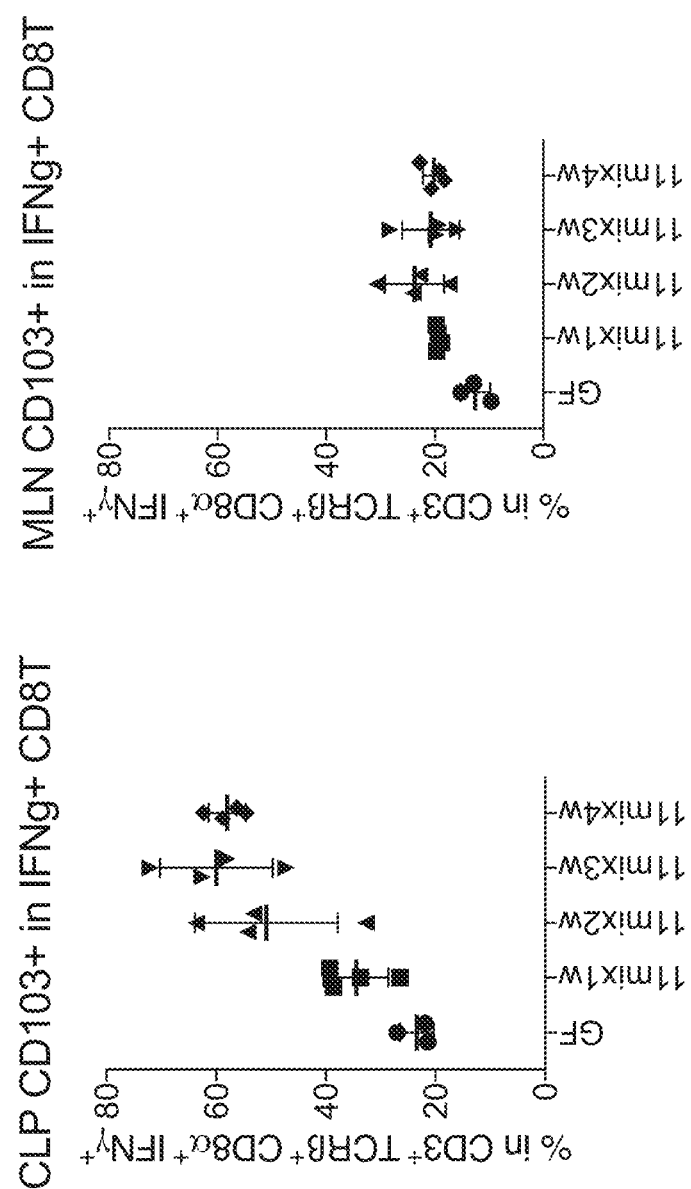

Example 11: Selective and Temporal Activation of Subsets of Lamina Propria Dendritic Cells As CD8 cells can be activated through certain subclasses of dendritic cells, the number and activation state of lamina propria CD11b− CD103+ dendritic cells was investigated following administration of the 11-mix. As shown in FIG. 49, the administration of the 11-mix did not change the proportion of the lamina propria CD11b− CD103+ dendritic cell subset. The temporality/kinetics of activation was also investigated. GF mice were colonized with the 11-mix for 1, 2, 3, and 4 weeks. The frequency of colonic LP and MLN dendritic cells (DCs)/macrophage subsets were not affected by the colonization with 11 mix. However, expression of MHC class I on colonic LP DCs (but not MLN DCs), particularly on colonic LP CD103+ DC subset (namely, Batf3-dependent DC subset), was significantly enhanced by the colonization with 11-mix. Upregulation of MHC class I expression most strongly occurred at 1 week after colonization. (See FIGS. 50-54) Without being limited to a particular mechanism it is likely that induction of the CD8 positive T cells is mostly due to proliferation rather than antigen-specific de novo differentiation. Ki67 staining revealed that expansion of CD8 positive T cells occurred at 1 week, accompanied by increase with IFNγ+CD8+ T in the colonic LP (See FIG. 55). CD103 staining revealed that induced IFNγ+CD8+ T at 1 week post colonization were mostly CD103 negative, and that CD103+ IFNγ+CD8 T (tissue resident memory phenotype CD8+ T) were gradually increased (See FIGS. 56 and 57).

SEQUENCE LISTING

Sequence_List.TXT

The invention claimed is:

1. A method for treating cancer in a subject undergoing cancer immunotherapy, the method comprising administering to the subject a pharmaceutical composition comprising a purified bacterial mixture consisting of bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, in a therapeutically effective amount to treat the cancer, wherein the pharmaceutical composition is formulated for delivery to the intestine of the subject.

2. The method of claim 1, wherein said cancer immunotherapy comprises administering an anti-cancer agent to the subject.

3. The method of claim 2, wherein the anti-cancer agent is an immune checkpoint inhibitor.

4. The method of claim 3, wherein the immune checkpoint inhibitor is a PD-1 inhibitor.

5. The method of claim 3, wherein the immune checkpoint inhibitor is nivolumab.

6. The method of claim 3, wherein the immune checkpoint inhibitor is pembrolizumab.

7. The method of claim 3, wherein the immune checkpoint inhibitor is a CTLA-4 inhibitor.

8. The method of claim 1, further comprising administering an antibiotic prior to administering the pharmaceutical composition or administering multiple doses of an antibiotic prior to administering the pharmaceutical composition.

9. The method of claim 8, wherein the antibiotic is kanamycin, gentamicin, colistin, metronidazole, vancomycin, clindamycin, fidaxomicin or cefoperazone.

10. The method of claim 9, wherein the antibiotic is vancomycin.

11. The method of claim 1, wherein the cancer is a carcinoma or an adenocarcinoma.

12. The method of claim 1, wherein the cancer is melanoma, head and neck cancer, stomach cancer, esophageal cancer, non-small cell lung cancer or colorectal cancer.

13. The method of claim 12, wherein the cancer is head and neck cancer.

14. The method of claim 12, wherein the cancer is stomach cancer.

15. The method of claim 12, wherein the cancer is esophageal cancer.

16. The method of claim 12, wherein the cancer is non-small cell lung cancer.

17. The method of claim 12, wherein the cancer is colorectal cancer.

18. The method of claim 5, further comprising administering an antibiotic prior to administering the pharmaceutical composition.

19. The method of claim 18, wherein the antibiotic is vancomycin.

20. The method of claim 12, wherein the cancer is melanoma.

\* \* \* \* \*